US006492365B1

(12) United States Patent
Wetterau, II et al.

(10) Patent No.: US 6,492,365 B1
(45) Date of Patent: Dec. 10, 2002

(54) MICROSOMAL TRIGLYCERIDE TRANSFER PROTEIN

(75) Inventors: John R. Wetterau, II, Langhorne, PA (US); Daru Young Sharp, Perrineville; Richard E. Gregg, Pennington, both of NJ (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 08/486,929

(22) Filed: Jun. 7, 1995

Related U.S. Application Data

(60) Division of application No. 08/117,362, filed on Sep. 3, 1993, now Pat. No. 5,595,872, which is a continuation-in-part of application No. 08/015,449, filed on Feb. 22, 1993, now abandoned, which is a continuation-in-part of application No. 08/847,503, filed on Mar. 6, 1992, now abandoned.

(51) Int. Cl.$^7$ ............................................. C07D 261/06
(52) U.S. Cl. ....................................... 514/247; 514/277
(58) Field of Search .................................. 514/247, 277

(56) References Cited

U.S. PATENT DOCUMENTS 4,758,569 A * 7/1988 Swindell ..................... 514/222
5,302,613 A * 4/1994 Morris ........................ 514/451
5,321,031 A * 6/1994 Dugar ......................... 514/278

OTHER PUBLICATIONS

Harrity et al., Circulation vol. 94(8): I–632, 1996.*
Wetterau et al., Science vol. 282: 751–754, 1998.*
Agrawal "Antisense Oligonucleotides: Towards Clinical Trials" Tibtech vol. 14, 376–387, Oct. 1996.*
Branch "A Good Antisense is Hard to Find" TIBS vol. 23:45–50, Feb. 1998.*

* cited by examiner

Primary Examiner—Sean McGarry
(74) Attorney, Agent, or Firm—Christopher A. Klein

(57) ABSTRACT

Nucleic acid sequences, particularly DNA sequences, coding for all or part of the high molecular weight subunit of microsomal triglyceride transfer protein, expression vectors containing the DNA sequences, host cells containing the expression vectors, and methods utilizing these materials. The invention also concerns polypeptide molecules comprising all or part of the high molecular weight subunit of microsomal triglyceride transfer protein, and methods for producing these polypeptide molecules. The invention additionally concerns novel methods for preventing, stabilizing or causing regression of atherosclerosis and therapeutic agents having such activity. The invention concerns further novel methods for lowering serum liquid levels and therapeutic agents having such activity.

10 Claims, 8 Drawing Sheets

MICROSOMAL TRIGLYCERIDE TRANSFER PROTEIN

CROSS-REFERENCE TO RELATED APPLICATIONS

This is a divisional of U.S. Ser. No. 08/117,362, filed on Sep. 3, 1993 now U.S. Pat. No. 5,595,872.

This is a continuation-in-part of U.S. patent application Ser. No. 08/015,449 Filed Feb. 22, 1993 now abandoned, which is a continuation-in-part of U.S. patent application Ser. No. 08/847,503, filed Mar. 6, 1992, now abandoned, each of which is hereby incorporated by reference.

FIELD OF THE INVENTION

This invention relates to microsomal triglyceride transfer protein, genes for the protein, expression vectors comprising the genes, host cells comprising the vectors, methods for producing the protein, methods for detecting inhibitors of the protein, and methods of using the protein and/or its inhibitors.

BACKGROUND OF THE INVENTION

The microsomal triglyceride transfer protein (MTP) catalyzes the transport of triglyceride (TG), cholesteryl ester (CE), and phosphatidylcholine (PC) between small unilamellar vesicles (SUV). Wetterau & Zilversmit, *Chem. Phys. Lipids* 38, 205–22 (1985). When transfer rates are expressed as the percent of the donor lipid transferred per time, MTP expresses a distinct preference for neutral lipid transport (TG and CE), relative to phospholipid transport. The protein from bovine liver has been isolated and characterized. Wetterau & Zilversmit, *Chem. Phys. Lipids* 38, 205–22 (1985). Polyacrylamide gel electrophoresis (PAGE) analysis of the purified protein suggests that the transfer protein is a complex of two subunits of apparent molecular weights 58,000 and 88,000, since a single band was present when purified MTP was electrophoresed under nondenaturing condition, while two bands of apparent molecular weights 58,000 and 88,000 were identified when electrophoresis was performed in the presence of sodium dodecyl sulfate (SDS). These two polypeptides are hereinafter referred to as 58 kDa and 88 kDa, respectively, or the 58 kDa and the 88 kDa component of MTP, respectively, or the low molecular weight subunit and the high molecular weight subunit of MTP, respectively.

Characterization of the 58,000 molecular weight component of bovine MTP indicates that it is the previously characterized multifunctional protein, protein disulfide isomerase (PDI). Wetterau et al., *J. Biol. Chem.* 265, 9800–7 (1990). The presence of PDI in the transfer protein is supported by evidence showing that (1) the amino terminal 25 amino acids of the bovine 58,000 kDa component of MTP is identical to that of bovine PDI, and (2) disulfide isomerase activity was expressed by bovine MTP following the dissociation of the 58 kDa–88 kDa protein complex. In addition, antibodies raised against bovine PDI, a protein which by itself has no TG transfer activity, were able to immunoprecipitate bovine TG transfer activity from a solution containing purified bovine MTP.

PDI normally plays a role in the folding and assembly of newly synthesized disulfide bonded proteins within the lumen of the endoplasmic reticulum. Bulleid & Freedman, *Nature* 335, 649–51 (1988). It catalyzes the proper pairing of cysteine residues into disulfide bonds, thus catalyzing the proper folding of disulfide bonded proteins. In addition, PDI has been reported to be identical to the beta subunit of human prolyl 4-hydroxylase. Koivu et al., *J. Biol. Chem.* 262, 6447–9 (1987). The role of PDI in the bovine transfer protein is not clear. It does appear to be an essential component of the transfer protein as dissociation of PDI from the 88 kDa component of bovine MTP by either low concentrations of a denaturant (guanidine HCl), a chaotropic agent (sodium perchlorate), or a nondenaturing detergent (octyl glucoside) results in a loss of transfer activity. Wetterau et al., *Biochemistry* 30, 9728–35 (1991). Isolated bovine PDI has no apparent lipid transfer activity, suggesting that either the 88 kDa polypeptide is the transfer protein or that it confers transfer activity to the protein complex.

The tissue and subcellular distribution of MTP activity in rats has been investigated. Wetterau & Zilversmit, *Biochem. Biophys. Acta.* 875, 610–7 (1986). Lipid transfer activity was found in liver and intestine. Little or no transfer activity was found in plasma, brain, heart, or kidney. Within the liver, MTP was a soluble protein located within the lumen of the microsomal fraction. Approximately equal concentrations were found in the smooth and rough microsomes.

Abetalipoproteinemia is an autosomal recessive disease characterized by a virtual absence of plasma lipoproteins which contain apolipoprotein B (apoB). Kane & Havel in The *Metabolic Basis of Inherited Disease*, Sixth edition, 1139–64 (1989). Plasma TG levels may be as low as a few mg/dL, and they fail to rise after fat ingestion. Plasma cholesterol levels are often only 20–45 mg/dL. These abnormalities are the result of a genetic defect in the assembly and/or secretion of very low density lipoproteins (VLDL) in the liver and chylomicrons in the intestine. The molecular basis for this defect has not been previously determined. In subjects examined, triglyceride, phospholipid, and cholesterol synthesis appear normal. At autopsy, subjects are free of atherosclerosis. Schaefer et al., *Clin. Chem.* 34, B9–12 (1988). A link between the apoB gene and abetalipoproteinemia has been excluded in several families. Talmud et al., *J. Clin. Invest.* 82, 1803–6 (1988) and Huang et al., *Am. J. Hum. Genet.* 46, 1141–8 (1990).

Subjects with abetalipoproteinemia are afflicted with numerous maladies. Kane & Havel, supra. Subjects have fat malabsorption and TG accumulation in their enterocytes and hepatocytes. Due to the absence of TG-rich plasma lipoproteins, there is a defect in the transport of fat-soluble vitamins such as vitamin E. This results in acanthocytosis of erythrocytes, spinocerebellar ataxia with degeneration of the fasciculus cuneatus and gracilis, peripheral neuropathy, degenerative pigmentary retinopathy, and ceroid myopathy. Treatment of abetalipopmteinemic subjects includes dietary restriction of fat intake and dietary supplementation with vitamins A, E and K.

To date, the physiological role of MTP has not been demonstrated. In vitro, it catalyzes the transport of lipid molecules between phospholipid membranes. Presumably, it plays a similar role in vivo, and thus plays some role in lipid metabolism. The subcellular (lumen of the microsomal fraction) and tissue distribution (liver and intestine) of MTP have led to speculation that it plays a role in the assembly of plasma lipoproteins, as these are the sites of plasma lipoprotein assembly. Wetterau & Zilversmit, *Biochem. Biophys. Acta.* 875, 610–7 (1986). The ability of MTP to catalyze the transport of TG between membranes is consistent with this hypothesis, and suggests that MTP may catalyze the transport of TG from its site of synthesis in the endoplasmic reticulum (ER) membrane to nascent lipoprotein particles within the lumen of the ER.

Olofsson and colleagues have studied lipoprotein assembly in HepG2 cells. Bostrom et al., *J. Biol. Chem.* 263, 4434–42 (1988). Their results suggest small precursor lipoproteins become larger with time. This would be consistent with the addition or transfer of lipid molecules to nascent lipoproteins as they are assembled. MTP may play a role in this process. In support of this hypothesis, Howell and Palade, *J. Cell Biol.* 92, 833–45 (1982), isolated nascent lipoproteins from the hepatic Golgi fraction of rat liver. There was a spectrum of sizes of particles present with varying lipid and protein compositions. Particles of high density lipoprotein (HDL) density, yet containing apoB, were found. Higgins and Hutson, *J. Lipid Res.* 25 1295–1305 (1984), reported lipoproteins isolated from Golgi were consistently larger than those from the endoplasmic reticulum, again suggesting the assembly of lipoproteins is a progressive event. However, there is no direct evidence in the prior art demonstrating that MTP plays a role in lipid metabolism or the assembly of plasma lipoprotein.

SUMMARY OF THE INVENTION

The present invention concerns an isolated nucleic acid molecule comprising a nucleic acid sequence coding for all or part of the high molecular weight subunit of MTP and/or intron, 5', or 3' flanking regions thereof. Preferably, the nucleic acid molecule is a DNA (deoxyribonucleic acid) molecule, and the nucleic acid sequence is a DNA sequence. Further preferred is a nucleic acid having all or part of the nucleotide sequence as shown in SEQ. ID. NOS. 1, 2, 5, 7, 8, 1 together with 5, 2 together with 7, the first 108 bases of 2 together with 8, the first 108 bases of 2 together with 7 and 8, or 8 together with 31 and 32.

The present invention also concerns a nucleic acid molecule having a sequence complementary to the above sequences and/or intron, 5', or 3' flanking regions thereof.

The present invention further concerns expression vectors comprising a DNA sequence coding for all or part of the high molecular weight subunit of MTP.

The present invention additionally concerns prokaryotic or eukaryotic host cells containing an expression vector that comprises a DNA sequence coding for all or part of the high molecular weight subunit of MTP.

The present invention additionally concerns polypeptides molecules comprising all or part of the high molecular weight subunit of MTP. Preferably, the polypeptide is the high molecular weight subunit of human MTP or the recombinantly produced high molecular weight subunit of bovine MTP.

The present invention also concerns methods for detecting nucleic acid sequences coding for all or part of the high molecular weight subunit of MTP or related nucleic acid sequences.

The present invention further concerns methods for detecting inhibitors of MTP and, hence, anti-atherosclerotic and lipid lowering agents.

The present invention further concerns a novel method for treatment of atherosclerosis, or for lowering the level of serum lipids such as serum cholesterol, TG, PC, or CE in a mammalian species comprising administration of a therapeutically effective amount of an agent that decreases the activity or amount of MTP. Such agents would also be useful for treatment of diseases associated or affected by serum lipid levels, such as pancreatitis, hyperglycemia, obesity and the like. In particular, this invention concerns a method of treatment wherein the agent that decreases the activity of MTP is a compound of the formula

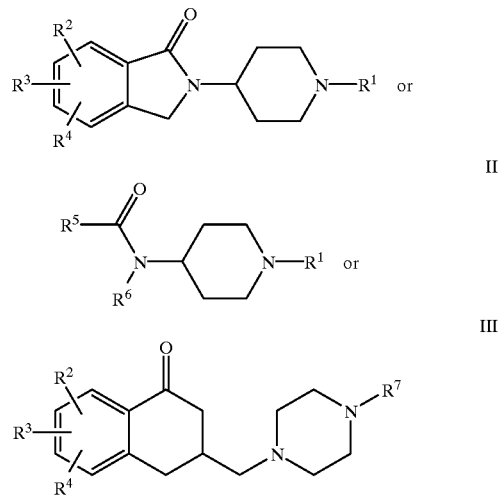

wherein:

$R^1$ is alkyl, alkenyl, alkynyl, aryl, heteroaryl, arylalkyl, heteroarylalkyl, cycloalkyl, cycloalkylalkyl (all optionally substituted through available carbon atoms with 1, 2, or 3 groups selected from halo, alkyl, alkenyl, alkoxy, aryloxy, aryl, arylalkyl, alkylmercapto, arylmercapto, cycloalkyl, cycloalkylalkyl, heteroaryl, heteroarylalkyl);

$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl;

$R^5$ and $R^6$ are independently hydrogen, alkyl, alkenyl, aryl, heteroaryl, arylalkyl, heteroarylalkyl, cycloalkyl, cycloalkylalkyl (all optionally substituted through available carbon atoms with 1, 2, or 3 groups selected from hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl; with the proviso that when $R^5$ is $CH_3$, $R^6$ is not hydrogen.

$R^7$ is alkyl (optionally substituted with oxo), aryl, or arylalkyl (wherein the alkyl portion is optionally substituted with oxo). Examples of such oxo-sustituted groups are described in Cortizo, L., *J. Med. Chem.* 34, 2242–2247 (1991).

Also in accordance with the present invention are novel compounds of formula I, wherein $R^1$ is alkyl, alkenyl, aryl, heteroaryl, arylalkyl (wherein the alkyl comprises at least two carbon atoms), heteroarylalkyl (wherein the alkyl comprises at least two carbon atoms), cycloalkyl, or cycloalkylalkyl, all optionally substituted as described above.

The present invention further concerns novel compounds of formula II wherein $R^1$ is arylalkyl or heteroarylalkyl, wherein the alkyl portion of each comprises at least two carbon atoms and wherein each is optionally substituted as described above.

Further still in accordance with the present invention are novel compounds of the formula

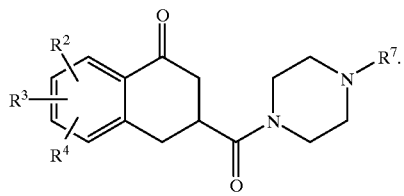

DETAILED DESCRIPTION OF THE INVENTION

DEFINITION OF TERMS

Figure 1:
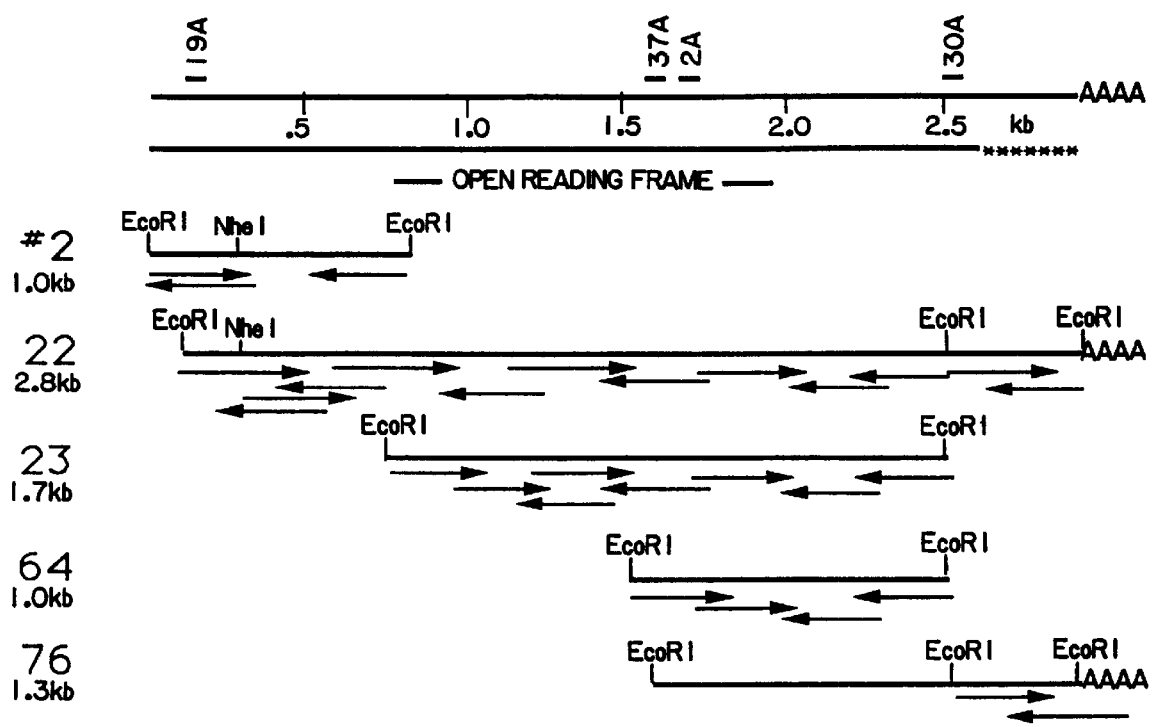
FIG. 1 shows bovine cDNA clones. The five bovine cDNA inserts are illustrated. The continuous line at the top of the figure represents the total cDNA sequence isolated. Small, labeled bars above this line map peptide and probe sequences. The open reading frame is indicated by the second line, followed by  corresponding to 3' noncoding sequences. Clone number and length are indicated to the left of each line representing the corresponding region of the composite sequence. Clones 64 and 76 were isolated with probe 2A, clones 22 and 23 with probe 37A and clone 2 with probe 19A. Eco RI linkers added during the cDNA library construction contribute the Eco RI restriction sites at the 5' and 3' ends of each insert. The internal Eco RI site in inserts 22 and 76** is encoded by the cDNA sequence. The Nhe I restriction site was utilized in preparing probes for isolation of human cDNA clones (below). The arrows under each insert line indicate individual sequencing reactions.

The following definitions apply to the terms as used throughout this specification, unless otherwise limited in specific instances.

The term "MTP" refers to a polypeptide or protein complex that (1) if obtained from an organism (e.g., cows, humans, etc.), can be isolated from the microsomal fraction of homogenized tissue; and (2) stimulates the transport of triglycerides, cholesterol esters, or phospholipids from synthetic phospholipid vesicles, membranes or lipoproteins to synthetic vesicles, membranes, or lipoproteins and which is distinct from the cholesterol ester transfer protein [Drayna et al., Nature 327, 632–634 (1987)] which may have similar catalytic properties. However, the MTP molecules of the present invention do not necessarily need to be catalytically active. For example, catalytically inactive MTP or fragments thereof may be useful in raising antibodies to the protein.

The term "modified", when referring to a nucleotide or polypeptide sequence, means a nucleotide or polypeptide sequence which differs from the wild-type sequence found in nature.

The term "related", when referring to a nucleotide sequence, means a nucleic acid sequence which is able to hybridize to an oligonucleotide probe based on the nucleotide sequence of the high molecular weight subunit of MTP.

The phrase "control regions" refers to nucleotide sequences that regulate expression of MTP or any subunit thereof, including but not limited to any promoter, silencer, enhancer elements, splice sites, transcriptional initiation elements, transcriptional termination elements, polyadenylation signals, translational control elements, translational start site, translational termination site, and message stability elements. Such control regions may be located in sequences 5' or 3' to the coding region or in introns interrupting the coding region.

The phrase "stabilizing" atherosclerosis as used in the present application refers to slowing down the development of and/or inhibiting the formation of new atherosclerotic lesions.

The phrase "causing the regression of" atherosclerosis as used in the present application refers to reducing and/or eliminating atherosclerotic lesions.

The terms "alkyl" and "alk" refer to straight and branched chain hydrocarbon radicals of up to 20 carbon atoms, with 1 to 12 carbon atoms preferred and 1 to 8 carbon atoms most preferred. Exemplary alkyl groups are methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like.

The term "alkylene" refers to alkyl groups having single bonds for attachment to other groups at two different carbon atoms. Exemplary alkylene groups are —CH—CH$_2$CH$_2$CH—, —CH—CH(CH$_3$)—CH$_2$—CH—, and the like.

The term "alkenyl" refers to both straight and branched chain hydrocarbon groups of up to 20 carbon atoms, with 1 to 12 carbon atoms preferred and 1 to 8 carbon atoms most preferred, having at least one double bond. The term "cis-alkenyl" refers to alkenyl groups having a cis double bond orientation.

The term "alkenylene" refers to alkenyl groups having single bonds for attachment at two different carbon atoms. Exemplary alkenylene groups are —CH$_2$—CH=CH—CH$_2$—, —CH$_2$—CH(CH$_3$)—CH=CH—CH$_2$—CH$_2$—, and the like. The term "cis-alkenylene" refers to alkenylene groups having a cis double bond orientation.

The term "alkynyl" refers to both straight and branched chain hydrocarbon groups of up to 20 carbon atoms, with 1 to 12 carbon atoms preferred and 1 to 8 carbon atoms most preferred, having at least one triple bond.

The term "cycloalkyl" refers to saturated cyclic hydrocarbon groups containing 3 to 20 carbons, preferably 3 to 12 carbons. Exemplary cycloalkyl groups include cyclopropyl, cyclobutyl, cyclopentyl, cyclohexyl, cycloheptyl, cyclooctyl, cyclodecyl, and cyclododecyl.

The terms "aryl" or "ar" as employed herein refer to monocyclic or bicyclic aromatic groups containing from 6 to 10 carbon atoms in the ring portion, such as phenyl or napthyl, may be optionally substituted.

The term "heteroaryl" refers to (1) 5- or 6-membered aromatic rings having 1 or 2 heteroatoms in the ring wherein the heteroatoms are selected from nitrogen, oxygen, and sulfur, (2) such rings fused to an aryl (e.g., benzothiophenyl, indolyl). Exemplary heteroaryl groups include pyrrolyl, furanyl, thiophenyl, imidazolyl, oxazolyl, thiazolyl, pyrazolyl, pyridyl, pyrimidinyl, and the like, and may be optionally substituted and/or fused to an aryl as in indolyl and benzothiophenyl.

Preferred Moities

For methods of use and novel compounds in accordance with the present invention, the following moities of formulae I and II are preferred:

R$^1$ is —R$^v$—R$^w$ or

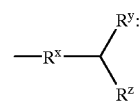

R$^v$ and R$^x$ are each independently alkylene or cis-alkenylene of up to 6 carbon atoms;

R$^w$ is aryl or heteroaryl; and

R$^y$ and R$^z$ are each independently alkyl, alkenyl, aryl, arylalkyl, heteroaryl, heteroarylalkyl, cycloalkyl, or cycloalkylalkyl.

For the methods of use and novel compounds of formulae I and II, $R^y$ and $R^z$ are most preferred to be independently aryl, arylalkyl, heteroaryl, or heteroarylalkyl.

Use and Utility

The nucleic acids of the present invention can be used in a variety of ways in accordance with the present invention. For example, they can be used as DNA probes to screen other cDNA and genomic DNA libraries so as to select by hybridization other DNA sequences that code for proteins related to the high molecular weight subunit of MTP. In addition, the nucleic acids of the present invention coding for all or part of the high molecular weight subunit of human or bovine MTP can be used as DNA probes to screen other cDNA and genomic DNA libraries to select by hybridization DNA sequences that code for MTP molecules from other organisms. The nucleic acids may also be used to generate primers to amplify cDNA or genomic DNA using polymerase chain reaction (PCR) techniques. The DNA sequences of the present invention can also be used to identify adjacent sequences in the cDNA or genome; for example, those that encode the gene, its flanking sequences and its regulatory elements.

The polypeptides of the present invention are useful in the study of the characteristics of MTP; for example, its structure, mechanism of action, and role in lipid metabolism or lipoprotein particle assembly.

Various other methods of using the nucleic acids, polypeptides, expression vectors and host cells are described in detail below.

In carrying out the methods of the present invention, the agents that decrease the activity or amount of MTP can be administered to various mammalian species, such as monkeys, dogs, cats, rats, humans, ect., in need of such treatment. These agents can be administered systemically, such as orally or parenterally.

The agents that decrease the activity or amount of MTP can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), antioxidants (ascorbic acid or sodium bisulfite) or the like. Oral dosage forms are preferred, although parenteral forms are quite satisfactory as well.

The dose administered must be carefully adjusted according to the age, weight, and condition of the patient, as well as the route of administration, dosage form and regimen, and the desired result. In general, the dosage forms described above may be administered in single or divided doses of one to four times daily.

DETAILED DESCRIPTION OF SPECIFIC EMBODIMENTS

Nucleic Acids

The present invention concerns an isolated nucleic acid molecule comprising a nucleic acid sequence coding for all or part of the high molecular weight subunit of MTP. Preferably, the nucleic acid molecule is a DNA molecule and the nucleic acid sequence is a DNA sequence. Further preferred is a nucleic acid sequence having the nucleotide sequence as shown in SEQ. ID. NOS. 1, 2, 5, 7, 8, 1 together with 5, 2 together with 7, the first 108 bases of 2 together with 8, or the first 108 bases of 2 together with 7 and 8, or 8 together with 31 and 32 or any part thereof, or a nucleic acid sequence complementary to one of these DNA sequences. In the case of a nucleotide sequence (e.g., a DNA sequence) coding for part of the high molecular weight subunit of MTP, it is preferred that the nucleotide sequence be at least about 15 sequential nucleotides in length, more preferably at least about 20 to 30 sequential nucleotides in length.

The following text shows a bovine cDNA nucleotide sequence (SEQ. ID. NO. 1), a human cDNA sequence (SEQ. ID. NO. 2), a comparison of the human and bovine cDNA sequences, the bovine amino acid sequence(SEQ. ID. NO. 3), the human amino acid sequence (SEQ. ID. NO. 4), and a comparison of the human and bovine amino acid sequences. In the sequence comparisons, boxed regions represent perfect identity between the two sequences.

| BOVINE cDNA SEQUENCE (SEQ. ID. NO. 1) | | | | | |
|---|---|---|---|---|---|
| 10<br>1234567890 | 20<br>1234567890 | 30<br>1234567890 | 40<br>1234567890 | 50<br>1234567890 | |
| AAACTCACAT | ACTCCACTGA | AGTTTTTCTC | GATCGGGCA | AAGGAAACCT | 50 |
| CCAAGACAGT | GTGGGCTACC | GAATTTCATC | CAATGTGGAT | GTCGCTTTAC | 100 |
| TGTGGAGGAG | TCCTGATGGT | GATGATAACC | AACTGATCCA | AATTACGATG | 150 |
| AAAGATGTAA | ACCTTGAAAA | TGTGAATCAA | CAGAGAGGAG | AGAAGAGCAT | 200 |
| TTTCAAAGGA | AAAAAGTCAT | CTCAAATCAT | AAGAAAGGAA | AACTTGGAAG | 250 |
| CAATGCAAAG | ACCTGTGCTC | CTTCATCTAA | TTCATGGAAA | GATCAAAGAG | 300 |
| TTCTACTCAT | ATCAAAATGA | ACCAGCAGCC | ATAGAAAATC | TCAAGAGAGG | 350 |
| CCTGGCTAGC | CTATTTCAGA | TGCAGTTAAG | CTCTGGAACT | ACCAATGAGG | 400 |
| TAGACATCTC | TGGAGATTGT | AAAGTGACCT | ACCAGGCTCA | TCAAGACAAA | 450 |
| GTGACCAAAA | TTAAGGCTTT | GGATTCATGC | AAAATAGAGA | GGGCTGGATT | 500 |
| TACGACCCCA | CATCAGGTCT | TGGGTGTCAC | TTCGAAAGCC | ACATCTGTCA | 550 |

-continued

BOVINE cDNA SEQUENCE (SEQ. ID. NO. 1)

| 10 | 20 | 30 | 40 | 50 | |
|---|---|---|---|---|---|
| CTACCTATAA | GATAGAAGAC | AGCTTTGTTG | TAGCTGTGCT | CTCAGAAGAG | 600 |
| ATACGTGCTT | TAAGGCTCAA | TTTTCTACAA | TCAATAGCAG | GCAAAATAGT | 650 |
| ATCGAGGCAG | AAACTGGAGC | TGAAAACCAC | GGAAGCAAGC | GTGAGACTGA | 700 |
| AGCCAGGAAA | GCAGGTTGCA | GCCATCATTA | AAGCAGTCGA | TTCAAAGTAC | 750 |
| ACGGCCATTC | CCATTGTGGG | GCAGGTCTTC | CAGAGCAAGT | GCAAAGGATG | 800 |
| CCCTTCTCTC | TCAGAGCACT | GGCAGTCCAT | CAGAAAACAC | CTGCAGCCTG | 850 |
| ACAACCTCTC | CAAGGCTGAG | GCTGTCAGAA | GCTTCCTGGC | CTTCATCAAG | 900 |
| CACCTCAGGA | CGGCAAAGAA | AGAAGAGATC | CTCCAAATTC | TAAAGGCAGA | 950 |
| AAACAAGGAA | GTACTACCCC | AGCTAGTGGA | TGCTGTCACC | TCTGCTCAGA | 1000 |
| CACCAGACTC | ATTAGACGCC | ATTTTGGACT | TTCTGGATTT | CAAAAGCACC | 1050 |
| GAGAGCGTTA | TCCTCCAGGA | AAGGTTTCTC | TATGCCTGTG | CATTTGCCTC | 1100 |
| ACATCCTGAT | GAAGAACTCC | TGAGAGCCCT | CATTAGTAAG | TTCAAAGGTT | 1150 |
| CTTTTGGAAG | CAATGACATC | AGAGAATCTG | TTATGATCAT | CATCGGGGCC | 1200 |
| CTTGTCAGGA | AGTTGTGTCA | GAACCAAGGC | TGCAAACTGA | AAGGAGTAAT | 1250 |
| AGAAGCCAAA | AAGTTAATCT | TGGGAGGACT | TGAAAAAGCA | GAGAAAAAAG | 1300 |
| AGGACATCGT | GATGTACCTG | CTGGCTCTGA | AGAACGCCCG | GCTTCCAGAA | 1350 |
| GGCATCCCGC | TCCTTCTGAA | GTACACAGAG | ACAGGAGAAG | GCCCATTAG | 1400 |
| CCACCTTGCC | GCCACCACAC | TCCAGAGATA | TGATGTCCCT | TTCATAACTG | 1450 |
| ATGAGGTAAA | GAAGACTATG | AACAGGATAT | ACCACCAGAA | TCGTAAAATA | 1500 |
| CATGAAAAAA | CTGTGCGTAC | TACTGCAGCT | GCCATCATTT | TAAAAAACAA | 1550 |
| TCCATCCTAC | ATGGAAGTAA | AAAACATCCT | GCTCTCTATT | GGGGAACTTC | 1600 |
| CCAAAGAAAT | GAATAAGTAC | ATGCTCTCCA | TTGTCCAAGA | CATCCTACGT | 1650 |
| TTTGAAACAC | CTGCAAGCAA | AATGGTCCGT | CAAGTTCTGA | AGGAAATGGT | 1700 |
| CGCTCATAAT | TACGATCGTT | TCTCCAAGAG | TGGGTCCTCC | TCTGCATATA | 1750 |
| CTGGCTACGT | AGAACGGACT | TCCCATTCGG | CATCTACTTA | CAGCCTTGAC | 1800 |
| ATTCTTTACT | CTGGTTCTGG | CATTCTAAGG | AGAAGTAATC | TGAACATCTT | 1850 |
| TCAGTATATT | GAGAAAACTC | CTCTTCATGG | TATCCAGGTG | GTCATTGAAG | 1900 |
| CCCAAGGACT | GGAGGCATTA | ATTGCAGCCA | CTCCTGATGA | GGGGAAGAG | 1950 |
| AACCTTGACT | CCTATGCTGG | CTTGTCACGT | CTCCTCTTTG | ATGTTCAGCT | 2000 |
| CAGACCTGTC | ACTTTTTTCA | ACGGGTACAG | TGATTTGATG | TCCAAAATGC | 2050 |
| TGTCAGCATC | TAGTGACCCT | ATGAGTGTGG | TGAAAGGACT | TCTTCTGCTA | 2100 |
| ATAGATCATT | CCCAGGAGCT | TCAGCTGCAA | TCTGGACTTA | AGGCCAATAT | 2150 |
| GGATGTTCAA | GGTGGTCTAG | CTATTGATAT | TACAGGTGCC | ATGGAGTTTA | 2200 |
| GTCTATGGTA | TCGTGAATCT | AAAACCCGAG | TGAAAAATCG | GGTAAGTGTG | 2250 |
| TTAATAACTG | GTGGCATCAC | GGTGGACTCC | TCTTTTGTGA | AAGCTGGCTT | 2300 |
| GGAAATTGGT | GCAGAAACAG | AAGCAGGCTT | GGAGTTTATC | TCCACGGTGC | 2350 |
| AGTTTTCTCA | GTACCCATTT | TTAGTTTGTC | TGCAGATGGA | CAAGGAAGAT | 2400 |

-continued

BOVINE cDNA SEQUENCE
(SEQ. ID. NO. 1)

```
         10         20         30         40         50
1234567890 1234567890 1234567890 1234567890 1234567890

GTTCCATACA GGCAGTTTGA GACAAAATAT GAAAGGCTGT CCACAGGCAG  2450
AGGTTACATC TCTCGGAAGA GAAAAGAAAG CCTAATAGGA GGATGTGAAT  2500
TCCCGCTGCA CCAAGAGAAC TCTGACATGT GCAAGGTGGT GTTTGCTCCT  2550
CAACCAGAGA GCAGTTCCAG TGGTTGGTTT TGAAACTGAT GGGGGCTGTT  2600
TCATTAGACT TCATCTCGCC AGAAGGGATA AGACGTGACA TGCCTAAGTA  2650
TTGCTCTCTG AGAGCACAGT GTTTACATAT TTACCTGTAT TTAAGAGTTT  2700
TGTAGAACGT GATGAAAAAC CTCACATAAT TAAGTTTGGG CCTGAATCAT  2750
TTGATACTAC CTACAGGGTC ATTCTGAGCC ACTCTATGTG ATACTTTAGT  2800
AGCGTTCTGT TTTCCTGCAT CTCTCTCAAA TCACATTTAC TACTGTGAAA  2850
CTAGTTCTGC CCTAAGAAGA AACCATTGTT TAAAAAAAAA AAAAAAAAA   2900
```

HUMAN cDNA SEQUENCE
(SEQ. ID. NO. 2)

```
         10         20         30         40         50
1234567890 1234567890 1234567890 1234567890 1234567890

GTGACTCCTA GCTGGGCACT GGATGCAGTT GAGGATTGCT GGTCAATATG    50
ATTCTTCTTG CTGTGCTTTT TCTCTGCTTC ATTTCCTCAT ATTCAGCTTC   100
TGTTAAAGGT CACACAACTG GTCTCTCATT AAATAATGAC CGGCTGTACA   150
AGCTCACGTA CTCCACTGAA GTTCTTCTTG ATCGGGCAA  AGGAAAACTG   200
CAAGACAGCG TGGGCTACCG CATTTCCTCC AACGTGGATG TGGCCTTACT   250
ATGGAGGAAT CCTGATGGTG ATGATGACCA GTTGATCCAA ATAACGATGA   300
AGGATGTAAA TGTTGAAAAT GTGAATCAGC AGAGAGGAGA GAAGAGCATC   350
TTCAAAGGAA AAAGCCCATC TAAAATAATG GGAAAGGAAA ACTTGGAAGC   400
TCTGCAAAGA CCTACGCTCC TTCATCTAAT CCATGGAAAG GTCAAAGAGT   450
TCTACTCATA TCAAAATGAG GCAGTGGCCA TAGAAAATAT CAAGAGAGGT   500
CTGGCTAGCC TATTTCAGAC ACAGTTAAGC TCTGAACCA  CCAATGAGGT   550
AGATATCTCT GGAAATTGTA AAGTGACCTA CCAGGCTCAT CAAGACAAAG   600
TGATCAAAAT TAAGGCCTTG GATTCATGCA AAATAGCGAG GTCTGGATTT   650
ACGACCCCAA ATCAGGTCTT GGGTGTCAGT TCAAAAGCTA CATCTGTCAC   700
CACCTATAAG ATAGAAGACA GCTTTGTTAT AGCTGTGCTT GCTGAAGAAA   750
CACACAATTT TGGACTGAAT TTCCTACAAA CCATTAAGGG GAAAATAGTA   800
TCGAAGCAGA AATTAGAGCT GAAGACAACC GAAGCAGGCC CAAGATTGAT   850
GTCTGGAAAG CAGGCTGCAG CCATAATCAA AGCAGTTGAT TCAAAGTACA   900
CGGCCATTCC CATTGTGGGG CAGGTCTTCC AGAGCCACTG TAAAGGATGT   950
CCTTCTCTCT CGGAGCTCTG GCGGTCCACC AGGAAATACC TGCAGCCTGA  1000
CAACCTTTCC AAGGCTGAGG CTGTCAGAAA CTTCCTGGCC TTCATTCAGC  1050
```

-continued

HUMAN cDNA SEQUENCE
(SEQ. ID. NO. 2)

| 10 | 20 | 30 | 40 | 50 |
|1234567890|1234567890|1234567890|1234567890|1234567890|

| | | | | | |
|---|---|---|---|---|---|
| ACCTCAGGAC | TGCGAAGAAA | GAAGAGATCC | TTCAAATACT | AAAGATGGAA | 1100 |
| AATAAGGAAG | TATTACCTCA | GCTGGTGGAT | GCTGTCACCT | CTGCTCAGAC | 1150 |
| CTCAGACTCA | TTAGAAGCCA | TTTTGGACTT | TTTGGATTTC | AAAAGTGACA | 1200 |
| GCAGCATTAT | CCTCCAGGAG | AGGTTTCTCT | ATGCCTGTGG | ATTTGCTTCT | 1250 |
| CATCCCAATG | AAGAACTCCT | GAGAGCCCTC | ATTAGTAAGT | TCAAAGGTTC | 1300 |
| TATTGGTAGC | AGTGACATCA | GAGAAACTGT | TATGATCATC | ACTGGGACAC | 1350 |
| TTGTCAGAAA | GTTGTGTCAG | AATGAAGGCT | GCAAACTCAA | AGCAGTAGTG | 1400 |
| GAAGCTAAGA | AGTTAATCCT | GGGAGGACTT | GAAAAAGCAG | AGAAAAAAGA | 1450 |
| GGACACCAGG | ATGTATCTGC | TGGCTTTGAA | GAATGCCCTG | CTTCCAGAAG | 1500 |
| GCATCCCAAG | TCTTCTGAAG | TATGCAGAAG | CAGGAGAAGG | GCCCATCAGC | 1550 |
| CACCTGGCTA | CCACTGCTCT | CCAGAGATAT | GATCTCCCTT | TCATAACTGA | 1600 |
| TGAGGTGAAG | AAGACCTTAA | ACAGAATATA | CCACCAAAAC | CGTAAAGTTC | 1650 |
| ATGAAAAGAC | TGTGCGCACT | GCTGCAGCTG | CTATCATTTT | AAATAACAAT | 1700 |
| CCATCCTACA | TGGACGTCAA | GAACATCCTG | CTGTCTATTG | GGGAGCTTCC | 1750 |
| CCAAGAAATG | AATAAATACA | TGCTCGCCAT | TGTTCAAGAC | ATCCTACGTT | 1800 |
| TTGAAATGCC | TGCAAGCAAA | ATTGTCCGTC | GAGTTCTGAA | GGAAATGGTC | 1850 |
| GCTCACAATT | ATGACCGTTT | CTCCAGGAGT | GGATCTTCTT | CTGCCTACAC | 1900 |
| TGGCTACATA | GAACGTAGTC | CCCGTTCGGC | ATCTACTTAC | AGCCTAGACA | 1950 |
| TTCTCTACTC | GGGTTCTGGC | ATTCTAAGGA | GAAGTAACCT | GAACATCTTT | 2000 |
| CAGTACATTG | GGAAGGCTGG | TCTTCACGGT | AGCCAGGTGG | TTATTGAAGC | 2050 |
| CCAAGGACTG | GAAGCCTTAA | TCGCAGCCAC | CCCTGACGAG | GGGGAGGAGA | 2100 |
| ACCTTGACTC | CTATGCTGGT | ATGTCAGCCA | TCCTCTTTGA | TGTTCAGCTC | 2150 |
| AGACCTGTCA | CCTTTTTCAA | CGGATACAGT | GATTTGATGT | CCAAAATGCT | 2200 |
| GTCAGCATCT | GGCGACCCTA | TCAGTGTGGT | GAAAGGACTT | ATTCTGCTAA | 2250 |
| TAGATCATTC | TCAGGAACTT | CAGTTACAAT | CTGGACTAAA | AGCCAATATA | 2300 |
| GAGGTCCAGG | GTGGTCTAGC | TATTGATATT | TCAGGTGCAA | TGGAGTTTAG | 2350 |
| CTTGTGGTAT | CGTGAGTCTA | AACCCGAGT | GAAAAATAGG | GTGACTGTGG | 2400 |
| TAATAACCAC | TGACATCACA | GTGGACTCCT | CTTTTGTGAA | AGCTGGCCTG | 2450 |
| GAAACCAGTA | CAGAAACAGA | AGCAGGCTTG | GAGTTTATCT | CCACAGTGCA | 2500 |
| GTTTTCTGAG | TACCCATTCT | TAGTTTGCAT | GCAGATGGAC | AAGGATGAAG | 2550 |
| CTCCATTCAG | GCAATTTGAG | AAAAAGTACG | AAAGGCTGTC | CACAGGCAGA | 2600 |
| GGTTATGTCT | CTCAGAAAAG | AAAAGAAAGC | GTATTAGCAG | GATGTGAATT | 2650 |
| CCCGCTCCAT | CAAGAGAACT | CAGAGATGTG | CAAAGTGGTG | TTTGCCCCTC | 2700 |
| AGCCGGATAG | TACTTCCAGC | GGATGGTTTT | GAAACTGACC | TGTGATATTT | 2750 |
| TACTTGAATT | TGTCTCCCCG | AAAGGGACAC | AATGTGGCAT | GACTAAGTAC | 2800 |
| TTGCTCTCTG | AGAGCACAGC | GTTTACATAT | TTACCTGTAT | TTAAGATTTT | 2850 |

-continued

HUMAN cDNA SEQUENCE
(SEQ. ID. NO. 2)

| 10 | 20 | 30 | 40 | 50 | |
|---|---|---|---|---|---|
| 1234567890 | 1234567890 | 1234567890 | 1234567890 | 1234567890 | |
| TGTAAAAAGC | TACAAAAAAC | TGCAGTTTGA | TCAAATTTGG | GTATATGCAG | 2900 |
| TATGCTACCC | ACAGCGTCAT | TTTGAATCAT | CATGTGACGC | TTTCAACAAC | 2950 |
| GTTCTTAGTT | TACTTATACC | TCTCTCAAAT | CTCATTTGGT | ACAGTCAGAA | 3000 |
| TAGTTATTCT | CTAAGAGGAA | ACTAGTGTTT | GTTAAAAACA | AAAATAAAAA | 3050 |
| CAAAACCACA | CAAGGAGAAC | CCAATTTTGT | TTCAACAATT | TTTGATCAAT | 3100 |
| GTATATGAAG | CTCTTGATAG | GACTTCCTTA | AGCATGACGG | GAAAACCAAA | 3150 |
| CACGTTCCCT | AATCAGGAAA | AAAAAAAAA | AAAAA | | 3185 |

BOVINE/HUMAN cDNA SEQUENCE COMPARISON

| | Sequence | Position |
|---|---|---|
| BOVINE | ------------------------------------------------------------------------- | 75 |
| HUMAN  | GTGACTCCTAGCTGGGCACTGGATGCAGTTGAGGATTGCTGGTCAATATGATTCTTCTTGCTGTGCTTTTTCT | 1 / 150 |
| BOVINE | ------------------------------------------------------------------------A | 76 |
| HUMAN  | GCTTCATTTCCTCATATTCAGCTTCTGTTAAAGGTCACACAACTGGTCTCTCATTAATAATGACCGGCTGTACA | 225 |
| BOVINE | A A CTCAC A TACTCCACTGAAGTT T TTCT C GATCGGGGCAAAGGAAA C CT G CAAGACAG T GTGGGCTACCG A ATTT | 151 |
| HUMAN  | A G CTCAC G TACTCCACTGAAGTT C TTCT T GATCGGGGCAAAGGAAA A CT G CAAGACAG C GTGGGCTACCG C ATTT | 300 |
| BOVINE | C A TCCAA A TGTGGATGT C GC T TTACT G TGGAGGA G TCCTGATGGTGATGAT A ACCA AC TGATCCAAAT T ACGATGA | 226 |
| HUMAN  | C C TCCAA C GTGGATGT G GC C TTACT A TGGAGGA A TCCTGATGGTGATGAT G ACCA GT TGATCCAAAT A ACCATGA | 375 |
| BOVINE | A A GATGTAAA CC TTGAAAATGTGAATCA A CAGAGAGGAGAGAGAGCAT T TTCAAAGGAAAAA AGT CATCT C AAA | 301 |
| HUMAN  | A G GATGTAAA TG TTGAAAATGTGAATCA G CAGAGAGGAGAGAAGAGCAT C TTCAAAGGAAAAA GCC CATCT A AAA | 450 |
| BOVINE | T C AT AA GAAAGGAAAACTTGGAAGC GT GCTCCTTCATCTAAT T CATGAAAAG A TCAAAGAGT | 376 |
| HUMAN  | T AT GG GAAAGGAAAACTTGGAAGC AC GCTCCTTCATCTAAT C CATGAAAAG G TCAAAGAGT | 525 |
| BOVINE | TCTACTCATATCAAAATGA AC CAG CA GCCATAGAAAAT C TCAAGAGAGG C CTGGCTAGCCTATTTCAGA TG CAGT | 451 |
| HUMAN  | TCTACTCATATCAAAATGA GG CAG TG GCCATAGAAAAT A TCAAGAGAGG T CTGGCTAGCCTATTTCAGA CA CAGT | 600 |
| BOVINE | TAAGCTCTGGAAC T ACCAATGAGGTAGA C ATCTCTGGA G ATTGTAAAGTGACCTACCAGGTCATCAAGACAAAG | 526 |
| HUMAN  | TAAGCTCTGGAAC C ACCAATGAGGTAGA T ATCTCTGGA A ATTGTAAAGTGACCTACCAGGTCATCAAGACAAAG | 675 |
| BOVINE | TGA C CAAAATTAAGGC T TTTGGATTCATGCAAAATAG A GAGG C CTGGATTTACGACCCCA C ATCAGGTCTTGGGTG | 601 |
| HUMAN  | TGA T CAAAATTAAGGC C TTGGATTCATGCAAAATAG C GAGG G CTGGATTTACGACCCCA A ATCAGGTCTTGGGTG | 750 |
| BOVINE | TCA C TTC C AAAGC C ACATCTGTCAC T ACCTATAAGATAGAAGACAGCTTTGTT G TAGCTGTGCT CT C A GAAGA G A | 676 |
| HUMAN  | TCA G TTC A AAAGC C ACATCTGTCAC C ACCTATAAGATAGAAGACAGCTTTGTT A TAGCTGTGCT TG C T GAAGA A A | 825 |
| BOVINE | T AC GTGC TTT AA G G CT C AATTT C C AT AGCA GG G C AAAAATAGTATCGA G GCAGAA C TT C GAGCTGAA A A | 751 |
| HUMAN  | C AC ACAA TTT TG A CT A AATTT C C TAAG GG G AAAAATAGTATCGA A GCAGAA TT A GAGCTGAA G A | 900 |
| BOVINE | C C AC G GAAGCA A GC GTG AGA C TGA A G C A GGAAAGCAGG C TGCAGCCAT C AT T AAAGCAGT C GATTCAAAGTACA | |
| HUMAN  | C A AC C GAAGCA G GC CCA AGA T TGA T G C T GGAAAGCAGG C TGCAGCCAT A AT C AAAGCAGT T GATTCAAAGTACA | |

BOVINE/HUMAN cDNA SEQUENCE COMPARISON

| | | | | | | | | |
|---|---|---|---|---|---|---|---|---|
| BOVINE | CGGCCATTCCCATTGTGGGCAGGTCTTCCAGAGC | A A | G TG | C | AAAGGATG | C | CCTTCTCTC | A GAGC | A | CTGGC | A GT | 826 |
| HUMAN | CGGCCATTCCCATTGTGGGCAGGTCTTCCAGAGC | C A | C TG | T | AAAGGATG | T | CCTTCTCTC | G GAGC | G | CTGGC | G GT | 975 |
| BOVINE | CCA | T CAG | A AAA | C | ACCTGCAGCCTGACAACCT | C | TCCAAGGCTGAGGCTGTCAGAA | G | CTTCCTGCCTTCAT | CA AGC | 901 |
| HUMAN | CCA | C CAG | G AAA | T | ACCTGCAGCCTGACAACCT | T | TCCAAGGCTGAGGCTGTCAGAA | A | CTTCCTGCCTTCAT | TC AGC | 1050 |
| BOVINE | AGCTCAGGAC | G GC | A | AAGAAGAAGAGATCCT | C | CAAAT | T | CTAAAG | GCA | GAAAA | C | AAGGAAGTA | C | CAGCT | A G | 976 |
| HUMAN | AGCTCAGGAC | T GC | G | AAGAAAGAAGAGATCCT | T | CAAAT | A | CTAAAG | ATG | GAAAA | T | AAGGAAGTA | T | CAGCT | C G | 1125 |
| BOVINE | TGGATGCTGTCACCTCTGCTCAGAC | AC | CAGACTCATTAGA | C | GCCATTTTGACTTT | C | TGGATTTCAAAAG | CAC | C G | 1051 |
| HUMAN | TGGATGCTGTCACCTCTGCTCAGAC | CT | CAGACTCATTAGA | A | GCCATTTTGACTTT | T | TGGATTTCAAAAG | TGA | C A | 1200 |
| BOVINE | AG | AGC | G | TTATCCTCCAGA | A | AGGTTTCTCTATGCCTGTG | C | ATTTGC | C TC | A | CATCC | TG | ATGAAGAACTCCTGAGAG | 1126 |
| HUMAN | GC | AGC | A | TTATCCTCCAGA | G | AGGTTTCTCTATGCCTGTG | G | ATTTGC | T TC | T | CATCC | CA | ATGAAGAACTCCTGAGAG | 1275 |
| BOVINE | CCCTCATTAGTAAGTTCAAAGTTCT | T | TTGG | A | AGCA | A | TGACATCAGAGAA | T | CTGTTTATGATCATCA | TC | GGG | G | C | C | 1201 |
| HUMAN | CCCTCATTAGTAAGTTCAAAGTTCT | A | TTGG | T | AGCA | G | TGACATCAGAGAA | A | CTGTTTATGATCATCA | CT | GGG | A | C | AC | 1350 |
| BOVINE | TTGTCAG | G | AAGTTGTGTCAGAA | CC | AAGGCTGCAAACT | G | AAAG | A | AGTA | A | T | A | GAAGC | T | AAGTTAATC | T | TGGGAG | 1276 |
| HUMAN | TTGTCAG | A | AAGTTGTGTCAGAA | TG | AAGGCTGCAAACT | C | AAAG | C | AGTA | G | T | G | GAAGC | C | AAGTTAATC | C | TGGGAG | 1425 |
| BOVINE | GACTTGAAAAAGCAGAGAAAAAGAGGACA | TC | GT | GATGTA | C | CTGCTGGCT | C | TGAAGAA | C | GCCC | T | GCTTCCAGAAG | 1351 |
| HUMAN | GACTTGAAAAGCAGAGAAAAAGAGGACA | C C | AG | GATGTA | T | CTGCTGGCT | T | TGAAGAA | T | GCCC | T | GCTTCCAGAAG | 1500 |
| BOVINE | GCATCCC | GCTC | CTTCTGAAGTA | CA | CAGA | GA | CAGGAGAGGGCCCAT | T | GC | CG | CCAC | CA | C | A | CTCCAGA | 1426 |
| HUMAN | GCATCCC | AAGT | CTTCTGAAGTA | TG | CAGA | AG | CAGGAGAGGGCCCAT | C | GC | TA | CCAC | TG | C | T | CTCCAGA | 1575 |
| BOVINE | GATATGAT | G | TCCCTTTCATAACTGATGAGT | A | AAGAAGAC | TA | G | AACAG | A | ATATACCACCA | G | AA | T | CGTAAA | A T | A C | 1501 |
| HUMAN | GATATGAT | C | TCCCTTTCATAACTGATGAGT | G | AAGAAGAC | CT | A | AACAG | A | ATATACCACCA | A | AA | C | CGTAAA | G T | T C | 1650 |
| BOVINE | ATGAAAA | A | ACTGTGCG | T | ACT | A | CTGCAGCTGC | T | ATCATTTTAAA | A | AACAATCCATCCTACATGGA | A | GT | A AA | A | AACA | 1576 |
| HUMAN | ATGAAAA | G | ACTGTGCG | C | ACT | G | CTGCAGCTGC | T | ATCATTTTAAA | T | AACAATCCATCCTACATGGA | C | GT | C AA | G | AACA | 1725 |
| BOVINE | TCCTGCT | C | TCTATTGGGA | A | CTTCCC | A | AAGAAATGAATAA | G | TACATGCTC | T | CCATTGT | C | CAAGACATCCTACGTT | 1651 |
| HUMAN | TCCTGCT | G | TCTATTGGGA | G | CTTCCC | C | AAGAAATGAATAA | A | TACATGCTC | G | CCATTGT | T | CAAGACATCCTACGTT | 1800 |
| BOVINE | TTGAAA | CA | CCTGCAAGCAAAAT | G | GTCCGTC | A | AGTTCTGAAGGAAATGGTCGCTCA | C | AATTA | C GA | T | CGTTTCTCCA | 1726 |
| HUMAN | TTGAAA | TG | CCTGCAAGCAAAAT | T | GTCCCGTC | G | AGTTCTGAAGGAAATGGTCGCTCA | T | AATTA | T GA | C | CGTTTCTCCA | 1875 |

BOVINE/HUMAN cDNA SEQUENCE COMPARISON

| | | |
|---|---|---|
| BOVINE<br>HUMAN | A GAGTGG G TC C TC C TCTGC C TA T C TAGAACG C ACTGGCTAC G A C T CCC A TTCGGCATCTACTTACAGCCT T GACA<br>G GAGTGG A TC T TC T TCTGC C TA C A TAGAACG T A G T C CCCC G TTCGGCATCTACTTACAGCCT A GACA | 1801<br>1950 |
| BOVINE<br>HUMAN | TTCT T TACTC T GGTTCTGGCATTCTAAGGAGAAGTAA T CTGAACATCTTTCAGTA T ATTG A GAA AA CT CC TCTTC<br>TTCT C GGTTCTGGCATTCTAAGGAGAAGTAA C CTGAACATCTTTCAGTA C ATTG G GAA GG CT GG TCTTC | 1876<br>2025 |
| BOVINE<br>HUMAN | A T GGTA T CCAGGTGGT C ATTGAAGCCCAAGGACTGGA G GC A TTAAT T GCAGCCAC T CCTGA T GAGGGGGA A GAGA<br>A C GGTA G CCAGGTGGT T ATTGAAGCCCAAGGACTGGA A GC C TTAAT C GCAGCCAC C CCTGA C GAGGGGGA G GAGA | 1951<br>2100 |
| BOVINE<br>HUMAN | ACCTTGACTCCTATGCTGG CT TGTCAGC TC TCCTCTTTTGATGTTCAGCTCAGACCTGTCAC T TTTTTTCAACGG G T<br>ACCTTGACTCCTATGCTGG TA TGTCAGC CA TCCTCTTTTGATGTTCAGCTCAGACCTGTCAC C TTTTTTCAACGG A T | 2026<br>2175 |
| BOVINE<br>HUMAN | ACAGTGATTTGATGTCCAAAATGCTGTCAGCATCT A G T GACCCTAT G AGTGTGGTGAAAGGACTT C TTCTGCTAA<br>ACAGTGATTTGATGTCCAAAATGCTGTCAGCATCT C G C GACCCTAT C AGTGTGGTGAAAGGACTT A TTCTGCTAA | 2101<br>2250 |
| BOVINE<br>HUMAN | TAGATCATTC C CAGGA G CTTCAGC C T C CAATCTGGACT T AA A GCCAATAT G GA T GT T CA A GGTGGTCTAGCTATTG<br>TAGATCATTC T CAGGA A CTTCAGC T T A CAATCTGGACT A AA A GCCAATAT A GA G GT C CA G GGTGGTCTAGCTATTG | 2176<br>2325 |
| BOVINE<br>HUMAN | ATATT A CAGGTGC C ATGGAGTTTAG TC T A TGGTATCGTGA A TCTAAAACCCGAGTGAAAAAT C GGGT A A G TGTG T<br>ATATT T CAGGTGC A ATGGAGTTTAG CT T G TGGTATCGTGA G TCTAAAACCCGAGTGAAAAAT A GGGT G A C TGTG G | 2251<br>2400 |
| BOVINE<br>HUMAN | TAATAAC TGG TG G CATCAC G GTGGACTCCTCTTTTTGTGAAAGCTGGC T TGGAAA TTG GT G CAGAAACAGAAGCAG<br>TAATAAC CAC TG A CATCAC A GTGGACTCCTCTTTTTGTGAAAGCTGGC C TGGAAA CCA GT A CAGAAACAGAAGCAG | 2326<br>2475 |
| BOVINE<br>HUMAN | GCTTGGAGTTTATCTCCAC C GTGCAGTTTTTCTCAGTACCCATT T TTAGTTTG TC TGCAGATGGACAAGGA A GA TG<br>GCTTGGAGTTTATCTCCAC A GTGCAGTTTTTCTCAGTACCCATT C TTAGTTTG CA TGCAGATGGACAAGGA T GA AG | 2401<br>2550 |
| BOVINE<br>HUMAN | T TCCAT A CAGGCA C TTTGAGA C AAA A TA T GAAAGGCTGTCCACAGGCAGAGTTA CA TCTCTC G GAA G AGAAAAG<br>C TCCAT T CAGGCA T TTTGAGA A AAA G TA C GAAAGGCTGTCCACAGGCAGAGTTA TG TCTCTC A GAA A AGAAAAG | 2476<br>2625 |
| BOVINE<br>HUMAN | AAAGC C TA A TAG G AGGATGTGAATTCCCGCT G CA C CAAGAGAACTC T GA C ATGTGCAA G GTGTGTTTGC T CCTC<br>AAAGC G TA T TAG C AGGATGTGAATTCCCGCT C CA T CAAGAGAACTC A GA G ATGTGCAA A GTGTGTTTGC C CCTC | 2551<br>2700 |
| BOVINE<br>HUMAN | A A CC A GA G AG C A TTCCAG T TGG T TGGTTTTGAAACTGA TGG G GG C TG TTT CA TTT A GA C TT CA TCTC G CC AG AAGG<br>A G CC G GA T AG T A C TTCCAG C TGG A TGGTTTTGAAACTGA CCT G TG A TA TTT T AC TTT GA A TTT TG TCTC C CC GA AAGG | 2626<br>2775 |

BOVINE/HUMAN cDNA SEQUENCE COMPARISON

| | | |
|---|---|---|
| BOVINE | GA T A AG A C GTG A CATG C CTAAGTA - TTGCTCTCTGAGAGCACAG T GTTTACATATTTACCTGTATTTAAGA G TTTT | 2700 |
| HUMAN | GA C A CA A T GTG G CATG A CTAAGTA C TTGCTCTCTGAGAGCACAG C GTTTACATATTTACCTGTATTTAAGA T TTTT | 2850 |
| BOVINE | TGTA G AA A C G TG A C G TG A TG AAAAAC CT CA -CA T A AT T AA G TTTGGG CC T G A AT CA T T TG AT A CTACC T ACAC G GTCATT C | 2774 |
| HUMAN | TGTA A AA A G CT A CA AAAAAC TG CA GTT T G AT C AA A TTTGGG TA TT A TG CA G T -- AT G CTACC C ACAC C GTCATT T | 2922 |
| BOVINE | TGA GC CA C TC T ATGTGA TA CTTT - A GT A G CGTTCT - GTTT T C C TT GC A T CTCTCTCAAATC A CATTT AC TAC T GT | 2846 |
| HUMAN | TGA AT CA - TC - ATGTGA CG CTTT C A AC A A CGTTCT TA GTTT A C TTT AT A C CTCTCTCAAATC T CATTT GG TAC A GT | 2995 |
| BOVINE | G A A C TAGTT C T G C C CTAAGA A GAAAC C A T TGTTT AAA AAAAA A AAAAA A AAAA ------- | 2900 |
| HUMAN | C A G A TAGTT A TT T C T T CTAAGA G GAAAC T A G TGTTT GTT AAAAA C AAAAA T AAAA ACAAAACCACACAAGGAGAAC | 3070 |
| BOVINE | ------------------------------------------------------ | 2900 |
| HUMAN | CCAATTTTGTTTCAACAATTTTTGATCAATGTATATGAAGCTCTTGATAGGACTTCCTTAAGCATGACGGGAAAA | 3145 |
| BOVINE | ------------------------------------- | 2900 |
| HUMAN | CCAAACACGTTCCCTAATCAGGAAAAAAAAAAAAAAAAA | 3185 |

BOVINE PROTEIN SEQUENCE (SEQ. ID. NO. 3)

```
         10         20         30         40         50
 1234567890 1234567890 1234567890 1234567890 1234567890

KLTYSTEVFL DRGKGNLQDS VGYRISSNVD VALLWRSPDG DDNQLIQITM   50
 KDVNLENVNQ QRGEKSIFKG KKSSQIIRKE NLEAMQRPVL LHLIHGKIKE  100
 FYSYQNEPAA IENLKRGLAS LFQMQLSSGT TNEVDISGDC KVTYQAHQDK  150
 VTKIKALDSC KIERAGFTTP HQVLGVTSKA TSVTTYKIED SFVVAVLSEE  200
 IRALRLNFLQ SIAGKIVSRQ KLELKTTEAS VRLKPGKQVA AIIKAVDSKY  250
 TAIPIVGQVF QSKCKGCPSL SEHWQSIRKH LQPDNLSKAE AVRSFLAGIK  300
 HLRTAKKEEI LQILKAENKE VLPQLVDAVT SAQTPDSLDA ILDFLDFKST  350
 ESVILQERFL YACAFASHPD EELLRALISK FKGSFGSNDI RESVMIIIGA  400
 LVRKLCQNQG CKLKGVIEAK KLILGGLEKA EKKEDIVMYL LALKNARLPE  450
 GIPLLLKYTE TGEGPISHLA ATTLQRYDVP FITDEVKKTM NRIYHQNRKI  500
 HEKTVRTTAA AIILKNNPSY MEVKNILLSI GELPKEMNKY MLSIVQDILR  550
 FETPASKMVR QVLKEMVAHN YDRFSKSGSS SAYTGYVERT SHSASTYSLD  600
 ILYSGSGILR RSNLNIFQYI EKTPLHGIQV VIEAQGLEAL IAATPDEGEE  650
 NLDSYAGLSA LLFDVQLRPV TFFNGYSDLM SKMLSASSDP MSVVKGLLLL  700
 IDHSQELQLQ SGLKANMDVQ GGLAIDITGA MEFSLWYRES KTRVKNTVSV  750
 LITGGITVDS SFVKAGLEIG AETEAGLEFI STVQFSQYPF LVCLQMDKED  800
 VPYRQFETKY ERLSTGRGYI SRKRKESLIG GCEFPLHQEN SDMCKVVFAP  850
 QPESSSSGWF 860
```

HUMAN PROTEIN SEQUENCE (SEQ. ID. NO. 4)

```
         10         20         30         40         50
 1234567890 1234567890 1234567890 1234567890 1234567890

MILLAVLFLC FISSYSASVK GHTTGLSLNN DRLYKLTYST EVLLDRGKGK   50
 LQDSVGYRIS SNVDVALLWR NPDGDDDQLI QITMKDVNVE NVNQQRGEKS  100
 IFKGKSPSKI MGKENLEALQ RPTLLHLIHG KVKEFYSYQN EAVAIENIKR  150
 GLASLFQTQL SSGTTNEVDI SGNCKVTYQA HQDKVIKIKA LDSCKIARSG  200
 FTTPNQVLGV SSKATSVTTY KIEDSFVIAV LAEETHNFGL NFLQTIKGKI  250
 VSKQKLELKT TEAGPRLMSG KQAAAIIKAV DSKYTAIPIV GQVFQSHCKG  300
 CPSLSELQRS TRKYLQPDNL SKAEAVRNFL AFIQHLRTAK KEEILQILKM  350
 ENKEVLPQLV DAVTSAQTSD SLEAILDFLD FKSDSSIILQ ERFLYACGFA  400
 SHPNEELLRA LISKFKGSIG SSDIRETVMI ITGTLVRKLC QNEGCKLKAV  450
 VEAKKLILGG LEKAEKKEDT RMYLLALKNA LLPEGIPSLL KYAEAGEGPI  500
 SHLATTALQR YDLPFITDEV KKTLNRIYHQ NRKVHEKTVR TAAAAIILNN  550
 NPSYMDVKNI LLSIGELPQE MNKYMLAIVQ DILRLEMPAS KIVRRVLKEM  600
 VAHNYDRFSR SGSSSAYTGY IERSPRSAST YSLDILYSGS GILRRSNLNI  650
```

HUMAN PROTEIN SEQUENCE
(SEQ. ID. NO. 4)

```
          10          20          30          40          50
     1234567890  1234567890  1234567890  1234567890  1234567890

FQYIGKAGLH  GSQVVIEAQG  LEALIAATPD  EGEENLDSYA  GMSAILFDVQ  700

LRPVTFFNGY  SDLMSKMLSA  SGDPISVVKG  LILLIDHSQE  LQLQSGLKAN  750

IEVQGGLAID  ISGAMEFSLW  YRESKTRVKN  RVTVVITTDI  TVDSSFVKAG  800

LETSTETEAG  LEFISTVQFS  QYPFLVCMQM  DKDEAPFRQF  EKKYERLSTG  850

RGYVSQKRKE  SVLAGCEFPL  HQENSEMCKV  VFAPQPDSTS  TGWF        894
```

BOVINE/HUMAN PROTEIN COMPARISON

| | | |
|---|---|---|
| BOVINE | ---------- ---------- ---------- ---- KLTYST EV F LDRGKG N | 16 |
| HUMAN | MILLAVLFLC FISSYSASVK GHTTGLSLNN DRLY KLTYST EV L LDRGKG K | 50 |
| | | |
| BOVINE | LQDSVGYRIS SNVDVALLWR S PDGDD N QLI QITMKDVN L E NVNQQRGEKS | 66 |
| HUMAN | LQDSVGYRIS SNVDVALLWR N PDGDD D QLI QITMKDVN V E NVNQQRGEKS | 100 |
| | | |
| BOVINE | IFKGK KS S C I IR KENLEA M Q RP V LLHLIHG K T KEFYSYQN E PA AIEN L KR | 116 |
| HUMAN | IFKGK SP S K I MG KENLEA L Q RP I LLHLIHG K V KEFYSYQN E AV AIEN I KR | 150 |
| | | |
| BOVINE | GLASLFQ M QL SSGTTNEVDI SG D CKVTYQA HQDKV I KIKA LDSCKI E R A G | 166 |
| HUMAN | GLASLFQ I QL SSGTTNEVDI SG N CKVTYQA HQDKV I KIKA LDSCKI A R S G | 200 |
| | | |
| BOVINE | FTTP H QVLGV I SKATSVTTY KIEDSFV V AV L SEE IRALR L NFLQ S I A GKI | 216 |
| HUMAN | FTTP N QVLGV S SKATSVTTY KIEDSFV I AV L AEE THNFG L NFLQ I I K GKI | 250 |
| | | |
| BOVINE | VS R QKLELKT TEA SV RL KP G KQ V AAIIKAV DSKYTAIPIV GQVFQS K CKG | 266 |
| HUMAN | VS K QKLELKT TEA GR RL MS G KQ A AAIIKAV DSKYTAIPIV GQVFQS H CKG | 300 |
| | | |
| BOVINE | CPSLSE H W Q S IRK H LQPDNL SKAEAVR S FL AFI K HLRTAK KEEILQILK A | 316 |
| HUMAN | CPSLSE L W R S IRK Y LQPDNL SKAEAVR N FL AFI Q HLRTAK KEEILQILK M | 350 |
| | | |
| BOVINE | ENKEVLPQLV DAVTSAQT P D SL D AILDFLD FKS TE S V ILQ ERFLYAC A FA | 366 |
| HUMAN | ENKEVLPQLV DAVTSAQT S D SL E AILDFLD FKS DS S I ILQ ERFLYAC G FA | 400 |
| | | |
| BOVINE | SHP C EELLRA LISKFKGS F G S N DIRE S VMI I G A LVRKLC QN Q GCKLK G V | 416 |
| HUMAN | SHP N EELLRA LISKFKGS I G S S DIRE I VMI I G I LVRKLC QN E GCKLK A V | 450 |
| | | |
| BOVINE | I EAKKLILGG LEKAEKKED I V MYLLALKNA R LPEGIP L LL KY T E T GEGPI | 466 |
| HUMAN | V EAKKLILGG LEKAEKKED T R MYLLALKNA L LPEGIP S LL KY A E A GEGPI | 500 |
| | | |
| BOVINE | SHLA A T T LQR YD V PFITDEV KKT M NRIYHQ NRK I HEKTVR T T AAAIIL K N | 516 |
| HUMAN | SHLA T T A LQR YD L PFITDEV KKT L NRIYHQ NRK V HEKTVR T A AAAIIL N N | 550 |
| | | |
| BOVINE | NPSYM E VKNI LLSIGELP K E MNKYML S IVQ DILRFE I PAS K M VR Q VLKEM | 566 |
| HUMAN | NPSYM C VKNI LLSIGELP C E MNKYML A IVQ DILRFE M PAS K I VR R VLKEM | 600 |
| | | |
| BOVINE | VAHNYDRFS K SGSSSAYTGY V ER TSH SAST YSLDILYSGS GILRRSNLNI | 616 |
| HUMAN | VAHNYDRFS R SGSSSAYTGY I ER SPR SAST YSLDILYSGS GILRRSNLNI | 650 |
| | | |
| BOVINE | FQYI E K TP LH G I QVVIEAQG LEALIAATPD EGEENLDSYA G L SA L LFDVQ | 666 |
| HUMAN | FQYI G K AG LH G S QVVIEAQG LEALIAATPD EGEENLDSYA G M SA I LFDVQ | 700 |

-continued

BOVINE/HUMAN PROTEIN COMPARISON

| | | | | | | | | | | |
|---|---|---|---|---|---|---|---|---|---|---|
| BOVINE | LRPVTFFNGY SDLMSKMLSA S | S | DP | M | SVVKG L | L | LLIDHSQE LQLQSGLKAN | | | 716 |
| HUMAN | LRPVTFFNGY SDLMSKMLSA S | G | DP | I | SVVKG L | I | LLIDHSQE LQLQSGLKAN | | | 750 |
| BOVINE | MD | VQGGLAID I | I | GAMEFSLW YRESKTRVKN RV | S | V | L | IT | GG | I TVDSSFVKAG | 766 |
| HUMAN | IE | VQGGLAID I | S | GAMEFSLW YRESKTRVKN RV | I | V | V | IT | TD | I TVDSSFVKAG | 800 |
| BOVINE | LE | IGA | ETEAG LEFISTVQFS QYPFLVC | L | QM DK | EDV | P | Y | RQF E | I | KYERLSTG | 816 |
| HUMAN | LE | TST | ETEAG LEFISTVQFS QYPFLVC | K | QM DK | DEA | P | F | RQF E | K | KYERLSTG | 850 |
| BOVINE | RGY | I | S | R | KRKE S | LIG | GCEFPL HQENS | C | MCKV VFAPQP | E | S | S | S SGWF | 860 |
| HUMAN | RGY | V | S | Q | KRKE S | VLA | GCEFPL HQENS | E | MCKV VFAPQP | D | S | I | S SGWF | 894 |

The bovine cDNA is a 2900 base composite of the cDNA sequences of clones 2 and 22 and has an open reading frame between bases 1 and 2580, predicting a translation product of 860 amino acids, followed by a TGA stop codon, 298 bases of 3 prime non-coding sequence, and a poly A region.

In the human cDNA, the 3185 bases predict an 894 amino acid translation product from bases 48 to 2729, followed by a TGA stop codon, 435 bases of 3 prime non-coding sequence, and a poly A region.

In the cDNA comparison, there is about an 88% identity between overlapping sequences in the coding region (bovine bases 1–2583 and human bases 150–2732). It is not necessary to introduce any gaps to attain this alignment within the coding region. The homology is somewhat weaker in the 3' noncoding region, including the introduction of several gaps to obtain optimal alignment.

The bovine protein sequence (SEQ. ID. NO. 3) is the 860 amino acid translation product of the combined sequence of bovine cDNA clones 2 and 22. Sequences for the peptide fragments used to design oligonucleotide probes are as follows: peptide 19A is found between residues 37 and 51, peptide 37A between residues 539 and 550, and peptide 2A between residues 565 and 572.

The human protein sequence (SEQ. ID. NO. 4) is the 894 amino acid translation product of human cDNA clone 693.

In the amino acid comparison, the bovine protein shows about 86% identity to the human translation product. When considering highly conserved substitutions at nonidentical residues, the two proteins are about 94% homologous.

The inventors extended their knowledge of the 5' end of the foregoing bovine cDNA sequence with the sequence shown below, 5' to 3'. The top line shows the nucleotide sequence (SEQ. ID. NO. 5), and the bottom line the amino acid sequence (SEQ. ID. NO. 6). The new sequence obtained (83 bases) is underlined.

```
TT TTT CTC TGC TTC ATT TCC TCA TAT TCA GCT TCT
   F   L   C   F   I   S   S   Y   S   A   S

GTT AAA GGT CAC ACA ACT GGT CTC TCA TTA AAT AAT
 V   K   G   H   T   T   G   L   S   L   N   N

GAC CGA CTA TAC AAA CTC ACA TAC TCC ACT GAA GTT
 D   R   L   Y   K   L   T   Y   S   T   E   V
```

The inventors have also extended their knowledge of the 5' end of the foregoing human cDNA sequence. The additional sequence (SEQ. ID. NO. 7) is as follows:

AGAGTCCACTTCTCA

This sequence extends the 5' end of the human MTP cDNA sequence by 15 bases. These sequences were generated from human liver cDNA clone 754 isolated during the initial human cDNA cloning (see Example 3), but were characterized after clone 693.

The inventors have also elucidated a partial human genomic DNA sequence (SEQ. ID. NO. 8) for the high molecular weight subunit of MTP as shown below. Vertical lines indicate intron/exon boundaries. Exon sequences are in plain type, intron sequences in bold. Arrows indicate portions of the introns for which the sequence is not reported (arrow lengths do not indicate the size of the introns). The numbers in the right column indicate the first and last base of each exon relative to the human cDNA sequence shown supra. The inventors have also extended their knowledge of the human genomic DNA sequence flanking and including the cDNA sequences corresponding to bases 1 to 108 of the human MTP gene (SEQ. ID. NO. 31, below). The known intron/exon boundary is indicated at base 108. Plain type represents the corresponding cDNA sequence. This extended genomic nucleic acid, as well as the extended cDNA, and fragments thereof are useful in the present invention.

(SEQ. ID. NO. 8)

```
AAGGTTCCTGAGCCCCACTGTGGTAGAGAGATGCACTGATGGTGAGACAG
CATGTTCCCTTACAATGAAAACTGGATATGTGTCATTATCTTTATGCAGG       109
TCACACAACTGGTCTCTCATTAAATAATGACCGGCTGTACAAGCTCACGT
ACTCCACTGAAGTTCTTCTTGATCGGGGCAAAGGAAAACTGCAAGACAGC     EXON 2
GTGGGCTACCGCATTTCCTCCAACGTGGATGTGGCCTTACTATGGAGGAA
TCCTGATGGTGATGATGACCAGTTGATCCAAATAACGGTGGGCATTTTCT       296
ACCAGATAAATGCAAAGATTAGATATCAGAAGTTTTTGGAGAAGTGTACC
ATTGGACAGCACTTGTATTGGGTTCCCGTTTATAATCCATTAGTTTCTTA
TCTATCACTAAAACAAGCAGGTCTTTGTTTTAAGGTTTGGTGATGAAAG    ⟶
TTATTTTAAGCCTAAAGTCACAGAGTTCTTTAAGTATTGCTATTTTTGCC
TTATTAAAAAACCTAGTTTATAAATACCTTCTCCATTCTTTTAAAGTGAG
TGGCAAGGTCCTATAAATCATGAATTGAAAAATGACAGAAGAAATTGTGG

CCAACTCTTTCTGTTTCTTTATCATTTTATTTTCAGAGATACTCTGATGA
AGACAGATATAGGAAGTTTTTTTTAACAGCTTTCTTTCTGTTACTCCAGA       297
                                                        EXON 3
TGAAGGATGTAAATGTTGAAAATGTGAATCAGCAGAGAGGAGAGAAGAGC
ATCTTCAAAGGAAAAAGCCCATCTAAAATAATGGGAAAGGAAAACTTGGA
AGCTCTGCAAAGACCTACGCTCCTTCATCTAATCCATGGAAAGGTAAAGG       440
GGCGTTTAGATTCCACAACTTTTTCTCCAACTTCATATTTTTCTTCCCTT
CAGTAGATATTATTTTGAGGTAATCACATTGTAACTACTTTTATGGTAAA
TGGAATTTCTTCAAGAACTAAAGAACAGAGGTTGTAAATTAAATGTTTCC
AAACTGAATCAATGCCCTGAGTTCCCTTACATTTACTAGCCAATTTGTTT
CCTATTTTTCTGGAAATCTTTATAGTGGAATGAAGTATTTATTTATTGAT
GAAAGGCATTATTAAAAGGTAAATTTCTCATCAAATTATAAGGGATTACA
AACATAATGTAACAAAGCAAGTCATCAAAGCATGATTGGATGAATTC     ⟶
TCTGATAAATGATGCATTTTTGCTTCATTTGTGTTCTGTTCCCCTCTCCC

CACCAGGTCAAAGAGTTCTACTCATATCAAAATGAGGCAGTGGCCATAGA       441
AAATATCAAGAGAGGTCTGGCTAGCCTATTTCAGACACAGTTAAGCTCTG     EXON 4
GAACCACCAATGAGGTACTTACCAATATTAATAAGGATTCAGCATCTCAA       548
TAAAATTTGTAAGGATTTCTACTTATACAATTTCAGTAGAAGAGTTACTA
CTAAGGTAATGCTCAGAAAAGGTGACTTGTGTAG    ⟶
TCCCCTATGGCCTATTAGAGACCTCAATTTTCAAGCCACTTCTCACTAGA
ATTCAAATGGCCCACAAGGAATCCCAAGCATTATGCCCTTGCCTTTCTTT
TTAGGTAGATATCTCTGGAAATTGTAAAGTGACCTACCAGGCTCATCAAG       549
ACAAAGTGATCAAAATTAAGGCCTTGGATTCATGCAAAATAGCGAGGTCT     EXON 5
GGATTTCAGACCCCAAATCAGGTATGATAGATGTCACTTTCTTTGAGGCA       665
TTAAAATAATTACATTTTGTAGAGACTAATTTA    ⟶
```

```
CGATGATTACTTGTTATAAAGATGGCTATTTATTTATTTAG|GTCTTGGGT   666
GTCAGTTCAAAAGCTACATCTGTCACCACCTATAAGATAGAAGACAGCTT
TGTTATAGCTGTGCTTGCTGAAGAAACACACAATTTTGGACTGAATTTCC                EXON 6
TACAAACCATTAAGGGGAAAATAGTATCGAA|GTAAGATAATGCTAAAATT   805
TTTATTTTCTTTGCTATTCTTTGTTATATTATTATACTTGATTTGT    ⎯⎯⎯⎯→
ATGATTATAATATAGCATTTCCCTTTGGTATTATGCAG|GCAGAAATTAGA   806
GCTGAAGACAACCGAAGCAGGCCCAAGATTGATGTCTGGAAAGCAGGCTG
CAGCCATAATCAAAGCAGTTGATTCAAAGTACACGGCCATTCCCATTGTG                EXON 7
GGGCAGGTCTTCCAGAGCCACTGTAAAGGATGTCCTTCT|GTAAGTGCAGA   956
CAAATATGGGAATAATCATGACATCAGACTCTGTTTTCATTTTGTCTCCA
GTGAAAGCATCAACTCATTCA    ⎯⎯⎯⎯⎯⎯⎯⎯⎯⎯⎯⎯⎯⎯⎯⎯⎯⎯⎯→
GGAGAACACCCTTTGTAAATGTGGATGTTCACAGTTATGAGTGGGGTATG
AGCCTGCAGTGTATGTTTTGCAG|CTCTCGGAGCTCTGGCGGTCCACCAGG   957
AAATACCTGCAGCCTGACAACCTTTCCAAGGCTGAGGCTGTCAGAAACTT
CCTGGCCTTCATTCAGCACCTCAGGACTGCGAAGAAAGAAGAGATCCTTC                EXON 8
AAATACTAAAGATGGAAAATAAGGAAGTATT|GTAAGTTCCCCAACCTTTG   1114
TGTGGGGTTGTCTGTCAGAAACATTTCTGGAGTG   ⎯⎯⎯⎯⎯⎯→
GATATCCATGATTATGCCTTTTTTTATAG|ACCTCAGCTGGTGGATGCTGT   1115
CACCTCTGCTCAGACCTCAGACTCATTAGAAGCCATTTTGGACTTTTTGG
ATTTCAAAAGTGACAGCAGCATTATCCTCCAGGAGAGGTTTCTCTATGCC                EXON 9
TGTGGATTTGCTTCTCATCCCAATGAAGAACTCCTGAGAGCCCTCATT|GT   283
AAGTCAAATAGAAAATAAAGACCCTCAACTCCTATAAAACTTCTTAAGAA
TATTAACAGTAATTAAAAGTTTCTTAGATCCGAATTCTTCGCCCTATAGT
GAGTCA   ⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯⎯→
CTATTTTATCCCTGGGTGGTTAATAG|AGTAAGTTCAAAGGTTCTATTGGT   1284
AGCAGTGACATCAGAGAAACTGTTATGATCATCACTGGGACACTTGTCAG              EXON 10
AAAGTTGTGTCAGAATGAAGGCTGCAAACTCAAA|GTAAGTGCAAATCCAA   1391
TCTCATGTATTACATCATTCTACACCATTGTCCATTTGATACTCACCATG
CTGCCTACTATTGGCACTCCTAATTCTCTTTACTCTATTCTACTTACCTT
ATTTGNATAGCAAT   ⎯⎯⎯⎯⎯⎯⎯⎯⎯⎯⎯⎯⎯→
AACACAATATGCCCATTATTGATAATACTCATTGCTTCTTAAGAATGTAT
ATGTATTTTTTTAAAAAAAGCATAACACCTTTATCAAGCTTTACTTGTT
TGCTTTTATTCCACTGTGTGCCTCAGTCAAGCAACCAATGCAAAACTTTG
TAAAACTGTAGGTTGCTTTCTTGGACCCAAGAATAAAGCCAGTCTCACCC
AAGTCTTCTTCAATGTATGGTCATGCATATATCTAAGGTATATGATTTTT
CAG|GCAGTAGTGGAAGCTAAGAAGTTAATCCTGGGAGGACTTGAAAAAGC   1392
```

```
AGAGAAAAAAGAGGACACCAGGATGTATCTGCTGGCTTTGAAGAATGCCC
                                                   EXON 11
TGCTTCCAGAAGGCATCCCAAGTCTTCTGAAGTATGCAGAAGCAGGAGAA

GGGCCCATCAGCCACCTGGCTACCACTGCTCTCCAGAGATATGATCTCCC

TTTCATAACTGATGAG|GTAAAATCTCCAAGAATATTTGCAACATTTACAG 1504

AAGAAAAAAAAAAAGCATGCTGAACATGAGTCAAATGCAAATTCCGCTCA

AGTCACTCTGTATTTTCCCCAAATAGTCTTCTCTCCTGCTTAAAAATAAC

TCTTAAATTGCATTTGGGGCTATTCTAA ─────────────────────▶

ATGTTTAATTTCTCAGGCTATGCCTAATGTGCATAAGGAAGTATGTGGTC

TGAAGTTCACTACAGTCATGGAAGAAAGAGATGGAGAAAGCCACCAGCTC

TTAACGGCCTCAGCCTAGAAGTGATCCTCATAGATTCTATCCATGGCGTA

TTAGCCAGAACTAGTCACGTGGCCCCCACCAAATCACAAAGGAATCTGGG

AAATGTAGTAACACATGTATATTTTTATGAACACTCACTATTCCTGCTAT

TCCTGCTGAAATGTCCATTTTAAAAATCTAGATGTGCACTAAGTTTGAAC

ATCTTATGAACAG|GTGAAGAAGACCTTAAACAGAATATACCACCAAAACC 1605

GTAAAGTTCATGAAAAGACTGTGCGCACTGCTGCAGCTGCTATCATTTTA

AATAACAATCCATCCTACATGGACGTCAAGAACATCCTGCTGTCTATTGG EXON 12

GGAGCTTCCCCAAGAAATGAATAAATACATGCTCGCCATTGTTCAAGACA

TCCTACGTTTTGAAATGCCTGCAAG|GTATAATACATTGCACATGTCTCTC 1816

TGTGTATTCAAGCTTATTTGTGTGTTCATGGGGTACCGATGTAGCTAATA

ATAATGATGTGGTCATTATGCAA ──────────────────────▶

AGCTGGACACCCTTGCCTTGCTGTCATTTTGATAGCAAACTAAATTTCAA

ATATCTGAGTAATGAAGGGGCTAGCCCTAATCCTGATGCTACCACGCCAG

CTGGCACCACCCTGGCTCTTGGAAAGGCATGAGGAAAATTTGGCTTCCTC

TTTTTTCCACTGAGGATTTTTTTTTTCCAAATTTGACTTGGGAAACAGTC

ATTACAATGAATGTGCAGCTTTTTTTTTCCTCATATGTTGCAGCAAAATT 1817

GTCCGTCGAGTTCTGAAGGAAATGGTCGCTCACAATTATGACCGTTTCTC EXON 13

CAGGAGTGGATCTTCTTCTGCCTACACTGGCTACATAGAAC|GTATGTACA 1914

CCAAAAAGAGGTTCTCCTTCCATACCCCACAACTTAGCATTGCTGGAACT

GCTATTAAATTACAGTTATTGTGTGTCATCAG|GTAGTCCCCGTTCGGCAT 1915
                                                   EXON 14
AGTAACCTGAACATCTTTCAGTACATTGGGAAGGCTGGTCTTCACGGTAG

CCAG|GTAACTCACTTCTCATGGATTTTGCTTAATAAAGTATGCAAGAAAT 2036

CAGGCTGAGGTAAAATAAAACATATATGCTGTGGGTAATGCTATAGAATG

TATAAGTTAATGGTGGCTTCTGTCATATTTTGCCCATGATTTCCTTATCT

GTAAGAGGCTGTATGGTTTATAGTCACTCAGAGAAAGTTTCGAATTTGAA

CTTGAAACCTAAGTAATTTGATCCATTGAACTTGACAAATGTCCATT ───▶

TGGCCCCTTGAGAAGTTCTAGCTGCAGCTCAGAAGCTTCACCATTATTTA
```

-continued

CAGAGCAGGCAGGGAGCTTGCGTCATGAACATTATATTGATTTTATCCAG

GTGGTTATTGAAGCCCAAGGACTGGAAGCCTTAATCGCAGCCACCCCTGA 2037

CGAGGGGAGGAGAACCTTGACTCCTATGCTGGTATGTCAGCCATCCTCT

TTGATGTTCAGCTCAGACCTGTCACCTTTTTCAACGGATACAGTGATTTG EXON 15

ATGTCCAAAATGCTGTCAGCATCTGGCGACCCTATCAGTGTGGTGAAAGG

ACTTATTCTGCTAATAGATCATTCTCAGGTAATTCANYCAGTCTGTGAGT 2264

ATTTATTGAGTCCCTAAACTACGCCAGGCACGTA ⟶

ATCAACACAACTCAAATGGAATTATCTACAGCAGGAGGTCAAATGTNCCA

TTGGAAAGGGGGTTAACTAAATTGTACTTATTATTTTTATAACTATTATT

ATGCTTTTTTCTTCTAGGAACTTCAGTTACAATCTGGACTAAAAGCCAAT 2265

ATAGAGGTCCAGGGTGGTCTAGCTATTGATATTTCAGGTGCAATGGAGTT EXON 16

TAGCTTGTGGTATCGTGAGTCTAAAACCCGAGTGAAAAATAGGTAAGTGT 2389

TTATGCATTATACATTTATGAATTACATATAAGACTATAT ⟶

CTTGGGTATTTCTGACCTGCTGAGAGGACCTGGGTTCCAAGAATGTTTTT

CATTTTGGTCTTTGTTATGCCCATACGAAACAATGTAGTATCTTACAGAC

ACTCCCCACATCTGCAACTGAAGGCAGGGGAGAGCTCAGGGGAAGGGCAA

ACCTTCCCTGCCCAATATCTGAGACTCACCAGGCCCTGGTTACCAGCAGA

ACTCTAAGCACATCCAGGTCACCTCTGAATCCCTTAAGTGTTTCCTTCCA

GTCACTGGCATCATACGTTCAGACCCTGTAAAGTTACAGCTGTTAGTCCA

ATACCATTAAATATAATATGAACAAGTTTTTTCTTTTTTTCTCAAATGTT

TAGGGTGACTGTGGTAATAACCACTGACATCACAGTGGACTCCTCTTTTG 2390

TGAAAGCTGGCCTGGAAACCAGTACAGAAACAGAAGCAGGTTTGGAGTTT

ATCTCCACAGTGCAGTTTTCTCAGTACCCATTCTTAGTTTGCATGCAGAT EXON 17

GGACAAGGATGAAGCTCCATTCAGGTAAGATGCAGCGTACAGGTCATGTT 2560

CCAGGACCATCCCCAGTGCACCAGGAACTTGCATTCAGTTTAGAACATTC

AGTTTCAGAATTAAAACAAAACAGTAGAAACCCAGGGAAAGATGAATTTT

CTTTAAATGAGTAGAAGAATAATTGATAAGGCCAAAAAAAGTCAGTTTCT

GGGATACCAAAAAAAAATCTAATGACTAGTTCATGTGATTCTGGAGATAG

TTATCATATTCTAATCCAGAAACAATTT ⟶

TGCTTTGGAACAGAAACTTCAAGTACATTCAGTAACTTGGCTGGAGAGGT

ATAGGGTGACTTAACTGTGTGTGTAATTCTGTTAATGTTGCTGTTGTTGT

ACAGGCAATTTGAGAAAAAGTACGAAAGGCTGTCCACAGGCAGAGGTTAT 2561

GTCTCTCAGAAAAGAAAAGAAAGCGTATTAGCAGGATGTGAATTCCCGCT

CCATCAAGAGAACTCAGAGATGTGCAAAGTGGTGTTTGCCCCTCAGCCGG

ATAGTACTTCCAGCGGATGGTTTTGAAACTGACCTGTGATATTTTACTTG

AATTTGTCTCCCCGAAAGGGACACAATGTGGCATGACTAAGTACTTGCTC
EXON 18
TCTGAGAGCACAGCGTTTACATATTTACCTGTATTTAAGATTTTTGTAAA

```
AAGCTACAAAAAACTGCAGTTTGATCAAATTTGGGTATATGCAGTATGCT

ACCCACAGCGTCATTTTGAATCATCATGTGACGCTTTCAACAACGTTCTT

AGTTTACTTATACCTCTCTCAAATCTCATTTGGTACAGTCAGAATAGTTA

TTCTCTAAGAGGAAACTAGTGTTTGTTAAAAACAAAAATAAAAACAAAAC

CACACAAGGAGAACCCAATTTTGTTTCAACAATTTTTCATCAATGTATAT

GAAGCTCTTGATAGGACTTCCTTAAGCATGACGGGAAAACCAAACACGTT

CCCTAATCAGGAAAAAAAAAAAAAAAAAAAAGGTAGGACACAACCAACCCAT

TTTTTTTCTCTTTTTTTGGACTTGGGGGCCCAGGGAGAAGGGACAAGACT

TTTAAAAGACTTGTTAGCCAACTTCAAGAATTAATATTTATGTCTCTGTT

ATTGTTAGTTTTAAGCCTTAAGGTAGAAGGCACATAGAAATAACATCTCA

TCTTTCTGCTGACCATTTTAGTGAGGTTGTTCCAAAGACATTCAGGTCTC

TACCTCCAGCCCTGCAAAAATATTGGACCTAGCACAGAGGAATCAGGAAA

ATTAATTTCAGAAACTCCATTTGATTTTTCTTTTGCTGTGTCTTTTTGAG

ACTGTAATATGGTACACTGTCCTCTAAGGGACATCCTCATTTTATCTCAC

CTTTTTGGGGGTGAGAGCTCTAGTTCATTTAACTGTACTCTGCACAATAG

CTAGGATGACTAAGAGAACATTGCTTCAAGAAACTGGTGGATTTGGATTT

CCAAAATATGAAATAAGGAAAAAAATGTTTTTATTTGTATGAATTAAAAG

ATCCATGTTGAACATTTGCAAATATTTATTAATAAACAGATGTGGTGATA

AACCCAAAACAAATGACAGGTCCTTATTTTCCACTAAACACAGACACATG

AAATGAAAGTTTAGCTAGCCCACTATTTGTTGTAAATTGAAAACGAAGTG

TGATAAAATAAATATGTAGAAATCATATTGAATTC
```

CCCCTCTTAATCTCTTCCTAGAAATGAGATTCAGAAAGGACAGGACTGCA   SEQ. ID. NO. 31

TCCAGCCTGTTTGGGAACTCAGACAAATGTGTGTTGTCACAGACACAAAT

AGAGGTCTACTATGAAATAATTGGCTTGCTAGTGTGCTAATGACAGACAA

TGCTGATTTGCTCCAACCTCATACAGTTTCACACATAAGGACAATCATCT

ATGTTTCATGAAAGTTCTATCTACTTTAACATTATTTTGAAGTGATTGGT

GGTGGTATGAATTAACAGTTTAAATTTAAATCCTAAAATTCAGTGTGAAT

TTTTTATAATAGCATAAAAATTCAAAGATGTCCATACAAGAAAAATTAAA

ATTTGGTTAGGTTTAGCAGAGTTTGAGAATCCTTACTACCCTCCCACATA

GTATTGTAATGTGAATATAGGCAGTTACTATTACAGGCATAATGATGATT

ATGTATTAAGCAGAAAGAAGTATCACCACCAGTTTTTTTCTTTGAATGCC

CCTCAGTACTTCTGCATTTATAGGATGGTAGACTGGTTTGGTTTAGCTCT

CAAAAGTGAAAACATTTAAAGTTTCCTCATTGGGTGAAAAAAATTAAAAA

GAGTGAGAGACTGAAAACTGCAGCCCACCTACGTTTAATCATTAATAGTG

AGCCCTTCAGTGAACTTAGGTCCTGATTTTGGAGTTTGGAGTCTGACCTT

TCCCCAAAGATAAACATGATTGTTGCAGGTTCTGAAGAGGGTCACTCCCT

```
CACTGGCTGCCATTGAAAGAGTCCACTTCTCAGTGACTCCTAGCTGGGCA  1

CTGGATGCAGTTGAGGATTGCTGGTCAATATGATTCTTCTTGCTGTGCTT  EXON 1

TTTCTCTGCTTCATTTCCTCATATTCAGCTTCTGTTAAAGGTAAGTTTGT  108

GTTGCCTTTTGCTAAACTTTAATTTCCATCTTTGGAGTTGGAGGCAGATA

CGTGCGTGTGTGTGTTTGTGTGAGTGAATAGTGAAAGAGTTTCTGACT

AAACTATCTTCAAAACCATGTAACTTTGGAATGTTTGTGAAAGCATGGCT
GAGTTGAAATGAAAACCAAATTCAAATCCCTACAAACATTAAGAAAACAG

ATATTTCTTTTAGTTTCAGTTCCTCAGACCAGTGTGTTCTTGCTTCAATT

TCTCATTCATGGTCTGTTTTTAAAAGAAGGAAAAAAGATACCCACTATTG

TTACCTGCTGTTGTTGGTCACATTGAATGCAGCTCCTTCATTTGAATTGT

AAATGAGGATTTTTTTTAAAAACCGAGTTCTTAAATTTTCTTTTAGTTGC
TTAGCAATGTGACCTCAAGAAGAATTAGACCCAATGAAAAAGGCATTTGA

TTTGCCAAAGAATTATGAATGAAATGGCACAACATATATTTAATTCCGTT

ACAATTAAAAAATGATA
```

The inventors have further determined the sequence of a 564 base pair region of intron 10 of the foregoing genomic DNA sequence. This region, shown below (SEQ. ID. NO. 32) has a CA repeat sequence with the structure $(CA)_4AA(CA)_3GA(CA)_4TA(CA)_nTACA$ wherein $(CA)_n$ varies from n=8 to n=17 in genes sequenced to date. Variation in this motif allows these sequences to be used as allelic markers for the MTP gene.

(1) the isolation of a double-stranded DNA sequence from genomic DNA or complementary DNA (cDNA) which contains the sequence;
(2) the chemical synthesis of the DNA sequence; and
(3) the synthesis of the DNA sequence by polymerase chain reaction (PCR).

In the first method, a genomic or cDNA library can be screened in order to identify a DNA sequence coding for all or part of the high molecular weight subunit of MTP. For example, bovine or human cDNA libraries can be screened

```
ACTTTTCAAATATGTTCTACAATCAGAAAAGTCCTTTTGTCCTAGTCTGA      50   SEQ. ID. NO. 32

GAAAAAGGGGGATTGAGTGTAAGTTAATAGTTTAATGGGAAAGCAAATTA     100

GAAATAGGGACATCTGGGTTCTGGTCTTATATTTGCCACTACATATGTTT     150

TAGAGGCTTCAGTTTCATGTTTAAAATAAAGATTCTTTGTATGACAGAGT     200

CTAGGCTGAAAAATTTTTTAAAAATAAAGGGTTTTAAGATCTAATTCATC     250

CACAGGATTCATAACCTCTGAAATTAGGCTACAAGCACACACAAACACAC     300

AGACACACACATACACACACACACACACACACACACACACACATACATGG     350

GGTTGGGGAGAATGGATGATATGGGGAAGAGTGGAGAAGTATTAACAAAA     400

GCTCCCAATAGAAGGAAAGATGCTAAACATCACACTTAATCAGAGAAGTG     450

ACATTTCTCAACTATCAAATTGGTGAAAAATTCAAAAGTTTGCTAACATA     500

TTTTGTAGGTGAGACTATGGGGAAATAGGCCTTTTCATAAATTGCTGATG     550

AAAGCCTAAAATGG                                         564
```

The nucleic acids of the present invention can be isolated from a variety of sources, although the presently preferred sequences have been isolated from human and bovine cDNA and human genomic libraries. The exact amino acid sequence of the polypeptide molecule produced will vary with the initial DNA sequence.

The nucleic acids of the present invention can be obtained using various methods well-known to those of ordinary skill in the art. At least three alternative principal methods may be employed:

in order to identify a DNA sequence coding for all or part of MTP. Various cDNA libraries, for example, a bovine small intestine lambda gt10 library (Clontech Laboratories, Inc. Palo Alto, Calif.), a human liver lambda UNI-ZAP™ XR library (Stratagene Cloning Systems, La Jolla, Calif.), or a human intestine lambda gt10 library (Clontech), can be used.

Various techniques can be used to screen genomic DNA or cDNA libraries for target sequences that code for the high molecular weight subunit of MTP. This technique may, for example, employ a labeled single-stranded DNA probe with a sequence complementary to a sequence that codes for the high molecular weight subunit of MTP. For example, DNA/DNA hybridization procedures may be used to identify the sequence in the cloned copies of genomic DNA or cDNA which have been denatured to a single-stranded form. Suitable probes include cDNA for the high molecular weight subunit of MTP acquired from the same or a related species, synthetic oligonucleotides, and the like.

A genomic DNA or cDNA library can also be screened for a genomic DNA or cDNA coding for all or part of the high molecular weight subunit of MTP using immunoblotting techniques.

In one typical screening method suitable for the hybridization techniques, a genomic DNA or cDNA library is first spread out on agarose plates, and then the clones are transferred to filter membranes, for example, nitrocellulose membranes. The genomic library is usually contained in a vector such as EMBL 3 or EMBL 4 or derivatives thereof (e.g., lambda DASH™). The cDNA library is usually contained in a vector such as λgt10, λgt11, or lambda ZAP. A DNA probe can then be hybridized to the clones to identify those clones containing the genomic DNA or cDNA coding for all or part of the high molecular weight subunit of MTP. Alternatively, appropriate *E. coli* strains containing vectors λgt11 or lambda ZAP can be induced to synthesize fusion proteins containing fragments of proteins corresponding to the cDNA insert in the vector. The fusion proteins may be transferred to filter membranes, for example, nitrocellulose. An antibody may then be bound to the fusion protein to identify all or part of the high molecular weight subunit of MTP.

In the second method, the nucleic acids of the present invention coding for all or part of MTP can be chemically synthesized. Shorter oligonucleotides, such as 15 to 50 nucleotides, may be directly synthesized. For longer oligonucisotides, the DNA sequence coding for the high molecular weight subunit of MTP can be synthesized as a series of 50–100 base oligonucleotides that can then be sequentially ligated (via appropriate terminal restriction sites) so as to form the correct linear sequence of nucleotides.

In the third method, the nucleic acids of the present invention coding for all or part of the high molecular weight subunit of MTP can be synthesized using PCR. Briefly, pairs of synthetic DNA oligonucleotides generally at least 15 bases in length (PCR primers) that hybridize to opposite strands of the target DNA sequence are used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the PCR primers. S White, T. J. et al., *Trends Genet.* 5, 185–9 (1989).

The nucleic acids of the present invention coding for all or part of MTP can also be modified (i.e., mutated) to prepare various mutations. Such mutations may change the amino acid sequence encoded by the mutated codon, or they may be silent and not change the amino acid sequence. These modified nucleic acids may be prepared, for example, by mutating the nucleic acid coding for the high molecular weight subunit of MTP so that the mutation results in the deletion, substitution, insertion, inversion or addition of one or more amino acids in the encoded polypeptide using various methods known in the art. For example, the methods of site-directed mutagenesis described in Taylor, J. W. et al., *Nucl. Acids Res.* 13, 8749–64 (1985) and Kunkel, J. A., *Proc. Natl. Acad. Sci. USA* 82, 482–92 (1985) may be employed. In addition, kits for site-directed mutagenesis may be purchased from commercial vendors. For example, a kit for performing site-directed mutagenesis may be purchased from Amersham Corp. (Arlington Heights, Ill.). In addition, disruption, deletion and truncation methods as described in Sayers, J. R. et al., *Nucl. Acids Res.* 16, 791–800 (1988) may also be employed. Mutations may be advantageous in producing or using the polypeptides of the present invention. For example, these mutations may modify the function of the protein (e.g., result in higher or lower activity), permit higher levels of protein production or easier purification of the protein, or provide additional restriction endonuclease recognition sites in the nucleic acid. All such modified nucleic acids and polypeptide molecules are included within the scope of the present invention.

Expression Vectors

The present invention further concerns expression vectors comprising a DNA sequence coding for all or part of the high molecular weight subunit of MTP or a protein complex comprising both the high and low molecular weight subunits or portions thereof. The expression vectors preferably contain all or part of the DNA sequence having the nucleotide sequence shown in SEQ. ID. NOS. 1, 2, 5, 7, 8, 1 together with 5, 2 together with 7, the first 108 bases of 2 together with 8, the first 108 bases of 2 together with 7 and 8, or 8 together with 31 and 32. Further preferred are expression vectors comprising one or more regulatory DNA sequences operatively linked to the DNA sequence coding for all or part of the high molecular weight subunit of MTP. As used in this context, the term "operatively linked" means that the regulatory DNA sequences are capable of directing the replication and/or the expression of the DNA sequence coding for all or part of the high molecular weight subunit of MTP.

Expression vectors of utility in the present invention are often in the form of "plasmids", which refer to circular double stranded DNA loops that, in their vector form, are not bound to the chromosome. However, the invention is intended to include such other forms of expression vectors which serve equivalent functions and which become known in the art subsequently hereto. The expression vectors of the present invention may also be used to stably integrate the DNA sequence encoding the high molecular weight subunit of MTP into the chromosome of an appropriate host cell (e.g.,COS or HepG2 cells).

Expression vectors useful in the present invention typically contain an origin of replication, a promoter located 5' to (i.e., upstream on the DNA sequence, followed by the DNA sequence coding for all or part of the high molecular weight subunit of MTP, transcription termination sequences, and the remaining vector. The expression vectors may also include other DNA sequences Known in the art, for example, stability leader sequences which provide for stability of the expression product, secretory leader sequences which provide for secretion of the expression product, sequences which allow expression of the structural gene to be modulated (e.g., by the presence or absence of nutrients or other inducers in the growth medium), marking sequences which are capable of providing phenotypic selection in transformed host cells, sequences which provide sites for cleavage by restriction endonucleases, and sequences which allow expression in various types of hosts, including but not limited to prokaryotes, yeasts, fungi, plants and higher eukaryotes. The characteristics of the actual expression vector used must be compatible with the host cell which is to be employed. For example, when expressing DNA sequences in a mammalian cell system, the expression vector should contain promoters isolated from the genome of mammalian cells, (e.g., mouse metallothionien promoter), or from viruses that grow in these cells (e.g., vaccinia virus 7.5 K promoter). An expression vector as contemplated by the present invention is at least capable of directing the replication, and preferably the expression, of the nucleic acids of the present invention. Suitable origins of replication include, for example, the Col E1, the SV4O viral and the M13 orgins of replication. Suitable promoters include, for example, the cytomegalovirus promoter, the lac Z promoter, the gal 10 promoter and the Autographa californica multiple nuclear polyhedrosis virus (AcMNPV) polyhedral promoter. Suitable termination sequences include, for example, the bovine growth hormone, SV40, lac Z and AcMNPV polyhedral polyadenylation signals. Examples of selectable markers include neomycin, ampicillin, and hygromycin resistance and the like. All of these materials are known in the art and are commercially available.

Suitable commercially available expression vectors into which the DNA sequences of the present invention may be inserted include the mammalian expression vectors pcDNAI or pcDNA/Neo, the baculovimus expression vector pBlueBac, the prokaryotic expression vector pcDNAII and the yeast expression vector pYes2, all of which may be obtained from Invitrogen Corp., San Diego, Calif.

Suitable expression vectors containing the desired coding and control sequences may be constructed using standard recombinant DNA techniques known in the art, many of which are described in Sambrook, et al., Molecular Cloning: A Laboratory Manual, Second Edition, Cold Spring Harbor Laboratory, Cold Spring Habor, N.Y. (1989).

Host Cells

The present invention additionally concerns host cells containing an expression vector which comprises a DNA sequence coding for all or part of the high molecular weight subunit of MTP. See, for example the host cells of Example 4 hereinbelow, which are preferred. The host cells preferably contain an expression vector which comprises all or part of the DNA sequence having the nucteotide sequence substantially as shown in SEQ. ID. NOS. 1, 2, 5, 7, 8, 1 together with 5, 2 together with 7, the first 108 bases of 2 together with 8, the first 108 bases of 2 together with 7 and 8, or 8 together with 31 and 32. See, for example, the expression vector appearing in Example 4 hereinbelow, which is preferred. Further preferred are host cells containing an expression vector comprising one or more regulatory DNA sequences capable of directing the replication and/or the expression of and operatively linked to a DNA sequence coding for all or part of the high molecular weight subunit of MTP. Suitable host cells include both prokaryotic and eukaryotic cells. Suitable prokaryotic host cells include, for example, *E. coli* strains HB101, DH5a, XL1 Blue, Y1090 and JM101. Suitable eukaryotic host cells include, for example, Spodoptera frugiperda insect cells, COS-7 cells, human skin fibroblasts, and Saccharomyces cerevisiae cells.

Expression vectors may be introduced into host cells by various methods known in the art. For example, transfection of host cells with expression vectors can be carried out by the calcium phosphate precipitation method. However, other methods for introducing expression vectors into host cells, for example, electroporation, liposomal fusion, nuclear injection, and viral or phage infection can also be employed.

Once an expression vector has been introduced into an appropriate host cell, the host cell may be cultured under conditions permitting expression of large amounts of the desired polypeptide, in this case a polypeptide molecule comprising all or part of the high molecular weight subunit of MTP.

Host cells containing an expression vector that contains a DNA sequence coding for all or part of the high molecular weight subunit of MTP may be identified by one or more of the following six general approaches: (a) DNA-DNA hybridization; (b) the presence or absence of marker gene functions; (c) assessing the level of transcription as measured by the production of mRNA transcripts encoding the high molecular weight subunit of MTP in the host cell; (d) detection of the gene product immunologically; (e) enzyme assay; and (f) PCR.

In the first approach, the presence of a DNA sequence coding for all or part of the high molecular weight subunit of MTP can be detected by DNA-DNA or RNA-DNA hybridization using probes complementary to the DNA sequence.

In the second approach, the recombinant expression vector host system can be identified and selected based upon the presence or absence of certain marker gene functions (e.g., thymidine kinase activity, resistance to antibiotics, etc.). A marker gene can be placed in the same plasmid as the DNA sequence coding for all or part of the high molecular weight subunit of MTP under the regulation of the same or a different promoter used to regulate the MTP coding sequence. Expression of the marker gene indicates expression of the DNA sequence coding for all or part of the high molecular weight subunit of MTP.

In the third approach, the production of mRNA transcripts encoding the high molecular weight subunit of MTP can be assessed by hybridization assays. For example, polyadenylated RNA can be isolated and analyzed by Northern blotting or a nuclease protection assay using a probe complementary to the RNA sequence. Alternatively, the total RNA of the host cell may be extracted and assayed for hybridization to such probes.

In the fourth approach, the expression of all or part of the high molecular weight subunit of MTP can be assessed immunologically, for example, by immunoblotting with antibody to MTP (Western blotting).

In the fifth approach, expression of the high molecular weight subunit of MTP can be measured by assaying for MTP enzyme activity using known methods. For example, the assay described herein below may be employed.

In the sixth approach, oligonucleotide primers homologous to sequences present in the expression system (i.e., expression vector sequences or MTP sequences) are used in a PCR to produce a DNA fragment of predicted length, indicating incorporation of the expression system in the host cell.

The DNA sequences of expression vectors, plasmids or DNA molecules of the present invention may be determined by various methods known in the art. For example, the dideoxy chain termination method as described in Sanger et al., *Proc. Natl. Acad. Sci. USA* 74, 5463–7 (1977), or the Maxam-Gilbert method as described in *Proc. Natl. Acad. Sci. USA* 74, 560–4 (1977) may be employed.

In order to express catalytically active MTP, it may be necessary to produce a protein complex containing both the high and low molecular weight subunits of MTP. The low molecular weight subunit of MTP is the previously characterized protein, protein disulfide isomerase (PDI). PDI cDNAs have been cloned from human [Pihlajaniemi et al., *EMBO J.* 6, 643–9 (1987)], bovine [Yamaguchi et al., *Biochem. Biophys. Res. Comm.* 146, 1485–92 (1987)], rat [Edman et al., *Nature* 317 267–70 (1985)] and chicken [Kao et al., *Connective Tissue Research* 18, 157–74 (1988)]. Various approaches can be used in producing a protein containing both the high and low molecular weight subunits of MTP. For example, cDNA sequences encoding the subunits may be inserted into the same expression vector or different expression vectors and expressed in an appropriate host cell to produce the protein.

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

Polypeptides

The present invention further concerns polypeptide molecules comprising all or part of the high molecular weight subunit of MTP, said polypeptide molecules preferably having all or part of the amino acid sequence as shown in SEQ. ID. NOS. 3, 4, or 3 together with 6. In the case of polypeptide molecules comprising part of the high molecular weight subunit of MTP, it is preferred that potypeptide molecules be at least about 5 to 8 sequential amino acids in length, more preferably at least about 15 to 20 sequential amino acids in length. Also preferred are polypeptides at least about 180 sequential amino acids in length, which may approximate the size of a structural domain within the protein.

All amino acid sequences are represented herein by formulas whose left to right orientation is in the conventional direction of amino-terminus to carboxy-terminus.

The polypeptides of the present invention may be obtained by synthetic means, i.e., chemical synthesis of the polypeptide from its component amino acids, by methods known to those of ordinary skill in the art. For example, the solid phase procedure described by Houghton et at., *Proc. Natl. Acad. Sci.* 82, 5131–5 (1985) may be employed. It is preferred that the polypeptides be obtained by production in prokaryotic or eukaryotic host cells expressing a DNA sequence coding for all or part of the high molecular weight subunit of MTP, or by in vitro translation of the mRNA encoded by a DNA sequence coding for all or part of the high molecular weight subunit of MTP. For example, the DNA sequence of SEQ. ID. NOS. 1, 2, 5, 7, 8, 1 together with 5, 2 together with 7, the first 108 bases of 2 together with 8, the first 108 bases of 2 together with 7 and 8, 8 together with 31 and 32 or any part thereof may be synthesized using PCR as described above and inserted into a suitable expression vector, which in turn may be used to transform a suitable host cell. The recombinant host cell may then be cultured to produce the high molecular weight subunit of MTP. Techniques for the production of polypeptides by these means are known in the art, and are described herein.

The polypeptides produced in this manner may then be isolated and purified to some degree using various protein purification techniques. For example, chromatographic procedures such as ion exchange chromatography, gel filtration chromatography and immunoaffinity chromatography may be employed.

The polypeptides of the present invention may be used in a wide variety of ways. For example, the polypeptides may be used to prepare in a known manner polyclonal or monoclonal antibodies capable of binding the polypeptides. These antibodies may in turn be used for the detection of the polypeptides of the present invention in a sample, for example, a cell sample, using immunoassay techniques, for example, radioimmunoassay, enzyme immunoassay, or immunocytochemistry. The antibodies may also be used in affinity chromatography for isolating or purifying the polypeptides of the present invention from various sources.

The polypeptides of the present invention have been defined by means of determined DNA and deduced amino acid sequencing. Due to the degeneracy of the genetic code, other DNA sequences which encode the same amino acid sequences depicted in SEQ. ID. NOS. 3, 4, 3 together with 6, or any part thereof may be used for the production of the polypeptides of the present invention.

It should be further understood that allelic variations of these DNA and amino acid sequences naturally exist, or may be intentionally introduced using methods known in the art. These variations may be demonstrated by one or more amino acid changes in the overall sequence, such as deletions, substitutions, insertions, inversions or addition of one or more amino acids in said sequence. Such changes may be advantageous in producing or using the polypeptides of the present invention; for example in isolation of MTP or the polypeptides by affinity purification. Amino acid substitutions may be made, for example, on the basis of similarity in polarity, charge, solubility, hydrophobicity, hydrophilicity and/or the amphiphathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine; asparagine, glutamine; serine, threonine; phenylalanine, tyrosine. Other contemplated variations include salts and esters of the aforementioned polypeptides, as well as precursors of the aforementioned polypeptides, for example, precursors having N-terminal substituents such as methionine, N-formylmethionine and leader sequences. All such variations are included within the scope of the present invention.

Method For Detection of Nucleic Acids

The present invention further concerns a method for detecting a nucleic acid sequence coding for all or part of the high molecular weight subunit of MTP or a related nucleic acid sequence, comprising contacting the nucleic acid sequence with a detectable marker which binds specifically to at least a portion of the nucleic acid sequence, and detecting the marker so bound. The presence of bound marker indicates the presence of the nucleic acid sequence. Preferably, the nucleic acid sequence is a DNA sequence having all or part of the nucleotide sequence substantially as shown in SEQ. ID. NOS. 1, 2, 5, 7, 8, 1 together with 5, 2 together with 7, the first 108 bases of 2 together with 8, the first 108 bases of 2 together with 7 and 8, or 8 together with 31 and 32, or is complementary thereto.

A DNA sample containing the DNA sequence can be isolated using various methods for DNA isolation which are well-known to those of ordinary skill in the art. For example, a genomic DNA sample may be isolated from tissue by rapidly freezing the tissue from which the DNA is to be isolated, crushing the tissue to produce readily digestible pieces, placing the crushed tissue in a solution of proteinase K and SDS, and incubating the resulting solution until most of the cellular protein is degraded. The genomic DNA is then deproteinized by successive phenol/chloroform/isoamyl alcohol extractions, recovered by ethanol precipitation, and dried and resuspended in buffer.

Also preferred is the method in which the nucleic acid sequence is an RNA sequence. Preferably, the RNA sequence is an mRNA sequence. Additionally preferred is the method in which the RNA sequence is located in the cells of a tissue sample. An RNA sample containing the RNA sequence may be isolated using various methods for RNA isolation which are well-known to those of ordinary skill in the art. For example, an RNA sample may be isolated from cultured cells by washing the cells free of medium and then lysing the cells by placing them in a 4 M guanidinium solution. The viscosity of the resulting solution is reduced by drawing the lysate through a 20-gauge needle. The RNA is then pelleted through a cesium chloride step gradient, and the supernatant fluid from the gradient carefully removed to allow complete separation of the RNA, found in the pellet, from contaminating DNA and protein.

The detectable marker useful for detecting a nucleic acid sequence coding for all or part of the high molecular weight subunit of MTP or a related nucleic acid sequence, may be a labeled DNA sequence, including a labeled cDNA sequence, having a nucleotide sequence complementary to at least a portion of the DNA sequence coding for all or part of the high molecular weight subunit of MTP.

The detectable marker may also be a labeled RNA having a sequence complementary to at least a portion of the DNA sequence coding for all or part of the high molecular weight subunit of MTP.

The detectable markers of the present invention may be labeled with commonly employed radioactive labels, such as $^{32}P$ and $^{35}S$, although other labels such as biotin or mercury may be employed. Various methods well-known to those of ordinary skill in the art may be used to label the detectable markers. For example, DNA sequences and RNA sequences may be labeled with $^{32}P$ or $^{35}S$ using the random primer method.

Once a suitable detectable marker has been obtained, various methods well-known to those of ordinary skill in the art may be employed for contacting the detectable marker with the sample of interest. For example, DNA-DNA, RNA-RNA and DNA-RNA hybridizations may be performed using standard procedures known in the art. In a typical DNA-DNA hybridization procedure for detecting DNA sequences coding for all or part of MTP in genomic DNA, the genomic DNA is first isolated using known methods, and then digested with one or more restriction enzymes. The resulting DNA fragments are separated on agarose gels, denatured in situ, and transferred to membrane filters. After prehybridization to reduce nonspecific hybridization, a radiolabeled nucleic acid probe is hybridized to the immobilized DNA fragments. The membrane is then washed to remove unbound or weakly bound probe, and is then autoradiographed to identify the DNA fragments that have hybridized with the probe.

The presence of bound detectable marker may be detected using various methods well-known to those of ordinary skill in the art. For example, if the detectable marker is radioactively labeled, autoradiography may be employed. Depending on the label employed, other detection methods such as spectrophotometry may also be used.

It should be understood that nucleic acid sequences related to nucleic acid sequences coding for all or part of the high molecular weight subunit of MTP can also be detected using the methods described herein. For example, a DNA probe that has conserved regions of the gene for the high molecular weight subunit of human or bovine MTP can be used to detect and isolate related DNA sequences (e.g., a DNA sequence coding for the high molecular weight subunit of MTP from mice, rats, hamsters, or dogs). All such methods are included within the scope of the present invention.

Methods For Detecting MTP Inhibitors

The present invention further concerns methods for detecting inhibitors of MTP. In particular, the present invention concerns a process for detecting an inhibitor of MTP comprising: (a) incubating a sample thought to contain an inhibitor of MTP with detectably labeled lipids in donor particles, acceptor particles and MTP; and (b) measuring the MTP stimulated transfer of the detectably labeled lipids from the donor particles to the acceptor particles. In this assay, an inhibitor would decrease the rate of MTP-stimulated transfer of detectable labeled lipid from donor to acceptor particles. The detection may be carried out by nuclear magnetic resonance (NMR), electron spin resonance (ESR), radiolabeling (which is preferred), fluorescent labeling, and the like. The donor and acceptor particles may be membranes, HDL, low density lipoproteins (LDL), SUV, lipoproteins and the like. HDL and SUV are the preferred donor particles; LDL and SUV are the preferred acceptor particles.

The foregoing procedure was carried out to identify the MTP inhibitor

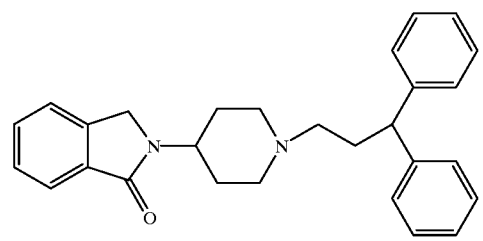

which has the name 2-[1-(3,3-diphenylpropyl)-4-piperdinyl]-2,3-dihydro-3-oxo-1H-isoindole hydrochloride (herein referred to as "compound A"). The foregoing procedure also identified the MTP inhibitor

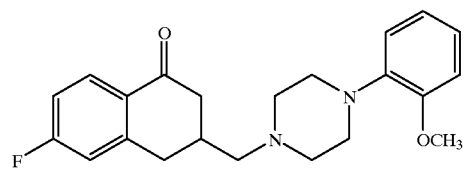

which has the name 1-[3-(6-fluoro-1-tetralanyl)methyl]-4-O-methoxyphenyl piperazine (herein referred to as "compound B"). These compounds were identified by the procedures described in the working examples hereinafter. The foregoing procedures further were used to identify the MTP inhibitors falling within Formulae I, II, and III.

Method of Preparation of Inhibitors

The compounds of formulae I, II, and III may be prepared by the exemplary processes described in the following reaction schemes. Exemplary reagents and procedures for these reactions appear hereinafter and in Examples 10 et seq.

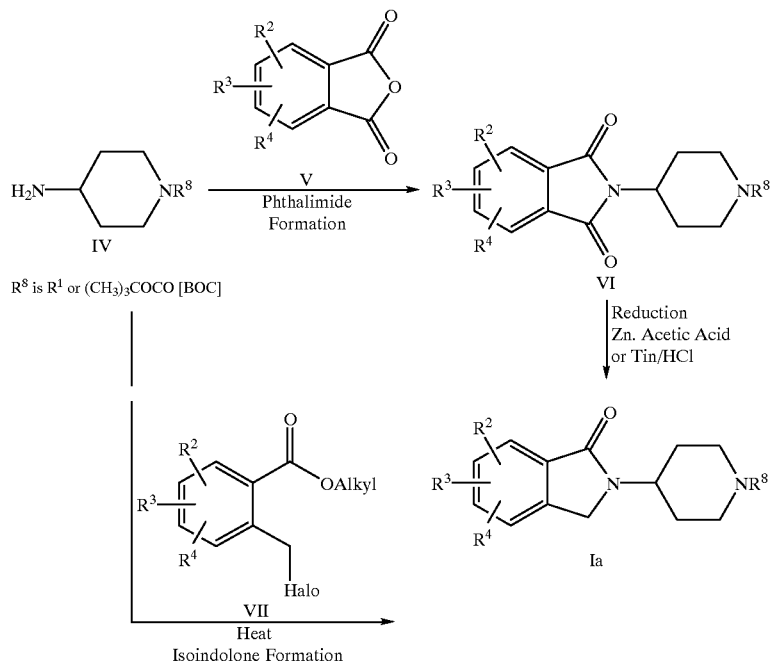
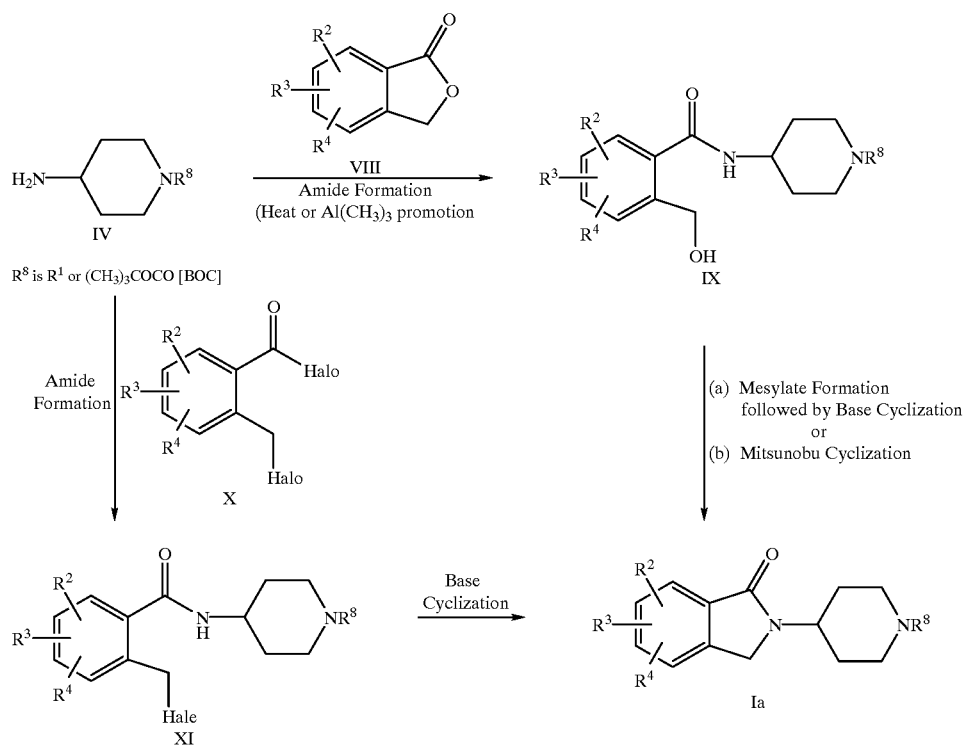

Scheme III
Introduction of R¹ by Alkylation or Arylation
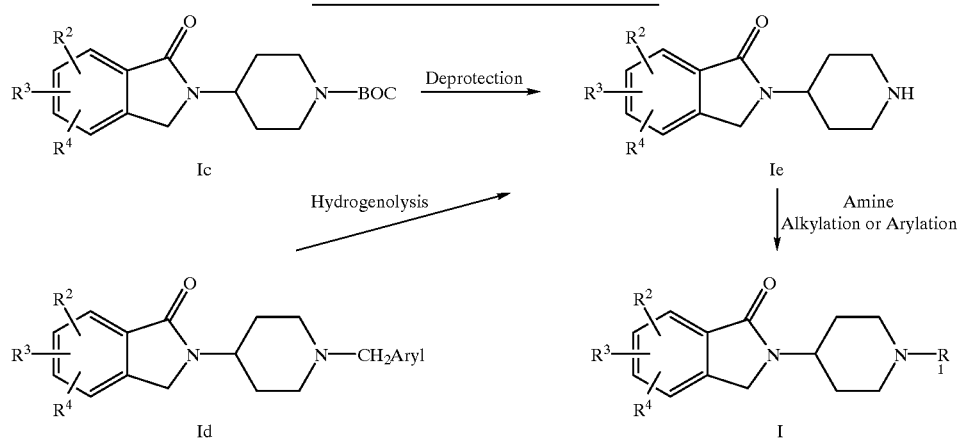
SCHEME IV
Routes to Starting Materials IVb and IVc
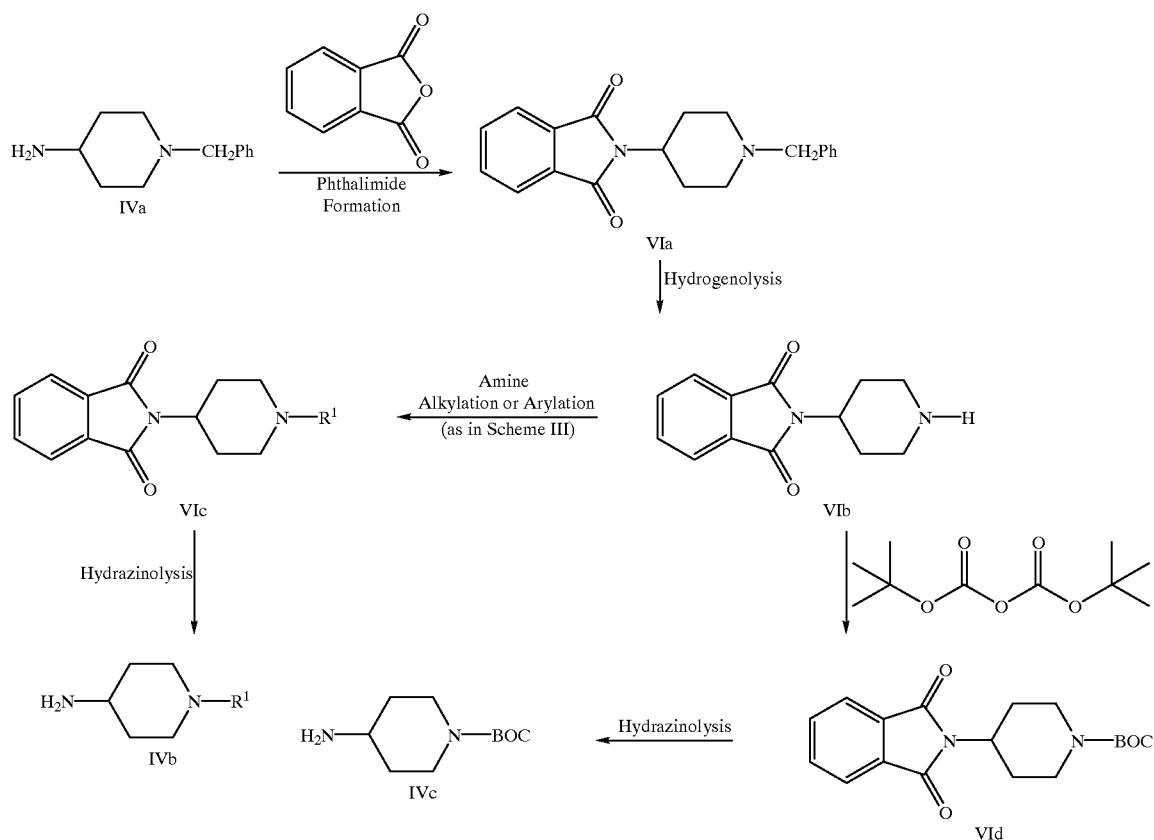

Scheme V
General Routes to Starting Materials IVb
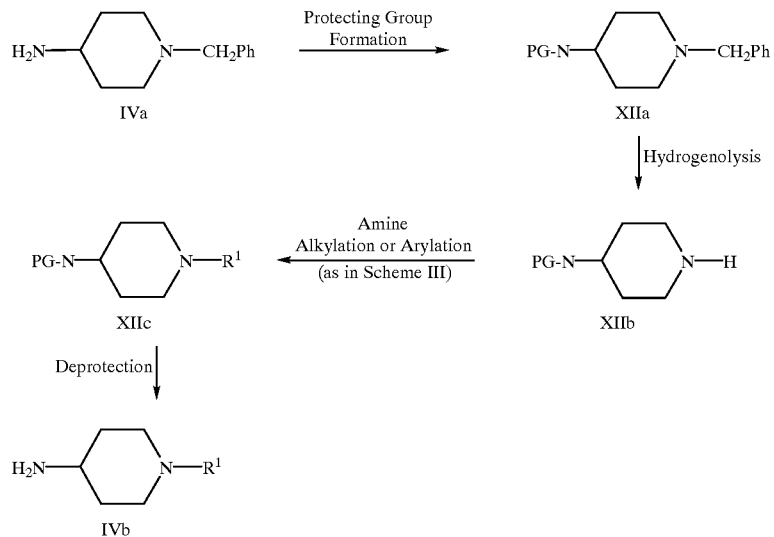
Scheme VI
General Routes to II
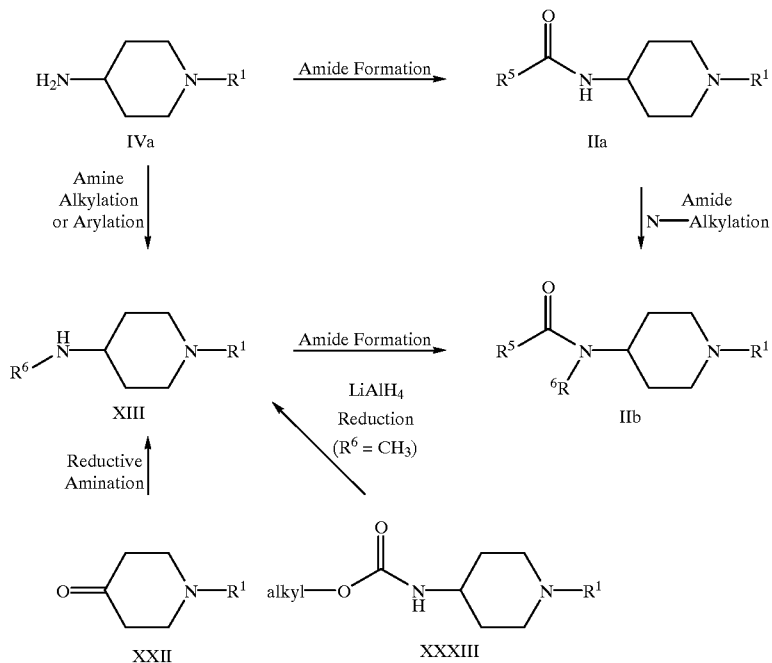

Scheme VII
General Route to III

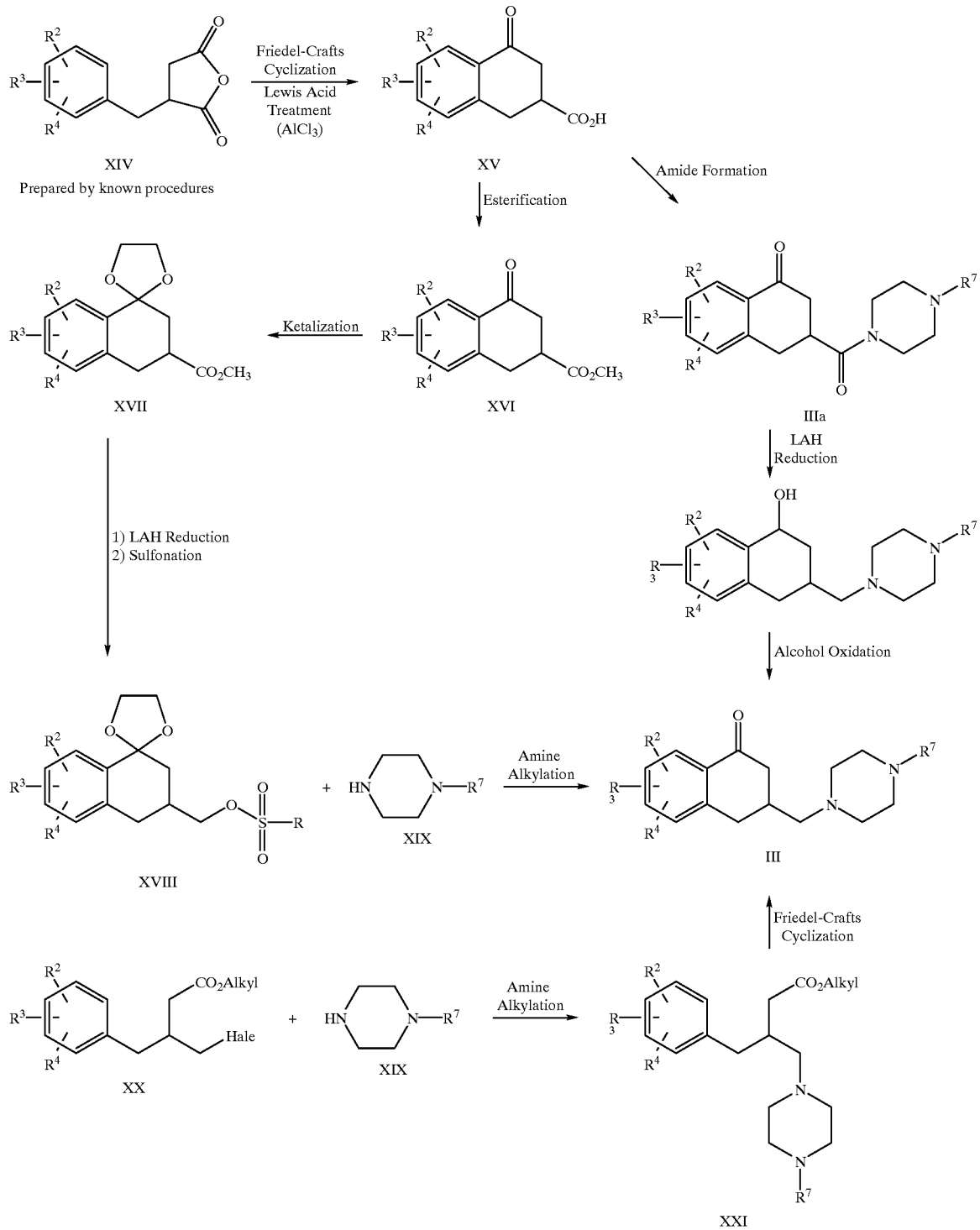

Phthalimide formation (Reaction Schemes I, IV) may be carried out by heating to about 80 to 150° C. in an oil bath optionally in an inert solvent or by varous other procedures known in the art. See, e.g., Example 13 hereinafter.

Reduction (Reaction Scheme I) may be carried out by treatment with such reducing agents as zinc in the presence of acetic acid or tin in the presence of hydrochloric acid under an inert atmoshphere (e.g., argon).

Isoindolone formation (Reaction Scheme I) may be carried out by heating in the range of about 50 to 150° C. in an organic solvent (e.g., toluene, ethanol, dimethylformamide) optionally in the presence of a salt (e.g., potassium carbonate) or a tertiary amine base (e.g., 2,6-di-t-butylpyridine or triethylamine).

Amide formation (Reaction Schemes II, VI, VII) may be carried out by a number of methods known in the art. For example, an amine substrate may be treated with (1) an acid halide $R^5C(O)$halo or compound X in an aprotic solvent, optionally in the presence of a tertiary amine base (e.g., triethylamine); (2) the acid halide in the presence of an aqueous base under Schotten-Baumann conditions; (3) a free carboxylic acid ($R^5CO_2H$) in the presence of a coupling agent such as dicyclohexylcarbodiimide (DCC) or 1-(3-dimethylaminopropyl)-3-ethylcarbodiimide hydrochloride (WSC), optionally in the presence of 1-hydroxybenzotriazole (HOBT); (4) the free acid in the presence of N,N-carbonyldiimidazole in an aprotic organic solvent followed by the amine substrate; (5) trialkylaluminum (e.g., $Al(CH_3)_3$) in an aprotic solvent, followed by an ester (e.g., $R^5CO_2$alkyl or compound VIII) or (6) mixed anhydride formation, by reacting the acid with an acid chloride (e.g., isobutyl chloroformate or bis-(2-oxo-3-oxazolidinyl)phosphinic chloride (Bop-Cl)) in the presence of a tertiary amine base (e.g., treithylamine) followed by treatment with the amine substrate.

Mesylate formation (Reaction Scheme II) may be carried out by treatment of the amine-alcohol substrate with methanesulfonyl chloride and triethylamine or pyridine or in an aprotic solvent, such as dichloromethane.

Base cyclization (Reaction Scheme II) may be carried out by treatment with a base (e.g., potassium t-butoxide or sodium hydride) in an inert solvent (e.g., dimethylformamide, tetrahydrofuran, dimethoxymethane, or toluene). Mitsunobu cyclization (Reaction Scheme II) may be carried out by procedures generally known in the art. See, e.g., R. K. Olsen, *J. Org. Chem.*, 49, 3527 (1984); Genin, M. J., et al., *J. Org. Chem.*, 58, 2334–7 (1993).

Alternatively, a mixture of compounds IV and VIII can be converted to compound Ia in a single pot by heating the mixture in a protic solvent (e.g., water, methanol, ethenyl or isopropanol or mixtures thereof) at 100 to 200° C. See, e.g., European patent application 81/26,749, FR 2, 548,666 (1983).

Protection and deprotection (Reaction Schemes III, IV, V) may be carried out by procedures generally known in the art. See, for example, T. W. Greene, *Protecting Groups in Organic Synthesis*. Second edition, 1991. PG in Scheme V denotes a nitrogen-protecting group. One particularly useful group is tert-butoxycarbonyl (BOC) which can be derived from the associated anhydride as shown in Scheme IV. BOC-protected amines may typically be deprotected by treatment with acid (e.g., trifluoroacetic acid or hydrochloric acid) in procedures well understood by those having ordinary skill in the art.

Hydrogenolysis (Reaction Schemes III, IV, V) may be carried out with $H_2$ using a balloon apparatus or a Parr Shaker in the presence of a catalyst (e.g., palladium on activated carbon).

Amine alkylation and arylation (Reaction Schemes III, IV, VII) may be carried out by methods known in the art. Suitable procedures are described in Cortizo, L., *J. Med. Chem.* 34, 2242–2247 (1991). For example, the alkylation or arylation may be carried out by treating the amine substrate with a halide (e.g., $R^1$-halo) or an oxytosylate (e.g., $R^1$-O-tosylate) in an aprotic solvent (e.g., dimethylformamide), optionally in the presence of a tertiary amine (e.g., triethylamine) or an inorganic base (e.g., potassium carbonate).

Reductive amination may be employed as an alternative to the foregoing amine alkylation and arylation procedures when $R^1$, $R^6$ or $R^7$ is $R^9R^{10}CH$—and $R^9$ and $R^{10}$ are each independently hydrogen, alkyl, alkenyl, aryl, heteroaryl, arylalkyl, heteroarylalkyl, cycloalkyl, or cycloalkylalkyl, or $R^9$ and $R^{10}$ together are alkylene (i.e., $R^9R^{10}CH$— forms a cycloalkyl group). Such reductive amination may be carried out by treating the amine with (a) a ketone or aldehyde ($R^9$—C(O)—$R^{10}$), (b) $NaBH_4$, $NaBH_3CN$ or NaB(acetoxy)$_3$H, (c) a protic solvent (e.g., methanol) or a dipolar aprotic solvent (e.g., acetonitrile), and, optionally, (d) an acid (e.g., acetic acid, trifluoroacetic acid, hydrochloric acid, or titanium isopropoxide).

When $R^1$ is aryl or heteroaryl, transition metals (e.g., palladium or copper salts or complexes) may be used to promote the arylation reaction.

Hydrazinolysis of phthalimides may be carried out by standard means known in the art. See, e.g., T. W. Greene, *Protecting Groups in Organic Synthesis*, Second edition, 1991.

Amide N-alkylation (Reaction Scheme VI) may be carried out by base treatment (e.g., NaH, KH, $KN[Si(CH_3)_3]_2$, $K_2CO_3$, P4-phosphazene base, or butyl lithium) in an aprotic organic solvent, followed by treatment with $R^6$-halo or $R^6$-O-tosylate. Use of P-phosphazene base is described in T. Pietzonka, D. Seebach, *Angew. Chem. Int. Ed. Engl.* 31, 1481, 1992.

In Scheme VII, the Friedel-Crafts cyclization may be carried out with, for example, aluminum chloride, boron trifluoride or polyphosphoric acid and aprotic solvents such as nitrobenzene, nitromethane or carbon disulfide at about −20° C. to 80° C. The esterification may be carried out with a common esterifying agent (e.g., sulfuric acid in methanol) with heating to reflux. Ketalization may be carried out by treatment with such reagents as ethylene glycol in an organic solvent (e.g., benzene) in the presence of an acid catalyst (e.g., p-toluenesulfonic acid). Reduction with lithium aluminum hydride (LAH) may be carried out in an organic solvent (e.g., tetrahydrofuran) from 0° C. to 70° C. Oxidation of alcohols may be carried out by Oppenauer oxidation, such as treatment with potassium t-butoxide and benzophenone, or by other procedures known in the art. The sulfonation may be carried out with $RSO_2Cl$ wherein R is alkyl, haloalkyl or aryl in an organic solvent (e.g., pyridine, dichloromethine) in an inert atmosphere (e.g., nitrogen) optionally in the presence of a tertiary amine base (e.g., triethylamine).

Compound III can also be prepared from compound XX as described by Cortizo, L., *J. Med. Chem.* 34, 2242–2247 (1991).

Methods of Treatment

The present invention also concerns a novel method for preventing, stabilizing or causing regression of atherosclerosis in a mammalian species comprising administration of a therapeutically effective amount of an agent which decreases the amount or activity of MTP.

The present invention further concerns a novel method for lowering serum lipid levels, such as cholesterol or TG levels, in a mammalian species, which comprises administration of a therapeutically effective amount of an agent which decreases the amount or activity of MTP.

The treatment of various other conditions or diseases using agents which decrease the amount of activity of MTP is also contemplated by the present invention. For example, agents which decrease the amount or activity of MTP and therefore decrease serum cholesterol and TG levels, and TG, fatty acid and cholesterol absorption are likely to be useful in treating hypercholesterolemia, hypertriglyceridemia, hyperlipidemia, pancreatitis, hyperglycemia and obesity.

Compound III can also be prepared from compound XX as described by Cortizo, L., *J. Med. Chem.* 34, 2242–2247 (1991).

Various agents which effectively decrease the amount or activity of MTP can be used in practicing the methods of the present invention. MTP inhibitors can be isolated using the screening methodology described hereinabove and in Example 5 hereinbelow. Compounds such as A and B, which are identified as inhibitors of MTP (see Example 6 hereinbelow), are useful in specific embodiments of the foregoing methods of treatment.

Antisense molecules may be used to reduce the amount of MTP. [See, Toulme and Helene, *Gene* 72, 51–8 (1988); Inouye, *Gene* 72, 25–34 (1988); and Uhlmann and Peyman, *Chemical Reviews* 90, 543–584 (1990)]. MTP antisense molecules can be designed based on the foregoing genomic DNA and cDNA, corresponding 5' and 3' flanking control regions, other flanking sequences, or intron sequences. Such antisense molecules include antisense oligodeoxyribonucleotides, oligoribonucleotides, oligonucleotide analogues, and the like, and may comprise about 15 to 25 bases or more. Such antisense molecules may bind noncovalently or covalently to the DNA or RNA for the high molecular weight subunit of MTP. Such binding could, for example, cleave or facilitate cleavage of MTP DNA or RNA, increase degradation of nuclear or cytoplasmic mRNA, or inhibit transcription, translation, binding of transactivating factors, or pre-mRNA splicing or processing. All of these effects would decrease expression of MTP and thus make the antisense molecules useful in the foregoing methods of treatment.

Potential target sequences for an antisense approach include but are not limited to the DNA or RNA sequence encoding MTP, its 5' and 3' flanking control regions, other flanking sequences, and nonclassic Watson and Crick base pairing sequences used in formation of triplex DNA. Antisense molecules directed against tandem sequences for the high molecular weight subunit of MTP may be advantageous.

Antisense molecules may also contain additional functionalities that increase their stability, activity, transport into and out of cells, and the like. Such additional functionalities may, for example, bind or facilitate binding to target molecules, or cleave or facilitate cleavage of target molecules.

Vectors may be constructed that direct the synthesis of antisense DNA or RNA. In this case, the length of the antisense molecule may be much longer; for example, 400 bp.

Demonstration of Relationship Between MTP and Serum Cholesterol Levels, TG Levels, and Atherosclerosis The methods of the present invention for lowering serum cholesterol or TG levels or preventing, stabilizing or causing regression of atherosclerosis are based in part on the discovery by the inventors that the genetic disease abetalipoproteinemia is caused by a lack of functional MTP. The inventors have demonstrated a gene defect in two abetalipoproteinemic subjects by the following methods.

Assay For TG Transfer Activity in Abetalipoproteinemic Subjects

A. MTP Assay

TG transfer activity was measured as the protein-stimulated rate of TG transfer from donor SUV to acceptor SUV. To prepare donor and acceptor vesicles, the appropriate lipids in chloroform were mixed in a 16×125 mm borosilicate glass screw cap tube (Fisher Scientific Co., Pittsburg, Pa., Cat. no. 14–933-1A) and then dried under a stream of nitrogen. Two mL 15/40 buffer (15 mM Tris, pH 7.4, 40 mM sodium chloride, 1 mM EDTA, and 0.02% NaN$_3$) were added to the dried lipids (or 100 µL per assay, which ever is the least volume), a stream of nitrogen was blown over the buffer, then the cap was quickly screwed on to trap a nitrogen atmosphere over the lipid suspension. Lipids in the buffer were bath-sonicated in a Special Ultrasonic Cleaner (Cat. no. G112SP1, Laboratory Supplies Co., Hicksville, N.Y.). The donor and acceptor phosphatidylcholine (PC) (egg L-alpha-phosphatidylcholine, Sigma Chem. Co., St. Louis, Mo.) was radiolabeled by adding traces of [$^3$H] dipalmitoylphosphatidylcholine(phosphatidylcholine L-alpha-dipalmitoyl [2-palmitoyl-9,10, $^3$H (N)], 33 Ci/mmol, DuPont NEN) to an approximate specific activity of 100 cpm/nmol. Donor vesicles containing 40 nmol egg PC, 0.2 mol % [$^{14}$C]TG [mixture of labeled (triolein [carboxyl-$^{14}$C]-, about 100 mCi/mmol, DuPont NEN) and unlabeled (triolein, Sigma Chem. Co., St. Louis, Mo.) triolein for a final specific activity of about 200,000 cpm/nmol], and 7.3 mol % cardiolipin (bovine heart cardiolipin, Sigma Chemical Co.) and acceptor vesicles containing 240 nmol egg PC and 0.2 mol % TG were mixed with 5 mg fatty acid free bovine serum albumin (BSA) and an aliquot of the MTP samples in 0.7 to 0.9 mL 15/40 buffer and incubated for 1 hour at 37° C. The transfer reaction was terminated by the addition of 0.5 mL DEAE-cellulose suspension (1:1 suspension DE-52, preswollen DEAE-cellulose anion exchange, Fisher, Cat. no. 05720-5 to 15 mM Tris, pH 7.4, 1 mM EDTA, and 0.02% NaN$_3$). The reaction mixture was agitated for 5 minutes and the DEAE-cellulose with bound donor membranes (the donor membranes contained the negatively charged cardiolipin and bound to the DEAE) were sedimented by low speed centrifugation.

The $^{14}$C-TG and $^3$H-PC remaining in the supernatant were quantitated by scintillation counting. TG transfer was calculated by comparing the ratio of $^{14}$C-TG (transferred from the donor membranes to the acceptor membranes) to $^3$H-PC (a marker of acceptor vesicle recovery) present in the supernatant following a transfer reaction to the ratio of total donor $^{14}$C-TG to acceptor [$^3$H]PC in the assay before the transfer reaction. The percentage of $^{14}$C-TG transfer was calculated as follows:

$$\% \ TG \ \text{Transfer} = \frac{\left(^{14}C\text{-}TG/^3H\text{-}PC\right)_{sup}}{\left(^{14}C\text{-}TG_{don}/^3H\text{-}PC_{acc}\right)_{total}} \times 100\%$$

To calculate the MTP-stimulated rate of TG transfer, the TG transfer rate in the absence of MTP was subtracted from the TG transfer rate in the presence of MTP. First order kinetics was used to calculate total TG transfer.

B. Antibody Production

Anti-88 kDa antibodies were obtained from the University of Cincinnati. The production of anti-88 kDa has been previously described. Wetterau et al., *J. Biol. Chem.* 265, 9800–7 (1990). To help address the specificity of the antisera in human intestinal homogenates, affinity purified anti-88 kDa was generated. Eight to 10 mg of purified MTP was dialyzed into 0.1 M MOPS, pH 7.5 and then added to 4 mL Bio Rad Affigel 15 (Bio-Rad, Richmond, Calif.) which had been prewashed 3 times with water at 4° C. The MTP was allowed to couple to the matrix at room temperature for two hours and then it was placed at 4° C. overnight. The remaining reactive sites on the affigel were blocked by the addition of 0.1 mL 1 M ethanolamine, pH 8.0, per mL gel. Optical density measurements of eluted protein were performed according to the manufacturer's instructions and indicated that more than 90% of the MTP was coupled to the column. The column was washed with 50 mL 10 mM Tris, pH 7.5 followed by 50 mL 100 mM glycine, pH 2.5, followed by 50 mL 10 mM Tris, pH 8.8, followed by 50 mL 100 mM triethylamine, pH 11.5, and finally the column was reequilibrated in 10 mM Tris, pH 7.5.

The antibodies in the antiserum were partially purified by ammonium sulfate precipitation (226 mg ammonium sulfate per mL serum). The pellet was resuspended and dialyzed into 15 mM Tris, pH 7.5, 1 mM EDTA, 0.02% sodium azide, and 150 mM sodium chloride. The partially purified antibodies were slowly applied to the MTP-affigel column over a two-hour period (the antibodies were cycled through the column three times). The column was washed with 100 mL 10 mM Tris, pH 7.5, followed by 100 mL 10 mM Tris, pH 7.5, 500 mM sodium chloride, followed by 50 mL 100 mM glycine, pH 2.5 (this fraction was collected into 5 mL of 1 M Tris, pH 8.0), followed by 10 mM Tris, pH 8.8 until the column was at neutral pH, followed by 50 mL triethylamine pH 11.5 (this fraction was collected into 5 mL 1 M Tris, pH 8.0), and finally the column was reequilibrated with 10 mM Tris, pH 7.5. Antibodies which eluted in the acidic wash were retained and used for immunoblot analysis of protein fractions.

C. Western Blot With anti-88 kDa Antibodies

To confirm the specificity of the antibodies and to detect the 88 kDa component of MTP in tissue homogenates, purified bovine MTP or the fraction to be tested were fractionated by SDS-PAGE [essentially as described by Laemmli, *Nature* 227, 680–5 (1970)] using a 0.75 mm Hoeffer Scientific Instrument Gel Apparatus (San Francisco, Calif.). The protein was then transferred to nitrocellulose by Western blotting using a BioRad Trans-blot cell (Bio-Rad, Richmond, Calif.). The blotting buffer (25 mM Tris, 192 mM glycine, pH 8.3, 20% methanol) was precooled to 4° C. The proteins were transferred for 100 minutes at 250 milliamperes at room temperature. The membranes were blocked 5–10 minutes with blocking buffer (400 µL antifoam, about 10 mg of thimersal, and 200 g nonfat dry milk in 4 liters 50 mM Tris, pH 7.7, 150 mM sodium chloride). An aliquot of the antiserum (1:300 dilution) or affinity purified antibody (1:25 dilution of affinity-purified antibodies) was added and allowed to react overnight at room temperature. Following washing with blocking buffer, the secondary antibody, goat anti-rabbit IgG coupled to horseradish peroxidase (BioRad), was added at a dilution of 1:2000 and allowed to react for 3 hours at room temperature. Following a washing step, the secondary antibody was visualized with developer, 50 mg imidizale, 50 mg 3,3'diaminobenzidine tetrahydrochloride, and 50 µL $H_2O_2$ (30% solution) in 50 mL blocking buffer.

D. MTP in Intestinal Biosoles

Intestinal biopsies from fasted control and disease state subjects were frozen and shipped to Bristol-Myers Squibb, Princeton on dry ice. Biopsies were homogenized with a polytron (Polytron PT3000, Brinkmann Instrument, Inc., Westbury, N.Y.) at ½ maximal setting. Typically, one biopsy was homogenized in 0.25 mL homogenization buffer (50 mM Tris, pH 7.4, 50 mM KCl, 5 mM EDTA, 5 µg/mL leupeptin, and 2 mM PMSF). An aliquot of the protein was adjusted to 0.7 mL and 1.4% SDS and the protein concentration was measured by the method of Lowry et al., [*J. Biol. Chem.* 193, 265–75 (1951)]. The homogenate was diluted with homogenization buffer to about 1.75 mg protein/mL. In some cases, the protein was already more dilute and was used directly. To release the soluble proteins from the microsomal fraction, one part deoxycholate solution (0.56%, pH 7.5) was added to 10 parts diluted homogenate with vortexing. The sample was incubated at 4° C. for 30 minutes, then centrifuged at 103,000×g for 60 minutes. The supernatant was removed, diluted 1:1 with 15/40 buffer, and then dialyzed overnight into 15/40 buffer. Aliquots of the treated biopsies were assayed for TG transfer activity and Western blot analysis was used to detect 88 kDa protein. TG transfer activity was expressed as the percentage of donor TG transferred per hour as a function of homogenized intestinal biopsy protein.

E. Results with Abetalipoproteinemic Subjects

Figure 2:
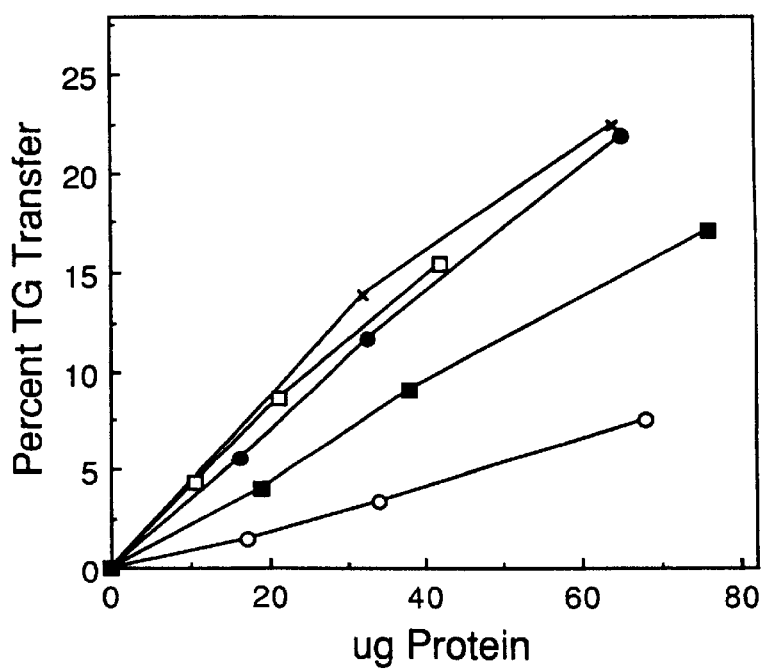
FIG. 2 shows TG transfer activity in normal subjects. Protein-stimulated transfer of $^{14}$C-TG from donor SUV to acceptor SUV was measured in homogenized intestinal biopsies obtained from five normal subjects. The results are expressed as the percentage of donor TG transferred per hour as a function of homogenized intestinal biopsy protein.

To investigate whether there is a relationship between detective MTP and abetalipoproteinemia, MTP activity in duodenal or duodenal-jejunal biopsies was measured from five control subjects and four abetalipoproteinemic subjects having the classic genetically recessive form of abetalipoproteinemia. Intestinal biopsies from the five normal subjects were homogenized and treated with detergent as described hereinabove. TG transfer activity was readily detectable in biopsies from all five subjects (FIG. 2).

The TG transfer activity in the biopsies was further characterized. To confirm that TG hydrolysis was not interfering with lipid transfer activity measurements, one subject's acceptor vesicles (which contained the transported lipid) were extracted after the transfer reaction, and the identity of the $^{14}$C-TG was confirmed by thin layer chromatography. All of the $^{14}$C-TG had a mobility identical to that of authentic TG, confirming that intact TG was being transported in the assay.

The human MTP was characterized for its heat stability. It was inactivated when heated to 60° C. for 5 minutes. The loss of activity demonstrates that the lipid transfer activity being measured was not from an intracellular form of the cholesteryl ester transfer protein (CETP), which is heat-stable under these conditions. Ihm et al., *J. Biol. Chem.* 257, 4818–27 (1982).

Figure 3:
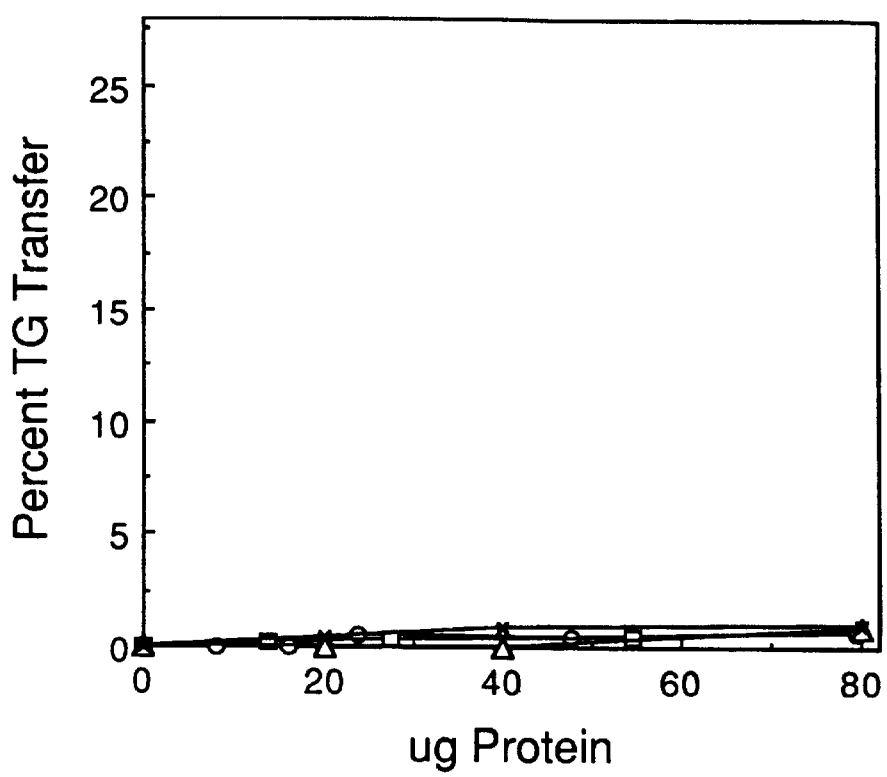
FIG. 3 shows TG transfer activity in abetalipoproteinemic subjects. Protein-stimulated transfer of $^{14}$C-TG from donor SUV to acceptor SUV was measured in homogenized intestinal biopsies obtained from four abetalipoproteinemic subjects. The results are expressed as the percentage of donor TG transferred/hour as a function of homogenized intestinal biopsy protein.

Intestinal biopsies from four abetalipoproteinemic subjects were obtained, homogenized, and TG transfer activity was measured as desribed herein above. No transfer activity was recovered from the biopsies of any of the four subjects (FIG. 3). The lack of detectable TG transfer activity could have been related to an inability to release MTP from the microsomes of the abetalipoproteinemic biopsies by deoxycholate treatment. To test this possibility, the microsomes from one subject were sonicated in addition to being treated with detergent. Bath sonication independently releases TG transfer activity comparable to that of detergent treatment. Even under these conditions, no TG transfer activity was detectable.

The next possibility considered was that the lack of detectable TG transfer activity was related to the inability to detect it in cells which contain large intracellular fat droplets such as those which occur in abetalipoproteinemia. To test this possibility, three controls were run. First, TG transfer activity was measured from a biopsy of a subject with chylomicron retention disease. Subjects with chylomicron retention desease have a defect in the assembly or secretion of chylomicrons and have large fat droplets in their enterocytes, analogous to abetalipoproteinemic subjects. In addition, TG transfer activity was measured from a biopsy taken from an individual who was not fasted prior to the biopsy and from a homozygous hypobetalipoproteinemic subject. Both these subjects also had fat-filled enterocytes.

Figure 4:
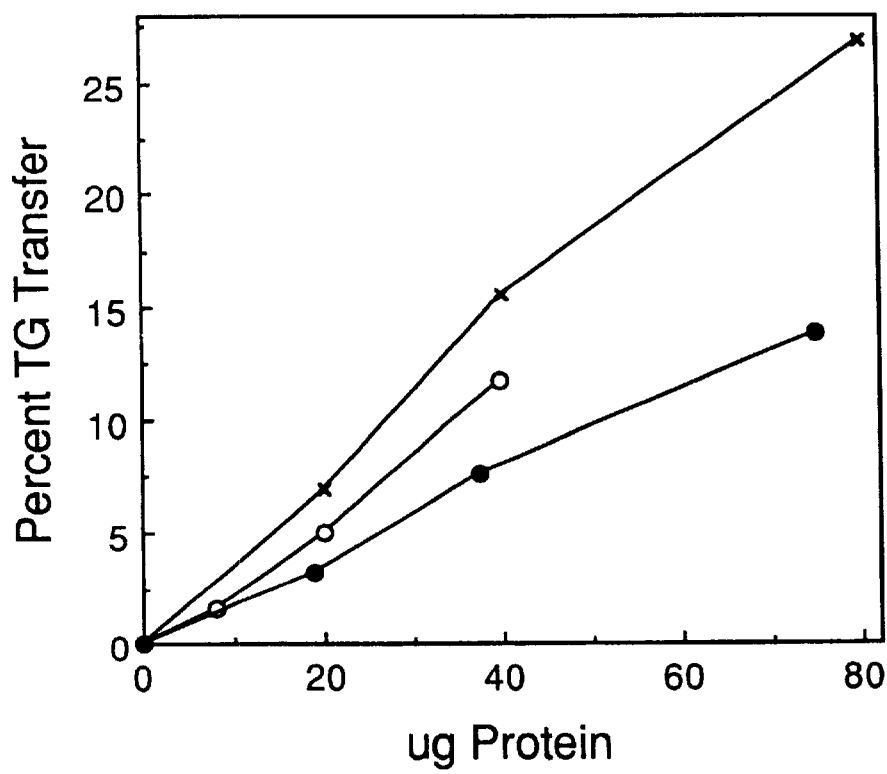
FIG. 4 shows TG transfer activity in control subjects. Protein stimulated transfer of $^{14}$C-TG from donor SUV to acceptor SUV in homogenized intestinal biopsies were obtained from three control subjects, one with chylomicron retention disease (open circles), one with homozygous hypobetalipoproteinemia (solid circles), and one non-fasted (x). The results are expressed as the percentage of donor TG transferred/hour as a function of homogenized intestinal biopsy protein.

In all three cases, TG transfer activity comparable to that of the normal subjects was found (FIG. 4), confirming that the presence of intracellular lipid droplets does not interfere with our ability to recover and detect TG transfer activity.

To establish the biochemical defect responsible for the absence of transfer activity, the soluble proteins following release of MTP from the microsomal fraction of the homogenized biopsy were analyzed by Western blot analysis with antibodies raised against the 88 kDa component of bovine MTP. When normal (FIG. 5) or control (FIG. 6) subjects were examined with a polyclonal anti-88 kDa antibody, a band comparable to that of the 88 kDa component of bovine MTP was observed. In addition, additional proteins of increased mobility also cross-reacted with this antibody. To confirm the identity of the 88 kDa component of human MTP, the antibody was affinity-purified on an MTP affinity column. Following this treatment, only the protein of molecular weight comparable to that of the 88 kDa component of bovine MTP was immunoreactive (FIG. 7).

Figure 5:
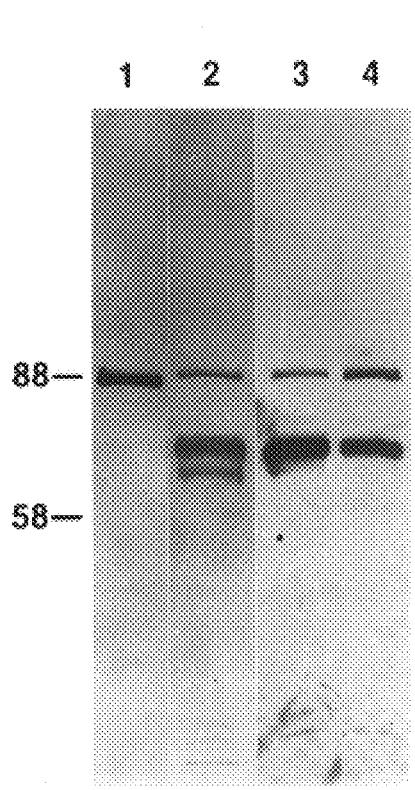
FIG. 5 shows western blot analysis of MTP in normal subjects. An aliquot of purified bovine MTP (lane 1) or the post 103,000×g proteins following deoxycholate treatment of 23 μg of homogenized intestinal biopsies from 3 normal subjects (lanes 2–4) were fractionated by SDS-PAGE and then transferred to nitrocellulose. The blots were probed with anti-88 kDa.
Figure 6:
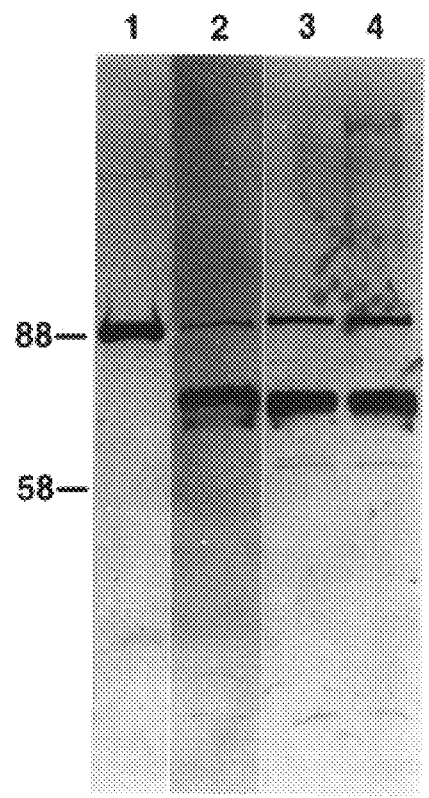
FIG. 6 shows western blot analysis of MTP in control subjects. An aliquot of purified bovine MTP (lane 1) or the post 103,000×g proteins following deoxycholate treatment of 15 μg, 25 μg, and 25 μg homogenized intestinal biopsies from a subject with chylomicron retention disease (lane 2), a subject with homozygous hypobetalipoproteinemia (lane 3), and a non-fasted subject (lane 4), respectively, were fractionated by SDS-PAGE and then transferred to nitrocellulose. The blots were probed with anti-88 kDa.
Figure 7:
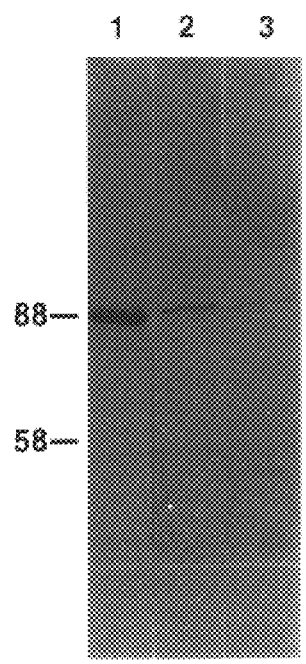
FIG. 7 shows western blot analysis of MTP in normal subjects with affinity-purified antibodies. An aliquot of purified bovine MTP (lane 1) or the post 103,000×g proteins following deoxycholate treatment of 34 μg (lane 2) or 25 μg (lane 3) of homogenized intestinal biopsies from 2 normal subjects were fractionated by SDS-PAGE and then transferred to nitrocellulose. The blots were probed with affinity purified anti-88 kDa.
Figure 8:
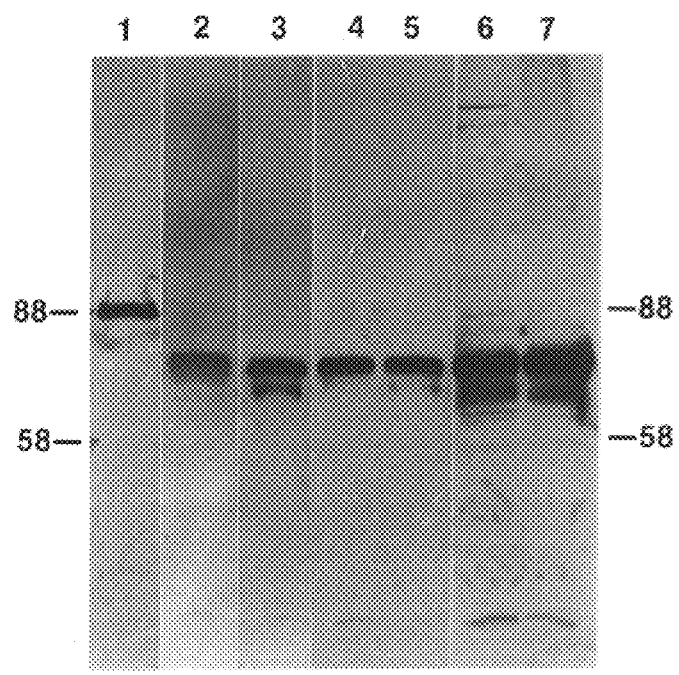
FIG. 8 shows western blot analysis of MTP in abetalipoproteinemic subjects. An aliquot of purified bovine MTP (lane 1) or post 103,000×g proteins following deoxycholate treatment of 18 μg (lane 2), 23 μg (lane 3), 23 μg (lane 4), 23 μg (lane 5) of homogenized intestinal biopsies from four different abetalipoproteinemic subjects were fractionated by SDS-PAGE and then transferred to nitrocellulose. In lanes 6 and 7, 100 μg of the whole intestinal homogenate (subjects corresponding to lane 4 and 5) was fractionated by SDS-PAGE and transferred to nitrocellulose. The blots were probed with anti-88 kDa.

Western blot analysis of the soluble proteins following detergent treatment of the microsomes of all five normal subjects and three control subjects demonstrated the presence of the 88 kDa component of MTP (FIGS. 5 to 7). In contrast, no protein corresponding to the 88 kDa component of bovine MTP was apparent in the abetalipoproteinemic subjects (FIG. 8). In addition, a similar analysis was performed with 100 µg protein from the whole intestinal homogenates from two abetalipoproteinemic subjects. Again, no band corresponding to the 88 kDa component of MTP was apparent (FIG. 8). As a control, immunoblot analysis with anti-PDI antibodies demonstrated the presence of PDI in the latter two abetalipoproteinemic subjects. These results demonstrate that the biochemical basis for the absence of MTP activity in the abetalipoproteinemic subjects is the marked deficiency or the absence of the 88 kDa component of MTP.

Demonstration of a Gene Defect in an Abetalipoproteinemic Subject

Amplification of mRNA and DNA by PCR

Two intestinal biopsies were obtained from the duodenal mucosa of a 39-year-old abetalipoproteinemic patient. Previous analysis demonstrated that neither MTP activity nor the 88 kDa component of MTP were detectable in intestinal biopsies taken from this subject. Each biopsy weighed 5–10 mg and was stored frozen at −70° C. To isolate total RNA, one frozen biopsy was placed into a microfuge tube containing 0.8 mL of cold RNAzol B (CinnaBiotecx labs, Friendswood, Tex.). The biopsy was homogenized immediately by polytron (Brinkmann, Westbury, N.Y.) for 6 strokes on setting 10. Chloroform (80 µL) was added and the mixture inverted gently 20 times. After a 5-minute incubation on ice, the mixture was centrifuged at 14,000 rpm in an Eppendorf microfuge 5415 (Brinkmann) for 15 minutes at 4° C. Total RNA was precipitated by adding 350 µL isopropanol to the supernatant. The yield from the biopsy was 20 µg of total RNA, or about 2 µg RNA per mg of tissue (0.2%).

RNA (50 ng) was reverse transcribed into first strand cDNA using 2.5 µM random hexamer primers, 5 mM magnesium chloride, 1 mM each deoxynucleotide triphosphate (dNTP), 1 U/µL RNAsin, 2.5 U/µL Moloney Murine Leukemia Virus reverse transcriptase ((M-MLV-RT), and 1×PCR reaction buffer (Perkin-Elmer-Cetus RNA-PCR kit No. N808-0017). The 20 µL reaction was incubated at room temperature for 10 minutes to anneal the primers, and then at 42° C. for 30 minutes to reverse transcribe the RNA. The reaction was terminated by heating to 99° C. for 5 minutes and cooling to 5° C. The first strand cDNA was added to a 100 µL PCR containing 0.15 µM forward and reverse primers, 2 mM magnesium chloride, 0.2 mM each dNTP, and 2.5 U Taq polymerase in 1.25× PCR buffer. Amplification was conducted in a Perkin-Elmer GeneAmp PCR System 9600 model thermal cycler for 50 cycles consisting of 94° C. for 30 seconds, 50° C. for 30 seconds, and 72° C. for 1 minute. The reaction was then incubated at 72° C. for 7 minutes. The forward and reverse primers used to amplify the 5' region of the RNA encoding the 88 kDa component of MTP are shown below, 5' to 3'.

| Forward Primers | Sequence | | | SEQ. ID. NO. |
|---|---|---|---|---|
| 15F | 15 GGCACTGGATGCAGTTGAGGATTGCT | | 40 | 9 |
| 41F | 41 GGTCAATATCATTCTTCTTGCTGTGC | | 67 | 10 |
| 578F | CCG GAATTCCCTACCAGGCTCATCAAGACAAAG | 578 | 602 | 11 |
| 900F | 900 ACGGCCATTCCCATTGTGGGCAGGT | | 925 | 12 |

| Reverse Primers | Sequence | | | SEQ. ID. NO. |
|---|---|---|---|---|
| 678R | 678 TGACACCCAAGACCTGATTTGGGGTC | | 653 | 13 |
| 839R | 839 GCCTGCTTCGGTTGTCTTCAGCTCT | | 815 | 14 |
| 1029R | 1029 CGCGGATCCTTCTGACAGCCTCAGCCTTGGA | | 1006 | 15 |
| 1588R | 1588 GGGAGATCATATCTCTGGAGAGCAGT | | 1563 | 16 |
| 2117R | 2117 CGGCGGATCCAGCATAGGAGTCAAGGTTCTC | | 2097 | 17 |

Shown below are the primer combinations used the PCR product length.

| Primer Pair | Product Length (bp) |
|---|---|
| 15F + 678R | 664 |
| 15F + 839R | 825 |
| 41F + 1029R | 998 |
| 578F + 1029R | 470 |
| 900F + 1588R | 689 |
| 900F + 2117R | 1228 |

The primer sequences are based on the normal human cDNA encoding the 88 kDa component of MTP. All primers are written 5' to 3'. F refers to the forward primer, and R to the reverse primer. The underlining identifies restriction sites recognized by Eco RI (primer 578F) or Bam HI (primers 1029R and 2117R), which were incorporated into the 5' end of the primers.

Subject genomic DNA was isolated from a second frozen intestinal biopsy. The biopsy was placed into a microfuge tube containing 400 µL extraction buffer (10 mM Tris.Cl, pH 8.0, 0.1 M EDTA, 0.5% SDS, 20 µg/mL RNAse 1) and homogenized immediately. Homogenization was by polytron for 5 strokes at setting 10. Proteinase K was added to a final concentration of 100 µg/ml and the reaction incubated at 50° C. for 3 hours. The mixture was swirled periodically.

After cooling the reaction to room temperature, 400 µL Tris-saturated pheno/chloroform (pH 8.0) was added. The tube was inverted gently for 5 minutes and then centrifuged for 5 minutes at 14,000 rpm at room temperature. 2 M sodium chloride (35 µL) and ethanol (0.7 ml) were added to the supernatant (350 μL) to precipitate the DNA. The DNA was centrifuged briefly, washed gently with 70% ethanol, dried briefly, and resuspended in 20 μL of deionized water (dH₂O). The yield of DNA was 20 μg, or about 2 μg DNA per mg tissue (0.2%).

Genomic DNA (0.5 μg) was heated to 95° C. for 5 minutes and added immediately to a 100 μL PCR reaction containing 0.15 μM forward and reverse primers, 2 mM magnesium chloride, 0.2 mM each dNTP, and 2.5 U Taq polymerase in 1.25× PCR buffer (Perkin-Elmer-Cetus). Amplification was conducted in a Perkin-Elmer GeneAmp PCR System 9600 model thermal cycler for 3 cycles consisting of 97° C. for 30 seconds, 50° C. for 30 seconds, and 72° C. for 1 minute. An additional 32 cycles consisting of 94° C. for 30 seconds, 50° C. for 30 seconds, and 72° C. for 1 minute were run. The reaction was then incubated at 72° C. for 7 minutes.

Exon 2 of the gene encodes bases 109–296 of the 88 kDa component of MTP RNA. The primers (SEQ. ID. NOS. 18 and 19) used to amplify exon 2 of the gene encoding the 88 kDa component of MTP from subject genomic DNA are shown below.

| Primer Pair | SEQ. ID. NO. |
|---|---|
| CCCTTACAATGAAAACTGG | 18 |
| GGTACACTTCTCCAAAAACTT | 19 |

These primers were designed based on the normal human DNA sequence encoding the 88 kDa component of MTP. The primers are complementary to the introns flanking the 188 bp exon 2 so that the entire exon is amplified in the PCR reaction. The amplification product size, including the primers and flanking intronic regions, is 292 bp long.

B. Sequencing of PCR Products

The PCR products obtained from both RNA- and DNA-PCR were electrophoresed on a 1.4% agarose gel in TAE buffer (40 mM Tris-acetate, 1 mM EDTA pH 8.0). The gel was stained for 5 minutes in 0.5 mg/mL ethidium bromide in water, and destained in water for 10 minutes. The DNA was visualized on an ultraviolet light box. The bands containing the desired PCR product were excised with a razor blade, and the DNA was purified by the GeneClean method (Bio 101, La Jolla, Calif.). The DNA was eluted from the silica matrix in 20 μL of distilled water. Each PCR reaction yielded approximately 1 μg of the desired DNA fragment. A portion of the purified DNA was sequenced directly by Taq polymerase cycle sequencing on an Applied Biosystems, Inc., 373 Automatic Sequencer, as described by Tracy and Mulcahy, *Biotechniques*, 11, 68 (1991).

The remaining DNA was prepared for cloning into a plasmid vector by producing blunt-ends with T4 DNA polymerase followed by phosphorylation with T4 polynucleotide kinase. DNA (500 ng) was added to a 50 μL reaction mixture containing 20 μM each dNTP, 1 mM ATP, 4.5 units T4 DNA polymerase, 5 units T4 polynucleotide kinase in 50 mM Tris HCl pH 7.5, 10 mM magnesium chloride, 1 mM dithiothreitol, and 50 μg/mL BSA. Incubation was at 37° C. for 1 hour. The DNA was then purified from the reaction mixture by GeneClean. The DNA was eluted in 10 μL dH₂O. The blunt-ended DNA was ligated into pUC18 cut previously with Sma I and dephosphorylated (Pharmacia). Dh5α cells (100 μL, Gibco-BRL) were transformed according to the protocol supplied by the manufacturer. Plasmid DNA was amplified and isolated by the alkaline lysis procedure described in *Molecular Cloning* (Sambrook, Fritsch, and Maniatis, eds.) Cold Spring Harbor Laboratory Press, 1.25–1.28 (1989). The plasmid clones were sequenced as described in Example 1.

Results

Direct sequence from three independent RNA-PCR reactions revealed a deleted cytosine at base 262 of the cDNA relative to the start site of translation in the abetalipoproteinemic subject. The one base deletion shifts the reading frame and leads to a stop codon (TGA) 21 bases downstream. Translation of the mutant RNA would terminate at amino acid residue 78. Below is a comparison of the normal and the abetalipoproteinemic subject's DNA and deduced amino acid sequences

```
Base 255                                            287
     AGG AAT CCT GAT GGT GAT GAT GAC CAG TTG ATC Normal
AA    R   N   P   D   G   D   D   D   Q   L   I Base 255                                           286
     AGG AAT C-TG ATG GTG ATG ATG ACC AGT TGA TG Abeta
AA    R   N   L   M   V   M   M   T   S  STOP
```

(SEQ. ID. NOS. 20 to 23, respectively).

Direct sequence analysis of 2 independent PCR amplifications of genomic DNA showed the deletion. This indicates that both alleles of the gene encoding the 88 kDa component of MTP in this subject exhibits the frameshift mutation. In addition, the DNA fragments were cloned into pUC18 for sequencing. Eight plasmid clones also exhibit the deleted cytosine further confirming the frameshift mutation on both alleles.

Demonstration of a Gene Defect in a Second Abetalipoproteinemic Subject

A. Methods

Genomic DNA was isolated from blood from a second abetalipoproteinemic subject using Qiagen (Chatsworth, Calif.) kit no. 13343, following the manufacturer's protocol. Like the first subject, we have previously demonstrated that neither MTP activity nor the 88 kDa component of MTP could be detected in intestinal biopsies from this subject. Three hundred μg of this genomic DNA was sent to Stratagene (La Jolla, Calif.) to be made into a genomic DNA library in the lambda DASH™ Vector(Stratagene). In addition, a normal genomic library in the lambda DASH™ vector was purchased from Stratagene (catalogue no. 943202).

Two million independent recombinant phage plaques from each library were screened for genomic DNA inserts containing sequences homologous to bovine MTP cDNA. The screening process was similar to that for the cDNA library screen in Example 1 except that the *E. coli* host strain was PLK 17, hybridization and wash temperatures were at 60° C., and the wash buffer was 1×SSC, 0.1% SDS. The probe for the genomic library screen was the 2.4 kb Eco RI fragment from the bovine cDNA clone no. 22, $^{32}$P-labeled exactly as in example 2. Putative positive clones (about 30 from each library) were rescreened and remained positive through two additional rounds of hybridization analysis. Following the tertiary screen, single, isolated positive plaques were excised from the agar plates and deposited into 1 mL of SM buffer with 50 μL chloroform. Phage titer was amplified for each phage stock following the "Small-scale liquid cultures" protocol from Sambrook, et al., supra, p 2.67. One hundred μL of the amplified stocks was mixed with 100 μL of prepared PLK 17 plating cells and 100 μL of 10 mM magnesium chloride, 10 mM calcium chloride and incubated at 37° C. for 15 minutes. This mixture was then used to inoculate 50 mL 2×NZY (Bethesda Research Laboratories) with 0.2% Casamino Acids (CAA, Fisher Scientific no. DF0288-01-2) and grown overnight at 37° C. Lambda DNA was isolated from the lysed cultures using the Qiagen kit no. 12543 using Qiagen buffers and protocol.

Direct DNA sequencing of the genomic DNA inserts was performed as described in Example 1 using lambda DNA as template. Oligonucleotides of about 20 bases, complementary to human cDNA sequence, were used as primers for sequencing normal or abetalipoproteinemic genomic clones. Characterization and sequencing of abetalipoproteinemic and normal genomic clones were performed in parallel (see Example 9). Intron-exon boundaries were identified by comparing genomic and cDNA sequences. Sequencing primers were designed against intron sequences 5' and 3' to each exon and used to confirm intron/exon boundaries by resequencing the boundaries. In addition, the coding sequence of both DNA strands for each exon of at least one abetalipoproteinemia genomic clone was sequenced. DNA sequence analysis of exon 13 of the abetalipoproteinemic subject revealed a C-to-T point mutation at base 1830 of the human cDNA. This base change introduces a stop codon at a site that normally encodes the amino acid residue Arg$_{595}$.

The nucleotide sequence around base 1830 encodes a Taq I endonuclease restriction site (TCGA) in the normal DNA sequence but not in the abetalipoproteinemic subject's DNA sequence (TTGA). To confirm this nucleotide change and address homozygosity of this allele, Taq I digests were performed on genomic DNA from a normal control, the abetalipoproteinemic subject and both parents of the abetalipoproteinemic subject. Genomic DNA was isolated from blood from a normal control, the abetalipoproteinemic subject and the abetalipoproteinemic subject's mother and father as described above. Ten μg of genomic DNA from each sample was digested with 100 units of Taq I (Bethesda Research Laboratories) in 100 μL 1×REact buffer no. 2 (Bethesda Research Laboratories) at 65° C. for 5 hours. Each digestion reaction was spun at 2,000 rpm in an Ultrafree-MC 10,000 NMWL filter unit (no. UFC3 TGC 00 from Millipore) with a molecular weight cut-off of 10,000, for 30 minutes to reduce the reaction volume to 50 μL. The restriction digest reactions were then subjected to agarose gel electrophoresis through a 1% gel in TEA buffer at 20 volts for 16 hours. The agarose gel was stained with ethidium bromide, photographed, and then transferred to a nitrocellulose membrane by the method of Southern. E. M. Southern, *J. Mol. Biol.* 98, 503–17 (1975).

The probe for the Southern hybridization was a PCR product containing exon 13 and some flanking intron sequences (see SEQ. ID NO.24, below). The PCR was performed using the GeneAmp Kit (Perkin-Elmer, Cetus Industries) components and protocol with 0.3 μg normal genomic DNA as template and 10 picomoles each of the forward and reverse primers in a 100 μL reaction volume. The reaction mix was incubated at 97° C. for two minutes, then subjected to 30 cycles consisting of 94° C. for 30 seconds, 45° C. for 30 seconds, and 72° C. for 1 minute, followed by one 7-minute incubation at 72° C. and storage at 4° C. The amplified DNA was subjected to electrophoresis through agarose as in example I and the expected 302 bp fragment was excised and eluted from the gel. This exon 13 PCR product was then $^{32}$P-labeled labeled as in example 2 and used as a probe for the Southern hybridization. Hybridization and wash conditions were as in example 2. The blot was exposed to X-ray film at −80° C. for 5 days.

B. Results

A human genomic library was generated from DNA isolated from a second abetalipoproteinemic subject. Two million phage were probed with a bovine cDNA probe and thirty phage with human genomic DNA inserts homologous to the bovine MTP cDNA were characterized.

DNA sequence analysis of the genomic DNA inserts from the abetalipoproteinemic subject revealed a C-to-T point mutation at base 1830 in exon 13 of the human MTP gene (exon 13 corresponds to bases 1817 to 1914 of the human cDNA). This C-to-T point mutation changes the normal CGA arginine codon at residue 595 to a TGA translational stop signal, resulting in a 300 amino acid truncation of this protein. This nucleotide change was found on all four independent genomic DNA inserts characterized from this individual.

Shown below is the position of the C-to-T mutation in exon 13 of an abetalipoproteinemic subject. The 302 base DNA sequence of the normal exon 13 with flanking intron sequence is shown. DNA corresponding to the forward (-->) and reverse (<--) PCR primers used to make the probe for the Southern hybridization are indicated above the appropriate arrows. Horizontal lines represent the intron/exon boundaries. The Taq I recognition sequence is boxed. An asterisk (*) designates base 1830, the site of the C-to-T mutation.

SEQ. ID. NO. 24.

```
ATTTGGCTTC    CTCTTTTTTC    CACTGAGGAT    TTTTTTTTCC    AAATTTGACT    50

TGGGAAACAG    TCATTACAAT    GAATGTGCAG    CTTTTTTTTT    CCTCATATGT    100

TGCAG CAAAA   TTGTCCG TCG   A GTTCTGAAG   GAATGTGTCG    CTCACAATTA    150
INTRON EXON
TGACCGTTTC    TCCAGGAGTG    GATCTTCTTC    TGCCTACACT    GGCTACATAG    200

AAC GTATGTA   CACCAAAAAG    AGGTTCTCCT    TCCATACCCC    ACAACTTAGC    250
EXON INTRON
ATTGCTGGAA    CTGCTATTAA    ATTACAGTTA    TAGTGTGTCA    TCAGGTAGTC    300

CC                                                                   302
```

The normal nucleotide sequence surrounding the C at base 1830 (TCGA) encodes a Taq I restriction site. In this abetalipoproteinemic subject, the sequence at this site is mutated (TTGA). Therefore, Taq I should cut exon 13 at this site in normal DNA, but not in DNA which contains the mutation. There is only one Taq I site in the normal exon 13.

Figure 9:
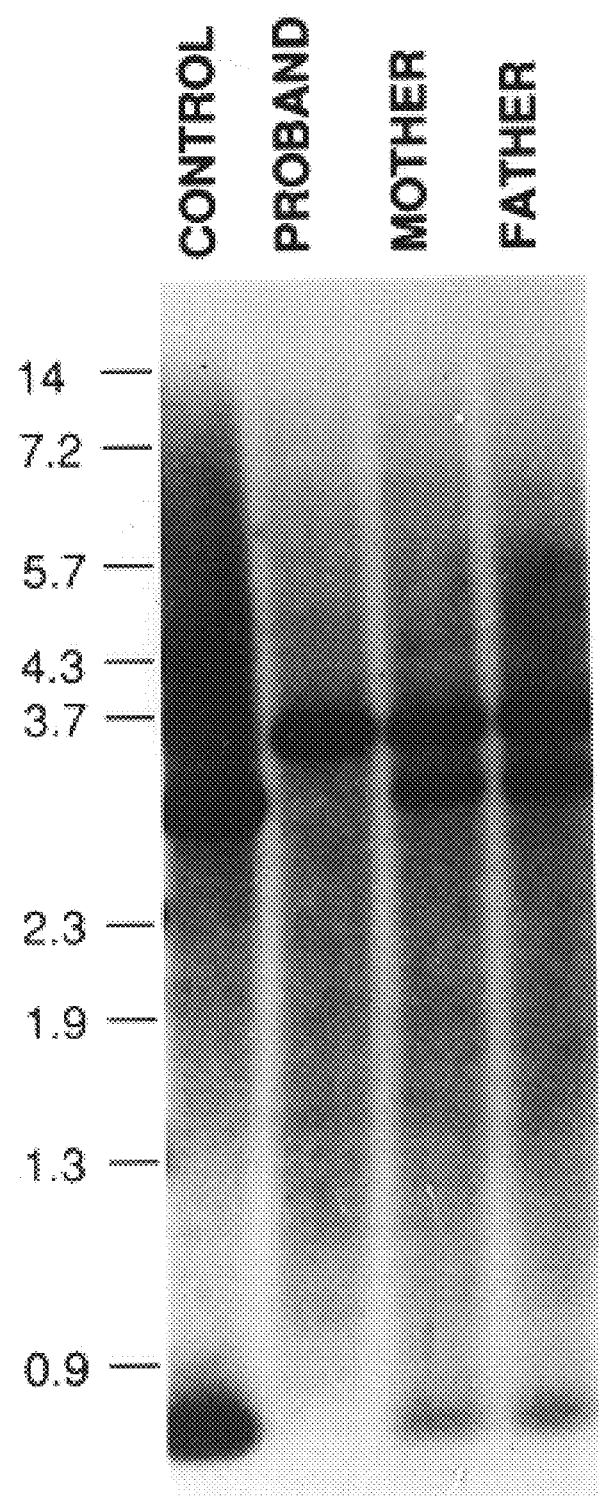
FIG. 9 shows a Southern blot analysis of a gene defect in an abetalipoproteinemic subject. Ten μg of genomic DNA from a control, the abetalipoproteinemic subject (proband), and from the subject's mother and father were cut to completion with Taq I, electrophoresed on 1% agarose and transferred to nitrocellulose. Southern hybridization was performed using exon 13 cDNA as a probe. Two hybridizing bands in the normal lane indicated the presence of a Taq I site in the normal exon 13. One hybridizing band in the abetalipoproteinemic subject lane demonstrated the absence of this restriction sequence in both alleles in exon 13, confirming a homozygous mutation in this subject. The heterozygous state in the mother and father is shown by the three hybridizing bands, corresponding to both the normal and the mutant restriction patterns.

A Southern blot confirms this nucleotide change (FIG. 9). The genomic DNA isolated from a control subject, the abetalipopmteinemic subject, and the subject's mother and father was cut to completion with Taq I and probed with sequences from exon 13. The normal DNA is cut by Taq I into two pieces which hybridize to exon 13; the abetalipoproteinemia DNA is not cut with Taq I, evidenced by only one hybridizing band. This result confirms the lack of a Taq I recognition sequence. The DNA from both parents exhibits a mixed pattern, demonstrating the presence of one normal allele and one mutated allele.

C. Analysis

The foregoing results and the conclusions drawn from them can be summarized as follows.

MTP activity and protein are undetectable in the abetalipoproteinemic subjects studied. Mutations in the MTP gene fully explain the lack of protein and activity. Previous results demonstrate that abetalipoproteinemia is a monogenetic disease Kane & Havel, supra. From these results, one can conclude that abetalipoproteinemia is caused by a loss of MTP activity.

These results demonstrate that MTP activity is required for the efficient assembly and secretion of lipoprotein particles which contain apolipoprotein B. Loss of MTP activity results in lower serum levels of cholesterol, triglycerides, phospholipids, and cholesterol esters. One can thus conclude that a decrease in the amount of activity of MTP will result in lower serum lipid levels.

Moreover, lower serum lipid levels are associated with prevention, stabilization, or regression of atherosclerosis. As discused above, loss of the amount or activity of MTP results in lower serum lipid levels. In addition, abetalipoproteinemic subjects lack atherosclerosis. Schaefer, supra; Dische and Porro, Am. J. Med. 49, 568–71 (1970); and Sobrevilla et al., Am. J. Med. 37, 821 (1964). One can thus also conclude that inhibition of MTP will result in the prevention, stabilization, or regression of atherosclerosis.

The following examples further illustrate the present invention. These examples are not intended to limit the scope of the present invention, and may provide further understanding of the invention.

EXAMPLE 1

Isolation and DNA Sequence Analysis of cDNA Clones Encoding the 88 kDa Component of the Bovine MTP A commercially available bacteriophage lambda gt10/ bovine small intestine cDNA library was purchased from Clontech. $1 \times 10^6$ independent recombinant phage plaques were screened for the cDNA corresponding to the 88 kDa component of bovine MTP.

An E. coli bacteria host, strain C600 (Clontech), was prepared for phage infection by growing overnight to saturation at 30° C. in 50 mL of Luria Broth (LB=10 g sodium chloride, 10 g Bacto-Tryptone and 5 g Yeast Extract per liter) supplemented with 0.2% maltose and 10 mM magnesium sulfate. The cells were pelleted by low speed centrifugation, resuspended in 20 mL of 10 mM magnesium sulfate and stored at 4° C. Twenty aliquots each of 50,000 phage and 300 µL of the C600 cells were incubated at 37° C. for 15 minutes, mixed with 7 mL LB+0.7% agarose and plated on 132 mm LB Plates. The plates were incubated for 7–10 hours at 37° C. until distinct phage plaques appeared, then transferred to 4° C.

Duplicate plaque transfers to nitrocellulose membranes were performed for each plate as follows. A nitrocellulose membrane (Schleicher & Schuell, Keene, N.H.) was placed directly on the phage for 1 minute (first transfer) or 3 minutes (second transfer). The phage DNA adhering to the membrane was then denatured for 1 minute in 0.5 N sodium hydroxide, 1.5 M sodium chloride, neutralized for 1 minute in 1 M Tris, pH 8.0, 1.5 M sodium chloride, and finally washed for 1 minute in 2×SSC (1×SSC=0.15 M sodium chloride, 0.015 M sodium citrate, pH 7.0). The DNA was then permanently fixed onto the nitrocellulose membrane by baking in an 80° C. vacuum oven for 2 hours.

The isolation of bovine MTP, including the 88 kDa component, has been previously described. See Wetterau and Zilversmit, Chem. Phys. Lipids 38, 205–72 (1985); Wetterau et al., J. Biol. Chem. 265, 9800–7 (1990). The sequences of internal peptides of the 88 kDa component were used to design oligonucleotides which would hybridize to cDNA that encodes the protein. See Lathe, R., J. Mol. Biol. 183, 1–12 (1985).

The procedures described herein employed probes having the following DNA sequences (listed 5' to 3'):

| Probe | Sequence | NO. |
|---|---|---|
| 2A | CTCTACCAGCGAGTATTAAT | 25 |
|    | T      C G G G |    |
| 37A | ACGTAGGATGTCTTGGACAATGGAGAGCATGTA | 26 |
| 19A | GATCAGTTGGTTATCATCACCATCAGGACT | 27 |

Probe 2A is a mixture of thirty-two twenty base oligonucleotides, each encoding the amino acid sequence of the peptide from which this probe was designed. Probe 37A is a unique 33 base sequence and probe 19A is a unique thirty-mer. These oligonucleotide sequences encode amino acid sequences that correspond to internal peptides.

Oligonucleotides were obtained from commercial sources as indicated herein or synthesized on a Milligen/Biosearch (Millipore Corp., Bedford, Mass.) 8700 DNA Synthesizer using beta-cyanoethyl phosphoramidite chemistry. Sequencing primers were desalted on NAP-10 columns (Pharmacia LKB Biotechnologies, Inc., Piscataway, N.J.) prior to use. Probes were purified on NENSORB Prep Resin (DuPont Company, NEN Research Products, Boston, Mass.).

Probe 2A was purchased from Genosys Biotechnologies, Inc. (The Woodlands, Tex.) and was labeled by incubating 1 μg of the oligonucleotide in 50 mM Tris-Cl, pH 7.5, 10 mM magnesium chloride, 5 mM dithiothreitol (DTT), 0.1 mM ethylenediaminetetraacetate (EDTA), and 0.1 mM spermidine with 10 units T4 polynucleotide kinase and 120 μCi of gamma labeled $^{32}$P-ATP in a 50 μL reaction volume at 37° C. for 30 minutes followed by heat inactivation of the kinase at 68° C. for 5 minutes. Unreacted ATP was removed utilizing a G-25 Sephadex spin column (Boehringer Mannheim Corp., Indianapolis, Ind.) following the manufacturer's instructions. The labeled oligonucleotide had a specific activity of approximately $2\times10^8$ dpm/μg.

The nitrocellulose membranes were prehybridized for 2 hours at 37° C. in 150 mL of hybridization buffer (6×SSC, 20 mM NaPO4, 2×Denhardts, 0.1% SDS, and 100 μL salmon sperm DNA) (See, Sambrook et al., supra, p. B15 for Denhardts). The hybridization buffer was replaced and the labeled oligonucleotide probe 2A was added and allowed to hybridize overnight at 37° C. The membranes were washed in 1 liter of 2×SSC, 0.1% SDS at 40° C., air-dried, and exposed to Kodak XAR-5 X-ray film for 5 days at −80° C., with a Dupont lightening plus intensifying screen (Dupont, NEN).

Putative positive clones (40) were rescreened with the same probe through two subsequent rounds of hybridization. Agar plugs corresponding to positive signals on the X-ray films were excised from the original plates and placed in 1 mL SM+5% CHCl$_3$ (SM=5.8 g sodium chloride, 2.0 g magnesium sulfate, 50 mL 1 M Tris-Cl pH 7.5, and 5 mL 2% gelatin per liter). The phage were replated by mixing 0.001 μL of phage stock with 100 μL C600 cells in 10 mM magnesium sulfate, incubating at 37° C. for 15 minutes, adding 3 mL LB+0.7% agarose and plating onto 82 mm LB plates. After overnight incubation at 37° C. followed by 1 hour at 4° C., the phage plaques were transferred to nitrocellulose, and reprobed as above to labeled oligonucleotide probe 2A. Following the tertiary hybridization screen, 16 phage plaques were isolated.

The inserts of each of the 16 recombinant phage were amplified by PCR using the commercially available lambda gt10 amplimers (Clontech) and the GeneAmp Kit (Perkin-Elmer, Cetus Industries, Norwalk, Conn.) following the manufacturer's protocols exactly. The amplified DNA was subjected to electrophoresis through 1.2% agarose gels in Tris-EDTA-Acetate (TEA=40 mM Tris-Acetate, 1 mM EDTA) buffer, for 2–3 hours at 100 volts. The agarose gels were then stained in ethidium bromide (EtBr), rinsed in water and photographed. The DNA was then transferred from the gel to a nitrocellulose membrane by the method of Southern. A Southern hybridization was performed using labeled oligonucleotide probe 2A in 50 mL hybrdizaiton buffer (above) at 40° C. overnight then washing at 45° C., 48° C. and 51° C. Two amplified inserts, corresponding to phage no. 64 and no. 76 (FIG. 1), hybridized to probe 2A at 51° C. in 2×SSC. Lambda DNA of these 2 clones was prepared following the plate lysate procedure (Sambrook, et al., supra, p. 2.118). One-tenth (5 mL of 50 ml) of the phage DNA was digested with 20 units of the restriction enzyme Eco RI (New England Biolabs, Beverly, Mass.) in the manufacturer's buffer at 37° C. for 2 hours and subjected to agarose gel electrophoresis. Upon EcoRI cleavage of these phage, no. 64 yielded a 1.0 kb insert fragment and the cDNA from phage no. 76 yielded two EcoRI pieces, of 0.9 kb and 0.4 kb. These bands were excised from the gel.

DNA was eluted from the agarose gel slices by first forcing the gel slices through a 21 gauge needle into 3 mL of $T_{10}E_1N_{.3}$(10 mM Tris-Cl pH 7.4, 1 mM EDTA pH 8.0 and 0.3 M sodium chloride) and freezing at −20° C. overnight. The samples were then thawed at 37° C. for 30 minutes, centrifuged to pellet the agarose, diluted 1:1 with water and passed through an Elu.Tip column (Schleicher & Schuell) following the manufacture's protocol. The DNA samples were then ethanol precipitated, ethanol washed, and resuspended to an approximate concentration of 0.05 pmoles/μL.

The plasmid vector bluescript SK+ (Stratagene) was prepared to receive the cDNA inserts by digestion with 20 units of the restriction endonuclease Eco RI (New England Biolabs) in the manufacturer's buffer at 37° C. for 2 hours, followed by a 30 minute treatment with 1 unit of calf alkaline phosphatase (Boehringer-Mannheim) which is added directly to the Eco RI reaction. This DNA was then electrophoresed through a 1.2% agarose/TEA gel at 100 volts for 2 hours. The linear plasmid band was excised, eluted and resuspended as above.

cDNA insert fragments were ligated into the prepared bluescript plasmid vector by mixing 0.05 pmole of vector with 0.10 pmoles of cDNA insert in 50 mM Tris-Cl pH 7.4, 10 mM magnesium chloride, 1 mM DTT, 1 mM ATP, and 40 units T4 DNA ligase (New England Biolabs). The 10 μL reaction was incubated at 15° C. overnight. The ligation reaction was then mixed with 100 μL of transformation competent *E. coli* cells, strain DH5a (Bethesda Research Laboratories), and the plasmid DNA transformed into the *E. coli* cells following the standard protocol of Sambrook et al., supra, p. 1.74. Transformed cells were plated on LB-agar plates containing 100 μg/mL ampicillin and grown overnight at 37° C.

Plasmid DNA was isolated from ampicillin resistant colonies following the alkaline lysis procedure of Birnboin and Doly [*Nucleic Acids Res.*, 7, 1513–23 (1979)]. The purified plasmid DNA was digested with Eco RI as above, subjected to agarose gel electrophoresis and analyzed for the generation of the correct size Eco RI cDNA insert fragment. Cells from a unique colony positive for a cDNA insert were used to innoculate 100 mL of LB containing 100 μg/mL ampicillin and grown to saturation at 37° C. Plasmid DNA was extracted using a Qiagen plasmid isolation kit no. 12143 (Qiagen, Inc., Chatsworth, Calif.) following the manufacturer's protocol.

Sequencing of cDNA clones was performed with the Applied Biosystems, Inc. (ABI, Foster City, Calif.) 373 Automated DNA Sequencer utilizing either dye-labeled primers or dye-labeled dideoxynucleotides. Cycle sequencing with dye-labeled primers was performed with Taq Dye Primer Cycle Sequencing Kits (ABI part nos. 401121 and 401122). One μg of double-stranded DNA was used per reaction. Methods used for cycling and concentration of sequencing samples were as described in the Cycle Sequencing of DNA with Dye Primers manual (ABI part no. 901482). Alternatively, cycle sequencing with dye-labeled dideoxynucleotides was performed using the Taq Dye Deoxy™ Terminator Cycle Sequencing Kit (ABI part no. 401113). Typically, 1.25 μg of template with 4 pmol of primer was used per reaction. The template and primer concentrations were varied as necessary to optimize sequencing reactions. Cycling of reactions was performed using a Perkin-Elmer Cetus thermal cycler (model 9810) as described in the Taq Dye Deoxy™ Terminator Cycle Sequencing Protocol (ABI part no. 901497).

Following the cycle reactions, Centri-Sep™ spin columns (Princeton Separations, Adelphia, N.J.) were used to remove excess dye terminators and primers. Spin column eluants were then precipitated and washed as described in the Taq Dye Deoxy™ Terminator Cycle Sequencing Protocol (ABI part no. 901497). A 6% acrylamide denaturing gel was prepared as described in the ABI 373A DNA Sequencing System User's Manual. Just prior to running the gel, samples were resuspended in 5 μL of deionized formamide/50 mM EDTA (pH 8.0) 5/1 (v/v). Samples were denatured at 90° C. for two minutes, cooled quickly on ice, then loaded onto a pre-run gel (gel was prerun for approximately 15–20 minutes). The gel was run for 12 hours at the following settings: 2500 volts, 40 amps, 30 watts, 40° C. Sequence analysis was performed with ABI 373A DNA Analysis software (version 1.0.2). Final sequence was obtained using ABI DNA Sequence Editor software seqEd™ (version 1.0) ABI, Inc.

The entire 1036 bp insert of clone no. 64 was sequenced. It encoded 936 bp of open reading frame continuing through the 3 prime end of the insert (corresponding to a polypeptide with a molecular weight of at least 34,000). Comparison of the sequence of this clone to available sequence in nucleotide sequence data banks revealed that the first 91 bases at the 5' end of the clone corresponded to the bovine mitochondrial genome. Therefore, the 1036 bp insert of clone no. 64 resulted from the ligation of two independent cDNAs during the construction of this library.

The 400 bp EcoRI fragment of clone no. 76 was sequenced entirely indicating 81 bp of open reading frame followed by 298 bases of 3 prime untranslated sequence and a poly A region.

The lambda gt10 bovine small intestine cDNA library was rescreened with an oligonucleotide probe 37A, an exact 33 bp match to the 5' most peptide sequence encoded by clone no. 64. Two positive clones, no. 22 and no. 23 (FIG. 1) were isolated through tertiary screens, subcloned and sequenced as for clone no. 64.

Clones no. 22 and 23 contained 2.8 kb and 1.7 kb cDNA inserts respectively. The 2.8 kb cDNA insert of clone no. 22 predicted a continuous open reading frame of 835 amino acids between bases 2 and 2506 (corresponding to a 93.2 kDa polypeptide), followed by 298 base of 3' untranslated sequences and a poly A region.

The lambda gt10 library was rescreened with probe 19A, an exact match to the sequence of clone no. 22 corresponding to the 5'-most peptide encoded by that clone, and clone no. 2 was isolated as above. DNA sequence analysis of the 1 kb cDNA insert from clone no. 2 indicated it overlapped clone no. 22 and extended the 5' end of the bovine cDNA by 100 bases. A composite of the DNA sequences of clones no. 2 and no. 22 and the predicted translation product is shown in SEQ. ID. NOS. 1 and 3, respectively.

In summary, sequencing of bovine small intestine cDNA clones corresponding to the 88 kDa component of MTP yielded 2900 bp of continuous sequence which encodes an open reading frame of 860 amino acids followed by a 298 bp 3' noncoding region and a poly A region. The predicted protein product of this composite sequence is 96.1 kDa.

EXAMPLE 2
DNA Hybridization Analysis of Related Species

Southern hybridization analysis was performed on DNAs from cow, human, mouse, hamster (Chinese hamster ovary or CHO cells), rat, and dog. 10 μg of each genomic DNA (Clontech) was digested with 140 units of Eco RI (New England Biolabs) in 100 μL 1×Eco RI buffer (New England Biolabs) at 37° C., overnight. Each digestion reaction was spun at 2,000 rpm in a Ultrafree-MC 10,000 NMWL filter unit (no. UFC3 TGC 00 from Millipore) with a molecular weight cut-off of 10,000, for 30 minutes to reduce the reaction volume to 50 μL. The restriction digest reactions were then subjected to agarose gel electrophoresis through a 0.75% gel in TEA buffer at 80 volts for 3 hours. The agarose gel was stained with ethidium bromide, photographed, and then transferred to a nitrocellulose membrane by the method of Southern.

A Southern hybrdization was performed using the 2.4 kb Eco RI fragment from the bovine cDNA clone no. 22 as a probe. Twenty-five ng of the DNA fragment was labeled using the Multiprime DNA Labelling System (Amersham Corp., Arlington Heights, Ill.) and 50 μCi of $^{32}$P-α-dCTP. Unincorporated $^{32}$P was separated from the labeled probe using a Sephadex G25 spin column as above. The nitrocellulose membranes was prehybrdized in 100 mL hybridization buffer (above) at 37° C. for 2 hours. The hybridization was performed overnight in 50 mL fresh hybridization buffer at 60° C. with 1.2×10$^7$ dpm denatured probe. The membrane was washed in 500 mL 1×SSC, 0.1% SDS at 65° C. for 1 hour, air-dried, and then exposed to X-ray film at −80° C. with an intensifying screen for 4 days. The 2.4 kb Eco RI fragment from bovine clone no. 22 specifically hybridized to at least two DNA bands in every species tested. Therefore, it was concluded that the hybridization conditions established for the bovine cDNA probe allows detection of homologous DNAs from other species, such as human, mouse, hamster, rat and dog.

EXAMPLE 3
Isolation and DNA Sequence Analysis of cDNA Clones Encoding the 88 kDa Component of Human MTP A. Cloning and Sequence Analysis To obtain the full coding sequence of the 88 kDa component of human MTP, a human liver cDNA library was screened with a bovine MTP cDNA insert described herein above. The library was obtained from Stratagene. It contained oligo dT primed liver cDNA directionally cloned (EcoRI to XhoI) into the lambda ZAP vector. The probe was obtained by digestion of 10 μg of bovine intestinal clone no. 22 above in universal buffer (Stratagene) with 50 units of EcoRI, electrophoresis at 80–150 volts through a gel consisting of 0.9% low melting point agarose (Bethesda Research Laboratories, Gaithersburg, Md.), TAE (40 mM Tris acetate, 1 mM EDTA), and 0.5 μg/mL ethidium bromide. The resulting 2.4 Kb fragment was purified by phenol extraction as described in Sambrook et al., supra, p. 6.30. The purified fragment was then radiolabelled with a multiprime DNA labelling kit and alpha $^{32}$P dCTP (Amersham) to 10$^9$ cpm/μg using the manufacturer's instructions. Unincorporated $^{32}$P was separated from the labeled probe using a Sephadex G-25 spin column as above.

10$^6$ plaques from the library were screened as follows according to the manufacturers instructions (Stratagene). *E. coli* bacteria, strain XL 1 Blue (Stratagene), were grown with shaking overnight at 37° C. in 50 mL LB broth (Bethesda Research Laboratories) supplemented with 0.2% maltose and 10 mM magnesium sulfate. The cells were sedimented by low speed centrifugation and then resuspended in 10 mM magnesium sulfate to an OD$_{600}$=0.5 and stored at 4° C. Phage were diluted to a concentration of 50,000 plaque forming units/25 μL SM buffer. For each plate, 600 μL of bacteria, and 25 μL of phage were mixed and incubated at 37° C. for 15 minutes. Top agar (6.5 mL) consisting of NZY broth (Bethesda Research Laboratories), 0.7% agarose (Bethesda Research Laboratories) preheated to 50° C., was added to the bacteria and phage mixture, and then plated onto a 150 mm NZY plate. The top agar was allowed to solidify and the plates were incubated overnight at 37° C.

The plates were then cooled to 4° C. for 2 hours and the plaques were lifted onto nitrocellulose filters. Duplicate lifts were performed in which the alignment of the membranes relative to the plate were recorded by placing needle holes through the filter into the agar plate. The filters were incubated 1 minute in 0.5 N sodium hydroxide, 1.5 M sodium chloride, 1 minute in 1 M Tris, pH 8.0, 3 M sodium chloride, and 1 minute in 2×SSC. Filters were then baked at 80° C. in a vacuum chamber for 2 hours. The filters were incubated for 2 hours at 60° C. in 5 mL per filter of hybridization buffer (6×SSC, 20 mM $NaPO_4$, 2×Dendardts, 0.1% SDS, and 100 µg/mL salmon sperm DNA). The buffer was replaced with an equal volume of hybridization buffer containing the probe at a concentration of $3.5×10^6$ cpm per filter and incubated overnight at 60° C. The filters were washed in 1×SSC, 0.1% SDS first at room temperature and then at 50° C. for 2 hours. Autoradiography revealed 56 positives.

A small plug of agarose containing each positive was incubated overnight at 4° C. with 1 mL of SM buffer and a drop of chloroform. The positive phage were purified by replating at a low density (approximately 50–500 per 100 mm plate), screening and isolating single positive plaques as described above.

When XL1 Blue cells are infected with the ZAP vector (Stratagene) and coinfected with a helper phage, the bluescript part of the vector is selectively replicated, circularized and packaged into a single stranded phagemid. This phagemid is converted to a double stranded plasmid upon subsequent infection into naive XL1 Blue cells. The cDNA insert of the resultant plasmid can be sequenced directly. Plasmids containing the positive human liver cDNA inserts were excised in this manner utilizing the helper phage provided by Stratagene according to the manufacturer's directions.

DNA from these clones was purified as follows. A single colony was inoculated into 2 mL of LB and incubated with shaking at 37° C. overnight. 1.5 mL of this was centrifuged and resuspended in 50 µL of LB. 300 µL of TENS (1×TE, 0.1 N sodium hydroxide, 0.5% SDS) was added and vortexed for 5 seconds. 150 µL of 3 M sodium acetate, pH 5.2 was added and vortexed for 5 seconds. The samples were then spun in a microfuge for 10 minutes. The supernatant was recovered, 0.9 mL of ethanol was added and the samples were spun in a microfuge for 10 minutes. The pellet was washed in 70% ethanol, dried, and resuspended in 20 µL of TE (10 mM Tris pH 7.4, 1 mM EDTA pH 8).

The DNA from the clones was characterized as follows. Five µL of the DNA from each clone were digested with 10 units Eco RI, 10 units XhoI, and 10 µg RNAse, and then fractionated and visualized by electrophoresis through a 1% agarose, TBE (45 mM Tris-Borate, 1 mM EDTA), 0.5 µg/mL ethidium bromide gel. A Southern blot of the gel was performed as described in Sambrook et al., supra, p. 9.41. This Southern blot was probed with a fragment of the bovine cDNA near the 5' end of the coding sequence. This 5' probe was prepared by digesting 25 µg of bovine intestinal clone no. 2 above with 50 units EcoR1 and 50 units of NheI, isolating as above the 376 base pair fragment from a 2% low melting point agarose, TBE, 0.5 ug/mL ethidium bromide gel, and radiolabelling as described above. The results are as follows: Clone no. 693, 3.7 kB insert, hybridizes with the 5' probe; Clone no. 754, 1.2 kB insert, hybridizes with the 5' probe; Clone no. 681, 1.8 kB insert, does not hybridize with the 5' probe.

Overnight cultures containing these three clones were grown in 200 mL of LB with 100 µg/mL ampicillin. Large amounts of plasmid were purified using a Qiagen plasmid maxiprep kit according to the manufacturer's instructions. The sequence of clone no. 693 reveals that it contained two inserts. The 5' 500 bp insert was homologous to haptoglobin and will not be discussed further. This was followed by a mutant XhoI and an EcoRI restriction site (the two sites used in the directional cloning). The 3' insert was the cDNA of interest. It contained some 5' untranslated sequence as indicated by the stop codons in all three reading frames. At bases 48–2729 there is an ATG-initiated open reading frame corresponding to 894 amino acids. The deduced amino acid sequence begins

MILLAVLFLCFI (SEQ. ID. NO. 28). The stop codon is found at bases 2730–2732 followed by a 3' untranslated region of 435 bases and a poly A region. The sequence of clone no. 681 confirmed the 3' 1768 bases of this clone, and clone no. 754 confirmed bases 1 through 442.

B. Tissue Localization of the 88 kDa mRNA

A MultiTissue Northern Blot (Clontech) contained 2 µg per lane of polyA⁺ RNA from human heart, brain, placenta, lung, liver, skeletal muscle, kidney or pancreas. Northern hybridization was performed as for the genomic Southern blot. Prehybridization was in 50 mL hybridization buffer at 37° C. for 2 hours followed by an overnight hybridization in 20 mL fresh buffer at 60° C. with $5.2×10^7$ dpm labeled 2.4 kb Eco RI fragment from the bovine intestinal clone no. 22 as above. The Northern blot was washed in 500 mL 0.2× SSC, 0.1% SDS at 60° C., 1 hour and subjected to autoradiography at −80° C. After a 20 hour exposure to X-ray film there is a predominant signal in the liver RNA lane at about 4.4 kb and no other detectable hybridization. Therefore, cross hybridization of the 2.4 kb fragment of the bovine cDNA detects a human liver RNA specifically. As liver and intestine are the only two tissues in which significant MTP activity has been reported, the cloning and northern blot analysis support the biochemical localization for MTP. Also, the results of the northern analysis extend this detection to include DNA:RNA hybrids as well as DNA:DNA interactions.

EXAMPLE 4

Expression of MTP in Human Fibroblast Cell Line

I. Methods

All standard molecular biology protocols were taken from Sambrook, supra, except where indicated below. All restriction enzymes used in this example were obtained from Bethesda Research Laboratories (BRL, Gaithersburg, Md.). A 3.2 kb fragment extending from nucleotide −64 to 3135 (relative to the translation start site with A of the translation start site ATG codon designated +1), was constructed from plasmids p754 (bases −64 to 384) and p693 (bases 385 to 3135) as follows. A 448 bp EcoRI-NcoI restriction endonuclease fragment and a 2750 bp NcoI-XhoI restriction endonuclease fragment were excised from p754 and p693, respectively. Following gel purification, the fragments were ligated into EcoRI-XhoI cut plasmid pBluescript-SK to yield plasmid pBS/hMTP. The entire hMTP fragment was isolated from pBS/hMTP by restriction endonuclease digestion with HindIII and XhoI and was subcloned into plasmid pcDNA/Neo (Invitrogen,San Diego, Calif.) to yield plasmid pcDNA/MTP. This places the full-length hMTP coding sequence under the transcriptional control of the highly active Cytomegalovirus promoter.

Plasmids were transfected into 1508T [*J. Biol. Chem.* 267, 13229–38 (1992)] transformed human skin fibroblasts by the lipofectin reagent (BRL). Cells were split into 100 mm dishes at a density of 25% of confluency, 24 hours prior to transfection. At the time of transfection, 50 µg of plasmid per 100 mm plate were dissolved in 1.5 mL of serum-free Dulbecco's Modified Eagles Medium (DMEM) and added dropwise to a solution of 120 µL lipofectin reagent in 1.5 mL of serum free DMEM. After a 15-minute incubation at room temperature, the transfection mixtures were added to the 1508T cultures containing 7 mL of serum free DMEM. Twenty four hours later, the transfection mixtures were removed and 10 mL of fresh DMEM containing 10% fetal bovine serum was added for an additional 24 hours. Cells were scraped from the dish and washed twice with ice cold phosphate buffered saline (PBS). Cell extracts, MTP activity measurements and Western analyses were carried out as described in the foregoing "Assay for TG transfer activity in Abetalipoproteinemic subjects" herein.

II. Results

The cDNA containing the full coding sequence for MTP was subcloned into expression vector pcDNA/Neo, yielding construct pcDNA/MTP. This plasmid was transiently expressed in 1508T transformed human skin fibroblasts [*J. Biol. Chem.* 267, 13229–38 (1992)] by liposome mediated transfection. Forty-eight hours after transfection, TG transfer activity was readily detectable above background levels assayed in extracts from cells transfected with the parent plasmid, pcDNA/Neo. Western blot analysis showed the presence of the the 88 kDa component of MTP in cells transfected with pcDNA/MTP but not in cells transfected with pcDNA/Neo. A comparison of the protein mass and activity in the transfected cells to that found in HepG2 cells suggests that the expressed MTP was efficiently incoporated into an active transfer protein complex with PDI.

EXAMPLE 5
Screen for Identifying Inhibitors of MTP

In this screen, the rate of detectably labeled lipid (for example, NMR, ESR, radio or fluorescently labeled TG, CE, or PC) transfer from donor particles (e.g., donor membranes, vesicles, or lipoproteins) to acceptor particles (e.g., acceptor membranes, vesicles, or lipoproteins) in the presence of MTP is measured. A decrease in the observed transfer rate in the presence of an inhibitor of MTP (e.g., contained in a natural products extract or known compounds) may be used as an assay to identify and isolate inhibitors of MTP function. A variety of assays could be used for this purpose, for example, the synthetic vesicle assays previously published by Wetterau & Zilversmit, *J. Biol. Chem.* 259, 10863–6 (1984) or Wetterau et al., *J. Biol. Chem.* 265, 9800–7 (1990) or the assay outlined hereinabove in the "Assay for TG transfer activity in Abetalipoproteinemic subjects." An example of one such assay is as follows.

A. Substrate Preparation

In a typical screen using labeled lipoproteins, labeling of lipoproteins with [$^3$H]-TG is accomplished by the lipid dispersion procedure described by Morton and Zilversmit [Morton, R. E. et al., *J. Biol, Chem.* 256, 1992–5 (1981)] using commercially available materials. In this preparation, 375 µCi of [$^3$H] triolein (Triolein, [9,10-$^3$H (N)]-, NEN Research Products, cat. no. NET-431), 1.5 mg of egg phosphatidylcholine and 160 µg of unlabeled trolein in chloroform are mixed and evaporated under a stream of nitrogen to complete dryness. Two mL of 50 mM Tris-HCl, 0.01% Na$_2$ EDTA, 1 mM dithiothreitol, pH 7.4, is added and the tube flushed with nitrogen. The lipids are resuspended by vortexing and the suspension is then sonicated for two 20-minutes intervals in a bath sonicator. The sonicated lipids are added to 75 mL rabbit plasma (Pel-Freez Biologicals, Rogers, Ariz.) with 5.8 mL of 8.2 mM diethyl p-nitrophenyl phophate (Sigma, Cat. No. D9286) and 0.5 mL of 0.4 M Na$_2$EDTA, 4% NaN$_3$. The plasma is then incubated under nitrogen for 16–24 hours at 37° C. Low density lipoproteins (LDL) and high density lipoproteins (HDL) are isolated from the incubation mixture and from control plasma which was not labeled by sequential ultracentrifugation [Schumaker & Puppion, *Methods Enzymology* 128, 155–170 (1986)]. Isolated lipoproteins are dialyzed at 4° C. against 0.9% sodium chloride, 0.01% Na$_2$EDTA, and 0.02% NaN$_3$ and stored at 4° C.

B. Transfer Assay

In a typical 150 µL assay, transfer activity is determined by measuring the transfer of radiolabeled TG from [$^3$H]-HDL (5 µg cholesterol) donor particles to LDL (50 µg cholesterol) acceptor particles at 37° C. for three hours in 15 mM Tris, pH 7.4, 125 mM MOPS, 30 mM Na acetate, 160 mM NaCl, 2.5 mM Na$_2$ EDTA, 0.02% NaN$_3$, 0.5% BSA with about 50–200 ng purified MTP in the well of a 96-well plate. The material to be tested (e.g., natural product extracts in an assay compatible solvent such as ethanol, methanol or DMSO (typically, 5 µL of material in 10% DMSO is added) can be screened by addition to a well prior to incubation. The transfer is terminated with the addition of 10 µL of freshly prepared, 4° C. heparin/MnCl$_2$ solution (1.0 g heparin, Sigma Cat. No. H3393 187 U/mg, to 13.9 mL, 1.5 M MnCl$_2$. 0.4% heparin (187 I.U.)/0.1 M MnCl$_2$) to precipitate the $^3$H-TG-LDL acceptor particles and the plate centrifuged at 800×g. An aliquot of the supernatant from each well containing the [$^3$H]-TG-HDL donor particles is transferred to scintillation cocktail and the radioactivity quantitated. The enzyme activity is based on the percentage of TG transfer and is calculated by the following equation:

$$\text{Enzyme activity} = 1 - \frac{[3H]\text{-}TG \text{ recovery } (+MTP)}{[3H]\text{-}TG \text{ recovery } (-MTP)} \times 100\%$$

In such an assay, the percent TG transfer will increase with increasing MTP concentration. An inhibitor candidate will decrease the percent TG transfer. A similar assay could be performed with labeled CE or PC.

EXAMPLE 6
Identification and Demonstration of the Activity of MTP Inhibitors

I. Methods

A. Identification of MTP Inhibitors

Using the method outlined in Example 5, MTP inhibitor compounds A and B were identified. The assay measured the bovine MTP-catalyzed rate of transport of radiolabeled TG from donor HDL to acceptor LDL. In this method, an inhibitor decreases the rate of radiolabeled TG transfer.

The MTP-inhibiting activity of these compounds was confirmed in an independent assay following the procedures outlined in the foregoing "Assay for TG transfer activity in abetalipoproteinemic subjects." That assay measured the bovine MTP-catalyzed transport of radiolabeled TG from donor to acceptor SUV.

B. Cell Culture

The human hepatoblastoma cell line, HepG2, was obtained from the American Type Culture Collection (Rockville, Md.; ATCC accession no. 8065). Cultures were maintained at 37° C. in a 5% carbon dioxide atmosphere in T-75 culture flasks with 12 mL of RPMI 1640 medium containing 10% fetal bovine serum (all cell culture media and buffers were obtained from GIBCO Life Technologies, Gaithersburg, Md.). Cells were subcultured 1:4 once a week and fed fresh medium 3 times a week.

Experiments to measure the effects of compounds A and B on protein secretion were carried out in 48-well plates. HepG2 cells were subcultured 1:2 and allowed to come to confluency at least 24 hours before drug treatment. Before commencement of drug treatment, culture medium was removed, the cells washed once with PBS and 1 mL of fresh medium was added quantitatively. Compound A was added to duplicate wells in 10 μL of dimethylsulfoxide (DMSO) to yield varying compound concentrations. DMSO alone (10 μL) was used as the negative control. (Note: DMSO at this concentration has negligible effect on HepG2 cells.) After a 16-hour incubation under standard cell culture conditions, the plates were centrifuged at 2,500 rpm for 5 minutes at 4° C. to sediment any loose cells. The media were diluted with cell culture medium 10 times for the apolipoprotein B (apoB) and human serum albumin (HSA) assays, and 20 times for the apolipoprotein Al (apoAl) assays. The cells were washed twice with cold PBS, and 0.5 mL of homogenization buffer was then added (0.1 M sodium phosphate, pH 8.0; 0.1% Triton X-100). The cells were homogenized by trituration with a 1 mL micropipettor, and protein was measured using the Coomassie reagent (Pierce Chemical Co, Rockford, Ill.) as described by the manufacturer.

C. ELISA Assays for ApoB and ApoAl and HSA

The ELISA assays to measure protein mass were of the "sandwich" design. Microtiter plates were coated with a monoclonal antibody (primary antibody), specific for the protein of interest (Biodesigns International, Kennebunkport, Me.), followed by the antigen or sample, a polyclonal antibody (secondary antibody) directed to the protein of interest (Biodesigns International), and a third antibody conjugated to alkaline phosphatase directed to the secondary antibody (Sigma Biochemical, St.Louis, Mo.). The 96-well microtiter plates (Corning no. 25801) were coated overnight at room temperature with 100 μL of diluted monoclonal antibody (final concentrations were 1 μg/mL, 2 μg/mL and 4 μg/mL for anti-apoB, apoAl and HSA, respectively, in 0.1 M sodium carbonate-sodium bicarbonate, pH 9.6 and 0.2 mg/mL sodium azide). Coating was carried out overnight at room temperature. After coating and between each subsequent incubation step, the plates were washed five times with 0.9% sodium chloride with 0.05% Tween 20. Duplicate aliquots (100 μL) of diluted culture media or standard (purified apoB, apoAl or HSA diluted to 0.3125–320 ng/mL with cell culture medium) were added to wells coated with monoclonal antibody. Following incubation for 1.5 hours at room temperature, the antigen or sample was removed and the wells washed. The secondary antibodies were diluted 1:500 in PBS+0.05% Tween 20 (Buffer III), then 100 μL was added to each well and incubated for 1 hour at room temperature. The antibody was removed and the wells were washed. All secondary antibodies were polyclonal antisera raised in goat against the human proteins. A rabbit anti-goat IgG, conjugated to alkaline phosphatase, was diluted 1:1000 with Buffer III and 100 μL was added to each well. Following incubation for 1 hour at room temperature, the antibody was removed and wells washed eight times. The substrate p-nitrophenylphosphate (Sigma Biochemical, St. Louis, Mo.) was added at 1 mg/mL in 0.05 M NaCarbonate-NaBicarbonate, pH 9.8+1 mM magnesium chloride. Following a 45-minute reaction at room temperature, the assay was stopped and the color stabilized with the addition of 100 μL of 0.1 M Tris, pH 8.0+0.1 M EDTA. The microtiter plates were read at 405 nm in a V-Max 96-well plate reader (Molecular Devices, Menlo Park, Calif.).

After subtraction of background, the standards were plotted on a semi-log graph and logarithmic regression was performed. The equation for the curve was used to calculate the concentration of apoB, apoAl and HSA. The protein concentration was normalized to total cell protein yielding concentrations with units of ng/ml/mg cell protein. Each drug treatment was performed in duplicate and the results were averaged. The apoB, apoAl, and HSA concentrations for each drug treatment were divided by the corresponding protein concentration in the DMSO control. The results were plotted as a percentage of control versus the drug concentration.

D. Lipid Analysis

HepG2 cells were subcultured into 6-well dishes and allowed to come to confluency at least 24 hours before drug treatment. Prior to addition of the drug, culture media were removed, cells washed once with PBS, and 1 mL of fresh medium (RPMI 1640+10% FBS) was added quatitatively. Compound A was added to duplicate wells in 10 μL of DMSO to yield varying compound concentrations. DMSO alone (10 μL) was used as the negative control. After a 16-hour incubation under standard cell culture conditions, the media were removed and 1 mL of labeling medium (RPMI 1640; 16.5 mg/mL fatty acid free BSA; 1 mM sodium oleate; 1 mM glycerol; 5 μCi/mL 3H-glycerol (Amersham, Arlington Heights, Ill., Catalog no. TRA.244) was added with a second addition of compound A. The cultures were incubated for 2 hours under standard cell culture conditions. Media (1 mL) were removed to 15-mL glass tubes and immediately diluted with 2 mL of ice cold methanol and 1 mL of dH2O. Cells were washed once with PBS and were processed for total protein measurements as described in section I-B.

Total lipids were extracted from the media and analyzed as follows. After addition of 5.0 mL of chloroform and 0.2 mL of 2% acetic acid, the tubes were vortexed for 1 minute and centrifuged at 2,000 rpm for 5 minutes to separate the aqueous and organic phases. The upper aqueous phase was removed and 3.6 mL of methanol:water (1:1) containing 0.1% acetic acid added. After briefly vortexing, the tubes were centrifuged as before and the aqueous phase again removed. The organic phase was quatitatively transferred to clean 15-mL glass tubes and the solvent evaporated under nitrogen. Dried lipids were dissolved in 0.1 mL of chloroform and 30 μL of each sample were spotted onto silica gel 60A, 19 channel thin layer chromatography plates (Whatman). 5–10 μg of TG in 10 μL of chloroform were added as carrier and the plates were developed in hexane-:diisopropyl ether:acetic acid (130:70:4, V/V). After drying, lipid was stained by exposing the plates to iodine. Bands corresponding to TG were scraped into scintillation vials. 0.5 mL of dH2O and 10 mL of EcoLite (ICN Biomedical) scintillation fluid were added and the samples vortexed vigorously. Raw data was normalized to cell protein and expressed as percent of DMSO control.

II. Results

A. Identification of MTP Inhibitors

The primary screen suggested that compound A inhibited the MTP-catalyzed transport of $^3$H-TG from HDL to LDL.

Figure 10:
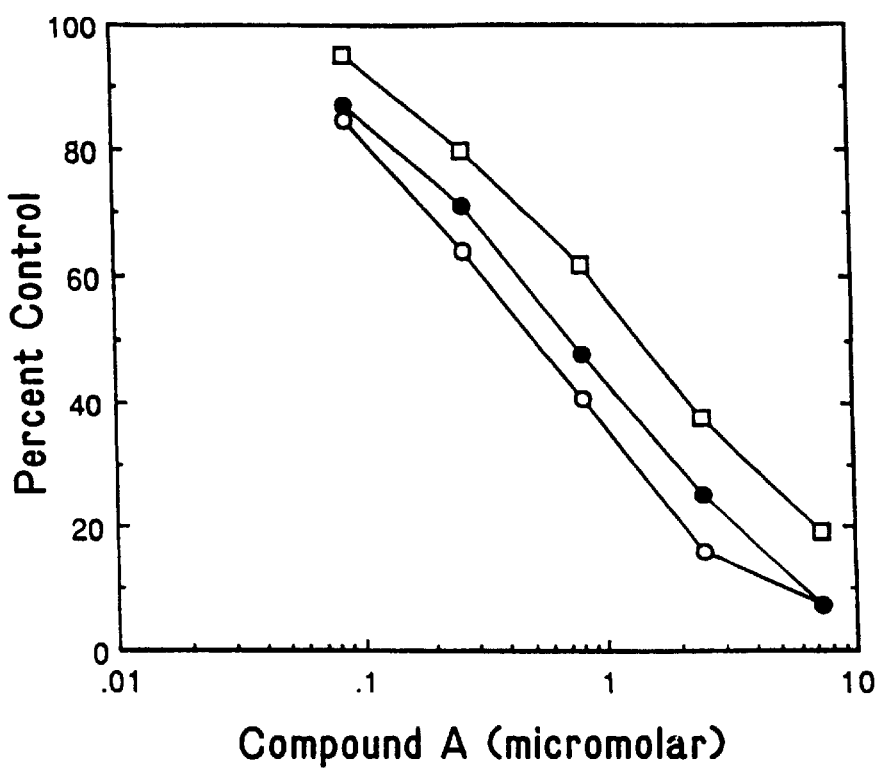
FIG. 10 shows inhibition in MTP-catalyzed transport of TG from donor SUV to acceptor SUV by compound A described hereinafter. Compound A was dissolved in DMSO and then diluted into 15/40 buffer. Aliquots were added to a lipid transfer assay to bring the compound to the indicated final concentrations. DMSO concentration in the assay never exceeded 2 μL/600 μL, a concentration that was independently determined to have minimal effect on the assay. MTP-catalyzed lipid transport was measured for 30 minutes at 37° C. TG transfer was calculated and compared to a control assay without inhibitor. Three independent assay conditions were used to demonstrate MTP inhibition by compound A. Assay conditions were: 8 nmol donor PC, 48 nmol acceptor PC, and 75 ng MTP (open circles); 24 nmol donor PC, 144 nmol acceptor PC, and 100 ng MTP (solid circles); 72 nmol donor PC, 432 nmol acceptor PC, and 125 ng MTP (open squares).

The ability of compound A to inhibit MTP-catalyzed lipid transport was confirmed in a second assay which measures the MTP-catalyzed transport of $^3$H-TG from donor SUV to acceptor SUV. The IC$_{50}$ for compound A is about 1 µM (FIG. 10).

B. Inhibition of apoB and TG Secretion

Figure 11:
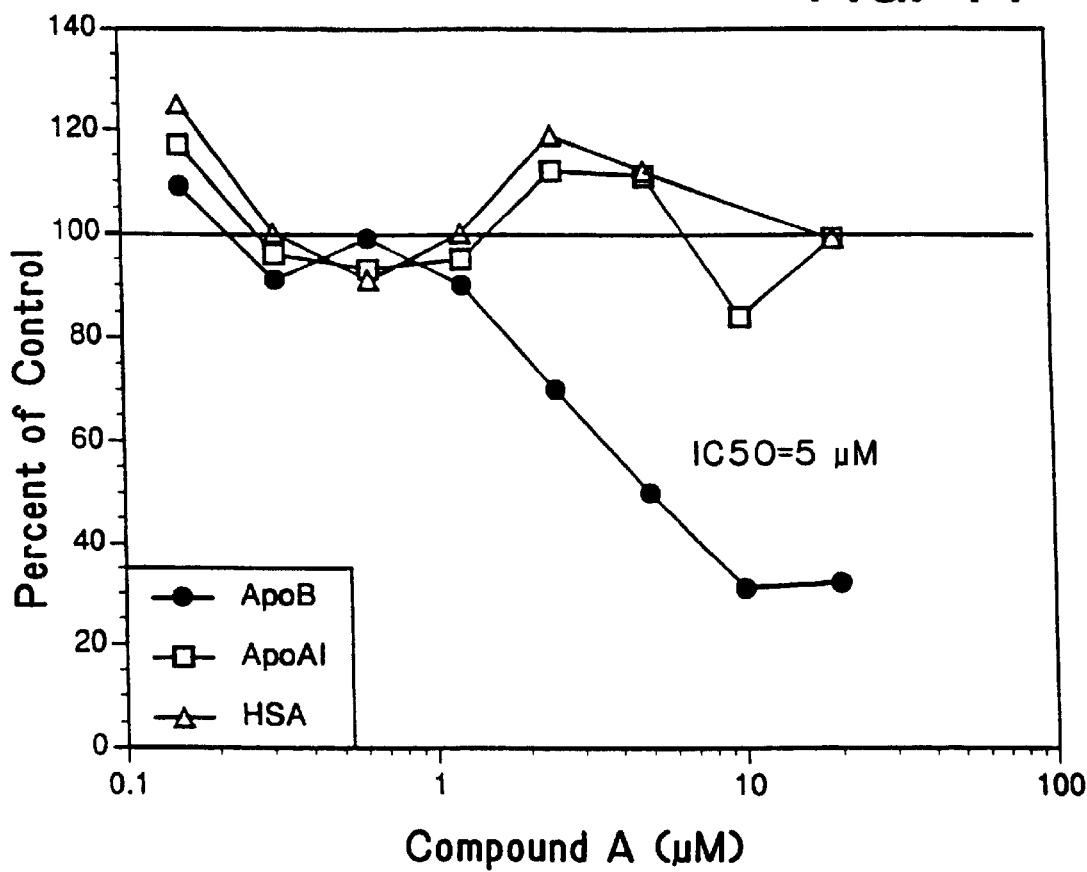
FIG. 11 shows the dose response of Compound A on ApoB, ApoAI and HSA secretion from HepG2 cells. HepG2 cells were treated with compound A at the indicated doses for 16 hours. The concentration in the cell culture media of apoB, apoAI and HSA after the incubation period was measured with the appropriate ELISA assay and normalized to total cell protein. The data shown are expressed as a percentage of the control (DMSO only).

Compound A was administered to HepG2 cells in a twofold dilution series ranging from 0.156 to 20 µM. After a 16-hour incubation under standard cell culture conditions, aliquots of the conditioned media were assayed by ELISA for apob, apoAl and HSA. ApoB secretion was inhibited in a dose-responsive manner with an IC$_{50}$ of 5 µM (FIG. 11). The secretion of apoAl and HSA was unaffected up to the maximum dose of 20 µM confirming that the inhibition was specific for apoB. These data indicate that addition of an MTP inhibitor to a human liver cell line inhibits the secretion of lipoproteins which contain apoB.

Figure 12:
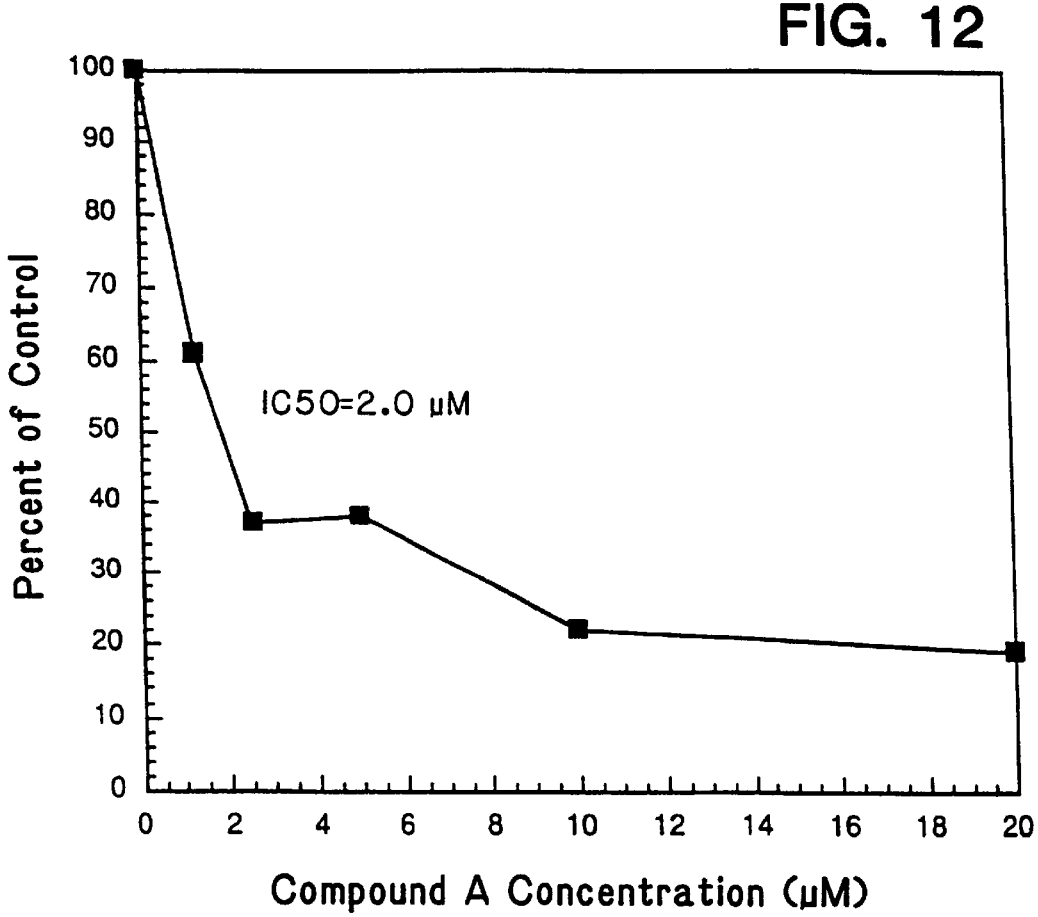
FIG. 12 shows the effect of compound A on TG secretion from HepG2 cells. HepG2 cells were treated with Compound A at the indicated doses for 18 hours, the last two hours of which were in the presence of 5 μCi/mL 3H-glycerol. The concentration of radiolabelled triglycerides in the cell culture media was measured by quantitative extraction, followed by thin layer chromatography analysis and normalization to total cell protein. The data shown are expressed as a percentage of the control (DMSO only).

HepG2 cells were treated with doses of compound A ranging from 1.25 µM–20 µM under conditions identical to those utilized for the apoB, apoAl and HSA secretion experiment. The intracellular pool of TG was radiolabelled for two hours with 3H-glycerol in the presence of vehicle or varying doses of compound A. The accumulation of radiolabelled TG in the medium was measured by quantitative extraction, followed by thin layer chromatography analysis and normalization to total cell protein. DMSO alone was used as a control. TG secretion was inhibited by compound A in a dose-dependent manner. The IC$_{50}$ was observed to be about 2.0 µM, which is similar to the IC$_{50}$ for inhibition of apoB secretion (FIG. 12). The data confirm that compound A inhibits the secretion of TG-rich lipoproteins that contain apoB.

Figure 13:
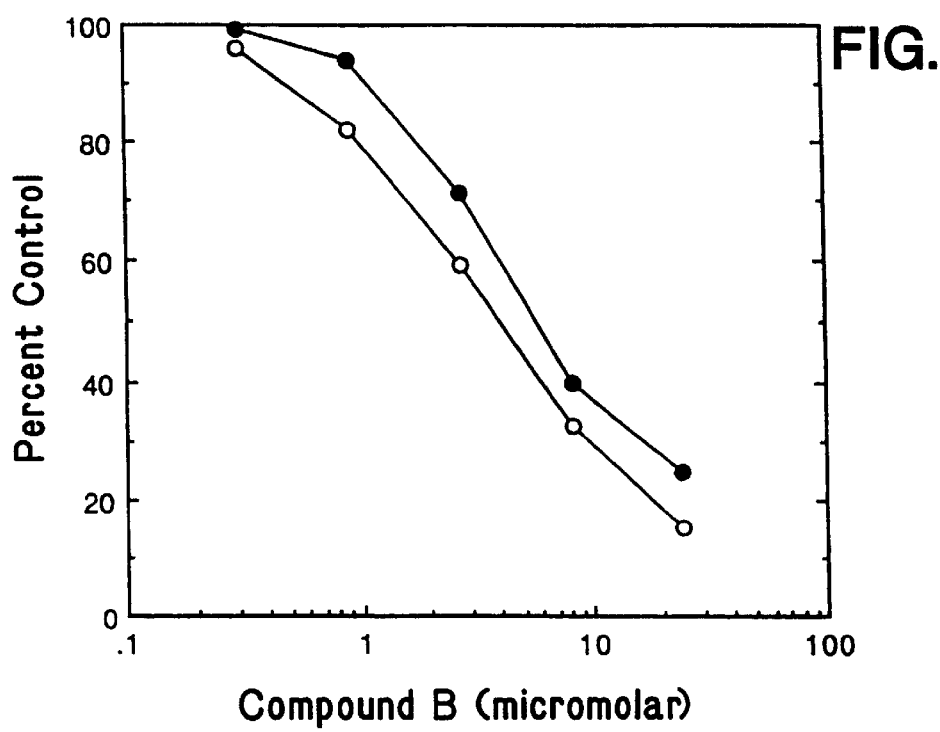
FIG. 13 shows inhibition in MTP-catalyzed transport of TG from donor SUV to acceptor SUV by compound B described hereinafter. Compound B was dissolved in DMSO and then diluted into 15/40 buffer. Aliquots were added to a lipid transfer assay to bring the compound to the indicated final concentrations. DMSO concentration in the assay never exceeded 2 µL/600 µL, a concentration that was independently determined to have minimal effect on the assay. MTP-catalyzed lipid transport was measured for 30 minutes at 37° C. TG transfer was calculated and compared to a control assay without inhibitor. Two independent assay conditions were used to demonstrate MTP inhibition by compound B. Assay conditions were: 24 nmol donor PC, 144 nmol acceptor PC, and 100 ng MTP (open circles); 72 nmol donor PC, 432 nmol acceptor PC, and 125 ng MTP (solid circles).
Figure 14:
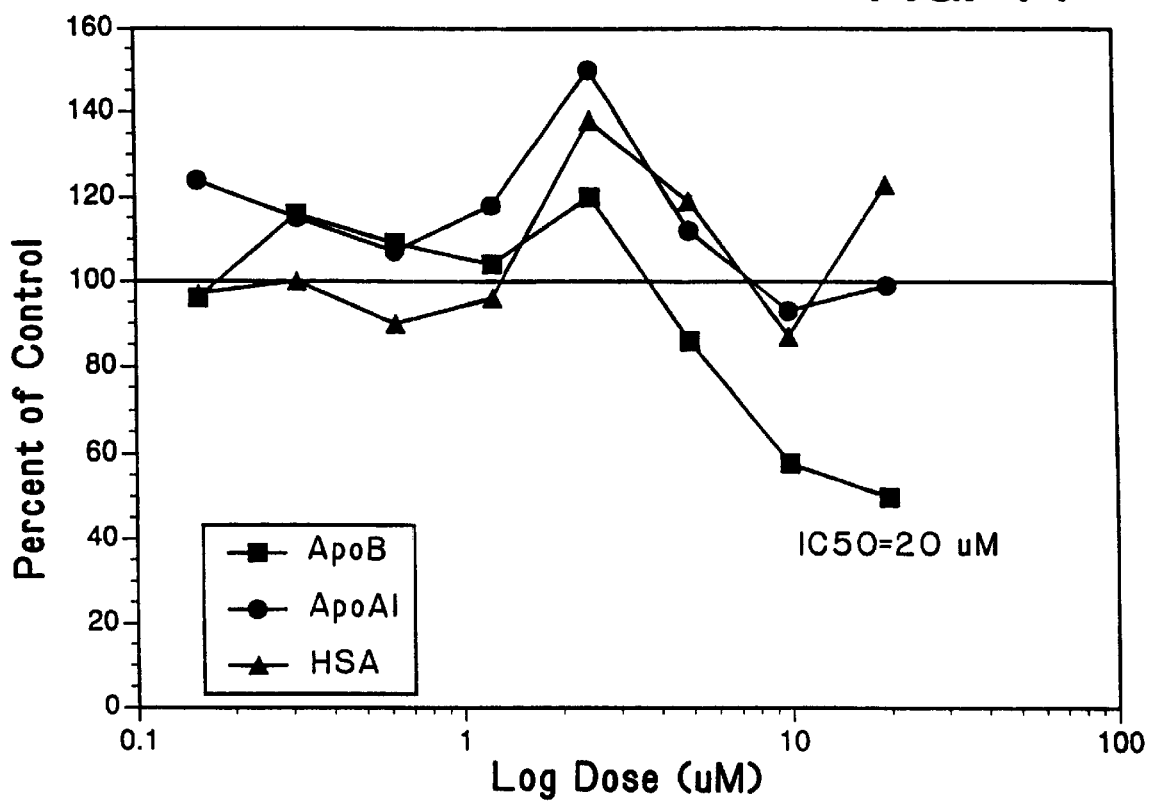
FIG. 14 shows the dose response of compound B on ApoB, ApoAI and HSA secretion from HepG2 cells. HepG2 cells were treated with compound B at the indicated doses for 16 hours. The concentration in the cell culture media of apoB, apoAI and HSA after the incubation period was measured with the appropriate ELISA assay and normalized to total cell protein. The data shown are expressed as a percentage of the control (DMSO only).

The foregoing procedures were repeated with compound B. Compound B inhibits MTP-catalyzed $^3$H-TG transport from donor SUV to acceptor SUV. The IC$_{50}$ is about 4 to 6 µM (FIG. 13). The secretion of lipoproteins that contain apoB is also inhibited in HepG2 cells by compound B (FIG. 14).

EXAMPLE 7

Inhibition of MTP-catalyzed CE and PC Transport

I. Methods

To measure the effect of compound A on bovine MTP-catalyzed transport of CE or PC between membranes, the lipid transfer assay which measures TG transfer between SUV was modified. The composition of the donor vesicles was the same, except 0.25 mol% $^{14}$C-CE or $^{14}$C-PC replaced the labeled TG. The composition of the acceptor vesicles were the same, except labeled PC and unlabeled TG were not included. Following precipitation of donor vesicles, the percentage of lipid transfer was calculated by comparing the $^{14}$C-CE or -PC in the acceptor vesicles in the supernatant following a transfer reaction to the total $^{14}$C-CE or -PC in the assay. The labeled lipid in the supernatant in the absence of MTP was subtracted from the labeled lipid in the presence MTP to calculate the MTP-catalyzed lipid transfer from donor SUV to acceptor SUV. The remainder of the assay was essentially as described previously.

II. Results

The ability of compound A to inhibit the MTP-catalyzed transport of radiolabeled CE and PC between membranes was also investigated. Compound A inhibited CE transfer in a manner comparable to its inhibition of TG transfer. Compound A inhibited PC transfer, but it was less effective at inhibiting PC transfer than CE and TG transfer. Approximately 40% of the PC transfer was inhibited at concentrations of inhibitor which decreased TG and CE transfer more than 80%.

EXAMPLE 8

Cloning of Bovine MTP-5' End

A bovine small intestinal cDNA library, packaged in lambda gt10, was obtained from Clontech (#BL1010A). The library was diluted in SM to contain 50,000 phage/100 µL (a 1:100,000 dilution). The diluted phage (100 µL) were mixed with 300 µL E. Coli C600 cells (Clontech) and incubated for 15 minutes at 37° C. After adding 7 mL of top agarose, the mixture was poured onto a 150 mm plate containing 75 mL of LB agarose. A total of 25 plates, each containing approximately 5×10$^4$ phage, were prepared in this manner. The plates were incubated overnight at 37° C.

To isolate phage DNA, 10 mL SM (no gelatin) was added to each plate. The plates were then rocked gently at room temperature for 2 hours. The eluted phage (approximately 8 mL/plate) were collected and pooled. E. Coli cells were sedimented by centrifugation for 10 minutes at 12,000×g.

Lambda DNA was isolated from the supernatant using the QIAGEN tip-100 (midi) preparation according to the protocol supplied by the manufacturer. The purified DNA was resuspended in a total of 200 µL TE (10 mM Tris.Cl pH 8.0, 1 mM EDTA).

1 µg lambda phage DNA (approximately 3×10$^7$ molecules) was added to a 100 µL PCR reaction containing 2 mM magnesium chloride, 0.2 mM each deoxynucleotide triphosphate, 1.25×buffer, and 2.5 units Taq polymerase (Perkin-Elmer Cetus, kit #N801-0555). The concentration of each primer was 0.15 mM. The sequence of the forward primer (SEQ. ID. NO. 29) was as follows:

```
         41                              66
         GGTCAATATGATTCTTCTTGCTGTGC.
```

The forward primers sequence was based on the human cDNA sequence encoding bases 41 to 66 of the 88 kDa component of MTP. The reverse primer (SEQ. ID. NO. 30) had the following sequence:

```
    658                         636  (bovine)
    807                         785  (human)
         CCCTCCATACTATTTTCCCTCCT
```

The reverse primer's sequence was based on the known bovine cDNA sequence encoding the 88 kDa component of MTP and hybridizes from base 658 to 636 of the bovine cDNA, which correspond to bases 807–785 of the human cDNA.

PCR-amplification was conducted in a Perkin-Elmer thermal cycler, model 9600. After a two-minute incubation at 97° C., the reaction was cycled at 94° C. for 30 seconds, 50° C. for 30 seconds, and 72° C. for one minute for 35 cycles. A final incubation at 72° C. for 7 minutes was performed.

The PCR product was electrophoresed on a 1% agarose gel in TAE buffer as described previously. The yield of the desired 766 base pair fragment was approximately 2 µg. The DNA was excised from the gel, purified using GeneClean (Bio101 La Jolla, Calif.), blunt-ended, cloned into pUC 18-Sma1 (Pharmacia), and sequenced as described previously.

The new sequence obtained from the bovine cDNA encoding the 5' region of the 88 kDa component of MTP is shown in SEQ. ID. NO. 5. The sequence adds 83 bases to the 5' end of the bovine cDNA reported previously.

EXAMPLE 9

Sequencing of Human Genomic DNA For the 88 kDa Component of MTP

Sequencing of human genomic DNA was carried out by the procedures described in "Demonstration of a gene defect in a second abetalipoproteinemic subject" and in Example 1. The result of this procedure is the human genomic sequence SEQ. ID. NO. 8.

MTP INHIBITORS

EXAMPLE 10

N-[1-(3,3-Diphenylpropyl)-4-piperidinyl]benzamide monohydrochloride

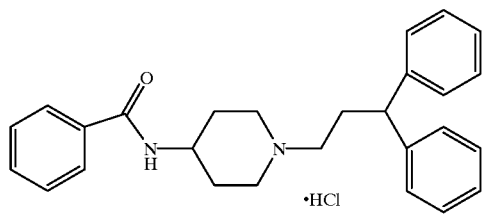

A. [1-(Phenylmethyl)-4-piperidinyl]carbamic acid, 1,1-dimethylethyl ester

To a solution of 4-amino-1-benzylpiperidine (20.0 g, 105 mmol) in dichloromethane (150 mL) was added dropwise a solution of di-tert-butyldicarbonate (25.2 g, 116 mmol) in dichloromethane (50 mL) at 0° C. After addition, the reaction was warmed to room temperature. The reaction was maintained at this temperature for 2 hours. The reaction was evaporated to dryness. The resulting residue was recrystallized from ethyl ether to give compound A (23.5 g, 76%) as a white solid (melting point 119–121° C.).

B. 4-Piperidinylcarbamic acid, 1,1-dimethylethyl ester

A suspension of 64.94 g (0.224 mol) of compound A and 25.6 mL (0.447 mol) of acetic acid in 500 mL of absolute ethanol was warmed to dissolve all solids. After cooling, 6.5 g (1 wt %) of 10% palladium on charcoal was added and the mixture was shaken on a Parr apparatus under initial hydrogen pressure of 40 psi for 23 hours. The catalyst was removed by filtration and the solution was concentrated to a clear oil which was dissolved in 1.5 L of chloroform. The organics were washed with a 3 N KOH solution saturated with NaCl (2×75 mL). The aqueous layer was back extracted with chloroform (5×200 mL). The combined organics were dried (sodium sulfate) and concentrated to provide 65 g of a white solid which was redissolved in 1.5 L of chloroform and washed with brine (2×200) mL to remove residual acetate. The combined aqueous layers were back extracted and the combined organics were dried (sodium sulfate) and concentrated to provide 40.15 g (90%) of compound B as a white solid (melting point 156–159° C.).

C. γ-Phenylbenzenepropanol, 4-methylbenzenesulfonate ester

To a solution of tosyl chloride (4.94 g, 25.9 mmol) in dichloromethane (10 mL) was added 3,3-diphenyl-1-propanol (5.00 g, 23.6 mmol) and pyridine (2.86 mL, 35.4 mmol) at room temperature. The reaction was stirred overnight at room temperature. Ethyl ether (200 mL) was added to dilute the reaction, and the organic layer was washed with 1 N HCl (50 mL×2), saturated sodium carbonate (50 mL×2), brine (50 mL×2) and dried over $MgSO_4$. Purification was performed by flash chromatography, loaded and eluted with 25% ethyl acetate in hexane. Pure fractions were combined and evaporated to give compound C (5.2 g, 60%) as a colorless oil.

D. [1-(3,3-Diphenylpropyl)-4-piperidinyl]carbamic acid, 1,1-dimethylethyl ester To a solution of compound C (1.83 g, 5.00 mmol) and compound B (1.00 g, 5.00 mmol) in isopropanol (25 mL) was added potassium carbonate (1.1 g, 8.00 mmol). The reaction was refluxed overnight. The reaction was cooled to room temperature and filtered, and the filtrate was evaporated to dryness. Purification was performed by flash chromatography, loaded and eluted with 2.5% methanol in dichloromethane. Pure fractions were combined and evaporated to give compound D (1.5 g, 76%) as a colorless oil.

E. 1-(3,3-Diphenylpropyl)-4-piperidinamine, hydrochloride

To a stirred solution of 9.21 g (23.34 mmol) of compound D in 60 mL of dioxane was added 58 mL (0.223 mol) of a 4.0 M HCl in dioxane solution. The mixture was stirred for 15 hours then concentrated to provide 8.45 g (100%) of compound E as a white solid containing 10 wt % of dioxane by $^1H$ NMR, melting point 123–126° C. A dioxane-free sample of the hydrochloride salt has a melting point of 192–194° C.

F. N-[1-(3,3-Diphenylpropyl)-4-piperidinyl]benzamide

To solution of compound E (100 mg, 0.30 mmol) and triethylamine (152 mg, 0.33 mmol) in dichloromethane (2 mL) was added a solution of benzoyl chloride (46.8 mg, 0.33 mmol) in dichloromethane (0.5 mL) at 0° C. After addition, the reaction was stirred at 0° C. for 10 minutes. The reaction was diluted with dichloromethane (50 mL), the organic layer was washed with saturated sodium bicarbonate solution (10 mL), water (10 mL) and dried over sodium sulfate. The solution was evaporated to dryness. The resulting residue was recrystallized from isopropanol to give compound F (100 mg, 84%) as a white solid (melting point 151–155° C.).

G. N-[1-(3,3-Diphenylpropyl)-4-piperidinyl]benzamide, monohydrochloride

Compound F (100 mg, 0.25 mmol) was dissolved in ethanol (2 mL) and 1 N HCl in diethyl ether (0.5 mL) was added. The mixture was evaporated to give Example 10 (100 mg, 100%) as a white solid, melting point 246–249° C.

Analysis for $C_{27}H_{31}ClN_2O \cdot 0.2H_2O$:

Calc'd C, 73.94; H, 7.22; N, 6.39; Cl, 8.08

Found: C, 73.90; H, 7.18; N, 6.40; Cl, 8.11

EXAMPLE 11

2-[1-(3,3-Diphenyl-2-propenyl)-4-piperidinyl]-2,3-dihydro-1H-isoindol-1-one, monohydrochloride

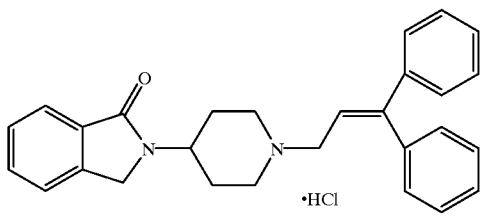

A. 2-(4-piperidinyl)-2,3-dihydro-1H-isoindol-1-one

To a solution of compound B from Example 13 (8.5 g, 26.4 mmol) in ethanol (65 mL) was added acetic acid (3.5 mL, 52.8 mmol), followed by 10% palladium on activated carbon (0.7 g) under argon. The slurry was purged with nitrogen and agitated under a pressure of 45 psi of hydrogen gas for 48 hours. The reaction mixture was filtered through Celite® and washed with ethanol. The filtrate was evaporated to dryness. The resulting residue was dissolved in chloroform (100 mL) and washed with 1 N KOH saturated with sodium chloride (2×30 mL) and dried over $MgSO_4$. The resulting clear solution was evaporated to dryness and azeotroped with toluene (2×30 mL) to give compound A (5.0 g, 77%) as a white solid, melting point 137–140° C.

B. 3,3-Diphenyl-2-propen-1-ol

To a solution of β-phenylcinnamaldehyde (5.0 g, 24.0 mmol) in toluene (100 mL) was added 1 M diisobutylaluminum hydride (26.4 mL, 26.4 mmol) at 0° C. The reaction was stirred at 0° C. for 15 minutes, and methanol (5 mL) was added slowly to quench the reaction. 1 M potassium sodium tartrate solution (150 mL) was added and the mixture was stirred at room temperature overnight. The reaction was diluted with ethyl ether (100 mL), and the organic layer was washed with brine (30 mL) and dried over $Na_2SO_4$. Evaporation gave compound B (3.95 g, 80%) as a pale yellow oil.

C. 1-Chloro-3,3-diphenyl-2-propene

To a solution of N-chlorosuccinimide (1.52 g, 11.4 mmol) in dichloromethane (40 mL) was added dimethyl sulfide (1.1 mL, 14.5 mmol) at −40° C. under argon. The reaction was stirred at −40° C. for 10 minutes then warmed to room temperature for 30 minutes. The white cloudy solution was recooled to −40° C., and a solution of compound B (2.17 g, 10.3 mmol) in dichloromethane (3 mL) was added dropwise. The reaction was stirred at −40° C. for 2 hours and then diluted with hexane (100 mL). The organic layer was washed with water (50 mL), brine (50 mL×2) and dried over $Na_2SO_4$. Evaporation gave compound C (1.9 g, 81%) as a colorless oil.

D. 2-[1-(3,3-Diphenyl-2-propenyl)-4-piperidinyl]-2,3-dihydro-1H-isoindol-1-one To a solution of compound A (1.63 g, 7.56 mmol) and compound C (1.90 g, 8.32 mmol) in dimethylformamide (35 mL), potassium carbonate (1.10 g, 7.94 mmol) was added at room temperature. The reaction was stirred at 50° C. overnight. The reaction was evaporated to dryness. The resulting residue was dissolved in dichloromethane (150 mL) and washed with water (50 mL×2), brine (50 mL×2) and dried over $MgSO_4$. Evaporation gave a crude solid. Purification was performed by flash chromatography, loaded and eluted with 3% methanol in dichloromethane. Pure fractions were combined and evaporated to give compound D (1.95 g, 63%) as a white solid, melting point 164–167° C.

Analysis for $C_{28}H_{28}N_2O \cdot 0.3\ H_2O$:

Calc'd: C, 81.24; H, 6.96; N, 6.77;

Found: C, 81.29; H, 6.88; N, 6.79.

E. 2-[1-(3,3-Diphenyl-2-propenyl)-4-piperidinyl]-2,3-dihydro-1H-isoindol-1-one, monohydrochloride To a solution of compound D (200 mg, 0.49 mmol) in methanol (2 mL) was added 1 N HCl in ethyl ether (0.5 mL) at room temperature. The resulting salt was filtered and washed with cold methanol (2×0.5 mL). After drying under high vacuum, Example 11 was obtained (160 mg, 80%) as a white solid, melting point 231–235° C.

Analysis for $C_{28}H_{29}ClN_2O \cdot 0.9\ H_2O$:

Calc'd: C, 72.92; H, 6.73; Cl, 7.69; N, 6.07;

Found: C, 72.99; H, 6.91; Cl, 7.36; N, 6.06.

EXAMPLE 12

2-[1-(3,3-Diphenylpropyl)-4-piperidinyl]-2,3-dihydro-1H-isoindol-1-one, monohydrochloride

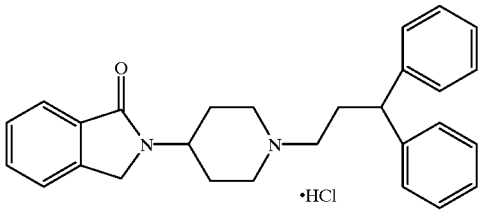

A. 2-[1-(3,3-Diphenylpropyl)-4-piperidinyl]-2,3-dihydro-1-1H-isoindol-1-one

To a solution of compound A from Example 11 (2.0 g, 9.26 mmol) and compound C from Example 10 (3.40 g, 9.26 mmol) in isopropanol (25 mL) was added potassium carbonate (2.05 g, 14.8 mmol). The reaction was refluxed overnight. The reaction was cooled to room temperature and filtered, and the filtrate was evaporated to dryness. Purification was performed by flash chromatography, loaded and eluted with 2.5% methanol in dichloromethane. Pure fractions were combined and evaporated to give compound A (2.82 g, 74%) as a colorless oil.

B. 2-[1-(3,3-Diphenylpropyl)-4-piperidinyl]-2,3-dihydro-1H-isoindol-1-one, monohydrochloride Compound A (1.0 g, 2.44 mmol) was dissolved in methanol (7.0 mL). 1 N HCl in ethyl ether (4.88 mL, 4.88 mmol) and stirred at room temperature overnight. The reaction was evaporated to dryness. The resulting residue was recrystallized from ethanol to give Example 12 (700 mg, 68%) as a white solid, melting point 237–241° C.

Analysis for $C_{28}H_{31}ClN_2O \cdot 0.6\ H_2O$:

Calc'd: C, 73.46; H, 7.09; N, 6.12;

Found: C, 73.32; H, 7.20; N, 5.96.

EXAMPLE 13

2,3-Dihydro-2-[1-(phenylmethyl)-4-piperidinyl]-1H-isoindol-1-one, monohydrochloride

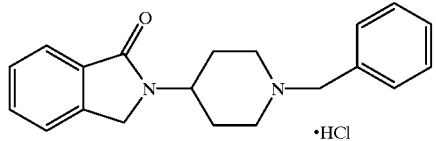

·HCl

A. 2-[1-(Phenylmethyl)-4-piperidinyl]-1H-isoindol-1,3(2H)-dione

A mixture of phthalic anhydride (15.0 g, 101 mmol) and 4-amino-1-benzylpiperidine (19.3 g, 101 mmol) was heated with stirring in an oil bath until the mixture melted (about 125° C.). The reaction was kept at this temperature until the mixture solidified again (about 30 minutes). The reaction was cooled to room temperature. Purification was performed by flash chromatography on 1 kg silica gel, loaded and eluted with 30% ethyl acetate in hexane. Pure fractions were combined and evaporated to give compound A (25 g, 77%) as a white solid, melting point 151–154° C.

B. 2,3-Dihydro-2-[1-(phenylmethyl)-4-piperidinyl]-1H-isoindol-1-one

To a solution of compound A (20.0 g, 62.5 mmol) in acetic acid (248 mL) was added zinc dust (28.6 g, 438 mmol) under argon. With mechanical stirring, the reaction was refluxed overnight. The reaction was filtered through Celite, then evaporated to dryness. Dichloromethane (500 mL) was added, and the organic layer was washed with saturated sodium bicarbonate (2×100 mL), brine (100 mL) and dried over $MgSO_4$. Evaporation gave a crude oil. The resulting residue was azeotroped with toluene (2×30 mL) to afford a white solid. The product was recrystallized from isopropanol to give compound B (16 g, 80%) as a white solid (melting point 130–133° C.).

C. 2,3-Dihydro-2-[1-(phenylmethyl)-4-piperidinyl]-1H-isoindol-1-one, monohydrochloride Compound B (200 mg, 0.62 mmol) was dissolved in ethanol (3 mL) and 4 N HCl in dioxane (1 mL) was added. After 2 minutes at room temperature, a white solid precipitated. The solid was filtered and pumped under high vaccum to give Example 13 (120 mg, 60%) as a white solid, melting point 271–274° C.

Analysis for $C_{20}H_{23}N_2OCl·0.8 H_2O$:

Calc'd. C, 67.22; H, 6.94; N, 7.84;

Found: C, 66.99; H, 7.05; N, 8.07.

EXAMPLE 14

2,3-Dihydro-2-[1-(3-phenylpropyl)-4-piperidinyl]-1H-isoindol-1-one, monohydrochloride

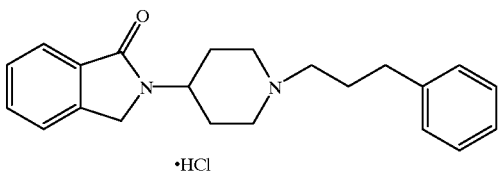

·HCl

A. 2,3-Dihydro-2-[1-(3-phenylpropyl)-4-piperidinyl]-1H-isoindol-1-one

To a solution of compound A from Example 11 (300 mg, 1.39 mmol) in dimethylformamide (8 mL) was added 1-bromo-3-phenylpropane (276 mg, 1.39 mmol, Aldrich) and potassium carbonate (201 mg, 1.46 mmol) at room temperature. The reaction was stirred at room temperature for 30 minutes, then the reaction was heated to 50° C. for 4 hours. The reaction was cooled to room temperature. Dichloromethane (100 mL) was added to dilute the reaction, and the organic layer was washed with water (50 mL×2), brine (50 mL×2) and dried over magnesium sulfate. Evaporation under reduced pressure gave a crude oil. Purification was performed by flash chromatography on silica gel (50 g), loaded and eluted with 0.5% methanol in dichloromethane (1.5 L) then 1.2% methanol in dichloromethane (1.0 L). Pure fractions were combined and evaporated to give compound A (400 mg, 84%) as a colorless oil.

B. 2,3-Dihydro-2-[1-(3-phenylpropyl)-4-piperidinyl]-1H-isoindol-1-one, monohydrochloride Compound A (400 mg, 1.20 mmol) was dissolved in 20% methanol in ethyl ether (2 mL). A solution of 1 M HCl in ethyl ether (4 mL, 4.0 mmol) was added. The HCl salt precipitated and was filtered and washed with ethyl ether. The resulting solid was dried under high vacuum at 60° C. overnight to give Example 14 (320 mg, 80%) as a white solid, melting point 229–231° C.

Analysis for $C_{22}H_{27}ClN_2O$:

Calc'd: C, 71.24; H, 7.34; N, 7.55; Cl, 9.56;

Found: C, 70.96; H, 7.42; N, 7.60; Cl, 9.63.

EXAMPLE 15

2-[1-(5,5-Diphenylpentyl)-4-piperidinyl]-2,3-dihydro-1H-isoindol-1-one, monohydrochloride

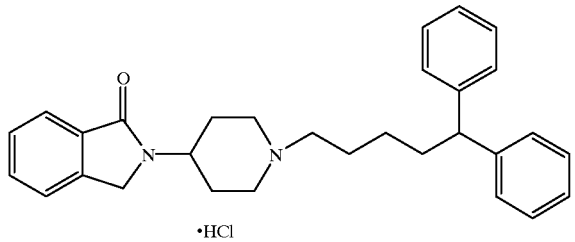

A. β-Phenylbenzenepropanal

To a solution of oxalyl chloride (2.0 M in dichloromethane, 1.53 mL, 30.7 mmol) in dichloromethane (100 mL) was added dropwise a solution of dimethyl sulfoxide (4.35 mL, 61.4 mmol) in dichloromethane (9 mL) at −70° C. After addition, the reaction was stirred at −70° C. for 30 minutes, then a solution of 3,3-diphenyl-1-propanol (5.0 g, 23.6 mmol) in dichloromethane (10 mL) was added dropwise. The reaction was stirred at −70° C. for 1 hour. Triethylamine (27 mL, 141 mmol) was added and the reaction mixture was warmed to room temperature. Ethyl ether (300 mL) was added to dilute the reaction, the organic layer was washed with water (2×100 mL), 1 N HCl (2×100 mL), saturated sodium bicarbonate solution (2×100 mL), brine (2×100 mL) and dried over MgSO$_4$. Evaporation gave compound A (5.0 g, 100%) as a yellowish oil.

B. (E)-5,5-Diphenyl-2-pentenoic acid, ethyl ester

To a suspension of sodium hydride (1.14 g, 28.6 mmol) in tetrahydrofuran (50 mL) was added dropwise a solution of triethyl phosphonoacetate (6.13 mL, 30.9 mmol) in tetrahydrofuran (5 mL) at 0° C. The reaction was stirred at room temperature for 20 minutes (the solution is clear) then recooled to −78° C. A solution of compound A (5.0 g, 23.8 mmol) in tetrahydrofuran (5 mL) was added dropwise. The reaction was warmed to room temperature and quenched with saturated ammonium chloride solution (5 mL). Ethyl ether (200 mL) was added to dilute the reaction, and the organic layer was washed with water (2×50 mL), brine (2×50 mL) and dried over MgSO$_4$. Evaporation gave a crude oil. Purification was performed by flash chromatography on 250 g silica gel, loaded and eluted with 6% ethyl acetate in hexane. Pure fractions were combined and evaporated to give compound B (5.0 g, 75%) as a colorless oil.

C. (E)-5,5-Diphenyl-2-penten-1-ol

To a solution of compound B (4.97 g, 17.8 mmol) in toluene (30 mL) at 0° C. was added dropwise diisobutyl aluminum hydride (1.0 M in toluene) (39.1 mL, 39.1 mmol). The reaction was stirred at 0° C. for 1 hour. The reaction was quenched with methanol (5 mL). Potassium sodium tartrate solution (1 M, 200 mL) was added, and the reaction mixture was stirred for 3.5 hours. Ethyl ether (200 mL) was added, and the organic layer was washed with water (2×50 mL), brine (2×50 mL) and dried over MgSO$_4$. Evaporation gave a crude oil. Purification was performed by flash chromatography on 300 g silica gel, loaded and eluted with 20% ethyl acetate in hexane. Pure fractions were combined and evaporated to give compound C as a colorless oil (3.6 g, 85%).

D. (E)-1-Chloro-5,5-diphenyl-2-pentene

To a solution of N-chlorosuccinimide (2.22 g, 16.6 mmol) in dichloromethane (50 mL) at −40° C. was added dropwise methyl sulfide (1.55 mL, 21.1 mmol). The reaction was stirred at −40° C. for 10 minutes then warmed to room temperature for 30 minutes. The reaction was recooled to −40° C., and a solution of compound C (3.6 g, 15.1 mmol) in dichloromethane (5 mL) was added dropwise. The reaction was stirred at −40° C. for 2 hours then warmed to room temperature for 30 minutes. Hexane (300 mL) was added to dilute the reaction and the organic layer was washed with water (2×50 mL), brine (2×50 mL) and dried over MgSO$_4$. Evaporation gave compound D (3.4 g, 87%) as a colorless oil.

E. (E)-2-[1-(5,5-Diphenyl-2-pentenyl)-4-piperidinyl]-2,3-dihydro-1H-isoindol-1-one To a solution of compound A from Example 11 (800 mg, 3.70 mmol) in dimethylformamide (20 mL) was added compound D (952 mg, 3.70 mmol) followed by anhydrous potassium carbonate (536 mg, 3.89 mmol). The reaction was stirred at 50° C. for 3 hours. The reaction was cooled to room temperature. Ethyl acetate (100 mL) was added to dilute the reaction, and the organic layer was washed with water (2×50 mL), brine (2×50 mL) and dried over Na$_2$SO$_4$. Evaporation gave a crude oil. Purification was performed by flash chromatography on 100 g of silica gel, loaded and eluted with 2% methanol in dichloromethane. Pure fractions were combined and evaporated to give compound E (1.0 g, 62%) as a white solid (melting point 136–141° C.).

F. 2-[1-(5,5-Diphenylpentyl)-4-piperidinyl]-2,3-dihydro-1H-isoindol-1-one

To a solution of compound E (500 mg, 1.36 mmol) in ethanol (10 mL) was added 10% palladium on activated carbon (50 mg) under argon at room temperature. A hydrogen balloon was connected to the solution. Hydrogenation was maintained overnight. The reaction was filtered through Celite, and the filtrate was evaporated to dryness. Purification was performed by flash chromatography on 100 g silica gel, loaded and eluted with 2.5% methanol in dichloromethane. Pure fractions were combined and evaporated to give compound F (400 mg, 80%) as a white solid, melting point 121–124° C.

G. 2-[1-(5,5-Diphenylpentyl)-4-piperidinyl]-2,3-dihydro-1H-isoindol-1-one, monohydrochloride Compound F (400 mg, 0.91 mmol) was dissolved in 20% methanol in ethyl ether (2 mL). A solution of 1 M HCl in ethyl ether (4 mL, 4.0 mmol) was added. The HCl salt precipitated and was filtered and washed with ethyl ether. The resulting solid was dried under high vacuum at 60° C. overnight to give Example 15 (320 mg, 80%) as a white solid (melting point 208–211° C.).

Analysis for $C_{30}H_{35}ClN_2O$:

Calc'd: C, 75.85; H, 7.43; N, 7.90; Cl, 7.46;

Found: C, 75.54; H, 7.54; N, 7.82; Cl, 7.56.

EXAMPLE 16

N-[1-(3,3-Diphenylpropyl)-4-piperidinyl] cyclohexane-carboxamide, monohydrochloride

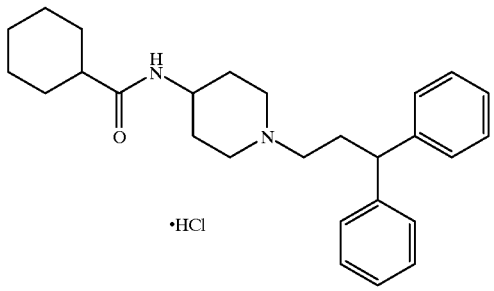

A. N-[1-(3,3-Diphenylpropyl)-4-piperidinyl] cyclohexanecarboxamide

To a stirred solution of 405 mg (1.22 mmol) of compound E from Example 10 and 7 mg (5 mol %) of 4-dimethylaminopyridine in 8 mL of methylene chloride at 0° C. under argon was added 171 μL (1.28 mmol) of cyclohexylcarbonyl chloride. After warming to room temperature, the mixture was stirred for one hour and diluted with methylene chloride and water. The organics were separated, and the aqueous layer was basified with 1 M KOH and extracted with methylene chloride. The combined organics were dried (sodium sulfate) and concentrated to provide a yellow solid which was dried under high vacuum. The crude product was purified by flash chromatograghy on silica gel (80 g) eluted with 9:1 methylene chloride/methanol. Pure fractions were combined and concentrated to yield 438 mg (88%) of compound A as a clear, glassy solid.

B. N-[1-(3,3-Diphenylpropyl)-4-piperidinyl] cyclohexane-carboxamide, monohydrochloride To a solution of 430 mg (1.06 mmol) of compound A in 4 mL of methylene chloride was added 2.12 mL (2.12 mmol) of a 1.0 M solution of hydrogen chloride in diethyl ether. The opaque white solution was concentrated and dried under vacuum to provide 375 mg (76%) of Example 16 as a white solid, melting point greater than 250° C.

Analysis for $C_{27}H_{37}N_2OCl$:

Calcd.: C, 73.53; H, 8.46; N, 6.35;Cl, 8.04;

Found: C, 73.38; H, 8.52; N, 6.16; Cl, 7.97.

EXAMPLE 17

2-[1-(3-Butylheptyl)-4-piperidinyl]-2,3-dihydro-1H-isoindol-1-one, monohydrochloride

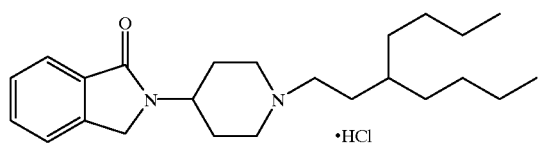

A. 3-Butyl-2-heptenoic acid, ethyl ester

To a suspension of sodium hydride (60% in mineral oil) (1.01 g, 25.3 mmol) in tetrahydrofuran (40 mL) was added dropwise a solution of triethyl phosphonoacetate (5.44 mL, 27.4 mmol) in tetrahydrofuran (5 mL) at 0° C. The reaction was warmed to room temperature and stirring was continued until the solution was clear. The reaction was recooled to −78° C., a solution of 5-nonanone (3.0 g, 21.1 mmol) in tetrahydrofuran (5 mL) was added dropwise. The reaction was stirred at −78° C. for 1 hour. The reaction was warmed to room temperature and quenched with saturated ammonium chloride (5 mL). Ethyl ether (200 mL) was added to dilute the reaction, and the organic layer was washed with water (2×50 mL), brine (2×50 mL) and dried over magnesium sulfate. Purification was performed by flash chromatography on 400 g silica gel, loaded and eluted with 15% ethyl acetate in hexane. Pure fractions were combined and evaporated to give compound A (1.63 g, 37%) as a colorless oil.

B. 3-Butyl-2-hepten-1-ol

To a solution of compound A (1.63 g, 7.69 mmol) in toluene (20 mL) at 0° C. was added a solution of diisobutylaluminum hydride (1 M solution in toluene, 16.9 mL, 16.9 mmol). The reaction was stirred at room temperature for 10 minutes and quenched with methanol (5 mL). Potassium sodium tartrate solution (1 M, 100 mL) was added, the mixture was stirred overnight. Ethyl ether (100 mL) was added, and the organic layer was washed with water (2×50 mL), brine (2×50 mL) and dried over magnesium sulfate. Evaporation gave compound B (1.30 g, 99%) as a colorless oil.

C. 3-Butyl-2-hepten-1-yl chloride

To a suspension of N-chlorosuccinimide (1.12 g, 8.42 mmol) in dichloromethane (20 mL) at −40° C. was added dropwise a solution of methyl sulfide (0.79 mL, 10.7 mmol) in dichloromethane (1 mL). After addition, the reaction was warmed to room temperature for 30 minutes. The reaction was recooled to −40° C., and a solution of 3 (1.3 g, 7.65 mmol) in dichloromethane (2 mL) was added. The reaction was stirred at −40° C. for 2 hours and warmed to room temperature. Hexane (150 mL) was added to dilute the reaction, and the organic layer was washed with water (2×50 mL), brine (2×50 mL) and dried over magnesium sulfate. Evaporation gave compound C (860 mg, 60%) as a cololess oil.

D. 2-[1-(3-Butyl-2-heptenyl)-4-piperidinyl]-2,3-dihydro-1H-isoindol-1-one

To a solution of compound A from Example 11 (974 mg, 4.51 mmol) in dimethylformamide (14 mL) was added a solution of compound C (850 mg, 4.51 mmol) in dimethylformamide (2 mL) followed by anhydrous potassium carbonate (653 mg, 4.74 mmol). The reaction was stirred at 50° C. for 3 hours. The reaction was cooled to room temperature. Ethyl acetate (100 mL) was added to dilute the reaction, and the organic layer was washed with water (2×50 mL), brine (2×50 mL) and dried over magnesium sulfate. Evaporation gave a crude oil. Purification was performed by flash chromatography on 100 g of silica gel, loaded and eluted with 2% methanol in dichloromethane. Pure fractions were combined and evaporated to give compound D (1.13 g, 68%) as a cololess oil.

E. 2-[1-(3-Butylheptyl)-4-piperidinyl]-2,3dihydro-1H-isoindol-1-one

To a solution of compound D (500 mg, 1.36 mmol) in ethanol (10 mL) was added 10% palladium on activated carbon (50 mg) under argon at room temperature. Argon on the reaction was replaced by hydrogen. A hydrogen balloon was connected to the solution. Hydrogenation was maintained overnight. The reaction was filtered through Celite, and the filtrate was evaporated to dryness. Purification was performed by flash chromatography on 100 g silica gel, loaded and eluted with 2.5% methanol in dichloromethane. Pure fractions were combined and evaporated to give compound F (480 mg, 95%) as a waxy solid.

F. 2-[1-(3-Butylheptyl)-4-piperidinyl]-2,3-dihydro-1H-isoindol-1-one, monohydrochloride Compound E (480 mg, 1.30 mmol) was dissolved in 20% methanol in ethyl ether (2 mL). A solution of 1 M HCl in ethyl ether (4 mL, 4.0 mmol) was added. The HCl salt precipitated and was filtered and washed with ethyl ether. The resulting solid was dried under high vacuum at 60° C. overnight to give Example 17 (300 mg, 62%) as a white solid (melting point 185–187° C.).

Analysis for $C_{24}H_{39}ClN_2O+0.5\ H_2O$:

Calc'd: C, 69.29; H, 9.69; N, 6.73; Cl, 8.52;

Found: C, 69.17; H, 9.75; N, 6.88; Cl, 8.91.

EXAMPLE 18

N-[1-(3,3-Diphenylpropyl)-4-piperidinyl]benzene acetamide, monohydrochloride

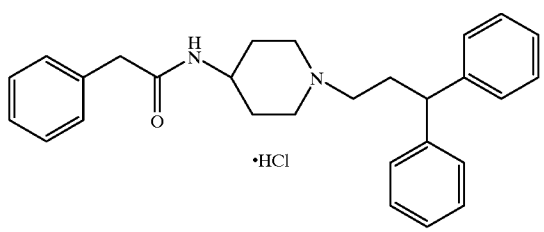

A. N-[1-(3,3-Diphenylpropyl)-4-piperidinyl] benzeneacetamide

To a stirred solution of 420 mg (1.27 mmol) of compound E from Example 10 in 8 mL of methylene chloride at 0° C. under argon was added 308 μL (3.81 mmol) of pyridine and 176 μL (1.33 mmol) of phenylacetyl chloride. After warming to room temperature, the mixture was stirred for one hour and diluted with methylene chloride and water. The organics were separated, and the aqueous layer was basified with 1 M KOH and extracted with methylene chloride. The combined organics were dried (sodium sulfate) and concentrated to provide a yellow oil which was dried under high vacuum. The crude product was purified by flash chromatography on silica gel (80 g) eluted with 98:2 methylene chloride/methanol. Pure product fractions were combined and concentrated to provide 366 mg of a yellow solid, which was further purified by recrystallization from methanol to afford 214 mg (41%) of compound A as white needles, melting point 141–143° C. (decomp.).

B. N-[1-(3,3-Diphenylpropyl)piperidinyl]benzene acetamide, monohydrochloride

To a solution of 214 mg (0.52 mmol) of compound A in 4 mL of methylene chloride was added 0.77 mL (0.77 mmol) of a 1.0 M solution of hydrogen chloride in diethyl ether. The opaque white solution was concentrated to a white solid which was purified by recrystallization from methanol and dried under vacuum to provide 194 mg (83%) of Example 18 as a white solid, melting point 109–115° C. (decomp.).

Analysis for $C_{28}H_{33}N_2OCl+0.94\ H_2O$:

Calc'd: C, 72.19; H, 7.54; N, 6.01; Cl, 7.61;

Found: C, 72.03; H, 7.58; N, 6.17; Cl, 7.60.

EXAMPLE 19

N-[1-(3,3-Diphenylpropyl)-4-piperidinyl]pentamide, monohydrochloride

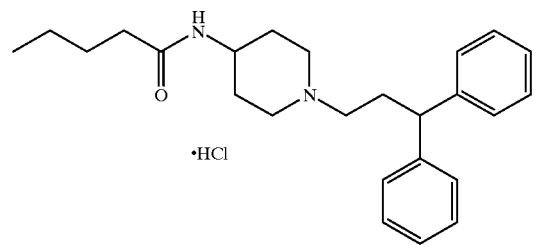

A. N-[1-(3,3-Diphenylpropyl)-4-piperidinyl] pentamide

To a stirred solution of 385 mg (1.16 mmol) of compound E from Example 10 and 7 mg (5 mol %) of 4-dimethylaminopyridine in 8 mL of methylene chloride at 0° C. under argon was added 147 μL (1.22 mmol) of cyclohexylcarbonyl chloride. After warming to room temperature, the mixture was stirred for one hour and diluted with methylene chloride and water. The organic layers were separated, and the aqueous layer was basified with 1 M KOH and extracted with methylene chloride. The combined organic layers were dried (sodium sulfate) and concentrated to provide a yellow solid which was dried under high vacuum. The crude product was purified by flash chromatography on silica gel (75 g) eluted with 95:5 methylene chloride/methanol. Pure fractions were combined and concentrated to yield 334 mg (76%) of compound A as a clear, glassy solid, meting point 126–128° C.

B. N-[1-(3,3-Diphenylpropyl)-4-piperidinyl] pentamide, monohydrochloride

To a solution of 319 mg (0.84 mmol) of compound A in 4 mL of methylene chloride was added 1.68 mL (1.68 mmol) of a 1.0 M solution of hydrogen chloride in diethyl ether and the heterogeneous mixture was stirred for thirty minutes. The resulting precipitate was filtered, washed with ether, and dried under vacuum to provide 327 mg (72%) of Example 19 as a yellow solid, melting point 189–191° C.

Analysis for $C_{25}H_{35}N_2OCl+0.3\ H_2O$:

Calc'd: C, 71.41; H, 8.54; N, 6.66; Cl, 8.43;

Found: C, 71.56; H, 8.46; N, 6.51; Cl, 8.66.

EXAMPLE 20

(E)-2,3-Dihydro-2-[1-[3-(2-phenoxyphenyl)-2-propenyl]-4-piperidinyl]-1H-isoindol-1-one, monohydrochloride

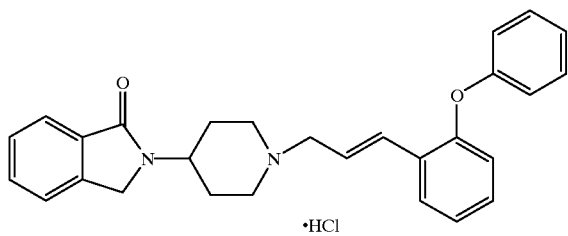

A. 2-Phenoxybenzenemethanol

To a solution of 2-phenoxybenzoic acid (5.0 g, 23.3 mmol) in tetrahydrofuran (50 mL) was added dropwise at 0° C. lithium aluminum hydride solution (1 M in tetrahydrofuran, 23.3 mL, 23.3 mmol). The reaction was warmed to room temperature and stirring was continued for 8 hours. The reaction was quenched with methanol (5 mL), and 1 M potassium sodium tartrate solution (100 mL) was added. The mixture was stirred at room temperature overnight. Ethyl ether (200 mL) was added, and the organic layer was washed with water (2×50 mL), brine (2×50 mL) and dried over magnesium sulfate. Evaporation gave compound A (4.65 g, 99%) as a colorless oil.

B. 2-Phenoxybenzaldehyde

To a solution of oxalyl chloride (2.0 M in dichloromethane, 15.1 mL, 30.3 mmol) in dichloromethane (100 mL) at −70° C. was added dropwise a solution of dimethyl sulfoxide (4.25 mL, 60.6 mmol) in dichloromethane (5 mL). After addition, the reaction was stirred at −70° C. for 30 minutes, then a solution of compound A (4.65 g, 23.3 mmol) in dichloromethane (10 mL) was added dropwise. The reaction was stirred at −70° C. for 1 hour. Triethylamine (27 mL) was added and the reaction mixture was warmed to room temperature. Ethyl ether (300 mL) was added to dilute the reaction, and the organic layer was washed with water (2×100 mL), 1 N HCl (2×100 mL), saturated sodium bicarbonate solution (2×100 mL) and brine (2×100 mL) and dried over MgSO$_4$. Evaporation gave compound B as a yellowish oil (4.63 g, 100%).

C. (E)-3-(2-Phenoxyphenyl)-2-propenoic acid, ethyl ester

To suspension of sodium hydride (1.12 g, 28.1 mmol) in tetrahydrofuran (50 mL) was added dropwise a solution of triethyl phosphonoacetate (6.04 mL, 30.4 mmol) in tetrahydrofuran (5 mL) at 0° C. Then the reaction was stirred at room temperature for 20 minutes (the solution was clear). The reaction was recooled to −78° C., and a solution of compound A (4.63 g, 23.4 mmol) in tetrahydrofuran (5 mL) was added dropwise. The reaction was warmed to room temperature and quenched with saturated ammonium chloride solution (5 mL). Ethyl ether (200 mL) was added to dilute the reaction, and the organic layer was washed with water (2×50 mL), brine (2×50 mL) and dried over MgSO$_4$. Evaporation gave a crude oil. Purification was performed by flash chromatography on 500 g silica gel, loaded and eluted with 10% ethyl acetate in hexane. Pure fractions were combined and evaporated to give compound C (6.0 g, 96%) as a colorless oil.

D. (E)-3-(2-Phenoxyphenyl)-2-propenol

To a solution of compound C (2.5 g, 9.33 mmol) in toluene at 0° C. was added dropwise a diisobutyl aluminum hydride (1.0 M in toluene) (20.5 mL, 20.5 mmol) solution. The reaction was stirred at 0° C. for 1 hour. The reaction was quenched with methanol (5 mL). 1 M potassium sodium tartrate solution (100 mL) was added, and the reaction mixture was stirred for 3.5 hours. Ethyl ether (200 mL) was added, and the organic layer was washed with water (2×50 mL), brine (2×50 mL) and dried over MgSO$_4$. Evaporation gave a crude oil. Purification was performed by flash chromatography on 300 g silica gel, loaded and eluted with 20% ethyl acetate in hexane. Pure fractions were combined and evaporated to give compound D (1.85 g, 88%) as a colorless oil.

E. (E)-1-(3-Chloro-1-propenyl)-2-phenoxybenzene

To a solution of N-chlorosuccinimide (1.11 g, 8.33 mmol) in dichloromethane (20 mL) was added dropwise methyl sulfide (0.78 mL, 10.6 mmol) at −40° C. The reaction was stirred at −40° C. for 10 minutes then warmed to room temperature for 30 minutes. The reaction was recooled to −40° C., and a solution of compound D (1.71 g, 7.57 mmol) in dichloromethane was added dropwise. The reaction was stirred at −40° C. for 3 hours, then warmed to room temperature for 30 minutes. Hexane (100 mL) was added to dilute the reaction, and the organic layer was washed with water (2×50 mL), brine (2×50 mL) and dried over MgSO$_4$. Evaporation gave compound E (1.72 g, 93%) as a colorless oil.

F. (E)-2,3-Dihydro-2-[1-[3-(2-phenoxyphenyl)-2-propenyl]-4-piperidinyl]-1H-isoindol-1-one To a solution of compound A from Example 11 (0.88 g, 4.09 mmol) in dimethylformamide (10 mL) was added a solution of compound E (1.0 g, 4.09 mmol) in dimethylformamide (2 mL) followed by potassium carbonate (592 mg, 4.29 mmol). The reaction was stirred at 50° C. for 14 hours. The reaction was cooled to room temperature. Ethyl ether (100 mL) was added to dilute the reaction, and the organic layer was washed with water (2×50 mL), brine (2×50 mL) and dried over MgSO$_4$. Evaporation gave a crude oil. Purification was performed by flash chromatography on 150 g silica gel, loaded and eluted with 2% methanol in dichloromethane. Pure fractions were combined and evaporated to give compound F (1.1 g, 63%) as a colorless oil.

G. (E)-2,3-Dihydro-2-[1-[3-(2-phenoxyphenyl)-2-propenyl]-4-piperidinyl]-1H-isoindol-1-one, monohydrochloride To a solution of compound F (500 mg, 1.15 mmol) in ethyl ether:methanol (2 mL, 5:1) was added 1 M HCl in ethyl ether (1.5 mL, 1.5 mmol). The HCl salt precipitated from the solution. The salt was filtered and dried at 60° C. under vacuum to give Example 20 (300 mg, 55%) as a white solid, melting point 215–218° C.

Analysis for $C_{28}H_{29}ClN_2O_2$:

Calc'd: C, 72.95; H, 6.34; N, 6.08; Cl, 7.69;

Found: C, 72.49; H, 6.39; N, 6.04; Cl, 7.37.

EXAMPLE 21

2,3-Dihydro-2-[1-[3-(2-methoxyphenyl)propyl]-4-piperidinyl]-1H-isoindol-1-one, monohydrochloride

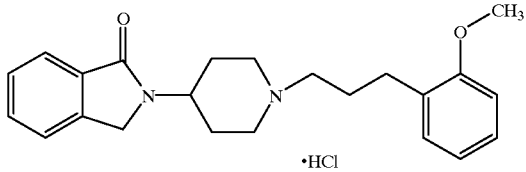

A. 2-Methoxybenzenepropanol

To a solution of 3-(2-methoxyphenyl)propionic acid (2.0 g, 11.1 mmol) in tetrahydrofuran (25 mL) was added dropwise at 0° C. lithium aluminum hydride solution (1 M in tetrahydrofuran, 11.1 mL, 11.1 mmol). The reaction was warmed to room temperature and stirring was continued overnight. The reaction was quenched with methanol (5 mL), and 1 M potassium sodium tartrate solution (100 mL) was added. The mixture was stirred at room temperature overnight. Ethyl ether (200 mL) was added, and the organic layer was washed with water (2×50 mL), brine (2×50 mL) and dried over magnesium sulfate. Evaporation gave compound A (1.5 g, 81%) as a colorless oil.

B. 1-(3-Bromopropyl)-2-methoxybenzene

To a solution of compound A (620 mg, 3.73 mmol) and triphenylphosphine (1.08 g, 4.11 mmol) in dichloromethane (10 mL) was added N-bromosuccinimide (731 mg, 4.11 mmol) at 0° C. The reaction was stirred at 0° C. for 2 hours. Dichloromethane (100 mL) was added to dilute the reaction, and the organic layer was washed with water (2×50 mL), brine (2×50 mL) and dried over MgSO$_4$. Purification was performed by flash chromatography on 100 g silica gel, loaded and eluted with 10% dichloromethane in hexane. Pure fractions were combined and evaporation to give compound B (582 mg, 68%) as a colorless oil.

C. 2,3-Dihydro-2-[1-[3-(methoxyphenyl)propyl]-4-piperidinyl]-1H-isoindol-1-one To a solution of compound A from Example 11 (549 mg, 2.54 mmol) in dimethylformamide (10 mL) was added a solution of compound B (582 mg, 2.54 mmol) in dimethylformamide (1 mL) followed by potassium carbonate (386 mg, 2.80 mmol). The reaction was stirred at 50° C. for 14 hours. The reaction was cooled to room temperature. Ethyl ether (100 mL) was added to dilute the reaction, and the organic layer was washed with water (2×50 mL), brine (2×50 mL) and dried over MgSO$_4$. Evaporation gave a crude oil. Purification was performed by flash chromatography on 150 g silica gel, loaded and eluted with 2% methanol in dichloromethane. Pure fractions were combined and evaporated to give compound C (560 mg, 61%) as a colorless oil.

D. 2,3-Dihydro-2-[1-[3-(2-methoxyphenyl)propyl]-4-piperidinyl]-1H-isoindol-1-one, monohydrochloride To a solution of compound C (500 mg, 1.37 mmol) in methanol (2 mL) was added 1 M HCl in ethyl ether (1.5 mL, 1.5 mmol). The mixture was evaporated and dried at 70° C. under vacuum to give Example 21 (300 mg, 60%) as a yellowish solid, melting point 191–195° C.

Analysis for $C_{23}H_{29}ClN_2O_2+0.3$ mol $H_2O$:
Calc'd: C, 67.98; H, 7.34; N, 6.89; Cl, 8.72;
Found: C, 67.92; H, 7.63; N, 6.75; Cl, 8.54

EXAMPLE 22

6-Fluoro-3,4-dihydro-3-[[4-(2-methoxyphenyl)-1-piperazinyl]-methyl]-1(2H)-naphthalenone

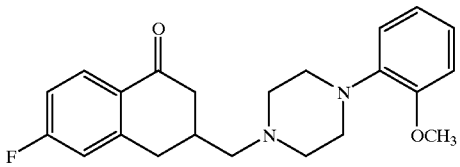

A. α-Acetyl-3-fluorobenzenepropanoic acid, ethyl ester

To a solution of 500 mL of 10% dimethylformamide in benzene was added 58.6% NaH (41 g, 1.0 mol) cooled in an ice bath was added ethyl acetoacetate (130 g, 1.0 mol) was added. The reaction was stirred at room temperature for 30 minutes, and m-fluorobenzyl chloride (145 g, 1.0 mol) was added. The reaction was heated to reflux for 3 hours and gave an NaCl precipitate which was then removed by filtration. The filtrated was poured into $H_2O$, acidified with concentrated HCl and was extracted with a mixture of ether and benzene. The organic layer was washed with $H_2O$, brine, dried over $Na_2SO_4$ and concentrated in vacuo. The crude product was purified by distillation (112–119° C./25 mmHg) to give 1 (133 g, 56%).

Analysis for $C_{13}H_{13}FO_3$:
Calc'd: C, 65.53; H, 6.35;
Found: C, 65.56; H 6.12.

B. 2-Acetyl-2-[(3-fluorophenyl)methyl]butanedioic acid, diethyl ester

This reaction procedure was followed as described above for the preparation of compound A. The reaction scale is as follows: Compound A (130 g, 0.546 mol), ethyl chloroacetate (67 g, 0.546 mol), 58.6% NaH (22.36 g, 0.546 mol) and 400 mL of 20% dimethylformamide in benzene. The reflux time in this reaction was 21 hours and the crude product was purified by distillation at 135–158° C./0.2 mmHg to give 2 (119 g, 67%).

C. 2-[(3-Fluorophenyl)methyl]butanedioic acid, diethyl ester

To a solution of compound B (119.3 g, 0.368 mol) in 550 mL $H_2O$ was added NaOH (45 g, 1.10 mol) and the reaction was reflux for 23 hours. The reaction was cooled to room temperature, and the reaction mixture was washed with ether. The aqueous layer was placed in the ice bath, acidified with concentrated HCl and gave a precipitate. The crude product was removed by filtration and recrystallized in hot benzene to give compound C (57.8 g, 69%), melting point 120.5–121.5° C.

Analysis for $C_{11}H_{11}FO_4$:
Calc'd: C, 58.41; H, 4.90;
Found: C, 58.91; H, 5.10.

D. 3-[(3-Fluorophenyl)methyl]-3,4-dihydro-2,5-furandione

To a solution of compound C (43.0 g, 0.19 mol) in 100 mL acetic anhydride was added 8 mL acetic acid. The reaction was heated to reflux for 20 minutes and concentrated in vacuo with dry benzene. The crude product was dissolved in 10 mL benzene, 70 mL skelly B was added and upon cooling in an ice bath, a crystalline solid formed. The crystals were collected by filtration and recrystallized in isopropanovskelly B to give compound D (24.0 g, 61%), melting point 55–57° C.

Analysis for $C_{11}H_9FO_3$:
Calc'd: C, 63.46; H, 4.36;
Found: C, 63.92; H, 5.25.

E. 7-Fluoro-1,2,3,4-tetrahydro-4-oxo-2-naphthalenecarboxylic acid

To 500 mL of nitrobenzene was slowly added $AlCl_3$ (30.66 g, 0.23 mol) and compound D (23.85 g, 0.115 mol) keeping the temperature between 20–25° C. The reaction was stirred at room temperature for 67 hours and was poured into a mixture of 360 g ice and 170 mL concentrated HCl. The nitrobenzene was then removed by distillation. The crude product was crystallized in the ice bath and was recrystallized from benzene/skelly B to give compound E (20.0 g, 84%), melting point 146–147° C.

Analysis for $C_{11}H_9FO_3$:
Calc'd: C, 63.46; H, 4.36
Found: C, 63.54; H, 4.48.

F. 7-Fluoro-1,2,3,4-tetrahydro-4-oxo-2-naphthalenecarboxylic acid, methyl ester To a solution of compound E (5.0 g, 0.024 mol) in 25 mL methanol was added 1 mL concentrated $H_2SO_4$. The reaction mixture heated to reflux for 40 hours. The reaction mixture was concentrated in vacuo and was partitioned between ethyl acetate and 5% $NaHCO_3$. The organic layer was washed further with $H_2O$, brine, dried over $Na_2SO_4$ and was concentrated in vacuo. The crude product was crystallized in a mixture of ethyl acetate and skelly B and was recrystallized in hot skelly B to give compound F (4.9 g, 92%), melting point 90–92° C.

Analysis for $C_{12}H_{11}FO_3$:
Calc'd: C, 64.86; H, 4.99;
Found: C, 65.21; H, 5.21.

G. 6-Fluoro-3',4'-dihydrospiro[1,3-dioxolane-2,1'(2'H)-naphthalene]-3'-carboxylic acid, methyl ester To a solution of compound F (103.4 g, 0.465 mol) in 700 mL of dry benzene was added ethylene glycol (78.5 mL, 1.395 mol), followed by a catalytic amount of p-toluenesulfonic acid. The reaction was heated to reflux for 66 hours. The reaction mixture was concentrated in vacuo, and the crude product was crystallized in methanol to give compound G (82 g, 66%), melting point 79–81° C.

Analysis for $C_{14}H_{15}FO_4$:
Calc'd: C, 63.15; H, 5.67;
Found: C, 63.13; H, 5.82.

H. 6-Fluoro-3',4'-dihydrospiro[1,3-dioxolane-2,1'(2'H)-naphthalene]-3'-methanol To a suspension of lithium aluminum hydride (11.25 g, 0.296 mol) in 700 mL of dry tetrahydrofuran was added a solution of compound G (78.8 g, 0.296 mol) in 300 mL tetrahydrofuran. The reaction was heated to reflux for 17 hours and 22.5 mL $H_2O$ and 18 mL 10% NaOH was added with cooling. The reaction was stirred at room temperature for 2 hours. The reaction mixture was filtered and the filtrate was concentrated in vacuo to give compound H (69.4 g, 78%).

Analysis for $C_{13}H_{15}FO_3$
Calc'd: C, 65.53; H, 6.35
Found: C, 65.82; H, 6.72.

I. 6-Fluoro-3',4'-dihydrospiro[1,3-dioxolane-2,1'(2'H)-naphthalene]-3'-methanol, methanesulfonate ester To a solution of compound H (61.1 g, 0.256 mol) in 175 mL dry pyridine under nitrogen was added methanesulfonyl chloride (27.15 mL, 0.358 mol) maintaining the temperature between 10 and 15° C. The reaction was stirred between 5–10° C. for 30 minutes and room temperature for 2.5 hours. The reaction mixture was poured into ice-water and extracted with $CH_2Cl_2$. The organic layer was further washed with $H_2O$, brine, dried over $Na_2SO_4$ and was concentrated in vacuo. The crude product was further evaporated with toluene at 35° C. under water pressure to give compound I (83.7 g, quant.).

J. 6-Fluoro-3,4-dihydro-3-[[4-(2-methoxyphenyl)-1-piperazinyl]-methyl]-1(2H)-naphthalenone To a solution of compound I (10.0 g, 0.0316 mmol) in 150 mL of 25% methyl isobutyl ketone in absolute ethanol was added $Na_2CO_3$ (2.7 g, 0.0316 mol) and 1-(2-methoxyphenyl)piperazine followed by a catalytic amount of KI. The reaction was heated to reflux for 25 hours and the mixture was filtered. The filtrate was concentrated in vacuo and dissolved in $CH_2Cl_2$. The organic layer was washed with $H_2O$, $NaHCO_3$, brine, dried over $Na_2SO_4$ and was concentrated in vacuo. 15% HCl (100 mL) was added to the crude and stirred at room temperature for 4 hours. The solution was filtered and was extracted with ethyl ether. The aqueous solution was then basified and extracted with ethyl ether. The final ethyl ether layer was washed with $H_2O$, brine, dried over $Na_2SO_4$ and was concentrated in vacuo. The crude product was recrystallized from methanol twice to give Example 22 (6.57 g, 56%), melting point 111–113° C.

Analysis for $C_{22}H_{25}N_2O_2F$:
Calc'd: C, 71.72; H, 6.84; N, 7.60;
Found: C, 70.1 1; H, 7.06, N, 7.83.

EXAMPLE 23

3,4-Dihydro-3-[(4-phenyl-1-piperazinyl)methyl]-1-(2H)-naphthalenone, monohydrochloride

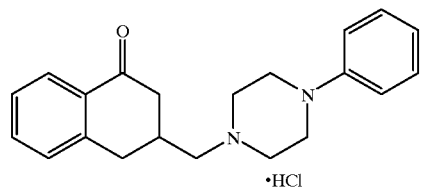

A. 2-Acetyl-2-(phenylmethyl)butanedioic acid, diethyl ester

This reaction procedure followed the procedure described in the preparation of compound B of Example 22. The reaction scale is as follows: Benzyl acetoacetate (180 g, 0.86 mol), ethyl chloroacetate (105 g, 0.86 mol), 58.6% NaH (35.2 g, 0.86 mol) and 300 mL of 10% dimethylformamide in dry benzene. The reflux time in this reaction was 3 hours and the crude product was purified by distillation at 148–159° C./0.3 mmHg to give compound A (164.7 g, 63%).

B. 2-(Phenylmethyl)butanedioic acid

This reaction procedure followed the procedure described in the preparation of compound C of Example 22. The reaction scale is as follows: compound A (164.7 g, 0.54 mol) and 1.5 L of 2 N NaOH. The reaction was reflux for 20 hours and gave compound B (95.8 g, 85%), melting point 152–156° C.

C. 3,4-Dihydro-3-(phenylmethyl)-2,5-furandione

This reaction procedure was followed as described in the preparation of compound D of Example 22. 95.8 g of compound B gave 72 g (82%) of compound C, boiling point 156° C. (0.4 mm), and the resulting solid was recrystallized from hot benzene, melting point 94–96° C.

D. 1,2,3,4-Tetrahydro-4-oxo-2-naphthalenecarboxylic acid

This reaction procedure was followed as described in the preparation of compound E of Example 22. The reaction scale is as follows: compound C (55.7 g, 0.29 mol), $AlCl_3$ (80 g, 0.6 mol) and 280 mL nitrobenzene. The nitrobenzene was removed by distillation and the aqueous was crystallized to give compound D (50.8 g, 91%), melting point 145–148° C.

E. 1,2,3,4-Tetrahydro-4-oxo-2-naphthalenecarboxylic acid, methyl ester

To a solution of N-nitro-N-methyl urea in 500 mL ether was added 135 mL of 40% KOH, followed by compound D (50.8 g, 0.27 mol), while cooling in an ice bath. The reaction was stirred at room temperature for 1 hour and acetic acid was added to react with excess diazomethane. The ethyl ether layer was washed with 200 mL of 5% NaOH, 200 mL of dilute acetic acid, 200 mL of dilute $NaHCO_3$, brine, dried over $Na_2SO_4$ and was concentrated in vacuo. The crude product was isolated by distillation at 124° C./0.15 mmHg to give compound E (50.3 g, 91%).

F. 3',4'-Dihydrospiro[1,3-dioxolane-2,1'(2'H)-naphthalene]-3'-carboxylic acid, methyl ester This reaction procedure was followed as described in the preparation of compound G of Example 22. The reaction scale is as follows: compound E (5.0 g, 0.025 mol), ethylene glycol (4.8 Ml, 0.075 mol), 40 mL dry benzene and a catatalytic amount p-toluenesulfonic acid. The reaction was reflux for 64 hours and was concentrated in vacuo to give compound F (6.0 g, 95%).

G. 3',4'-Dihydrospiro[1,3-dioxolane-2,1'(2'H)-naphthalene]-3'-methanol

This reaction procedure was followed as described in the preparation of compound H of Example 22. The reaction scale is as follows: compound F (7.3 g, 0.028 mol), lithium aluminum hydride (1.06 g, 0.028 mol) and 50 mL dry tetrahydrofuran. The crude product was isolated by distillation at 152–153° C./0.15 mmHg to give compound G (4.0 g, 62%).

Analysis for $C_{13}H_{16}O_3$:

Calc'd: C, 70.89; H, 7.32;

Found: C, 70.73; H 7.33.

H. 3',4'-Dihydrospiro[1,3-dioxolane-2,1'(2'H)-naphthalene]-3'-methanol, Methanesulfonate Ester This reaction procedure was followed as described in the preparation of compound I of Example 22. The reaction scale is as follows: compound G (3.16 g, 0.144 mol), methanesulfonyl chloride (1.6 mL, 0.202 mol) and 30 mL pyridine. The reaction was stirred at room temperature for 2 hours and the crude product was precipitated by pouring onto ice to give compound H (3.35 g, 78%), melting point 75–79° C.

I. 3,4-Dihydro-3-[(4-phenyl-1-piperazinyl)methyl]-1-(2H)-naphthalenone, monohydrochloride To a solution of compound H (1.43 g, 0.048 mmol) in 50 mL of a mixture of methyl isobutyl ketone and absolute ethanol was added $Na_2CO_3$ (0.71 g, 0.048 mol) and 1-phenylpiperazine (1.77 g, 0.011 mol). The reaction was heated to reflux for 20 hours and the particles was removed by filtration. The filtrate was concentrated in vacuo and dissolved in ethyl acetate. The organic layer was washed with $H_2O$, 5% $NaHCO_3$ and was concentrated in vacuo to dryness. 100 mL of 10% HCl was added to the crude and stirred at room temperature for 4 hours. The mixture was extracted with ethyl ether and the aqueous solution was then basified with concentrated $NH_4OH$ to pH 9 and extracted with ethyl ether. The ethyl ether layer was combined, washed with $H_2O$, brine, dried over $Na_2SO_4$ and concentrated in vacuo. The crude product was redissolved in 200 mL ethyl ether, saturated with HCl, and the solid precipitate was recrystallized from hot ethanol to give Example 23 (0.43 g, 23%), melting point 243–246° C.

Analysis for $C_{21}H_{24}N_2O \cdot HCl$:

Calc'd: C, 64.09; H, 6.67; N, 7.13; Cl, 9.95;

Found: C, 70.77; H, 7.10; N, 7.69; Cl, 10.69.

EXAMPLE 24

3,4-Dihydro-3-[[4-phenyl)-1-piperazinyl]carbonyl]-1 (2H)-naphthalenone, monohydrochloride

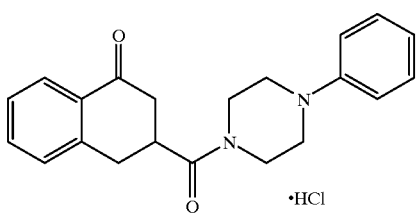

To a solution of compound D from Example 23 (1.4 g, 0.01 mol) and triethylamine (1.4 mL, 0.01 mol) in 35 mL $CH_2Cl_2$ was added ethyl chloroformate (0.98 mL, 0.01 mol). The reaction was stirred at 70° C. for 5 minutes and 1-phenylpiperzine (1.62 g, 0.01 mol) in 15 mL $CH_2Cl_2$ was added. The reaction was stirred at room temperature for 18 hours. The reaction mixture was washed with 5% $NaHCO_3$, $H_2O$, brine, dried over $Na_2SO_4$ and concentrated in vacuo to dryness. The crude product was dissolved in 200 mL ethyl ether, bubbled with HCl, filtered and was recrystallized from hot ethanol acidified with concentrated HCl to give Example 24 (2.73 g, 74%), melting point 188–191° C.

EXAMPLE 25

3,4-Dihydro-3-[[4-(2-methoxyphenyl)-1-piperazinyl]-carbonyl]-1(2H)-naphthalenone, monohydrochloride

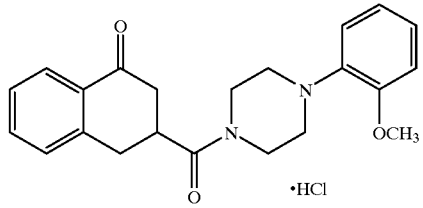

A. 1,2,3,4-Tetrahydro-4-oxo-2-naphthalenecarboxylic acid

To a solution of KOH (6.7 g, 0.12 mol) in 60 mL $H_2O$ was added compound E from Example 23 (10.0 g, 0.049 mol). The reaction was warmed gently for 30 minutes and was then cooled to room temperature and was acidified with 1 N HCl. The crude product was filtered, washed with cold $H_2O$ and dried over $P_2O_5$ to give compound A (8.68 g, 93%), melting point 148–150° C.

B. 3,4-Dihydro-3-[[4-(2-methoxyphenyl)-1-piperazinyl]carbonyl]-1(2H)-naphthalenone, monohydrochloride To a solution of compound A (9.5 g, 0.05 mmol) and triethylamine (8.38 mL, 0.05 mol) in 125 mL $CH_2Cl_2$ was added isobutyl chloroformate (6.58 mL, 0.05 mol) at −10° C. The reaction was stirred at −5 to −10° C. for 10 minutes and was followed by 1-(2-methoxyphenyl)piperazine (9.61 g, 0.05 mol) in 25 mL $CH_2Cl_2$. The ice bath was removed and the reaction was stirred at room temperature for 17 hours. The reaction mixture was washed with 5% $NaHCO_3$, $H_2O$, brine, dried over $Na_2SO_4$ and concentrated in vacuo. The crude product was dissolved in ethyl ether, bubbled with HCl and was filtered to give Example 25 (15.45 g, 85%), melting point 197–199° C.

Analysis for $C_{22}H_{24}N_2O_3 \cdot HCl$:

Calc'd: C, 65.89; H, 6.28; N, 6.99; Cl, 8.85;

Found: C, 66.27; H, 6.41; N, 7.35; Cl, 9.58.

EXAMPLE 26

3,4-Dihydro-3-[[4-(2-methoxyphenyl)-1-piperazinyl]methyl]-1(2H)-naphthalenone, dihydrochloride

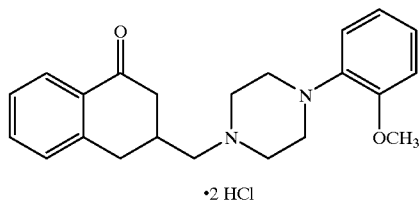

A. 1,2,3,4-Tetrahydro-3-[[4-(2-methoxyphenyl)-1-piperazinyl]methyl]-1-naphthalenol To a solution of the free base of compound B of Example 25 (11.74 g, 0.0322 mol) in 50 mL of dry tetrahydrofuran was added lithium aluminum hydride (2.45 g, 0.0644 mol) in 50 mL of dry tetrahydrofuran. The reaction was heated to reflux for 22 hours. The reaction was mixed with 5 mL $H_2O$, 4 mL of 10% NaOH and was stirred at room temperature for 2 hours. The solids were removed by filtration, washed with tetrahydrofuran and concentrated in vacuo to give compound A (10.1 g, 89%).

Analysis for $C_{22}H_{28}N_2O_2 \cdot 2$ HCl·$H_2O$:

Calc'd: C, 59.59; H, 7.27; N, 6.32; Cl, 15.99; KF, 4.06;

Found: C, 59.45; H, 7.10; N, 6.50; Cl, 16.49; KF, 4.36.

B. 3,4-Dihydro-3-[[4-(2-methoxyphenyl)-1-piperazinyl]methyl]-1(2H)-naphthalenone, dihydrochloride To a solution of compound A (4.91 g, 0.014 mmol) in 120 mL benzene was added potassium tert-butoxide (3.93 g, 0.035 mol) and benzophenone (11.8 g, 0.065 mol). The reaction was refluxed for 16 hours and washed with $H_2O$. The organic layer was washed further with brine, dried over $Na_2SO_4$ and concentrated in vacuo to dryness. The crude product was dissolved in ethyl ether, bubbled with HCl salt, recrystallized from methanol/ethyl ether to give Example 26 (5.2 g, 87%), melting point 218–219° C.

Analysis for $C_{22}H_{26}N_2O_2 \cdot 2$ HCl

Calc'd: C, 62.41; H, 6.67; N, 6.62; Cl, 16.75;

Found: C, 62.61; H, 6.87; N, 6.37.

EXAMPLE 27

3-[[4-[(4-Chlorophenyl)phenylmethyl]-1-piperazinyl]methyl]-6-fluoro-3,4-dihydro-1(2H)-naphthalenone, dihydrochloride

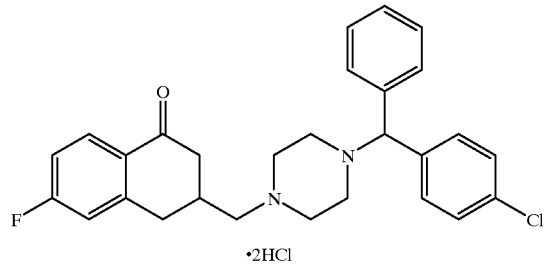

To a solution of compound I from Example 22 (10.10 g, 0.032 mmol) in 150 mL absolute ethanol was added $Na_2CO_3$ (3.40 g, 0.032 mol) and 1-[(4-chlorophenyl)phenylmethyl]piperazine (9.18 g, 0.032 mol), followed by a catalytic amound of KI. The reaction was heated to reflux for 19 hours and the particles were removed by filtration. The filtrate was concentrated in vacuo and dissolved in $CH_2Cl_2$. The organic layer was washed with $H_2O$, $NaHCO_3$, brine, dried over $Na_2SO_4$ and was concentrated in vacuo. 150 mL of 10% HCl was added to the crude and stirred at room temperature for 4 hours. The residue was filtered and dissolved in $CH_2Cl_2$, washed with $H_2O$ and brine, dried over $Na_2SO_4$, and concentrated in vacuo. The crude material was dissolved in 100 mL of absolute ethanol and 150 mL of 10% HCl was added. The reaction was stirred at room temperature for 18 hours. The reaction mixture was concentrated in vacuo to half volume and extracted with a mixture of $CH_2Cl_2$ and ethyl ether. The organic layer was concentrated in vacuo and dissolved in 100 mL ethanol which was then treated with concentrated $NH_4OH$ until basic. 400 mL of $H_2O$ was added and extracted with ethyl ether. The ethyl ether layer was then washed with $H_2O$, brine, dried over $Na_2SO_4$ and bubbled with HCl to give white solid. The HCl salt was collected by filtration and mixed with H₂O. The crude product was collected by filtration and was recrystallized from methanol to give Example 27 (1.55 g, 9%), melting point 211–212° C.

Analysis for C$_{28}$H$_{30}$N$_2$OCl$_3$F:

Calc'd: C, 62.75; H, 5.64; N, 5.33; Cl, 19.85;

Found: C, 62.62; H, 5.99; N, 4.83; Cl, 19.78.

EXAMPLE 28

N-[1-(Phenylmethyl)-4-piperidinyl]-1H-indole-3-acetamide

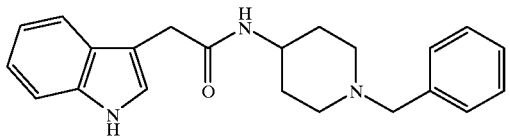

To a solution of indole-3-acetic acid (2.87 g, 0.0164 mol) in 50 mL dry tetrahydrofuran was added 1,1'-carbonyldiimidazole (2.90 g, 0.018 mol). The reaction was stirred at room temperature until CO$_2$ evolution ceased and 1-phenylmethyl-4-aminopiperidine (3.12 g, 0.0164 mol) was added. The reaction was stirred at room temperature for 16 hours, warmed to 50–55° C. and allowed to cool to room temperature over 1 hour. The reaction mixture was concentrated in vacuo and partitioned between CHCl$_3$ and H$_2$O. The CHCl$_3$ layer was further washed with H$_2$O and concentrated in vacuo. The crude product was recrystallized from methanol/CH$_3$CN and collected by filtration to provide 3.93 g (69%) of Example 28, melting point 153–154° C.

Analysis for C$_{22}$H$_{25}$N$_3$O:

Calc'd: C, 76.05; H, 7.25; N, 12.09;

Found: C, 75.86; H, 7.27; N, 12.08.

EXAMPLE 29

4-Methoxy-α-(4methoxyphenyl)-N-[1-(2-phenylethyl)-4-piperidinyl]benzeneacetamide, monohydrochloride

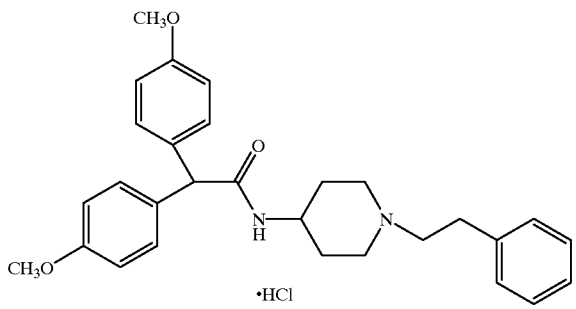

A. 1-(2-Phenylethyl)-4-piperidinone, oxime, hydrochloride

To a solution of 1-phenylethyl-4-piperidone (24.8 g, 0.122 mol) in 125 mL absolute ethanol was added hydroxylamine hydrochloride (8.48 g, 0.122 mol) with mechanically stirring. Additional of absolute ethanol was added and stirred for 1 hour. The reaction mixture was diluted with 300 mL ethyl ether and was collected by filtration to give compound A (26.1 g, 84%) as a solid, melting point 236–237° C.

B. 1-(2-Phenylethyl)-4-piperidinamine, dihydrochloride

To a solution of LiAlH$_4$ (5.82 g, 0.154 mol) in 250 mL ethyl ether under argon was added compound A (26.1 g, 0.1024 mol) portionwise. The reaction was warmed to reflux for 8 hours. The heating mantle was removed and was stirred at ambient temperature for 16 hours. The reaction mixture was washed with 50 mL H$_2$O and 50 mL of 10% NaOH solution. The ethyl ether layer was separated, dried over Mg$_2$SO$_4$ and was concentrated in vacuo. The crude was dissolved in 50 mL absolute ethanol and acidified to pH 1 with 5.6 N ethanolic HCl to give precipitation, followed by dilution with ether and filtration to isolate the solid. The precipitate was washed with hexane and ethyl ether to give compound B (16.72 g, 64%) as a solid, melting point 315° C.

C. 4-Methoxy-α-(4-methoxyphenyl)benzeneacetic acid

To neat morpholine (43.56 g, 0.5 mol) was added dichloroacetic acid (12.89 g, 0.1 mol) portionwise under argon, with ice bath. When the addition was finished, the ice bath was removed and the reaction was allowed to stand at ambient temperature for 16 hours. The reaction mixture was dissolved in a mixed solvent of 120 mL acetic acid and 12 mL H$_2$O and was stirred at room temperature until it was clear. To the reaction was then added anisole (43.2 g, 0.4 mol) followed by 100 mL concentrated H$_2$SO$_4$ with ice bath keeping temperature less then 25° C. The reaction was stirred at room temperature for 16 hours and warmed to 60° C. for 3 hours. The reaction mixture was poured over the ice and was extracted with CHCl$_3$. The CHCl$_3$ layer was then washed with 1 N NaOH then filtered. The aqueous solution was acidified with HCl to give a cloudy solution which crystallized upon standing at room temperature for 64 hours. The crystalline solid was filtered and rinsed with H$_2$O to give the acid (15.2 g, 55%).

D. 4-Methoxy-α-(4-methoxyphenyl)-N-[1-(2-phenylethyl)-4-piperidinyl]benzeneacetamide, monohydrochloride To a solution of the part C acid (1.8 g, 0.0066 mol) in 50 mL dry tetrahydrofuran was added 1,1'-carbonyldiimidazole (1.3 g, 0.008 mol). The reaction was stirred at room temperature for 1 hour and 50° C. for another hour. The amine was prepared by liberating the part B hydrochloride salt with 1 N NaOH and extracting with CH$_2$Cl$_2$ to give the free amine. The free amine (1.33 g, 0.066 mol) was then added to the reaction mixture at room temperature and stirred for 64 hours. The reaction was then warmed to 50° C. for 1 hour and concentrated in vacuo. The crude product was chromatographed using a mixture of 10% methanol and CHCl$_3$ as an eluting solvent and recrystallized in a mixture of ethyl ether and ethanolic HCl, followed by recrystallization form methanol to give Example 29 (0.64 g, 2%), melting point 180–182° C.

Analysis for C$_{29}$H$_{34}$N$_2$O$_3$+HCl+0.5 H$_2$O:

Calc'd: C, 69.10; H, 7.20; N, 5.56;

Found: C, 68.97; H, 7.12; N, 5.64.

EXAMPLE 30

α-Phenyl-N-[1-(phenylethyl)-4-piperidinyl]-benzeneacetamide, monohydrochloride

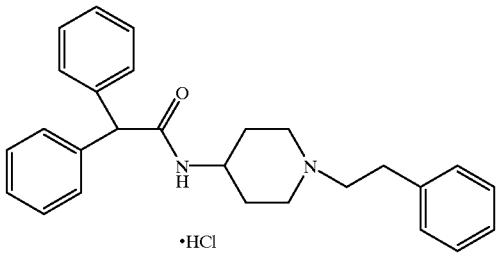

This reaction followed the procedure described in Example 29, part D. The reaction scale was as follows: diphenylacetic acid (2.1 g, 0.01 mol); 1,1'-carbonyldiimidazole (1.78 g, 0.011 mol) and the free amine derived from Example 29, part B hydrochloride (2.04 g, 0.01 mol). The reaction mixture was concentrated in vacuo and was partitioned between $CHCl_3$ and $H_2O$. The $CHCl_3$ layer was washed with diluted $NaHCO_3$, $H_2O$, dried over $Na_2SO_4$ and concentrated in vacuo. The crude product was dissolved in a mixture of methanol and ethyl ether and acidified with 5.6 N ethanolic HCl. More ethyl ether was added to increase precipitation which was then collected by filtration. The solid was recrystallized from methanol and ethyl ether to give Example 30 (1.05 g, 22%), melting point 263–264° C.

Analysis for $C_{27}H_{30}N_2O+HCl$:
Calc'd: C, 74.55; H, 7.18; N, 6.44;
Found: C, 74.85; H, 7.27; N, 6.39.

EXAMPLE 31

5-Chloro-2,3-dihydro-2-[1-(phenylmethyl)-4-piperidinyl]-1H-isoindol-1-one, monohydrochloride

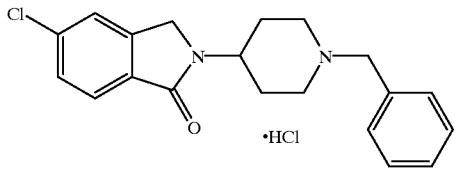

A. 5-Chloro-1,3-isobenzofurandione

4-Chlorophthalic acid (446.5 g, 2.23 mol) was heated neat until $H_2O$ was no longer released to give compound A (415.9 g, quantitative), melting point 138–140° C.

B. 5-Chloro-1H-isoindole-1,3(2H)-dione

A solution of compound A (415.9 g, 2.28 mol) and 1000 mL of 28% ammonium hydroxide was heated at 300° C. until $H_2O$ was no longer released to give compound B (361.0 g, 89%).

C. 5-Chloro-2-[1-(phenylmethyl)-4-piperidinyl]-1H-isoindole-1,3(2H)-dione

To a solution of compound B (10.0 g, 55.2 mmol) in 100 mL amyl alcohol was added 4-amino-1-benzylpiperidine (10.5 g, 55.2 mmol). The reaction was heated to reflux for 16 hours. The reaction mixture was concentrated in vacuo and dissolved in 250 mL $CHCl_3$. The $CHCl_3$ layer was washed with $H_2O$, dried over $Mg_2SO_4$ and was concentrated in vacuo. The crude product was dissolved in 400 mL isopropyl ether, treated with charcoal and filtered. The filtrate was acidified with 4 N HCl in dioxane to give compound C (19.0 g, 97%) as a white solid, melting point 233–234.5° C.

Analysis for $C_{20}H_{19}ClN_2O_2 \cdot HCl$:
Calc'd: C, 61.40; H, 5.16; N, 7.16;
Found: C, 62.04; H, 5.64; N, 7.31.

D. 5-Chloro-2,3-dihydro-2-[1-(phenylmethyl)-4-piperidinyl]-1H-isoindol-1-one, monohydrochloride To a solution of compound C (5.5 g, 14.1 mmol) in 40 mL acetic acid and 8.25 mL concentrated HCl was added tin (4.2 g, 35.3 mmol). The reaction was heated at 95–100° C. for 16 hours, treated with 5% NaOH to pH greater than 9, and extracted with $CHCl_3$. The organic layer was dried over $Mg_2SO_4$ and was concentrated in vacuo to the dryness. The crude product was dissolved in 200 mL $H_2O$ and treated with HCl in dioxane to give Example 31 (4.64 g, 87%), melting point 269–271° C.

Analysis for $C_{20}H_{21}ClN_2O+0.8$ HCl+0.2 $H_2O$:
Calc'd: C, 64.29; H, 5.99; N, 7.50; Cl, 17.08; $H_2O$, 0.96;
Found: C, 64.19; H, 6.05; N, 7.54; Cl, 16.96; $H_2O$, 0.95.

EXAMPLE 32

2-[1-(3-Butyl-2-heptenyl)-4-piperidinyl]-2,3-dihydro-1H-isoindol-1-one, monohydrochloride

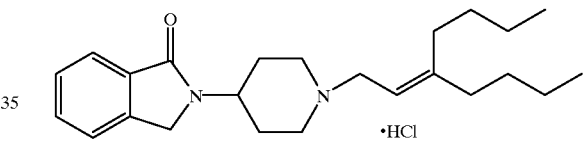

To a solution of Example 17, Part D amine (520 mg, 1.41 mmol) in ethyl ether/methanol (2 mL, 5:1) was added 1 M HCl in ethyl ether (1.5 mL, 1.5 mmol). The HCl salt precipitated from the solution. The salt was filtered and dried at 60° C. under vacuum to give Example 32 (300 mg, 58%) as a white solid, melting point 147–152° C.

Analysis for $C_{24}H_{37}ClN_2O+0.3$ $H_2O$:
Calc'd: C, 70.23; H, 9.23; N, 6.83; Cl, 8.64;
Found: C, 70.31; H, 9.17; N, 6.96; Cl, 8.50.

EXAMPLE 33

2-[1-(5,5-Diphenyl-2-pentenyl)-4-piperidinyl]-2,3-dihydro-1H-isoindol-1-one, monohydrochloride

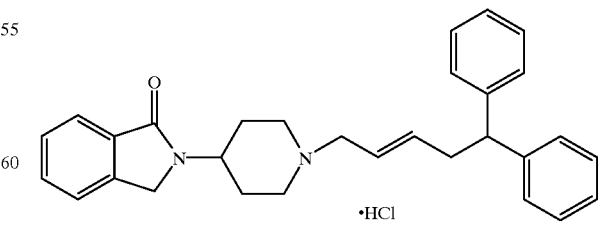

To a solution of Example 15, part E amine (500 mg, 1.15 mmol) in ethyl ether/methanol (2 mL, 5:1) was added 1 M HCl in ethyl ether (1.5 mL, 1.5 mmol). The HCl salt precipitated from the solution. The salt was filtered and dried at 60° C. under vacuum to give Example 33 (300 mg, 80%) as a white solid, melting point 127–134° C.

Analysis for $C_{30}H_{33}ClN_2O+1.4\ H_2O$:

Calc'd: C, 72.31; H, 7.24; N, 5.62; Cl, 7.12;

Found: C, 72.47; H, 7.49; N, 5.54; Cl, 7.33.

EXAMPLE 34

2,3-Dihydro-2-[1-[3-(2-phenoxyphenyl)propyl]-4-piperidinyl]-1H-isoindol-1-one, monohydrochloride

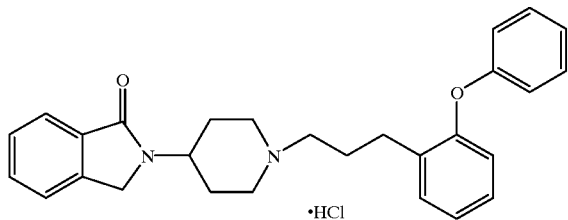

A. 2,3-Dihydro-2-[1-[3-(2-phenoxyphenyl)propyl]-4-piperidinyl]-1H-isoindol-1-one To a solution of compound F from Example 20 (450 mg, 1.06 mmol) in ethanol (10 mL) was added 10% palladium on activated carbon (45 mg) under argon at room temperature. Argon on the reaction was replaced by hydrogen. A hydrogen balloon was connected to the solution. Hydrogenation was maintained overnight. The reaction was filtered through Celite, and the filtrate was evaporated to dryness. Purification was performed by flash chromatography on 100 g silica gel, loaded and eluted with 1.5% methanol in dichloromethane. Pure fractions were combined and evaporated to give compound A (450 mg, 100%) as a colorless oil.

B. 2,3-Dihydro-2-[1-[3-(2-phenoxyphenyl)propyl]-4-piperidinyl]-1H-isoindol-1-one, monohydrochloride Compound A (450 mg, 1.06 mmol) was dissolved in 20% methanol in ethyl ether (2 mL). A solution of 1 M HCl in ethyl ether (2 mL, 2.0 mmol) was added. The HCl salt precipitated and was filtered and washed with ethyl ether. Dichloromethane (80 mL) was added to dissolve the solid, and the organic layer was washed with saturated sodium bicarbonate solution (2×30 mL). Evaporation gave a colorless oil. Purification was performed by flash chromatography, loaded and eluted with 1.5% methanol in dichloromethane. Pure fractions were combined and evaporated to give a colorless oil. The resulting oil was dissolved in 20% methanol in hexane. A solution of 1 M HCl in ethyl ether (1 mL, 1.0 mmol) was added. The HCl salt precipitated and was filtered and washed ethyl ether. The resulting solid was dried under high vacuum at 60° C. overnight to give Example 34 (160 mg, 35%) as a white solid, melting point 199–202° C.

Analysis. for $C_{28}H_{31}ClN_2O_2+0.5\ H_2O$:

Calc'd: C, 71.25; H, 6.83; N, 5.93;

Found: C, 71.13; H, 6.78; N, 5.93.

EXAMPLE 35

2,3-Dihydro-2-[1-(diphenylmethyl)-4-piperidinyl]-1H-isoindol-1-one, monohydrochloride

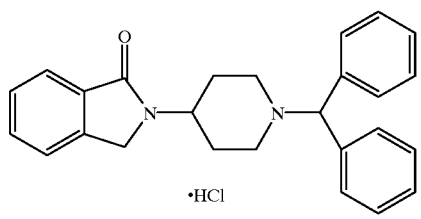

A. 2,3-Dihydro-2-[1-(diphenylmethyl)-4-piperidinyl]-1H-isoindol-1-one

To a solution of bromodiphenylmethane (572 mg, 2.31 mmol) in dimethylformamide (10 mL) was added a solution of compound A from Example 11 (500 mg, 2.31 mmol) in dimethylformamide (2 mL) followed by anhydrous potassium carbonate (351 mg, 2.54 mmol). The reaction was refluxed overnight. The reaction was cooled to room temperature. Ethyl ether (100 mL) was added to dilute the reaction, and the organic layer was washed with water (2×50 mL), brine (2×50 mL) and dried over magnesium sulfate. Evaporation gave a crude oil. Purification was performed by flash chromatography on 100 g of silica gel, loaded and eluted with 2% methanol in dichloromethane. Pure fractions were combined and evaporated to give compound A (520 mg, 59%) as a colorless oil.

B. 2,3-Dihydro-2-[1-(diphenylmethyl)-4-piperidinyl]-1H-isoindol-1-one, monohydrochloride To a solution of compound A (500 mg, 1.31 mmol) in ethyl ether/methanol (2 mL, 5:1) was added 1 M HCl in ethyl ether (3.0 mL, 3.0 mmol). The mixture was evaporated to dryness. The result solid was dried at 70° C. under vacuum to give Example 35 (300 mg, 60%) as a white solid, melting point 165–169° C.

Analysis for $C_{26}H_{27}ClN_2O+1.0\ H_2O$:

Calc'd: C, 71.46; H, 6.69; N, 6.41;

Found: C, 71.52; H, 6.87; N, 6.35.

EXAMPLE 36

(Z)-2,3-Dihydro-2-[1-(5,5-diphenyl-2-pentenyl)-4-piperidinyl]-1H-isoindol-1-one, monohydrochloride

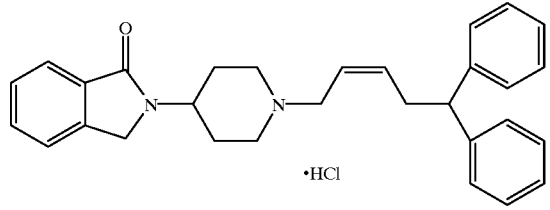

A. (Z)-5,5-Diphenyl-2-pentenoic acid, methyl ester

To a suspension of bis(2,2,2-trifluoroethyl) (methoxycarbonylmethyl)phosphonate (4.16 g, 13.1 mmol) and 18-crown-6 (3.46 g, 13.1 mmol) in tetrahydrofuran (65 mL) at 0° C. was added dropwise 0.5 M potassium bis (trimethylsilyl)amide in toluene (26.2 mL, 13.1 mmol). The reaction was stirred at 0° C. for 15 minutes, then cooled to −78° C. A solution of compound A from Example 15 (5.0 g, 23.8 mmol) in tetrahydrofuran (5 mL) was added dropwise. The reaction was stirred at −78° C. for 1 hour, then warmed to room temperature and quenched with saturated ammonium chloride solution (5 mL). Ethyl ether (200 mL) was added to dilute the reaction, and the organic layer was washed with water (2×50 mL), brine (2×50 mL) and dried over MgSO$_4$. Evaporation gave a crude oil. Purification was performed by flash chromatography on 250 g silica gel, loaded and eluted with 6% ethyl acetate in hexane. Pure fractions were combined and evaporated to give compound A (2.2 g, 70%) as a colorless oil.

B. (Z)-5,5-Diphenyl-2-penten-1-ol

To a solution of compound A (2.2 g, 8.27 mmol) in toluene (20 mL) at 0° C. was added dropwise diisobutylaluminum hydride (1.0 M in toluene, 18.2 mL, 18.2 mmol). The reaction was stirred at 0° C. for 1 hour. The reaction was quenched with methanol (5 mL). Potassium sodium tartrate solution (1 M, 200 mL) was added, and the reaction mixture was stirred for 3.5 hours. Ethyl ether (200 mL) was added, and the organic layer was washed with water (2×50 mL), brine (2×50 mL) and dried over MgSO$_4$. Evaporation gave a crude oil. Purification was performed by flash chromatography on 300 g silica gel, loaded and eluted with 20% ethyl acetate in hexane. Pure fractions were combined and evaporated to give compound B as a colorless oil (1.9 g, 97%).

C. (Z)-1-Chloro-5,5-diphenyl-2-pentene

To a solution of N-chlorosuccinimide (0.56 g, 4.16 mmol) in dichloromethane (12 mL) at −40° C. was added dropwise methyl sulfide (0.4 mL, 5.29 mmol). The reaction was stirred at −40° C. for 10 minutes then warmed to room temperature for 30 minutes. The reaction was recooled to −40° C., and a solution of compound B (0.9 g, 3.78 mmol) in dichloromethane (5 mL) was added dropwise. The reaction was stirred at −40° C. for 2 hours then warmed to room temperature for 30 minutes. Hexane (300 mL) was added to dilute the reaction and the organic layer was washed with water (2×50 mL), brine (2×50 mL) and dried over MgSO$_4$. Evaporation gave compound C (0.9 g, 93%) as a colorless oil.

D. (Z)-2,3-Dihydro-2-[1-(5,5-diphenyl-2-pentenyl)-4-piperidinyl]-1H-isoindol-1-one To a solution of compound A from Example 11 (756 mg, 3.50 mmol) in dimethylformamide (12 mL) was added compound C (900 mg, 3.50 mmol) followed by anhydrous potassium carbonate (531 mg, 3.85 mmol). The reaction was stirred at 50° C. overnight. The reaction was cooled to room temperature. Ethyl ether (100 mL) was added to dilute the reaction, and the organic layer was washed with water (2×50 mL), brine (2×50 mL) and dried over Na$_2$SO$_4$. Evaporation gave a crude oil. Purification was performed by flash chromatography on 100 g of silica gel, loaded and eluted with 2% methanol in dichloromethane. Pure fractions were combined and evaporated to give compound D (950 mg, 62%) as a white solid, melting point 138–140° C.

E. (Z)-2,3-Dihydro-2-[1-(5,5diphenyl-2-pentenyl)-4-piperidinyl]-1H-isoindol-1-one, monohydrochloride To a solution of compound D (500 mg, 1.15 mmol) in methanol (2 mL) was added 1 M HCl in ethyl ether (1.5 mL, 1.5 mmol). The mixture was evaporated to dryness. The resulting white solid was dried at 60° C. under vacuum to give Example 36 (300 mg, 80%) as a white solid, melting point 174–177° C.

Analysis for C$_{30}$H$_{33}$ClN$_2$O+1.2 H$_2$O:

Calc'd: C, 72.84; H, 7.21; N, 5.66; Cl, 7.17;

Found: C, 72.74; H, 6.88; N, 5.70; Cl, 7.42.

EXAMPLE 37

N-[1-(3,3-Diphenylpropyl)-4-piperidinyl)phenoxyacetamide, monohydrochloride

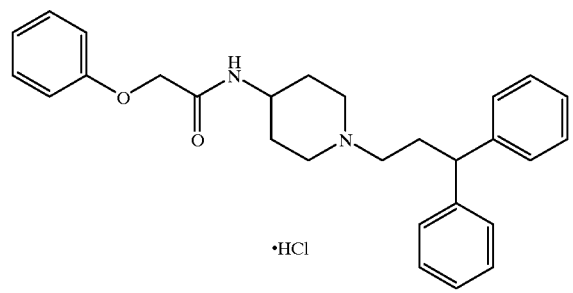

A. N-[1-(3,3-Diphenylpropyl)-4-piperidinyl)phenoxyacetamide

Compound A was prepared and purified as described for compound A in Example 18, using 517 mg (1.56 mmol) of compound E from Example 10, 380 μL (4.68 mmol) of pyridine, and 226 μL (1.64 mmol) of phenoxyacetyl chloride. The crude product was purified by flash chromatography on silica gel eluted with 98:2 methylene chloride/methanol to provide 491 mg (73%) of compound A as a yellow solid, melting point 83–86° C.

B. N-[1-(3,3-Diphenylpropyl)-4-piperidinyl)phenoxyacetamide, monohydrochloride To a solution of 485 mg (1.13 mmol) of compound A in 4 mL of methylene chloride was added 2.26 mL (2.26 mmol) of a 1.0 M solution of hydrogen chloride in diethyl ether. The opaque white mixture was concentrated to an orange solid which was purified by recrystallization from isopropanol. Removal of isopropanol remnants by co-evaporation with chloroform followed by methylene chloride and drying under vacuum provided 408 mg (78%) of Example 37 as an off-white solid, melting point 203–205° C.

Analysis for C$_{28}$H$_{33}$N$_2$OCl+0.94 H$_2$O:

Calc'd: C, 70.34; H, 7.26; N, 5.86;

Found: C, 70.37; H, 7.24; N, 5.83.

EXAMPLE 38

N-[1-(3,3-Diphenylpropyl)-4-piperidinyl]-2-methoxybenzamide, monohydrochloride

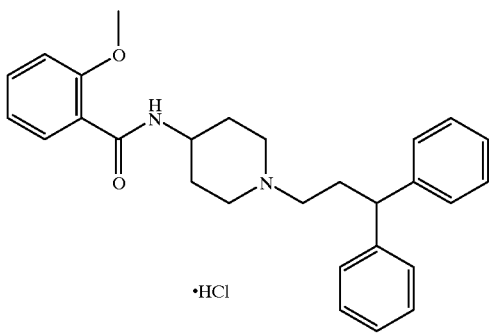

A. N-[1-(3,3-Diphenylpropyl)-4-piperidinyl]-2-methoxybenzamide

Compound A was prepared as described for compound A in Example 18, using 503 mg (1.52 mmol) of compound E from Example 10, 370 μL (4.58 mmol) of pyridine, and 238 μL (1.59 mmol) of O-anisoyl chloride. The crude product was purified by flash chromatography on silica gel eluted with 98:2 ethyl acetate/methanol to provide 336 mg (56%) of compound A as a yellow solid, melting point 96–98° C.

B. N-[1-(3,3-Diphenylpropyl)-4-piperidinyl]-2-methoxybenzamide, monohydrochloride To a solution of 364 mg (0.85 mmol) of compound A in 4 mL of methylene chloride was added a freshly prepared saturated solution of hydrogen chloride in diethyl ether. The opaque white mixture was concentrated and dried to provide 329 mg (83%) of Example 38 as an off-white solid, melting point 170–172° C.

Analysis for $C_{28}H_{33}N_2O_2Cl+1.11 H_2O$:
Calcd. C, 69.34; H, 7.32; N, 5.78;
Found C, 69.41; H, 7.31; N, 5.71.

EXAMPLE 39

N-[1-(3,3-Diphenylpropyl)-4-piperidinyl]-2-methylbenzamide, monohydrochloride

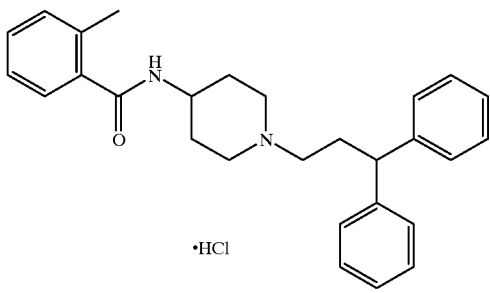

A. N-[1-(3,3-Diphenylpropyl)-4-piperidinyl]-2-methylbenzamide

Compound A was prepared as described for compound A in Example 18, using 485 mg (1.46 mmol) of compound E from Example 10, 336 μL (4.38 mmol) of pyridine, and 200 μL (1.54 mmol) of O-toluoyl chloride. The crude product was purified by flash chromatography on silica gel eluted with 98:2 ethyl acetate/methanol to provide 345 mg (67%) of compound A as a yellow solid.

B. N-[1-(3,3-Diphenylpropyl)-4-piperidinyl]-2-methylbenzamide, monohydrochloride To a solution of 342 mg (0.83 mmol) of compound A in 2 mL of methylene chloride was added a freshly prepared saturated solution of hydrogen chloride in diethyl ether. The opaque white mixture was concentrated, evaporated from methylene chloride to remove residual ether, and dried under vacuum to provide 348 mg (94%) of Example 39 as a white solid, meting point 237–239° C.

Analysis for $C_{28}H_{33}N_2OCl+1.15 H_2O$:
Calc'd: C, 71.60; H, 7.57; N, 5.96, Cl, 7.55;
Found: C, 71.59; H, 7.31; N, 5.97, Cl, 7.86.

EXAMPLE 40

N-[1-(3,3-Diphenylpropyl)-4-piperidinyl]-2-pyridineamide, monohydrochloride

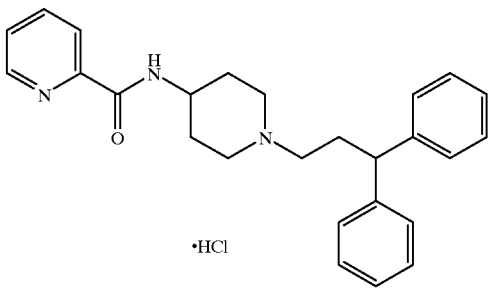

A. N-[1-(3,3-Diphenylpropyl)-4-piperidinyl]-2-pyridineamide

To a stirred suspension of 199 mg (1.62 mmol) of picolinic acid in 2.5 mL of methylene chloride at 0° C. was added 225 μL (1.62 mmol) of triethylamine. After all the solids had dissolved, the solution was treated with 412 mg (1.62 mmol) of bis(2-oxo-3-oxazolidinyl)phosphinic chloride, and stirred for 30 minutes. A methylene chloride solution of 535 mg (1.62 mmol) of compound E from Example 10 was converted to the free amine by washing with sodium bicarbonate and concentrating the organic layer to a brown oil which was redissolved in 1 mL of dry methylene chloride and added to the reaction mixture. After stirring at room temperature for 16 hours, the reaction was quenched with water and 4 M HCl and diluted with methylene chloride. The aqueous layer was basified with 1 N KOH and extracted two times. The combined organics were dried (sodium sulfate) and concentrated to provide 554 mg of a brown oil. The crude product was purified by flash chromatography on silica gel eluted with 98:2 ethyl acetate/methanol to provide 316 mg (58%) of compound A as a brown glass.

B. N-[1-(3,3-Diphenylpropyl)-4-piperidinyl]-2-pyridinamide, monohydrochloride The hydrochloride salt of compound A was prepared by the procedure used for compound B in Example 38, using 316 mg (0.83 mmol) of compound A, to afford 336 mg (83%) of Example 40 as a yellow solid, melting point 109–116° C.

Analysis for C$_{26}$H$_{30}$N$_3$OCl+1.42 H$_2$O
Calc'd: C 67.65, H 7.17, N 9.10;
Found: C 67.53, H 7.10, N 9.22.

EXAMPLE 41

N-[1-(3,3-Diphenylpropyl)-4-piperidinyl]-N-(phenylmethyl)acetamide, monohydrochloride

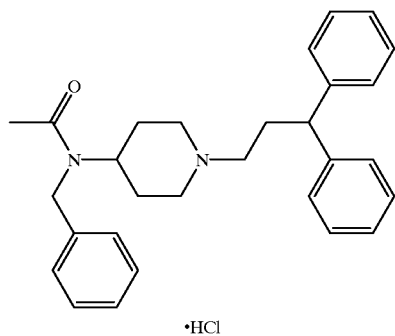

·HCl

A. 8-(3,3-Diphenylpropyl)spiro[1,3-dioxolane-2,4'-piperidine]

Toluenesulfonyl chloride (7.00 g, 36.7 mmol) was added to a solution of 7.09 g (33.4 mmol) of 3,3-diphenyl-1-propanol in dry pyridine (30 mL) at room temperature under argon. After 15 minutes, a precipitate began forming. The reaction was stirred at room temperature for a total of 7 hours, followed by addition of water (10 mL). The reaction was partitioned between diethyl ether (150 mL) and 1 M aqueous copper sulfate (50 mL). The organic layer was washed with 1 M aqueous copper sulfate (2×50 mL), 1 N HCl (50 mL), saturated sodium bicarbonate (50 mL), and brine (10 mL), then dried over Na$_2$SO$_4$. Evaporation gave 10.1 g of an orange solid mass. $^1$H NMR indicated approximately 10% remaining starting material.

A mixture of the crude tosylate prepared above, 1,4-dioxa-8-azaspiro[4.5]decane (4.78 g, 33.4 mmol), and potassium carbonate (6.91 g, 50.1 mmol) in isopropanol (70 mL) was maintained at reflux under argon for 8 hours, then cooled to room temperature. The reaction was filtered with the aid of CH$_2$Cl$_2$ (30 mL). Evaporation gave 11 g of a thick orange oil, which was purified by flash chromatography on silica gel (300 g) eluting with 4% methanol in CH$_2$Cl$_2$ to afford 8.33 g (74%) of compound A as an orange oil.

B. 1-(3,3-Diphenylpropyl)]-4-piperidinone

A mixture of 7.36 g (21.8 mmol) of compound A and 100 mL of 6 N HCl was heated at reflux under argon for 30 minutes, then cooled to room temperature. The reaction was made basic by slow addition of 1 N KOH (about 650 mL), and the cloudy mixture was extracted with CH$_2$Cl$_2$ (2×100 mL). Evaporation gave 6.13 g (97%) of compound B as an orange-brown solid.

C. 1-(3,3-Diphenylpropyl)-N-(phenylmethyl)-4-piperidinamine

To 750 mg (2.6 mmol, 1 eq) of compound B was added 279 µL (2.6 mmol, 1 eq) of benzylamine followed by 951 µL (3.2 mmol, 1.25 eq) of titanium isopropoxide. To obtain a homogeneous solution 5 mL of CH$_2$Cl$_2$ was added and the reaction was stirred at room temperature for 2 hours. Methanol (2 mL) was added to the reaction followed by 97 mg (2.6 mmol, 1 eq) of sodium borohydride. After 18 hours, the reaction was diluted with water (2 mL) and the resulting precipitate was removed by filtration and washed well with methanol. The filtrate was concentrated and the residual oil was dissolved in ethyl acetate. The resulting precipitate was again filtered and rinsed well with ethyl acetate. The ethyl acetate solution was concentrated to afford 1 g of a pale yellow oil which was chromatographed on silica gel (60 g) eluted initially with 5% methanol in CH$_2$Cl$_2$, followed by 10% methanol in CH$_2$Cl$_2$ to afford 960 mg (96%) of compound C as a pale yellow oil.

D. N-[1-(3,3-Diphenylpropyl)-4-piperidinyl]-N-(phenylmethyl)acetamide

To a solution of 460 mg (1.2 mmol, 1 eq) of compound C in 5 mL of CH$_2$Cl$_2$ at 0° C. was added 145 µL (1.8 mmol, 1.5 eq) of pyridine followed by dropwise addition of 94 µL (1.3 mmol, 1.1 eq) of acetyl chloride over 1 minute. The reaction was allowed to warm to room temperature. After 6 hours, the reaction was diluted with CH$_2$Cl$_2$ and washed with 1 N KOH. The organic layer was filtered through cotton and concentrated to afford 510 mg of an orange-brown oil which was chromatographed on silica gel (50 g) eluted with 2% methanol in t-butylmethylether to afford 490 mg (96%) of compound D as a yellow oil.

E. N-[1-(3,3-Diphenylpropyl)-4-piperidinyl]-N-(phenylmethyl)acetamide, monohydrochloride To a solution of 475 mg (1.1 mmol, 1 eq) of compound D in 5 mL of ether and 1 mL of CH$_2$Cl$_2$ was added an excess of HCl as a saturated solution in ether and the resulting heterogeneous mixture was stirred for 20 minutes. The solid was isolated by filtration, rinsed well with ether, concentrated and the solvent remnants were removed in a vacuum oven at 52° C. and full vacuum to afford 452 mg (89%) of Example 41 as a white solid, melting point 102–105° C.

Analysis for C$_{29}$H$_{35}$N$_2$OCl+0.67 H$_2$O:
Calc'd: C 73.31, H 7.71, N 5.90, Cl 7.46
Found: C 73.23, H 7.78, N 5.98, Cl 7.44

EXAMPLE 42

N-[1-(3,3-Diphenylpropyl)-4-piperidinyl]-N-(phenylmethyl)benzamide, monohydrochloride

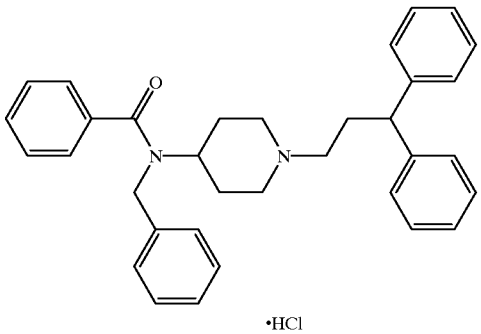

·HCl

A. N-[1-(3,3-Diphenylpropyl)-4-piperidinyl]-N-(phenylmethyl)benzamide

Compound A was prepared from 500 mg of compound C from Example 41 (1.3 mmol), 158 µL (2 mmol) of pyridine and 166 μL (1.3 mmol) of benzoyl chloride following the procedure described for preparation of compound D in Example 41. Flash chromatography on silica gel (75 g) eluted with 1% methanol in t-butylmethylether afforded 626 mg (98%) of compound A as a yellow oil.

B. N-[1-(3,3-Diphenylpropyl)-4-piperidinyl]-N-(phenylmethyl)benzamide, monohydrochloride Example 42 was prepared from 615 mg of compound A following the procedure described for compound E in Example 41 to afford 540 mg (82%) of Example 42 as a pale yellow solid; melting point 115–120° C.

Analysis for $C_{34}H_{37}N_2OCl+0.65\ H_2O$:

Calc'd: C 76.07, H 7.19, N 5.22, Cl 6.60

Found: C 76.09, H 7.25, N 5.21, Cl 6.35

EXAMPLE 43

N-[1-(3,3-Diphenylpropyl)-4-piperidinyl]-N-methylbenzamide, monohydrochloride

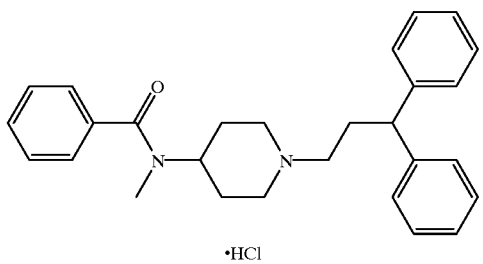

·HCl

A. N-[1-(3,3-Diphenylpropyl)-4-piperidinyl]-N-methylamine

To a solution of 550 mg (1.4 mmol, 1 eq) of compound D from Example 10 in 5 mL of tetrahydrofuran at 0° C. was added 8.4 mL (8.4 mmol, 6 eq) of a 1 M solution of lithium aluminum hydride in tetrahydrofuran and the reaction was allowed to warm to room temperature. After 15 hours, the reaction was heated at 60° C. for 4 hours, then quenched by slow addition of a saturated aqueous solution of $Na_2SO_4$. To the resulting heterogeneous mixture was added solid $Na_2SO_4$ and the mixture was stirred for 30 minutes. The solids were removed by filtration and rinsed well with ethyl acetate. Concentration of the organic filtrate afforded 400 mg (93%) of compound A as a viscous pale yellow oil which was used without further purification.

B. N-[1-(3,3-Diphenylpropyl)-4-piperidinyl]-N-methylbenzamide

Compound B was prepared from 390 mg (1.3 mmol) of compound A, 158 μL (1.4 mmol) of pyridine and 166 μL (1.4 mmol) of benzoyl chloride as described for compound D in Example 41. Flash chromatography on silica gel (75 g) eluted with 1.5% methanol in t-butylmethylether afforded 472 mg (88%) of compound B as a pale yellow oil.

C. N-[1-(3,3-Diphenylpropyl)-4-piperidinyl]-N-methylbenzamide, monohydrochloride Example 44 was prepared from 460 mg of compound B as described for compound E in Example 41 to afford 540 mg (82%) of Example 43 as a powdery white solid, melting point 216–217° C.

Analysis for $C_{34}H_{37}N_2OCl$:

Calc'd: C 74.90, H 7.41, N 6.24, Cl 7.90

Found: C 74.64, H 7.38, N 6.35, Cl 7.75

Additional compounds falling within the scope of the present invention are described by the following structures. Substituents for each example are identified in the table following each structure.

TABLE A

| $R^a$ | $R^b$ | $R^c$ | $R^d$ |
|---|---|---|---|
| H | F | H | H |
| F | H | H | H |
| F | H | H | F |
| H | Cl | Cl | H |
| H | $CF_3$ | H | H |
| H | phenoxy | H | H |
| H | phenyl | H | H |
| H | benzyl ($CH_2$-phenyl) | H | H |
| H | 4-pyridyl | H | H |
| H | 5-methyl-2-thienyl | H | H |
| H | H | phenoxy | H |
| H | pentyl | H | H |
| H | Isobutyl | H | H |
| $CH_3$ | H | H | $CH_3$ |
| H | 4-methylpent-3-enyl | H | H |
| H | H | $CH_3O$ | H |
| H | butylS | H | H |

TABLE A-continued

[Structure: isoindolinone with Rd, Re, Rb, Ra substituents on aromatic ring, N connected to piperidine-CH2CH2-CH(phenyl)2]

| Rª | Rᵇ | Rᶜ | Rᵈ |
|---|---|---|---|
| H | phenyl-S- | H | H |
| H | H | pyrrole-N-CH2- | H |

TABLE B

[Structure: X-piperidine-CH2CH2-CH(phenyl)2]

Examples of X

- 4-(trifluoromethyl)benzamide
- 4-chlorobenzamide
- 2,4,6-trichlorobenzamide
- 2,4,6-trimethylbenzamide (mesitylene carboxamide)

TABLE B-continued

[Structure: X-piperidine-CH2CH2-CH(phenyl)2]

Examples of X

- 2,6-dimethoxybenzamide
- 3,5-dimethylbenzamide
- N-phenylbenzamide
- N-allylcyclohexanecarboxamide
- N-phenylhexanamide
- 4-phenoxybenzamide TABLE B-continued
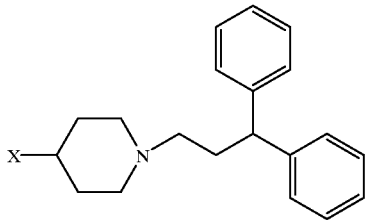
Examples of X
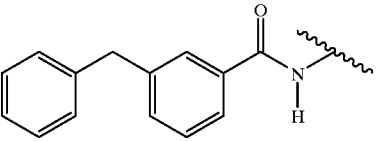
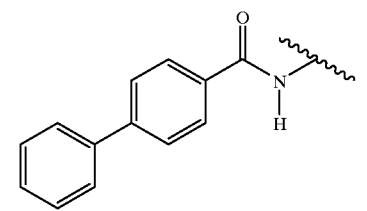
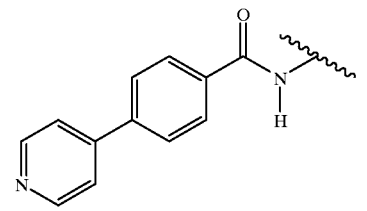
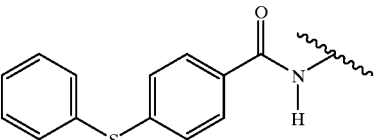
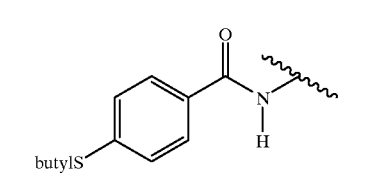
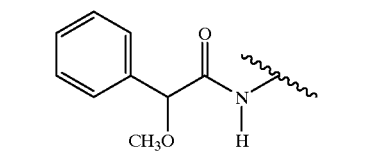
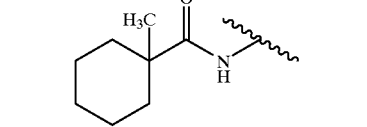
TABLE B-continued
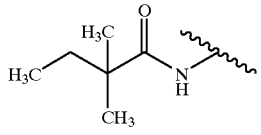
Examples of X
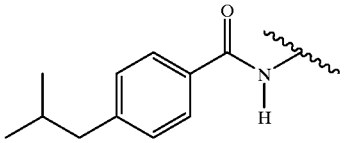
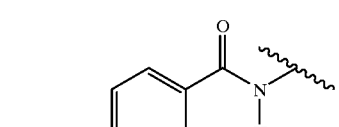
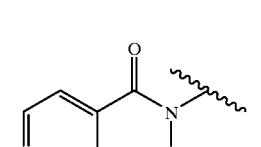
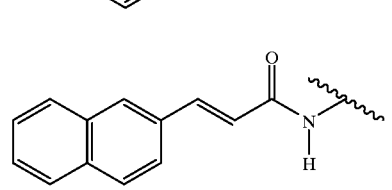
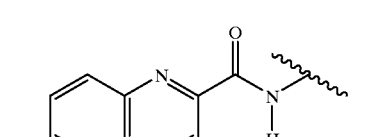
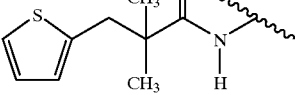
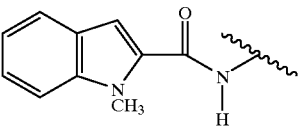

TABLE B-continued
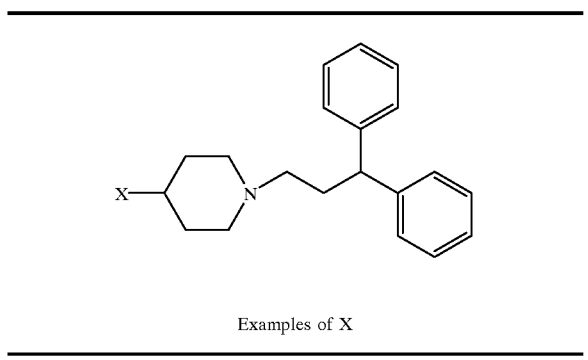
Examples of X
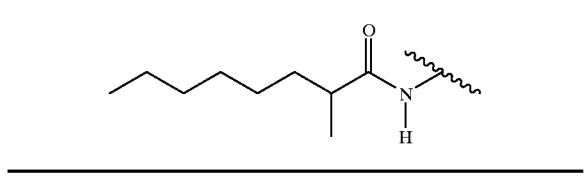
TABLE C
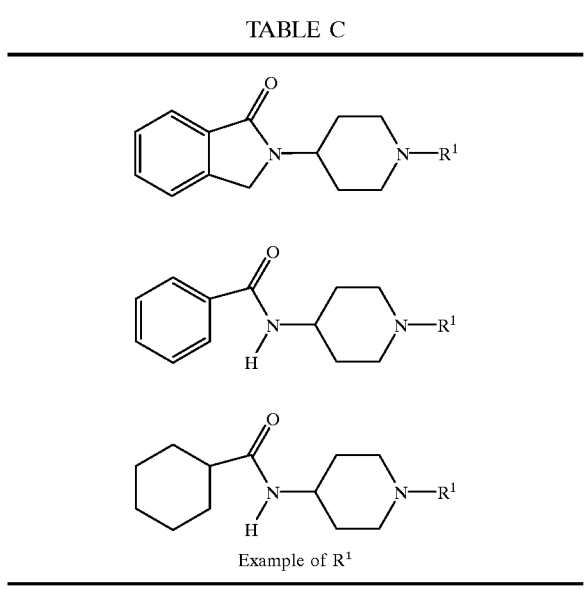
Example of R¹
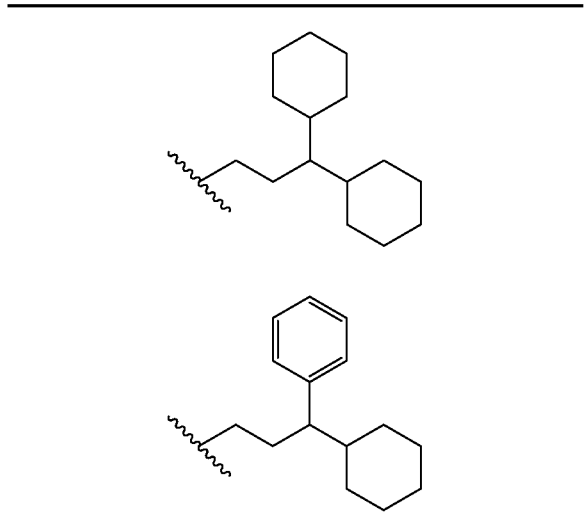
TABLE C-continued
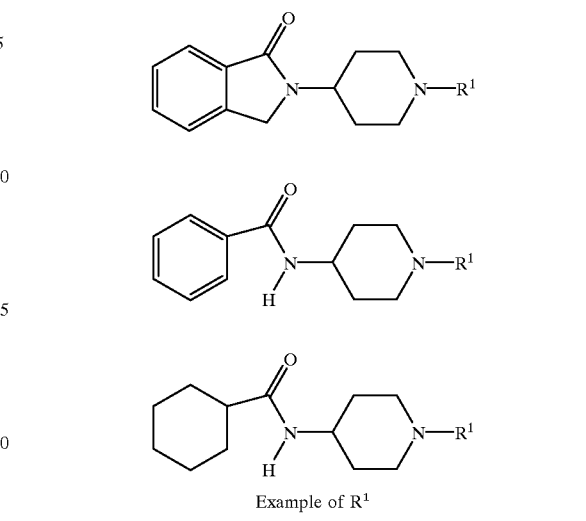
Example of R¹
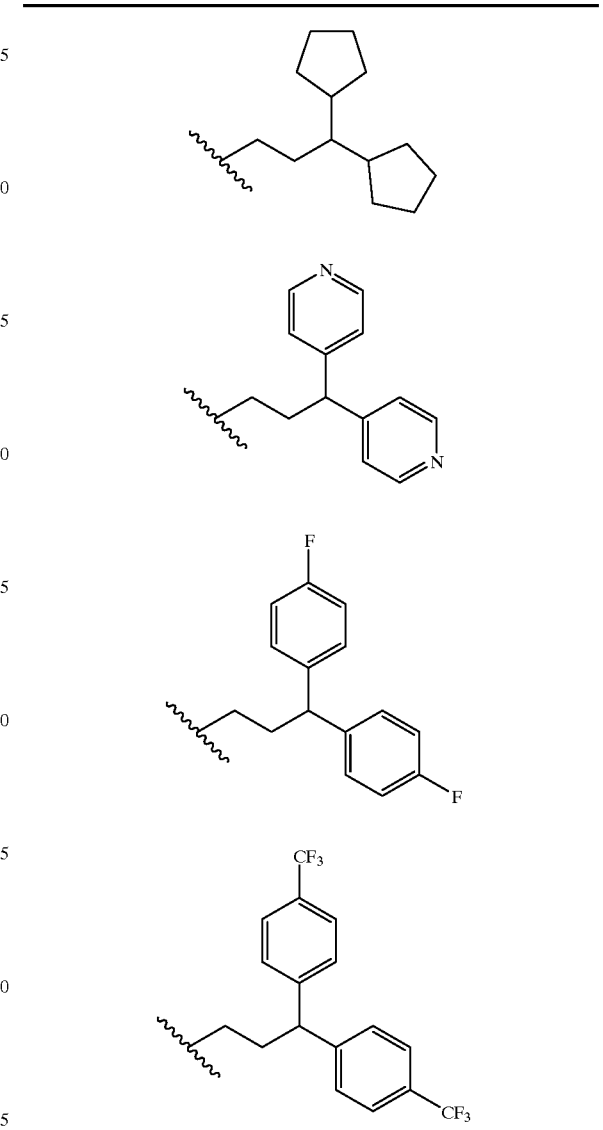

TABLE C-continued
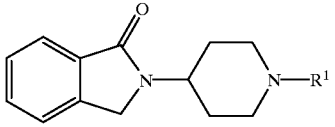
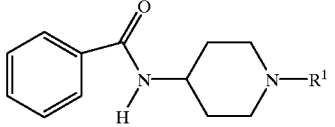
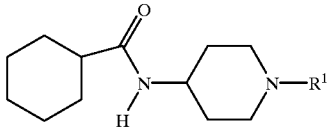
Example of R¹
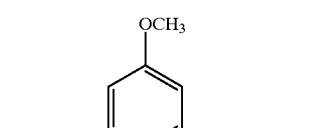
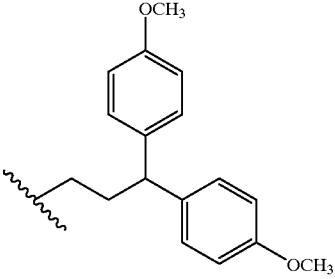
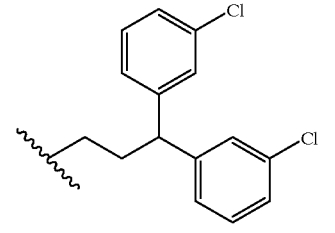
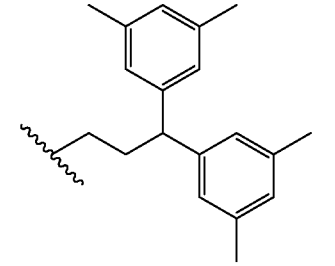
TABLE C-continued
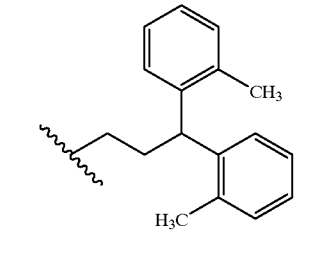
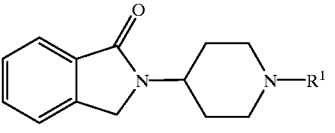
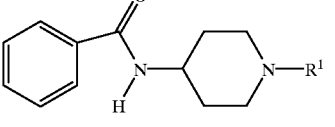
Example of R¹
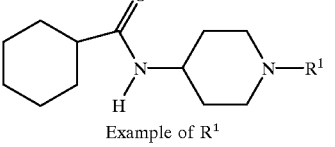
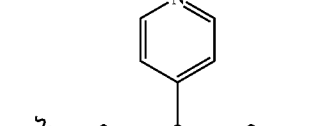
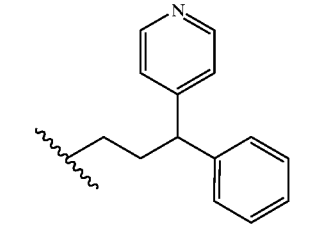
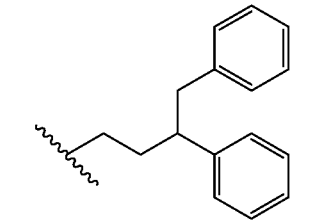
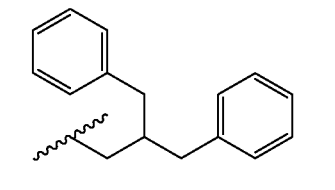

TABLE C-continued
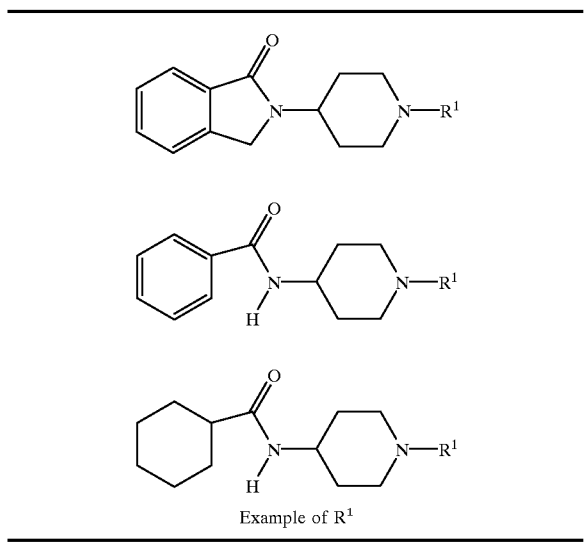
Example of R[1]
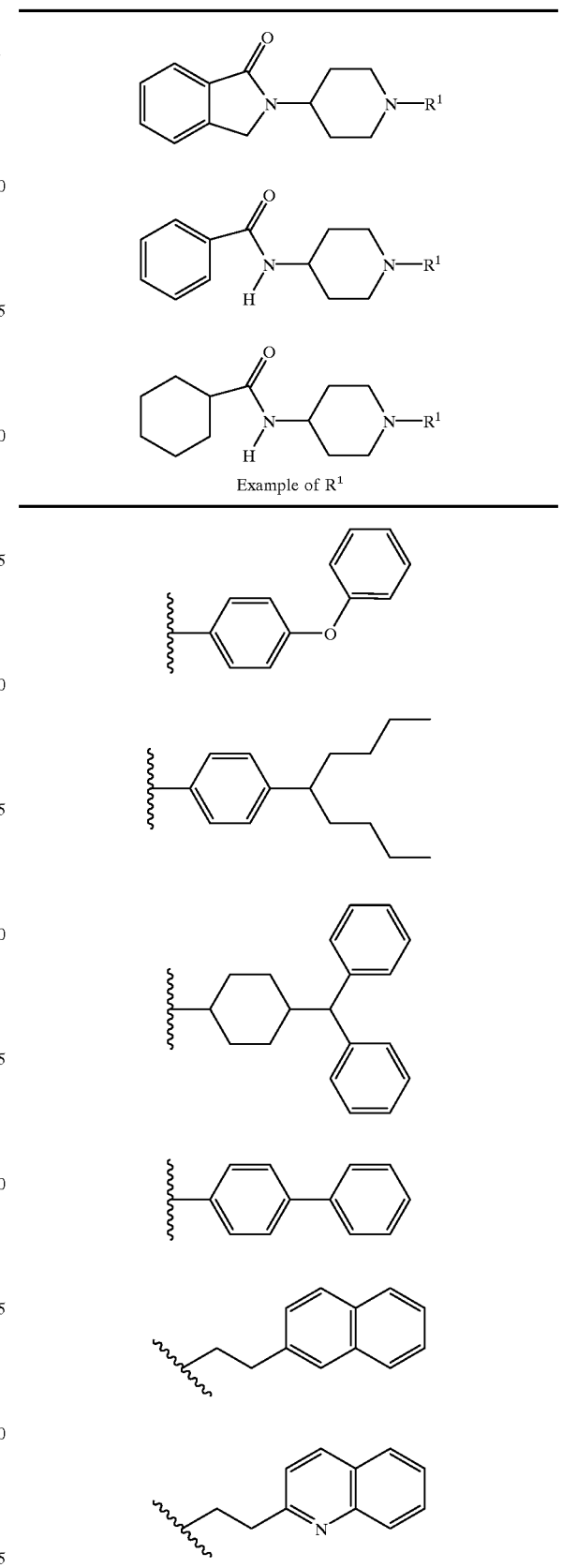
Example of R[1]

TABLE C-continued

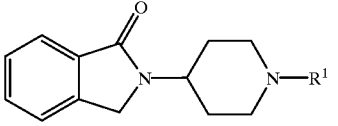

5

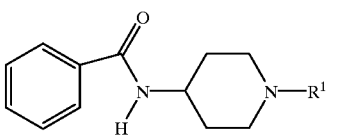

10

15

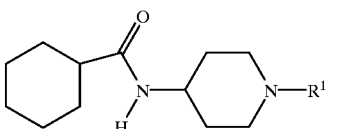

20

Example of $R^1$

25

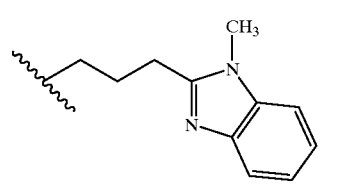

30

35

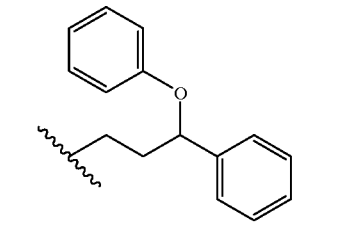

40

What is claimed is:

1. A method for treating atherosclerosis in a mammalian species comprising administration of a therapeutically effective amount of an agent which decreases the amount or activity of microsomal triglyceride transfer protein, wherein said agent is not a polynucleotide compound.

2. A method for decreasing serum lipid levels in a mammalian species, which comprises administration of a therapeutically effective amount of an agent which decreases the amount or activity of microsomal triglyceride transfer protein, wherein said agent is not a polynucleotide compound.

3. The method of claim 1 or 2, wherein the agent is a compound of the formula

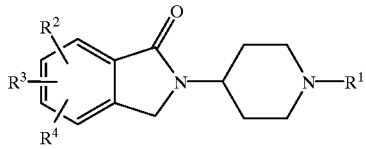

or a compound of the formula

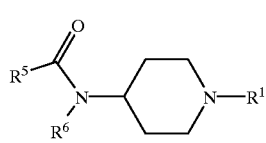

or a compound of the formula

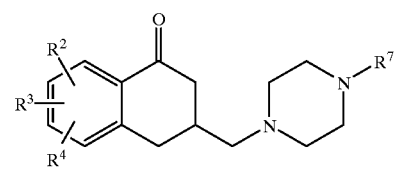

wherein:
R$^1$ is alkyl, alkenyl, alkynyl, aryl, heteroaryl, arylalkyl, heteroarylalkyl, cycloalkyl, cycloalkylalkyl (all optionally substituted through available carbon atoms with 1, 2, or 3 groups selected from halo, alkyl, alkenyl, alkoxy, aryloxy, aryl, arylalkyl, alkylmercapto, arylmercapto, cycloalkyl, cycloalkylalkyl, heteroaryl, heteroarylalkyl);
R$^2$, R$^3$, R$^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl;

R$^5$ and R$^6$ are independently hydrogen, alkyl, alkenyl, aryl, heteroaryl, arylalkyl, heteroarylalkyl, cycloalkyl, cycloalkylalkyl (all optionally substituted through available carbon atoms with 1, 2, or 3 groups selected from halo, alkyl, alkenyl, alkoxy, aryloxy, aryl, arylalkyl, alkylmercapto, arylmercapto, cycloalkyl, cycloalkylalkyl, heteroaryl, heteroarylalkyl; with the proviso that when R$^5$ is CH$_3$, R$^6$ is not hydrogen,
R$^7$ is alkyl (optionally substituted with oxo), aryl, or arylalkyl (wherein the alkyl portion is optionally substituted with oxo).

4. The method of claim 3, wherein the agent is a compound of the formula

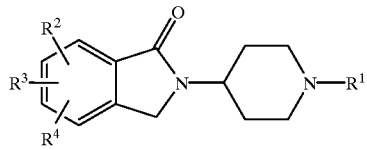

or a compound of the formula

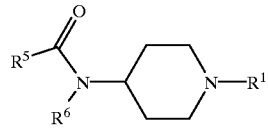

wherein:
R$^1$ is —R$^v$—R$^w$ or

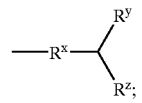

R$^v$ and R$^x$ are each independently alkylene or cis-alkenylene of up to 6 carbon atoms;
R$^w$ is aryl or heteroaryl; and
R$^y$ and R$^z$ are each independently alkyl, alkenyl, aryl, arylalkyl, heteroaryl, heteroarylalkyl, cycloalkyl, or cycloalkylalkyl.

5. The method of claim 4, wherein R$^y$ and R$^z$ are each independently aryl, arylalkyl, heteroaryl, or heteroarylalkyl.

6. A method for treating hyperglycemia in a mammalian species comprising administration of a therapeutically effective amount of an agent which decreases the amount or activity of microsomal triglyceride transfer protein, wherein said agent is not a polynucleotide compound.

7. A method for treating hypertriglyceridemia in a mammalian species comprising administration of a therapeutically effective amount of an agent which decreases the amount or activity of microsomal triglyceride transfer protein, wherein said agent is not a polynucleotide compound.

8. A method for treating hypercholesterolemia in a mammalian species comprising administration of a therapeutically effective amount of an agent which decreases the amount or activity of microsomal triglyceride transfer protein, wherein said agent is not a polynucleotide compound.

9. A method for treating hypertriglyceridemia and hypercholesterolemia in a mammalin species comprising administration of a therapeutically effective amount of an agent which decreases the amount or activity of microsomal triglyceride protein, wherein said agent is not a polynucleotide compound.

10. A method of reducing gastrointestinal triglyceride, fatty acid cholesterol absorption in a mammalian species comprising administration of a therapeutically effective amount of an agent which decreases the amount or activity of microsomal triglyceride transfer protein, wherein said agent is not a polynucleotide compound.

* * * * *

UNITED STATES PATENT AND TRADEMARK OFFICE
CERTIFICATE OF CORRECTION

PATENT NO.    : 6,492,365 B1
DATED         : December 10, 2002
INVENTOR(S)   : John R. Wetterau II et al.

Page 1 of 1

It is certified that error appears in the above-identified patent and that said Letters Patent is hereby corrected as shown below:

<u>Title page,</u>
Item [75], should read as follows:

-- Inventors: John R. Wetterau, II, Langhorne, PA (US); Daru Young Sharp, Perrineville; Richard E. Gregg, Pennington, both of NJ (US); Scott A. Biller, Ewing, NJ (US); John K. Dickson, Mount Holly, NJ (US); R. Michael Lawrence, Yardley, PA (US); John E. Lawson, Wallingford, CT (US); Henry M. Holava, Meriden, CT (US); Richard A. Partyka, Neshanic, NJ (US) --

Signed and Sealed this

Twenty-sixth Day of August, 2003

JAMES E. ROGAN
*Director of the United States Patent and Trademark Office*

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 2900 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
AAACTCACAT ACTCCACTGA AGTTTTTCTC GATCGGGGCA AAGGAAACCT CCAAGACAGT      60

GTGGGCTACC GAATTTCATC CAATGTGGAT GTCGCTTTAC TGTGGAGGAG TCCTGATGGT     120
```

```
GATGATAACC AACTGATCCA AATTACGATG AAAGATGTAA ACCTTGAAAA TGTGAATCAA    180

CAGAGAGGAG AGAAGAGCAT TTTCAAAGGA AAAAAGTCAT CTCAAATCAT AAGAAAGGAA    240

AACTTGGAAG CAATGCAAAG ACCTGTGCTC CTTCATCTAA TTCATGGAAA GATCAAAGAG    300

TTCTACTCAT ATCAAAATGA ACCAGCAGCC ATAGAAAATC TCAAGAGAGG CCTGGCTAGC    360

CTATTTCAGA TGCAGTTAAG CTCTGGAACT ACCAATGAGG TAGACATCTC TGGAGATTGT    420

AAAGTGACCT ACCAGGCTCA TCAAGACAAA GTGACCAAAA TTAAGGCTTT GGATTCATGC    480

AAAATAGAGA GGGCTGGATT TACGACCCCA CATCAGGTCT TGGGTGTCAC TTCGAAAGCC    540

ACATCTGTCA CTACCTATAA GATAGAAGAC AGCTTTGTTG TAGCTGTGCT CTCAGAAGAG    600

ATACGTGCTT TAAGGCTCAA TTTTCTACAA TCAATAGCAG GCAAAATAGT ATCGAGGCAG    660

AAACTGGAGC TGAAAACCAC GGAAGCAAGC GTGAGACTGA AGCCAGGAAA GCAGGTTGCA    720

GCCATCATTA AAGCAGTCGA TTCAAAGTAC ACGGCCATTC CCATTGTGGG GCAGGTCTTC    780

CAGAGCAAGT GCAAAGGATG CCCTTCTCTC TCAGAGCACT GGCAGTCCAT CAGAAAACAC    840

CTGCAGCCTG ACAACCTCTC CAAGGCTGAG GCTGTCAGAA GCTTCCTGGC CTTCATCAAG    900

CACCTCAGGA CGGCAAAGAA AGAAGAGATC CTCCAAATTC TAAAGGCAGA AAACAAGGAA    960

GTACTACCCC AGCTAGTGGA TGCTGTCACC TCTGCTCAGA CACCAGACTC ATTAGACGCC   1020

ATTTTGGACT TTCTGGATTT CAAAAGCACC GAGAGCGTTA TCCTCCAGGA AAGGTTTCTC   1080

TATGCCTGTG CATTTGCCTC ACATCCTGAT GAAGAACTCC TGAGAGCCCT CATTAGTAAG   1140

TTCAAAGGTT CTTTTGGAAG CAATGACATC AGAGAATCTG TTATGATCAT CATCGGGGCC   1200

CTTGTCAGGA AGTTGTGTCA GAACCAAGGC TGCAAACTGA AGGAGTAAT AGAAGCCAAA    1260

AAGTTAATCT TGGGAGGACT TGAAAAGCA GAGAAAAAG AGGACATCGT GATGTACCTG     1320

CTGGCTCTGA AGAACGCCCG GCTTCCAGAA GGCATCCCGC TCCTTCTGAA GTACACAGAG    1380

ACAGGAGAAG GGCCCATTAG CCACCTTGCC GCCACCACAC TCCAGAGATA TGATGTCCCT    1440

TTCATAACTG ATGAGGTAAA GAAGACTATG AACAGGATAT ACCACCAGAA TCGTAAAATA    1500

CATGAAAAAA CTGTGCGTAC TACTGCAGCT GCCATCATTT TAAAAAACAA TCCATCCTAC    1560

ATGGAAGTAA AAAACATCCT GCTCTCTATT GGGGAACTTC CCAAAGAAAT GAATAAGTAC    1620

ATGCTCTCCA TTGTCCAAGA CATCCTACGT TTTGAAACAC CTGCAAGCAA AATGGTCCGT    1680

CAAGTTCTGA AGGAAATGGT CGCTCATAAT TACGATCGTT TCTCCAAGAG TGGGTCCTCC    1740

TCTGCATATA CTGGCTACGT AGAACGGACT TCCCATTCGG CATCTACTTA CAGCCTTGAC    1800

ATTCTTTACT CTGGTTCTGG CATTCTAAGG AGAAGTAATC TGAACATCTT TCAGTATATT    1860

GAGAAAACTC CTCTTCATGG TATCCAGGTG GTCATTGAAG CCCAAGGACT GGAGGCATTA    1920

ATTGCAGCCA CTCCTGATGA GGGGAAGAG AACCTTGACT CCTATGCTGG CTTGTCAGCT    1980

CTCCTCTTTG ATGTTCAGCT CAGACCTGTC ACTTTTTTCA ACGGGTACAG TGATTTGATG    2040

TCCAAAATGC TGTCAGCATC TAGTGACCCT ATGAGTGTGG TGAAAGGACT TCTTCTGCTA    2100

ATAGATCATT CCCAGGAGCT TCAGCTGCAA TCTGGACTTA AGGCCAATAT GGATGTTCAA    2160

GGTGGTCTAG CTATTGATAT TACAGGTGCC ATGGAGTTTA GTCTATGGTA TCGTGAATCT    2220

AAAACCCGAG TGAAAAATCG GGTAAGTGTG TTAATAACTG GTGGCATCAC GGTGGACTCC    2280

TCTTTTGTGA AGCTGGCTT GGAAATTGGT GCAGAAACAG AAGCAGGCTT GGAGTTTATC    2340

TCCACGGTGC AGTTTCTCA GTACCCATTT TTAGTTTGTC TGCAGATGGA CAAGGAAGAT    2400

GTTCCATACA GGCAGTTTGA GACAAAATAT GAAAGGCTGT CCACAGGCAG AGGTTACATC    2460
```

| | |
|---|---|
| TCTCGGAAGA GAAAAGAAAG CCTAATAGGA GGATGTGAAT TCCCGCTGCA CCAAGAGAAC | 2520 |
| TCTGACATGT GCAAGGTGGT GTTTGCTCCT CAACCAGAGA GCAGTTCCAG TGGTTGGTTT | 2580 |
| TGAAACTGAT GGGGGCTGTT TCATTAGACT TCATCTCGCC AGAAGGGATA AGACGTGACA | 2640 |
| TGCCTAAGTA TTGCTCTCTG AGAGCACAGT GTTTACATAT TTACCTGTAT TTAAGAGTTT | 2700 |
| TGTAGAACGT GATGAAAAAC CTCACATAAT TAAGTTTGGG CCTGAATCAT TTGATACTAC | 2760 |
| CTACAGGGTC ATTCTGAGCC ACTCTATGTG ATACCTTAGT AGCGTTCTGT TTTCCTGCAT | 2820 |
| CTCTCTCAAA TCACATTTAC TACTGTGAAA CTAGTTCTGC CTAAGAAGA AACCATTGTT | 2880 |
| TAAAAAAAAA AAAAAAAAA | 2900 |

(2) INFORMATION FOR SEQ ID NO:2:

(i) SEQUENCE CHARACTERISTICS:
        (A) LENGTH: 3185 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

| | |
|---|---|
| GTGACTCCTA GCTGGGCACT GGATGCAGTT GAGGATTGCT GGTCAATATG ATTCTTCTTG | 60 |
| CTGTGCTTTT TCTCTGCTTC ATTTCCTCAT ATTCAGCTTC TGTTAAAGGT CACACAACTG | 120 |
| GTCTCTCATT AAATAATGAC CGGCTGTACA AGCTCACGTA CTCCACTGAA GTTCTTCTTG | 180 |
| ATCGGGCAA AGGAAAACTG CAAGACAGCG TGGGCTACCG CATTTCCTCC AACGTGGATG | 240 |
| TGGCCTTACT ATGGAGGAAT CCTGATGGTG ATGATGACCA GTTGATCCAA ATAACGATGA | 300 |
| AGGATGTAAA TGTTGAAAAT GTGAATCAGC AGAGAGGAGA GAAGAGCATC TTCAAAGGAA | 360 |
| AAAGCCCATC TAAAATAATG GGAAAGGAAA ACTTGGAAGC TCTGCAAAGA CCTACGCTCC | 420 |
| TTCATCTAAT CCATGGAAAG GTCAAAGAGT TCTACTCATA TCAAAATGAG GCAGTGGCCA | 480 |
| TAGAAAATAT CAAGAGAGGT CTGGCTAGCC TATTTCAGAC ACAGTTAAGC TCTGGAACCA | 540 |
| CCAATGAGGT AGATATCTCT GGAAATTGTA AAGTGACCTA CCAGGCTCAT CAAGACAAAG | 600 |
| TGATCAAAAT TAAGGCCTTG GATTCATGCA AAATAGCGAG GTCTGGATTT ACGACCCCAA | 660 |
| ATCAGGTCTT GGGTGTCAGT TCAAAAGCTA CATCTGTCAC CACCTATAAG ATAGAAGACA | 720 |
| GCTTTGTTAT AGCTGTGCTT GCTGAAGAAA CACACAATTT TGGACTGAAT TTCCTACAAA | 780 |
| CCATTAAGGG GAAAATAGTA TCGAAGCAGA AATTAGAGCT GAAGACAACC GAAGCAGGCC | 840 |
| CAAGATTGAT GTCTGGAAAG CAGGCTGCAG CCATAATCAA AGCAGTTGAT TCAAAGTACA | 900 |
| CGGCCATTCC CATTGTGGGG CAGGTCTTCC AGAGCCACTG TAAAGGATGT CCTTCTCTCT | 960 |
| CGGAGCTCTG GCGGTCCACC AGGAAATACC TGCAGCCTGA CAACCTTTCC AAGGCTGAGG | 1020 |
| CTGTCAGAAA CTTCCTGGCC TTCATTCAGC ACCTCAGGAC TGCGAAGAAA GAAGAGATCC | 1080 |
| TTCAAATACT AAAGATGGAA AATAAGGAAG TATTACCTCA GCTGGTGGAT GCTGTCACCT | 1140 |
| CTGCTCAGAC CTCAGACTCA TTAGAAGCCA TTTTGGACTT TTTGGATTTC AAAAGTGACA | 1200 |
| GCAGCATTAT CCTCCAGGAG AGGTTTCTCT ATGCCTGTGG ATTTGCTTCT CATCCCAATG | 1260 |
| AAGAACTCCT GAGAGCCCTC ATTAGTAAGT TCAAAGGTTC TATTGGTAGC AGTGACATCA | 1320 |
| GAGAAACTGT TATGATCATC ACTGGGACAC TTGTCAGAAA GTTGTGTCAG AATGAAGGCT | 1380 |
| GCAAACTCAA AGCAGTAGTG GAAGCTAAGA AGTTAATCCT GGGAGGACTT GAAAAGCAG | 1440 |
| AGAAAAAAGA GGACACCAGG ATGTATCTGC TGGCTTTGAA GAATGCCCTG CTTCCAGAAG | 1500 |

```
GCATCCCAAG TCTTCTGAAG TATGCAGAAG CAGGAGAAGG GCCCATCAGC CACCTGGCTA    1560

CCACTGCTCT CCAGAGATAT GATCTCCCTT TCATAACTGA TGAGGTGAAG AAGACCTTAA    1620

ACAGAATATA CCACCAAAAC CGTAAAGTTC ATGAAAAGAC TGTGCGCACT GCTGCAGCTG    1680

CTATCATTTT AAATAACAAT CCATCCTACA TGGACGTCAA GAACATCCTG CTGTCTATTG    1740

GGGAGCTTCC CCAAGAAATG AATAAATACA TGCTCGCCAT TGTTCAAGAC ATCCTACGTT    1800

TTGAAATGCC TGCAAGCAAA ATTGTCCGTC GAGTTCTGAA GGAAATGGTC GCTCACAATT    1860

ATGACCGTTT CTCCAGGAGT GGATCTTCTT CTGCCTACAC TGGCTACATA GAACGTAGTC    1920

CCCGTTCGGC ATCTACTTAC AGCCTAGACA TTCTCTACTC GGGTTCTGGC ATTCTAAGGA    1980

GAAGTAACCT GAACATCTTT CAGTACATTG GAAGGCTGG TCTTCACGGT AGCCAGGTGG    2040

TTATTGAAGC CCAAGGACTG GAAGCCTTAA TCGCAGCCAC CCCTGACGAG GGGGAGGAGA    2100

ACCTTGACTC CTATGCTGGT ATGTCAGCCA TCCTCTTTGA TGTTCAGCTC AGACCTGTCA    2160

CCTTTTTCAA CGGATACAGT GATTTGATGT CCAAAATGCT GTCAGCATCT GGCGACCCTA    2220

TCAGTGTGGT GAAAGGACTT ATTCTGCTAA TAGATCATTC TCAGGAACTT CAGTTACAAT    2280

CTGGACTAAA AGCCAATATA GAGGTCCAGG GTGGTCTAGC TATTGATATT TCAGGTGCAA    2340

TGGAGTTTAG CTTGTGGTAT CGTGAGTCTA AAACCCGAGT GAAAAATAGG GTGACTGTGG    2400

TAATAACCAC TGACATCACA GTGGACTCCT CTTTTGTGAA AGCTGGCCTG GAAACCAGTA    2460

CAGAAACAGA AGCAGGCTTG GAGTTTATCT CCACAGTGCA GTTTTCTCAG TACCCATTCT    2520

TAGTTTGCAT GCAGATGGAC AAGGATGAAG CTCCATTCAG GCAATTTGAG AAAAAGTACG    2580

AAAGGCTGTC CACAGGCAGA GGTTATGTCT CTCAGAAAAG AAAAGAAAGC GTATTAGCAG    2640

GATGTGAATT CCCGCTCCAT CAAGAGAACT CAGAGATGTG CAAAGTGGTG TTTGCCCCTC    2700

AGCCGGATAG TACTTCCAGC GGATGGTTTT GAAACTGACC TGTGATATTT TACTTGAATT    2760

TGTCTCCCCG AAAGGGACAC AATGTGGCAT GACTAAGTAC TTGCTCTCTG AGAGCACAGC    2820

GTTTACATAT TTACCTGTAT TTAAGATTTT TGTAAAAAGC TACAAAAAAC TGCAGTTTGA    2880

TCAAATTTGG GTATATGCAG TATGCTACCC ACAGCGTCAT TTTGAATCAT CATGTGACGC    2940

TTTCAACAAC GTTCTTAGTT TACTTATACC TCTCTCAAAT CTCATTTGGT ACAGTCAGAA    3000

TAGTTATTCT CTAAGAGGAA ACTAGTGTTT GTTAAAAACA AAATAAAAA CAAAACCACA     3060

CAAGGAGAAC CCAATTTTGT TTCAACAATT TTTGATCAAT GTATATGAAG CTCTTGATAG    3120

GACTTCCTTA AGCATGACGG GAAAACCAAA CACGTTCCCT AATCAGGAAA AAAAAAAAA    3180

AAAAA                                                              3185
```

(2) INFORMATION FOR SEQ ID NO:3:

(i) SEQUENCE CHARACTERISTICS:
        (A) LENGTH: 860 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Lys Leu Thr Tyr Ser Thr Glu Val Phe Leu Asp Arg Gly Lys Gly Asn
1               5                   10                  15

Leu Gln Asp Ser Val Gly Tyr Arg Ile Ser Ser Asn Val Asp Val Ala
            20                  25                  30

Leu Leu Trp Arg Ser Pro Asp Gly Asp Asp Asn Gln Leu Ile Gln Ile
        35                  40                  45
```

-continued

```
Thr Met Lys Asp Val Asn Leu Glu Asn Val Asn Gln Gln Arg Gly Glu
    50                  55                  60
Lys Ser Ile Phe Lys Gly Lys Ser Ser Gln Ile Ile Arg Lys Glu
65                  70                  75                  80
Asn Leu Glu Ala Met Gln Arg Pro Val Leu His Leu Ile His Gly
                85                  90                  95
Lys Ile Lys Glu Phe Tyr Ser Tyr Gln Asn Glu Pro Ala Ala Ile Glu
            100                 105                 110
Asn Leu Lys Arg Gly Leu Ala Ser Leu Phe Gln Met Gln Leu Ser Ser
            115                 120                 125
Gly Thr Thr Asn Glu Val Asp Ile Ser Gly Asp Cys Lys Val Thr Tyr
    130                 135                 140
Gln Ala His Gln Asp Lys Val Thr Lys Ile Lys Ala Leu Asp Ser Cys
145                 150                 155                 160
Lys Ile Glu Arg Ala Gly Phe Thr Thr Pro His Gln Val Leu Gly Val
                165                 170                 175
Thr Ser Lys Ala Thr Ser Val Thr Thr Tyr Lys Ile Glu Asp Ser Phe
            180                 185                 190
Val Val Ala Val Leu Ser Glu Glu Ile Arg Ala Leu Arg Leu Asn Phe
            195                 200                 205
Leu Gln Ser Ile Ala Gly Lys Ile Val Ser Arg Gln Lys Leu Glu Leu
    210                 215                 220
Lys Thr Thr Glu Ala Ser Val Arg Leu Lys Pro Gly Lys Gln Val Ala
225                 230                 235                 240
Ala Ile Ile Lys Ala Val Asp Ser Lys Tyr Thr Ala Ile Pro Ile Val
                245                 250                 255
Gly Gln Val Phe Gln Ser Lys Cys Lys Gly Cys Pro Ser Leu Ser Glu
            260                 265                 270
His Trp Gln Ser Ile Arg Lys His Leu Gln Pro Asp Asn Leu Ser Lys
    275                 280                 285
Ala Glu Ala Val Arg Ser Phe Leu Ala Phe Ile Lys His Leu Arg Thr
    290                 295                 300
Ala Lys Lys Glu Glu Ile Leu Gln Ile Leu Lys Ala Glu Asn Lys Glu
305                 310                 315                 320
Val Leu Pro Gln Leu Val Asp Ala Val Thr Ser Ala Gln Thr Pro Asp
                325                 330                 335
Ser Leu Asp Ala Ile Leu Asp Phe Leu Asp Phe Lys Ser Thr Glu Ser
            340                 345                 350
Val Ile Leu Gln Glu Arg Phe Leu Tyr Ala Cys Ala Phe Ala Ser His
            355                 360                 365
Pro Asp Glu Glu Leu Leu Arg Ala Leu Ile Ser Lys Phe Lys Gly Ser
    370                 375                 380
Phe Gly Ser Asn Asp Ile Arg Glu Ser Val Met Ile Ile Gly Ala
385                 390                 395                 400
Leu Val Arg Lys Leu Cys Gln Asn Gln Gly Cys Lys Leu Lys Gly Val
                405                 410                 415
Ile Glu Ala Lys Lys Leu Ile Leu Gly Gly Leu Glu Lys Ala Glu Lys
            420                 425                 430
Lys Glu Asp Ile Val Met Tyr Leu Leu Ala Leu Lys Asn Ala Arg Leu
            435                 440                 445
Pro Glu Gly Ile Pro Leu Leu Lys Tyr Thr Glu Thr Gly Glu Gly
    450                 455                 460
```

```
Pro Ile Ser His Leu Ala Ala Thr Thr Leu Gln Arg Tyr Asp Val Pro
465                 470                 475                 480

Phe Ile Thr Asp Glu Val Lys Lys Thr Met Asn Arg Ile Tyr His Gln
            485                 490                 495

Asn Arg Lys Ile His Glu Lys Thr Val Arg Thr Thr Ala Ala Ala Ile
                500                 505                 510

Ile Leu Lys Asn Asn Pro Ser Tyr Met Glu Val Lys Asn Ile Leu Leu
            515                 520                 525

Ser Ile Gly Glu Leu Pro Lys Glu Met Asn Lys Tyr Met Leu Ser Ile
            530                 535                 540

Val Gln Asp Ile Leu Arg Phe Glu Thr Pro Ala Ser Lys Met Val Arg
545                 550                 555                 560

Gln Val Leu Lys Glu Met Val Ala His Asn Tyr Asp Arg Phe Ser Lys
                565                 570                 575

Ser Gly Ser Ser Ser Ala Tyr Thr Gly Tyr Val Glu Arg Thr Ser His
            580                 585                 590

Ser Ala Ser Thr Tyr Ser Leu Asp Ile Leu Tyr Ser Gly Ser Gly Ile
            595                 600                 605

Leu Arg Arg Ser Asn Leu Asn Ile Phe Gln Tyr Ile Glu Lys Thr Pro
610                 615                 620

Leu His Gly Ile Gln Val Val Ile Glu Ala Gln Gly Leu Glu Ala Leu
625                 630                 635                 640

Ile Ala Ala Thr Pro Asp Glu Gly Glu Asn Leu Asp Ser Tyr Ala
                645                 650                 655

Gly Leu Ser Ala Leu Leu Phe Asp Val Gln Leu Arg Pro Val Thr Phe
                660                 665                 670

Phe Asn Gly Tyr Ser Asp Leu Met Ser Lys Met Leu Ser Ala Ser Ser
            675                 680                 685

Asp Pro Met Ser Val Val Lys Gly Leu Leu Leu Ile Asp His Ser
            690                 695                 700

Gln Glu Leu Gln Leu Gln Ser Gly Leu Lys Ala Asn Met Asp Val Gln
705                 710                 715                 720

Gly Gly Leu Ala Ile Asp Ile Thr Gly Ala Met Glu Phe Ser Leu Trp
                725                 730                 735

Tyr Arg Glu Ser Lys Thr Arg Val Lys Asn Arg Val Ser Val Leu Ile
            740                 745                 750

Thr Gly Gly Ile Thr Val Asp Ser Ser Phe Val Lys Ala Gly Leu Glu
            755                 760                 765

Ile Gly Ala Glu Thr Glu Ala Gly Leu Glu Phe Ile Ser Thr Val Gln
770                 775                 780

Phe Ser Gln Tyr Pro Phe Leu Val Cys Leu Gln Met Asp Lys Glu Asp
785                 790                 795                 800

Val Pro Tyr Arg Gln Phe Glu Thr Lys Tyr Glu Arg Leu Ser Thr Gly
                805                 810                 815

Arg Gly Tyr Ile Ser Arg Lys Arg Lys Glu Ser Leu Ile Gly Gly Cys
            820                 825                 830

Glu Phe Pro Leu His Gln Glu Asn Ser Asp Met Cys Lys Val Val Phe
            835                 840                 845

Ala Pro Gln Pro Glu Ser Ser Ser Gly Trp Phe
850                 855                 860
```

(2) INFORMATION FOR SEQ ID NO:4:

(i) SEQUENCE CHARACTERISTICS:

(A) LENGTH: 894 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:4:

```
Met Ile Leu Leu Ala Val Leu Phe Leu Cys Phe Ile Ser Ser Tyr Ser
1               5                   10                  15

Ala Ser Val Lys Gly His Thr Thr Gly Leu Ser Leu Asn Asn Asp Arg
            20                  25                  30

Leu Tyr Lys Leu Thr Tyr Ser Thr Glu Val Leu Leu Asp Arg Gly Lys
        35                  40                  45

Gly Lys Leu Gln Asp Ser Val Gly Tyr Arg Ile Ser Ser Asn Val Asp
50                  55                  60

Val Ala Leu Leu Trp Arg Asn Pro Asp Gly Asp Asp Gln Leu Ile
65                  70                  75                  80

Gln Ile Thr Met Lys Asp Val Asn Val Glu Asn Val Asn Gln Gln Arg
                85                  90                  95

Gly Glu Lys Ser Ile Phe Lys Gly Lys Ser Pro Ser Lys Ile Met Gly
            100                 105                 110

Lys Glu Asn Leu Glu Ala Leu Gln Arg Pro Thr Leu Leu His Leu Ile
        115                 120                 125

His Gly Lys Val Lys Glu Phe Tyr Ser Tyr Gln Asn Glu Ala Val Ala
130                 135                 140

Ile Glu Asn Ile Lys Arg Gly Leu Ala Ser Leu Phe Gln Thr Gln Leu
145                 150                 155                 160

Ser Ser Gly Thr Thr Asn Glu Val Asp Ile Ser Gly Asn Cys Lys Val
                165                 170                 175

Thr Tyr Gln Ala His Gln Asp Lys Val Ile Lys Ile Lys Ala Leu Asp
            180                 185                 190

Ser Cys Lys Ile Ala Arg Ser Gly Phe Thr Thr Pro Asn Gln Val Leu
        195                 200                 205

Gly Val Ser Ser Lys Ala Thr Ser Val Thr Thr Tyr Lys Ile Glu Asp
210                 215                 220

Ser Phe Val Ile Ala Val Leu Ala Glu Glu Thr His Asn Phe Gly Leu
225                 230                 235                 240

Asn Phe Leu Gln Thr Ile Lys Gly Lys Ile Val Ser Lys Gln Lys Leu
                245                 250                 255

Glu Leu Lys Thr Thr Glu Ala Gly Pro Arg Leu Met Ser Gly Lys Gln
            260                 265                 270

Ala Ala Ala Ile Ile Lys Ala Val Asp Ser Lys Tyr Thr Ala Ile Pro
        275                 280                 285

Ile Val Gly Gln Val Phe Gln Ser His Cys Lys Gly Cys Pro Ser Leu
290                 295                 300

Ser Glu Leu Trp Arg Ser Thr Arg Lys Tyr Leu Gln Pro Asp Asn Leu
305                 310                 315                 320

Ser Lys Ala Glu Ala Val Arg Asn Phe Leu Ala Phe Ile Gln His Leu
                325                 330                 335

Arg Thr Ala Lys Lys Glu Glu Ile Leu Gln Ile Leu Lys Met Glu Asn
            340                 345                 350

Lys Glu Val Leu Pro Gln Leu Val Asp Ala Val Thr Ser Ala Gln Thr
        355                 360                 365

Ser Asp Ser Leu Glu Ala Ile Leu Asp Phe Leu Asp Phe Lys Ser Asp
```

-continued

```
                 370                 375                 380
Ser Ser Ile Ile Leu Gln Glu Arg Phe Leu Tyr Ala Cys Gly Phe Ala
385                 390                 395                 400
Ser His Pro Asn Glu Glu Leu Leu Arg Ala Leu Ile Ser Lys Phe Lys
                    405                 410                 415
Gly Ser Ile Gly Ser Ser Asp Ile Arg Glu Thr Val Met Ile Ile Thr
                420                 425                 430
Gly Thr Leu Val Arg Lys Leu Cys Gln Asn Glu Gly Cys Lys Leu Lys
                435                 440                 445
Ala Val Val Glu Ala Lys Lys Leu Ile Leu Gly Gly Leu Glu Lys Ala
450                 455                 460
Glu Lys Lys Glu Asp Thr Arg Met Tyr Leu Leu Ala Leu Lys Asn Ala
465                 470                 475                 480
Leu Leu Pro Glu Gly Ile Pro Ser Leu Leu Lys Tyr Ala Glu Ala Gly
                    485                 490                 495
Glu Gly Pro Ile Ser His Leu Ala Thr Thr Ala Leu Gln Arg Tyr Asp
                500                 505                 510
Leu Pro Phe Ile Thr Asp Glu Val Lys Lys Thr Leu Asn Arg Ile Tyr
                515                 520                 525
His Gln Asn Arg Lys Val His Glu Lys Thr Val Arg Thr Ala Ala Ala
                530                 535                 540
Ala Ile Ile Leu Asn Asn Asn Pro Ser Tyr Met Asp Val Lys Asn Ile
545                 550                 555                 560
Leu Leu Ser Ile Gly Glu Leu Pro Gln Glu Met Asn Lys Tyr Met Leu
                    565                 570                 575
Ala Ile Val Gln Asp Ile Leu Arg Leu Glu Met Pro Ala Ser Lys Ile
                580                 585                 590
Val Arg Arg Val Leu Lys Glu Met Val Ala His Asn Tyr Asp Arg Phe
                    595                 600                 605
Ser Arg Ser Gly Ser Ser Ser Ala Tyr Thr Gly Tyr Ile Glu Arg Ser
                610                 615                 620
Pro Arg Ser Ala Ser Thr Tyr Ser Leu Asp Ile Leu Tyr Ser Gly Ser
625                 630                 635                 640
Gly Ile Leu Arg Arg Ser Asn Leu Asn Ile Phe Gln Tyr Ile Gly Lys
                    645                 650                 655
Ala Gly Leu His Gly Ser Gln Val Val Ile Glu Ala Gln Gly Leu Glu
                660                 665                 670
Ala Leu Ile Ala Ala Thr Pro Asp Glu Gly Glu Glu Asn Leu Asp Ser
                675                 680                 685
Tyr Ala Gly Met Ser Ala Ile Leu Phe Asp Val Gln Leu Arg Pro Val
                690                 695                 700
Thr Phe Phe Asn Gly Tyr Ser Asp Leu Met Ser Lys Met Leu Ser Ala
705                 710                 715                 720
Ser Gly Asp Pro Ile Ser Val Val Lys Gly Leu Ile Leu Leu Ile Asp
                    725                 730                 735
His Ser Gln Glu Leu Gln Leu Gln Ser Gly Leu Lys Ala Asn Ile Glu
                740                 745                 750
Val Gln Gly Gly Leu Ala Ile Asp Ile Ser Gly Ala Met Glu Phe Ser
                    755                 760                 765
Leu Trp Tyr Arg Glu Ser Lys Thr Arg Val Lys Asn Arg Val Thr Val
                770                 775                 780
Val Ile Thr Thr Asp Ile Thr Val Asp Ser Ser Phe Val Lys Ala Gly
785                 790                 795                 800
```

```
Leu Glu Thr Ser Thr Glu Thr Glu Ala Gly Leu Glu Phe Ile Ser Thr
            805                 810                 815
Val Gln Phe Ser Gln Tyr Pro Phe Leu Val Cys Met Gln Met Asp Lys
            820                 825                 830
Asp Glu Ala Pro Phe Arg Gln Phe Glu Lys Lys Tyr Glu Arg Leu Ser
            835                 840                 845
Thr Gly Arg Gly Tyr Val Ser Gln Lys Arg Lys Glu Ser Val Leu Ala
            850                 855                 860
Gly Cys Glu Phe Pro Leu His Gln Glu Asn Ser Glu Met Cys Lys Val
865                 870                 875                 880
Val Phe Ala Pro Gln Pro Asp Ser Thr Ser Thr Gly Trp Phe
            885                 890
```

(2) INFORMATION FOR SEQ ID NO:5:

(i) SEQUENCE CHARACTERISTICS:
        (A) LENGTH: 107 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..107

(xi) SEQUENCE DESCRIPTION: SEQ ID NO:5:

```
TT TTT CTC TGC TTC ATT TCC TCA TAT TCA GCT TCT GTT AAA GGT CAC         47
   Phe Leu Cys Phe Ile Ser Ser Tyr Ser Ala Ser Val Lys Gly His
   1               5                   10                  15

ACA ACT GGT CTC TCA TTA AAT AAT GAC CGA CTA TAC AAA CTC ACA TAC        95
Thr Thr Gly Leu Ser Leu Asn Asn Asp Arg Leu Tyr Lys Leu Thr Tyr
            20                  25                  30

TCC ACT GAA GTT                                                       107
Ser Thr Glu Val
        35
```

(2) INFORMATION FOR SEQ ID NO:6:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO:6:

```
Phe Leu Cys Phe Ile Ser Ser Tyr Ser Ala Ser Val Lys Gly His Thr
1               5                   10                  15
Thr Gly Leu Ser Leu Asn Asn Asp Arg Leu Tyr Lys Leu Thr Tyr Ser
            20                  25                  30
Thr Glu Val
        35
```

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

AGAGTCCACT TCTCA                                                               15

(2) INFORMATION FOR SEQ ID NO:8:

(i) SEQUENCE CHARACTERISTICS:
        (A) LENGTH: 8067 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: exon
        (B) LOCATION: 100..287

(ix) FEATURE:
        (A) NAME/KEY: -
        (B) LOCATION: 450..451

(ix) FEATURE:
        (A) NAME/KEY: exon
        (B) LOCATION: 700..844

(ix) FEATURE:
        (A) NAME/KEY: -
        (B) LOCATION: 1197..1198

(ix) FEATURE:
        (A) NAME/KEY: exon
        (B) LOCATION: 1253..1361

(ix) FEATURE:
        (A) NAME/KEY: -
        (B) LOCATION: 1481..1482

(ix) FEATURE:
        (A) NAME/KEY: exon
        (B) LOCATION: 1586..1702

(ix) FEATURE:
        (A) NAME/KEY: -
        (B) LOCATION: 1764..1765

(ix) FEATURE:
        (A) NAME/KEY: exon
        (B) LOCATION: 1805..1945

(ix) FEATURE:
        (A) NAME/KEY: -
        (B) LOCATION: 2010..2011

(ix) FEATURE:
        (A) NAME/KEY: exon
        (B) LOCATION: 2049..2199

(ix) FEATURE:
        (A) NAME/KEY: -
        (B) LOCATION: 2281..2282

(ix) FEATURE:
        (A) NAME/KEY: exon
        (B) LOCATION: 2355..2512

(ix) FEATURE:
        (A) NAME/KEY: -
        (B) LOCATION: 2565..2566

(ix) FEATURE:
        (A) NAME/KEY: exon
        (B) LOCATION: 2595..2763

(ix) FEATURE:
        (A) NAME/KEY: -
        (B) LOCATION: 2871..2872

```
(ix) FEATURE:
    (A) NAME/KEY: exon
    (B) LOCATION: 2898..3005

(ix) FEATURE:
    (A) NAME/KEY: -
    (B) LOCATION: 3135..3136

(ix) FEATURE:
    (A) NAME/KEY: exon
    (B) LOCATION: 3389..3601

(ix) FEATURE:
    (A) NAME/KEY: -
    (B) LOCATION: 3763..3764

(ix) FEATURE:
    (A) NAME/KEY: exon
    (B) LOCATION: 4077..4288

(ix) FEATURE:
    (A) NAME/KEY: -
    (B) LOCATION: 4386..4387

(ix) FEATURE:
    (A) NAME/KEY: exon
    (B) LOCATION: 4630..4727

(ix) FEATURE:
    (A) NAME/KEY: exon
    (B) LOCATION: 4819..4940

(ix) FEATURE:
    (A) NAME/KEY: -
    (B) LOCATION: 5183..5184

(ix) FEATURE:
    (A) NAME/KEY: exon
    (B) LOCATION: 5284..5511

(ix) FEATURE:
    (A) NAME/KEY: -
    (B) LOCATION: 5567..5568

(ix) FEATURE:
    (A) NAME/KEY: exon
    (B) LOCATION: 5685..5809

(ix) FEATURE:
    (A) NAME/KEY: -
    (B) LOCATION: 5857..5858

(ix) FEATURE:
    (A) NAME/KEY: exon
    (B) LOCATION: 6211..6381

(ix) FEATURE:
    (A) NAME/KEY: -
    (B) LOCATION: 6635..6636

(ix) FEATURE:
    (A) NAME/KEY: exon
    (B) LOCATION: 6740..8067

(ix) FEATURE:
    (A) NAME/KEY: repeat_region
    (B) LOCATION: 7347..7364

(xi) SEQUENCE DESCRIPTION: SEQ ID NO:8:
```

```
AAGGTTCCTG AGCCCCACTG TGGTAGAGAG ATGCACTGAT GGTGAGACAG CATGTTCCCT      60

TACAATGAAA ACTGGATATG TGTCATTATC TTTATGCAGG TCACACAACT GGTCTCTCAT     120

TAAATAATGA CCGGCTGTAC AAGCTCACGT ACTCCACTGA AGTTCTTCTT GATCGGGGCA     180

AAGGAAAACT GCAAGACAGC GTGGGCTACC GCATTTCCTC CAACGTGGAT GTGGCCTTAC     240
```

```
TATGGAGGAA TCCTGATGGT GATGATGACC AGTTGATCCA AATAACGGTG GGCATTTTCT    300

ACCAGATAAA TGCAAAGATT AGATATCAGA AGTTTTTGGA GAAGTGTACC ATTGGACAGC    360

ACTTGTATTG GGTTCCCGTT TATAATCCAT TAGTTTCTTA TCTTATCACT AAAACAAGCA    420

GGTCTTGTT TTAAGGTTTG GTGATGAAAG TTATTTTAAG CCTAAAGTCA CAGAGTTCTT     480

TAAGTATTGC TATTTTTGCC TTATTAAAAA ACCTAGTTTA TAAATACCTT CTCCATTCTT    540

TTAAAGTGAG TGGCAAGGTC CTATAAATCA TGAATTGAAA AATGACAGAA GAAATTGTGG    600

CCAACTCTTT CTGTTTCTTT ATCATTTTAT TTTCAGAGAT ACTCTGATGA AGACAGATAT    660

AGGAAGTTTT TTTTAACAGC TTTCTTTCTG TTACTCCAGA TGAAGGATGT AAATGTTGAA    720

AATGTGAATC AGCAGAGAGG AGAGAAGAGC ATCTTCAAAG GAAAAGCCC ATCTAAAATA     780

ATGGGAAAGG AAAACTTGGA AGCTCTGCAA AGACCTACGC TCCTTCATCT AATCCATGGA    840

AAGGTAAAGG GGCCTTTAGA TTCCACAACT TTTTCTCCAA CTTCATATTT TTCTTCCCTT    900

CAGTAGATAT TATTTTGAGG TAATCACATT GTAACTACTT TTATGGTAAA TGGAATTTCT    960

TCAAGAACTA AGAACAGAG GTTGTAAATT AAATGTTTCC AAACTGAATC AATGCCCTGA    1020

GTTCCCTTAC ATTTACTAGC CAATTTGTTT CCTATTTTTC TGGAAATCTT TATAGTGGAA   1080

TGAAGTATTT ATTTATTGAT GAAAGGCATT ATTAAAAGGT AAATTTCTCA TCAAATTATA   1140

AGGGATTACA AACATAATGT AACAAAGCAA GTCATCAAAG CATGATTGGA TGAATTCTCT   1200

GATAAATGAT GCATTTTTGC TTCATTTGTG TTCTGTTCCC CTCTCCCCAC CAGGTCAAAG   1260

AGTTCTACTC ATATCAAAAT GAGGCAGTGG CCATAGAAAA TATCAAGAGA GGTCTGGCTA   1320

GCCTATTTCA GACACAGTTA AGCTCTGGAA CCACCAATGA GGTACTTACC AATATTAATA   1380

AGGATTCAGC ATCTCAATAA AATTTGTAAG GATTCTACT TATACAATTT CAGTAGAAGA    1440

GTTACTACTA AGGTAATGCT CAGAAAAGGT GACTTGTGTA GTCCCCTATG GCCTATTAGA   1500

GACCTCAATT TTCAAGCCAC TTCTCACTAG AATTCAAATG GCCCACAAGG AATCCCAAGC   1560

ATTATGCCCT TGCCTTTCTT TTTAGGTAGA TATCTCTGGA AATTGTAAAG TGACCTACCA   1620

GGCTCATCAA GACAAAGTGA TCAAAATTAA GGCCTTGGAT TCATGCAAAA TAGCGAGGTC   1680

TGGATTTACG ACCCCAAATC AGGTATGATA GATGTCACTT TCTTTGAGGC ATTAAAATAA   1740

TTACATTTTG TAGAGACTAA TTTACGATGA TTACTTGTTA TAAAGATGGC TATTTATTTA   1800

TTTAGGTCTT GGGTGTCAGT TCAAAAGCTA CATCTGTCAC CACCTATAAG ATAGAAGACA   1860

GCTTTGTTAT AGCTGTGCTT GCTGAAGAAA CACACAATTT TGGACTGAAT TTCCTACAAA   1920

CCATTAAGGG GAAAATAGTA TCGAAGTAAG ATAATGCTAA AATTTTTATT TTCTTTGCTA   1980

TTCTTTGTTA TATTATTATA CTTGATTTGT ATGATTATAA TATAGCATTT CCCTTTGGTA   2040

TTATGCAGGC AGAAATTAGA GCTGAAGACA ACCGAAGCAG GCCCAAGATT GATGTCTGGA   2100

AAGCAGGCTG CAGCCATAAT CAAAGCAGTT GATTCAAAGT ACACGGCCAT TCCCATTGTG   2160

GGGCAGGTCT TCCAGAGCCA CTGTAAAGGA TGTCCTTCTG TAAGTGCAGA CAAATATGGG   2220

AATAATCATG ACATCAGACT CTGTTTTCAT TTTGTCTCCA GTGAAAGCAT CAACTCATTC   2280

AGGAGAACAC CCTTTGTAAA TGTGGATGTT CACAGTTATG AGTGGGTAT GAGCCTGCAG    2340

TGTATGTTTT GCAGCTCTCG GAGCTCTGGC GGTCCACCAG GAAATACCTG CAGCCTGACA   2400

ACCTTTCCAA GGCTGAGGCT GTCAGAAACT TCCTGGCCTT CATTCAGCAC CTCAGGACTG   2460

CGAAGAAAGA AGAGATCCTT CAAATACTAA AGATGGAAAA TAAGGAAGTA TTGTAAGTTC   2520

CCCAACCTTT GTGTGGGGTT GTCTGTCAGA AACATTTCTG GAGTGGATAT CCATGATTAT   2580

GCCTTTTTTT ATAGACCTCA GCTGGTGGAT GCTGTCACCT CTGCTCAGAC CTCAGACTCA   2640
```

```
TTAGAAGCCA TTTTGGACTT TTTGGATTTC AAAAGTGACA GCAGCATTAT CCTCCAGGAG    2700

AGGTTTCTCT ATGCCTGTGG ATTTGCTTCT CATCCCAATG AAGAACTCCT GAGAGCCCTC    2760

ATTGTAAGTC AAATAGAAAA TAAAGACCCT CAACTCCTAT AAAACTTCTT AAGAATATTA    2820

ACAGTAATTA AAAGTTTCTT AGATCCGAAT TCTTCGCCCT ATAGTGAGTC ACTATTTTAT    2880

CCCTGGGTGG TTAATAGAGT AAGTTCAAAG GTTCTATTGG TAGCAGTGAC ATCAGAGAAA    2940

CTGTTATGAT CATCACTGGG ACACTTGTCA GAAAGTTGTG TCAGAATGAA GGCTGCAAAC    3000

TCAAAGTAAG TGCAAATCCA ATCTCATGTA TTACATCATT CTACACCATT GTCCATTTGA    3060

TACTCACCAT GCTGCCTACT ATTGGCACTC CTAATTCTCT TTACTCTATT CTACTTACCT    3120

TATTTGNATA GCAATAACAC AATATGCCCA TTATTGATAA TACTCATTGC TTCTTAAGAA    3180

TGTATATGTA TTTTTTTTAA AAAAGCATA ACACCTTTAT CAAGCTTTAC TTGTTTGCTT    3240

TTATTCCACT GTGTGCCTCA GTCAAGCAAC CAATGCAAAA CTTTGTAAAA CTGTAGGTTG    3300

CTTTCTTGGA CCCAAGAATA AAGCCAGTCT CACCCAAGTC TTCTTCAATG TATGGTCATG    3360

CATATATCTA AGGTATATGA TTTTTCAGGC AGTAGTGGAA GCTAAGAAGT TAATCCTGGG    3420

AGGACTTGAA AAAGCAGAGA AAAAGAGGA CACCAGGATG TATCTGCTGG CTTTGAAGAA    3480

TGCCCTGCTT CCAGAAGGCA TCCCAAGTCT TCTGAAGTAT GCAGAAGCAG GAGAAGGGCC    3540

CATCAGCCAC CTGGCTACCA CTGCTCTCCA GAGATATGAT CTCCCTTTCA TAACTGATGA    3600

GGTAAAATCT CCAAGAATAT TTGCAACATT TACAGAAGAA AAAAAAAAAG CATGCTGAAC    3660

ATGAGTCAAA TGCAAATTCC GCTCAAGTCA CTCTGTATTT TCCCCAAATA GTCTTCTCTC    3720

CTGCTTAAAA ATAACTCTTA AATTGCATTT GGGGCTATTC TAAATGTTTA ATTTCTCAGG    3780

CTATGCCTAA TGTGCATAAG GAAGTATGTG GTCTGAAGTT CACTACAGTC ATGGAAGAAA    3840

GAGATGGAGA AAGCCACCAG CTCTTAACGG CCTCAGCCTA GAAGTGATCC TCATAGATTC    3900

TATCCATGGC GTATTAGCCA GAACTAGTCA CGTGGCCCCC ACCAAATCAC AAAGGAATCT    3960

GGGAAATGTA GTAACACATG TATATTTTTA TGAACACTCA CTATTCCTGC TATTCCTGCT    4020

GAAATGTCCA TTTTAAAAAT CTAGATGTGC ACTAAGTTTG AACATCTTAT GAACAGGTGA    4080

AGAAGACCTT AAACAGAATA TACCACCAAA ACCGTAAAGT TCATGAAAAG ACTGTGCGCA    4140

CTGCTGCAGC TGCTATCATT TTAAATAACA ATCCATCCTA CATGGACGTC AAGAACATCC    4200

TGCTGTCTAT TGGGGAGCTT CCCCAAGAAA TGAATAAATA CATGCTCGCC ATTGTTCAAG    4260

ACATCCTACG TTTTGAAATG CCTGCAAGGT ATAATACATT GCACATGTCT CTCTGTGTAT    4320

TCAAGCTTAT TTGTGTGTTC ATGGGGTACC GATGTAGCTA ATAATAATGA TGTGGTCATT    4380

ATGCAAAGCT GGACACCCTT GCCTTGCTGT CATTTTGATA GCAAACTAAA TTTCAAATAT    4440

CTGAGTAATG AAGGGGCTAG CCCTAATCCT GATGCTACCA CGCCAGCTGG CACCACCCTG    4500

GCTCTTGGAA AGGCATGAGG AAAATTTGGC TTCCTCTTTT TTCCACTGAG GATTTTTTTT    4560

TTCCAAATTT GACTTGGGAA ACAGTCATTA CAATGAATGT GCAGCTTTTT TTTTCCTCAT    4620

ATGTTGCAGC AAAATTGTCC GTCGAGTTCT GAAGGAAATG GTCGCTCACA ATTATGACCG    4680

TTTCTCCAGG AGTGGATCTT CTTCTGCCTA CACTGGCTAC ATAGAACGTA TGTACACCAA    4740

AAAGAGGTTC TCCTTCCATA CCCCACAACT TAGCATTGCT GGAACTGCTA TTAAATTACA    4800

GTTATTGTGT GTCATCAGGT AGTCCCCGTT CGGCATCTAC TTACAGCCTA GACATTCTCT    4860

ACTCGGGTTC TGGCATTCTA AGGAGAAGTA ACCTGAACAT CTTTCAGTAC ATTGGGAAGG    4920

CTGGTCTTCA CGGTAGCCAG GTAACTCACT TCTCATGGAT TTTGCTTAAT AAAGTATGCA    4980
```

```
AGAAATCAGG CTGAGGTAAA ATAAAACATA TATGCTGTGG GTAATGCTAT AGAATGTATA     5040

AGTTAATGGT GGCTTCTGTC ATATTTTGCC CATGATTTCC TTATCTGTAA GAGGCTGTAT     5100

GGTTTATAGT CACTCAGAGA AAGTTTCGAA TTTGAACTTG AAACCTAAGT AATTTGATCC     5160

ATTGAACTTG ACAAATGTCC ATTTGGCCCC TTGAGAAGTT CTAGCTGCAG CTCAGAAGCT     5220

TCACCATTAT TTACAGAGCA GGCAGGGAGC TTGCGTCATG AACATTATAT TGATTTTATC     5280

CAGGTGGTTA TTGAAGCCCA AGGACTGGAA GCCTTAATCG CAGCCACCCC TGACGAGGGG     5340

GAGGAGAACC TTGACTCCTA TGCTGGTATG TCAGCCATCC TCTTTGATGT TCAGCTCAGA     5400

CCTGTCACCT TTTTCAACGG ATACAGTGAT TTGATGTCCA AAATGCTGTC AGCATCTGGC     5460

GACCCTATCA GTGTGGTGAA AGGACTTATT CTGCTAATAG ATCATTCTCA GGTAATTCAN     5520

YCAGTCTGTG AGTATTTATT GAGTCCCTAA ACTACGCCAG GCACGTAATC AACACAACTC     5580

AAATGGAATT ATCTACAGCA GGAGGTCAAA TGTNCCATTG GAAAGGGGGT TAACTAAATT     5640

GTACTTATTA TTTTTATAAC TATTATTATG CTTTTTTCTT CTAGGAACTT CAGTTACAAT     5700

CTGGACTAAA AGCCAATATA GAGGTCCAGG GTGGTCTAGC TATTGATATT TCAGGTGCAA     5760

TGGAGTTTAG CTTGTGGTAT CGTGAGTCTA AAACCCGAGT GAAAAATAGG TAAGTGTTTA     5820

TGCATTATAC ATTTATGAAT TACATATAAG ACTATATCTT GGGTATTTCT GACCTGCTGA     5880

GAGGACCTGG GTTCCAAGAA TGTTTTTCAT TTTGGTCTTT GTTATGCCCA TACGAAACAA     5940

TGTAGTATCT TACAGACACT CCCCACATCT GCAACTGAAG GCAGGGGAGA GCTCAGGGGA     6000

AGGGCAAACC TTCCCTGCCC AATATCTGAG ACTCACCAGG CCCTGGTTAC CAGCAGAACT     6060

CTAAGCACAT CCAGGTCACC TCTGAATCCC TTAAGTGTTT CCTTCCAGTC ACTGGCATCA     6120

TACGTTCAGA CCCTGTAAAG TTACAGCTGT TAGTCCAATA CCATTAAATA TAATATGAAC     6180

AAGTTTTTTC TTTTTTTCTC AAATGTTTAG GGTGACTGTG GTAATAACCA CTGACATCAC     6240

AGTGGACTCC TCTTTTGTGA AAGCTGGCCT GGAAACCAGT ACAGAAACAG AAGCAGGTTT     6300

GGAGTTTATC TCCACAGTGC AGTTTTCTCA GTACCCATTC TTAGTTTGCA TGCAGATGGA     6360

CAAGGATGAA GCTCCATTCA GGTAAGATGC AGCGTACAGG TCATGTTCCA GGACCATCCC     6420

CAGTGCACCA GGAACTTGCA TTCAGTTTAG AACATTCAGT TTCAGAATTA AAACAAAACA     6480

GTAGAAACCC AGGGAAAGAT GAATTTTCTT TAAATGAGTA GAAGAATAAT TGATAAGGCC     6540

AAAAAAAGTC AGTTTCTGGG ATACCAAAAA AAAATCTAAT GACTAGTTCA TGTGATTCTG     6600

GAGATAGTTA TCATATTCTA ATCCAGAAAC AATTTTGCTT TGGAACAGAA ACTTCAAGTA     6660

CATTCAGTAA CTTGGCTGGA GAGGTATAGG GTGACTTAAC TGTGTGTGTA ATTCTGTTAA     6720

TGTTGCTGTT GTTGTACAGG CAATTTGAGA AAAAGTACGA AAGGCTGTCC ACAGGCAGAG     6780

GTTATGTCTC TCAGAAAAGA AAAGAAAGCG TATTAGCAGG ATGTGAATTC CCGCTCCATC     6840

AAGAGAACTC AGAGATGTGC AAAGTGGTGT TGCCCCTCA GCCGGATAGT ACTTCCAGCG     6900

GATGGTTTTG AAACTGACCT GTGATATTTT ACTTGAATTT GTCTCCCCGA AGGGACACA     6960

ATGTGGCATG ACTAAGTACT TGCTCTCTGA GAGCACAGCG TTTACATATT TACCTGTATT     7020

TAAGATTTTT GTAAAAGCT ACAAAAAACT GCAGTTTGAT CAAATTTGGG TATATGCAGT     7080

ATGCTACCCA CAGCGTCATT TTGAATCATC ATGTGACGCT TTCAACAACG TTCTTAGTTT     7140

ACTTATACCT CTCTCAAATC TCATTTGGTA CAGTCAGAAT AGTTATTCTC TAAGAGGAAA     7200

CTAGTGTTTG TTAAAAACAA AAATAAAAAC AAAACCACAC AAGGAGAACC CAATTTTGTT     7260

TCAACAATTT TTGATCAATG TATATGAAGC TCTTGATAGG ACTTCCTTAA GCATGACGGG     7320

AAAACCAAAC ACGTTCCCTA ATCAGGAAAA AAAAAAAAA AAAAGGTAGG ACACAACCAA     7380
```

```
CCCATTTTTT TTCTCTTTTT TTGGAGTTGG GGGCCCAGGG AGAAGGGACA AGACTTTTAA      7440

AAGACTTGTT AGCCAACTTC AAGAATTAAT ATTTATGTCT CTGTTATTGT TAGTTTTAAG      7500

CCTTAAGGTA GAAGGCACAT AGAAATAACA TCTCATCTTT CTGCTGACCA TTTTAGTGAG      7560

GTTGTTCCAA AGACATTCAG GTCTCTACCT CCAGCCCTGC AAAAATATTG GACCTAGCAC      7620

AGAGGAATCA GGAAAATTAA TTTCAGAAAC TCCATTTGAT TTTTCTTTTG CTGTGTCTTT      7680

TTGAGACTGT AATATGGTAC ACTGTCCTCT AAGGGACATC CTCATTTTAT CTCACCTTTT      7740

TGGGGGTGAG AGCTCTAGTT CATTTAACTG TACTCTGCAC AATAGCTAGG ATGACTAAGA      7800

GAACATTGCT TCAAGAAACT GGTGGATTTG GATTTCCAAA ATATGAAATA AGGAAAAAAA      7860

TGTTTTTATT TGTATGAATT AAAAGATCCA TGTTGAACAT TTGCAAATAT TTATTAATAA      7920

ACAGATGTGG TGATAAACCC AAAACAAATG ACAGGTCCTT ATTTTCCACT AAACACAGAC      7980

ACATGAAATG AAAGTTTAGC TAGCCCACTA TTTGTAAATT GAAAACGAAG TGTGATAAAA      8040

TAAATATGTA GAAATCATAT TGAATTC                                         8067

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

GGCACTGGAT GCAGTTGAGG ATTGCT                                            26

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GGTCAATATG ATTCTTCTTG CTGTGC                                            26

(2) INFORMATION FOR SEQ ID NO:11:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

CCGGAATTCC CTACCAGGCT CATCAAGACA AAG                                    33

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear
```

```
         (ii) MOLECULE TYPE: cDNA (xi) SEQUENCE DESCRIPTION: SEQ ID NO:12:

ACGGCCATTC CCATTGTGGG GCAGGT                                           26

(2) INFORMATION FOR SEQ ID NO:13:

(i) SEQUENCE CHARACTERISTICS:
                 (A) LENGTH: 26 base pairs
                 (B) TYPE: nucleic acid
                 (C) STRANDEDNESS: single
                 (D) TOPOLOGY: linear (ii) MOLECULE TYPE: cDNA (xi) SEQUENCE DESCRIPTION: SEQ ID NO:13:

TGACACCCAA GACCTGATTT GGGGTC                                           26

(2) INFORMATION FOR SEQ ID NO:14:

(i) SEQUENCE CHARACTERISTICS:
                 (A) LENGTH: 25 base pairs
                 (B) TYPE: nucleic acid
                 (C) STRANDEDNESS: single
                 (D) TOPOLOGY: linear (ii) MOLECULE TYPE: cDNA (xi) SEQUENCE DESCRIPTION: SEQ ID NO:14:

GCCTGCTTCG GTTGTCTTCA GCTCT                                            25

(2) INFORMATION FOR SEQ ID NO:15:

(i) SEQUENCE CHARACTERISTICS:
                 (A) LENGTH: 31 base pairs
                 (B) TYPE: nucleic acid
                 (C) STRANDEDNESS: single
                 (D) TOPOLOGY: linear (ii) MOLECULE TYPE: cDNA (xi) SEQUENCE DESCRIPTION: SEQ ID NO:15:

CGCGGATCCT TCTGACAGCC TCAGCCTTGG A                                     31

(2) INFORMATION FOR SEQ ID NO:16:

(i) SEQUENCE CHARACTERISTICS:
                 (A) LENGTH: 26 base pairs
                 (B) TYPE: nucleic acid
                 (C) STRANDEDNESS: single
                 (D) TOPOLOGY: linear (ii) MOLECULE TYPE: cDNA (xi) SEQUENCE DESCRIPTION: SEQ ID NO:16:

GGGAGATCAT ATCTCTGGAG AGCAGT                                           26

(2) INFORMATION FOR SEQ ID NO:17:

(i) SEQUENCE CHARACTERISTICS:
                 (A) LENGTH: 31 base pairs
                 (B) TYPE: nucleic acid
                 (C) STRANDEDNESS: single
                 (D) TOPOLOGY: linear (ii) MOLECULE TYPE: cDNA (xi) SEQUENCE DESCRIPTION: SEQ ID NO:17:
```

```
CGGCGGATCC AGCATAGGAG TCAAGGTTCT C                                   31

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

CCCTTACAAT GAAAACTGG                                                 19

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

GGTACACTTC TCCAAAAACT T                                              21

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..33

(xi) SEQUENCE DESCRIPTION: SEQ ID NO:20:

AGG AAT CCT GAT GGT GAT GAT GAC CAG TTG ATC                          33
Arg Asn Pro Asp Gly Asp Asp Asp Gln Leu Ile
 1               5                  10

(2) INFORMATION FOR SEQ ID NO:21:

(i) SEQUENCE CHARACTERISTICS:
        (A) LENGTH: 11 amino acids
        (B) TYPE: amino acid
        (D) TOPOLOGY: linear (ii) MOLECULE TYPE: protein (xi) SEQUENCE DESCRIPTION: SEQ ID NO:21:

Arg Asn Pro Asp Gly Asp Asp Asp Gln Leu Ile
 1               5                  10

(2) INFORMATION FOR SEQ ID NO:22:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA
```

(ix) FEATURE:
              (A) NAME/KEY: CDS
              (B) LOCATION: 1..27

(xi) SEQUENCE DESCRIPTION: SEQ ID NO:22:

AGG AAT CTG ATG GTG ATG ATG ACC AGT TGATG                              32
Arg Asn Leu Met Val Met Met Thr Ser
 1               5

(2) INFORMATION FOR SEQ ID NO:23:

(i) SEQUENCE CHARACTERISTICS:
              (A) LENGTH: 9 amino acids
              (B) TYPE: amino acid
              (D) TOPOLOGY: linear (ii) MOLECULE TYPE: protein (xi) SEQUENCE DESCRIPTION: SEQ ID NO:23:

Arg Asn Leu Met Val Met Met Thr Ser
 1               5

(2) INFORMATION FOR SEQ ID NO:24:

(i) SEQUENCE CHARACTERISTICS:
              (A) LENGTH: 302 base pairs
              (B) TYPE: nucleic acid
              (C) STRANDEDNESS: double
              (D) TOPOLOGY: linear (ii) MOLECULE TYPE: DNA (genomic)

(ix) FEATURE:
              (A) NAME/KEY: exon
              (B) LOCATION: 106..203

(ix) FEATURE:
              (A) NAME/KEY: mutation
              (B) LOCATION: replace(119, "")

(xi) SEQUENCE DESCRIPTION: SEQ ID NO:24:

ATTTGGCTTC CTCTTTTTTC CACTGAGGAT TTTTTTTTCC AAATTTGACT TGGGAAACAG         60

TCATTACAAT GAATGTGCAG CTTTTTTTTT CCTCATATGT TGCAGCAAAA TTGTCCGTCG        120

AGTTCTGAAG GAAATGGTCG CTCACAATTA TGACCGTTTC TCCAGGAGTG GATCTTCTTC        180

TGCCTACACT GGCTACATAG AAGGTATGTA CACCAAAAAG AGGTTCTCCT TCCATACCCC        240

ACAACTTAGC ATTGCTGGAA CTGCTATTAA ATTACAGTTA TAGTGTGTCA TCAGGTAGTC        300

CC                                                                      302

(2) INFORMATION FOR SEQ ID NO:25:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (xi) SEQUENCE DESCRIPTION: SEQ ID NO:25:

CTCTACCAGC GAGTATTAAT                                                    20

(2) INFORMATION FOR SEQ ID NO:26:

(i) SEQUENCE CHARACTERISTICS:
              (A) LENGTH: 33 base pairs
              (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO:26:

ACGTAGGATG TCTTGGACAA TGGAGAGCAT GTA                              33

(2) INFORMATION FOR SEQ ID NO:27:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

GATCAGTTGG TTATCATCAC CATCAGGACT                                  30

(2) INFORMATION FOR SEQ ID NO:28:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:28:

Met Ile Leu Leu Ala Val Leu Phe Leu Cys Phe Ile
1               5                   10

(2) INFORMATION FOR SEQ ID NO:29:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GGTCAATATG ATTCTTCTTG CTGTGC                                      26

(2) INFORMATION FOR SEQ ID NO:30:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

GCCTCGATAC TATTTTGCCT GCT                                         23

(2) INFORMATION FOR SEQ ID NO:31:

(i) SEQUENCE CHARACTERISTICS:
        (A) LENGTH: 1417 base pairs
        (B) TYPE: nucleic acid
        (C) STRANDEDNESS: double
        (D) TOPOLOGY: linear
```

(ii) MOLECULE TYPE: DNA (genomic)

(ix) FEATURE:
    (A) NAME/KEY: exon
    (B) LOCATION: 783..890

(xi) SEQUENCE DESCRIPTION: SEQ ID NO:31:

```
CCCCTCTTAA TCTCTTCCTA GAAATGAGAT TCAGAAAGGA CAGGACTGCA TCCAGCCTGT     60

TTGGGAACTC AGACAAATGT GTGTTGTCAC AGACACAAAT AGAGGTCTAC TATGAAATAA    120

TTGGCTTGCT AGTGTGCTAA TGACAGACAA TGCTGATTTG CTCCAACCTC ATACAGTTTC    180

ACACATAAGG ACAATCATCT ATGTTTCATG AAAGTTCTAT CTACTTTAAC ATTATTTTGA    240

AGTGATTGGT GGTGGTATGA ATTAACAGTT TAAATTTAAA TCCTAAAATT CAGTGTGAAT    300

TTTTTATAAT AGCATAAAAA TTCAAAGATG TCCATACAAG AAAAATTAAA ATTTGGTTAG    360

GTTTAGCAGA GTTTGAGAAT CCTTACTACC CTCCCACATA GTATTGTAAT GTGAATATAG    420

GCAGTTACTA TTACAGGCAT AATGATGATT ATGTATTAAG CAGAAAGAAG TATCACCACC    480

AGTTTTTTTC TTTGAATGCC CCTCAGTACT TCTGCATTTA TAGGATGGTA GACTGGTTTG    540

GTTTAGCTCT CAAAAGTGAA AACATTTAAA GTTTCCTCAT TGGGTGAAAA AAATTAAAAA    600

GAGTGAGAGA CTGAAAACTG CAGCCCACCT ACGTTAATC  ATTAATAGTG AGCCCTTCAG    660

TGAACTTAGG TCCTGATTTT GGAGTTTGGA GTCTGACCTT TCCCCAAAGA TAAACATGAT    720

TGTTGCAGGT TCTGAAGAGG GTCACTCCCT CACTGGCTGC CATTGAAAGA GTCCACTTCT    780

CAGTGACTCC TAGCTGGGCA CTGGATGCAG TTGAGGATTG CTGGTCAATA TGATTCTTCT    840

TGCTGTGCTT TTTCTCTGCT TCATTTCCTC ATATTCAGCT TCTGTTAAAG GTAAGTTTGT    900

GTTGCCTTTT GCTAAACTTT AATTTCCATC TTTGGAGTTG GAGGCAGATA CGTGCGTGTG    960

TGTGTGTTTG TGTGAGTGAA TAGTGAAAGA GTTTCTGACT AAACTATCTT CAAAACCATG   1020

TAACTTTGGA ATGTTTGTGA AAGCATGGCT GAGTTGAAAT GAAAACCAAA TTCAAATCCC   1080

TACAAACATT AAGAAAACAG ATATTTCTTT TAGTTTCAGT TCCTCAGACC AGTGTGTTCT   1140

TGCTTCAATT TCTCATTCAT GGTCTGTTTT TAAAAGAAGG AAAAAAGATA CCCACTATTG   1200

TTACCTGCTG TTGTTGGTCA CATTGAATGC AGCTCCTTCA TTTGAATTGT AAATGAGGAT   1260

TTTTTTTAAA AACCGAGTTC TTAAATTTTC TTTTAGTTGC TTAGCAATGT GACCTCAAGA   1320

AGAATTAGAC CCAATGAAAA AGGCATTTGA TTTGCCAAAG AATTATGAAT GAAATGGCAC   1380

AACATATATT TAATTCCGTT ACAATTAAAA AATGATA                            1417
```

(2) INFORMATION FOR SEQ ID NO:32:

(i) SEQUENCE CHARACTERISTICS:
        (A) LENGTH: 564 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: repeat_region
        (B) LOCATION: 286..347

(xi) SEQUENCE DESCRIPTION: SEQ ID NO:32:

```
ACTTTTCAAA TATGTTCTAC AATCAGAAAA GTCCTTTTGT CCTAGTCTGA GAAAAGGGG     60

GATTGAGTGT AAGTTAATAG TTTAATGGGA AAGCAAATTA GAAATAGGGA CATCTGGGTT   120

CTGGTCTTAT ATTTGCCACT ACATATGTTT TAGAGGCTTC AGTTTCATGT TTAAAATAAA   180
```

-continued

| | | | | |
|---|---|---|---|---|
| GATTCTTTGT | ATGACAGAGT | CTAGGCTGAA | AAATTTTTTA AAAATAAAGG | GTTTTAAGAT | 240 |
| CTAATTCATC | CACAGGATTC | ATAACCTCTG | AAATTAGGCT ACAAGCACAC | ACAAACACAC | 300 |
| AGACACACAC | ATACACACAC | ACACACACAC | ACACACACAC ACATACATGG | GGTTGGGGAG | 360 |
| AATGGATGAT | ATGGGGAAGA | GTGGAGAAGT | ATTAACAAAA GCTCCCAATA | GAAGGAAAGA | 420 |
| TGCTAAACAT | CACACTTAAT | CAGAGAAGTG | ACATTTCTCA ACTATCAAAT | TGGTGAAAAA | 480 |
| TTCAAAAGTT | TGCTAACATA | TTTTGTAGGT | GAGACTATGG GGAAATAGGC | CTTTTCATAA | 540 |
| ATTGCTGATG | AAAGCCTAAA | ATGG | | | 564 |